United States Patent
Teegarden et al.

(10) Patent No.: US 10,781,180 B2
(45) Date of Patent: *Sep. 22, 2020

(54) 3-PHENYL-PYRAZOLE DERIVATIVES AS MODULATORS OF THE 5-HT$_{2A}$ SEROTONIN RECEPTOR USEFUL FOR THE TREATMENT OF DISORDERS RELATED THERETO

(71) Applicant: Arena Pharmaceuticals, Inc., San Diego, CA (US)

(72) Inventors: Bradley Teegarden, San Diego, CA (US); Yifeng Xiong, San Diego, CA (US); Sonja Strah-Pleynet, Newton, MA (US); Honnappa Jayakumar, San Diego, CA (US); Peter I. Dosa, San Diego, CA (US); Konrad Feichtinger, San Diego, CA (US); Martin Casper, San Diego, CA (US); Juerg Lehmann, San Diego, CA (US); Robert M. Jones, San Diego, CA (US); David J. Unett, San Diego, CA (US); Jin Sun Karoline Choi, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,672

(22) Filed: Nov. 1, 2018

(65) Prior Publication Data

US 2019/0263757 A1 Aug. 29, 2019

Related U.S. Application Data

(63) Continuation of application No. 15/137,228, filed on Apr. 25, 2016, now abandoned, which is a continuation of application No. 12/976,887, filed on Dec. 22, 2010, now abandoned, which is a continuation of application No. 11/602,164, filed on Nov. 20, 2006, now Pat. No. 7,884,101, which is a continuation of application No. PCT/US2005/041726, filed on Nov. 17, 2005.

(Continued)

(51) Int. Cl.
*C07D 401/12* (2006.01)
*C07D 403/12* (2006.01)
(Continued)

(52) U.S. Cl.
CPC ........ *C07D 231/12* (2013.01); *A61K 31/5377* (2013.01); *C07D 231/16* (2013.01); *C07D 401/12* (2013.01); *C07D 403/12* (2013.01); *C07D 405/12* (2013.01); *C07D 409/12* (2013.01); *C07D 413/10* (2013.01); *C07D 413/12* (2013.01); *C07D 417/12* (2013.01); *C07D 487/08* (2013.01)

(58) Field of Classification Search
CPC ........................... C07D 401/12; C07D 403/12
See application file for complete search history.

(56) References Cited

U.S. PATENT DOCUMENTS

| | | |
|---|---|---|
| 4,099,012 A | 7/1978 | Gschwend |
| 4,405,644 A | 9/1983 | Kabbe et al. |

(Continued)

FOREIGN PATENT DOCUMENTS

| | | |
|---|---|---|
| EP | 1108720 | 6/2001 |
| EP | 1558582 | 8/2005 |

(Continued)

OTHER PUBLICATIONS

Adams et al., "APD791, a Novel 5-HT2A Receptor Antagonist: Pharmacological Profile, Pharmacokinetics, Platelet and Vascular Biology," JPET # 153189, published on Jul. 23, 2009, 38 pages.

(Continued)

*Primary Examiner* — Shawquia Jackson
(74) *Attorney, Agent, or Firm* — Fish & Richardson P.C.

(57) ABSTRACT

The present invention relates to certain 3-phenyl-pyrazole derivatives of Formula (Ia) and pharmaceutical compositions thereof that modulate the activity of the 5-HT$_{2A}$ serotonin receptor.

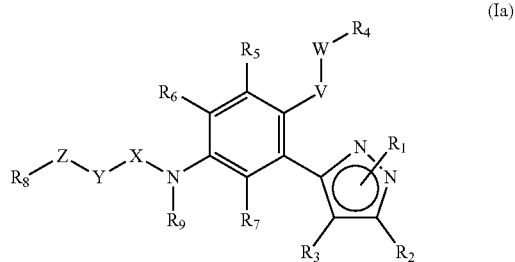

(Ia)

Compounds and pharmaceutical compositions thereof are directed to methods useful in the treatment of platelet aggregation, coronary artery disease, myocardial infarction, transient ischemic attack, angina, stroke, atrial fibrillation, reducing the risk of blood clot formation, asthma or symptoms thereof, agitation or a symptom, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, and sleep disorders, sleep disorders, diabetic-related disorders, progressive multifocal leukoencephalopathy and the like.

The present invention also relates to the methods for the treatment of 5-HT$_{2A}$ serotonin receptor mediated disorders in combination with other pharmaceutical agents administered separately or together.

39 Claims, 12 Drawing Sheets

Related U.S. Application Data

(60) Provisional application No. 60/733,165, filed on Nov. 4, 2005, provisional application No. 60/713,384, filed on Sep. 1, 2005, provisional application No. 60/658,384, filed on Mar. 2, 2005, provisional application No. 60/647,639, filed on Jan. 26, 2005, provisional application No. 60/629,774, filed on Nov. 19, 2004.

(51) Int. Cl.
*C07D 231/12* (2006.01)
*C07D 405/12* (2006.01)
*C07D 409/12* (2006.01)
*C07D 413/12* (2006.01)
*C07D 487/08* (2006.01)
*C07D 231/16* (2006.01)
*C07D 417/12* (2006.01)
*A61K 31/5377* (2006.01)
*C07D 413/10* (2006.01)

(56) References Cited

U.S. PATENT DOCUMENTS

| | | |
|---|---|---|
| 4,409,231 A | 10/1983 | Stenzel et al. |
| 4,985,352 A | 1/1991 | Julius et al. |
| 5,077,409 A | 12/1991 | Wissner |
| 5,128,351 A | 7/1992 | Wissner |
| 5,523,280 A | 6/1996 | Chene et al. |
| 5,661,024 A | 8/1997 | Kao et al. |
| 5,712,279 A | 1/1998 | Biller et al. |
| 5,739,135 A | 4/1998 | Biller et al. |
| 5,760,246 A | 6/1998 | Biller et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,085 A | 2/2000 | Bromibge |
| 6,054,472 A | 4/2000 | Armistead et al. |
| 6,140,509 A | 10/2000 | Behan et al. |
| 6,271,261 B1 | 8/2001 | Widdowson |
| 6,297,261 B1 | 10/2001 | Christopherson et al. |
| 6,417,393 B1 | 7/2002 | Christopherson et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,696,475 B2 | 2/2004 | Dahl et al. |
| 6,706,749 B2 | 3/2004 | Dahl et al. |
| 6,784,183 B2 | 8/2004 | Lavielle et al. |
| 7,884,101 B2 | 2/2011 | Teegarden et al. |
| 2002/0025965 A1 | 2/2002 | Lavielle et al. |
| 2004/0102636 A1 | 5/2004 | Miller et al. |
| 2005/0054691 A1 | 3/2005 | Potter et al. |
| 2005/0080124 A1 | 4/2005 | Teegarden et al. |
| 2005/0267097 A1 | 12/2005 | Pinto et al. |
| 2006/0014705 A1 | 1/2006 | Howitz et al. |
| 2006/0063754 A1 | 3/2006 | Edgar et al. |
| 2006/0205792 A1 | 9/2006 | Wong et al. |
| 2006/0229335 A1 | 10/2006 | Teegarden et al. |
| 2007/0037827 A1 | 2/2007 | Nunes et al. |
| 2007/0072857 A1 | 3/2007 | Teegarden et al. |
| 2007/0207994 A1 | 9/2007 | Teegarden et al. |
| 2007/0244086 A1 | 10/2007 | Teegarden et al. |
| 2008/0015223 A1 | 1/2008 | Strah-Pleynet et al. |
| 2008/0200530 A1 | 8/2008 | Unett et al. |
| 2009/0186895 A1 | 7/2009 | Teegarden et al. |
| 2009/0189935 A1 | 7/2009 | Kunimatsu |
| 2009/0197935 A1 | 8/2009 | Teegarden et al. |

FOREIGN PATENT DOCUMENTS

| | | |
|---|---|---|
| EP | 1734039 | 12/2006 |
| WO | WO 96/02138 | 2/1996 |
| WO | WO 96110559 | 4/1996 |
| WO | WO 97/03967 | 2/1997 |
| WO | WO 97/45111 | 12/1997 |
| WO | WO 98/24785 | 6/1998 |
| WO | WO 99/06354 | 2/1999 |
| WO | WO 99/32436 | 7/1999 |
| WO | WO 99/32463 | 7/1999 |
| WO | WO 99/52927 | 10/1999 |
| WO | WO 00/57877 | 10/2000 |
| WO | WO 00/64866 | 11/2000 |
| WO | WO 01/21160 | 3/2001 |
| WO | WO 01/29008 | 4/2001 |
| WO | WO 02/39987 | 5/2002 |
| WO | WO 02/051833 | 7/2002 |
| WO | WO 02/076464 | 10/2002 |
| WO | WO 03/062206 | 7/2003 |
| WO | WO 2004/028450 | 4/2004 |
| WO | WO 2004/045118 | 5/2004 |
| WO | WO 2004/058722 | 7/2004 |
| WO | WO 2004/071426 | 8/2004 |
| WO | WO 2004/085433 | 10/2004 |
| WO | WO 2004/096771 | 11/2004 |
| WO | WO 2005/012254 | 2/2005 |
| WO | WO 2005/077345 | 8/2005 |
| WO | WO 2005/103011 | 11/2005 |
| WO | WO 2006/018662 | 2/2006 |
| WO | WO 2006/049734 | 5/2006 |
| WO | WO 2006/049941 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 | 8/2006 |
| WO | WO 2006/086705 | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/120600 | 10/2007 |
| WO | WO 2007/129111 | 11/2007 |
| WO | WO 2007/136680 | 11/2007 |
| WO | WO 2007/136689 | 11/2007 |
| WO | WO 2007/136703 | 11/2007 |
| WO | WO 2007/136875 | 11/2007 |
| WO | WO 2008/027483 | 3/2008 |
| WO | WO 2008/042388 | 4/2008 |
| WO | WO 2008/054748 | 5/2008 |
| WO | WO 2009/023253 | 2/2009 |
| WO | WO 2011/075596 | 6/2011 |

OTHER PUBLICATIONS

Advisory Action dated Sep. 9, 2009 from U.S. Appl. No. 11/602,164.
Andrezejewska-Buczko, J. et al., "Serotonin in diabetic retinopathy," Klinika Oczna, 98(2):101-4 (1996) Abstract.
Antinori et al., "Diagnosis of AIDS-related focal brain lesions: a decision-making analysis based on clinical and neuroradiologic characteristics combined with polymerase chain reaction assays in CSF," Neurology, 48:687-694 (1997).
Berge, S. et al., "Pharmaceutical salts," Journal of Pharmaceutical Sciences, 66(1):1-19 (1977).
Berger et al., "Progressive multifocal leukoencephalopathy," Seminars in Neurology, 19: 193-200, (1999).
Blier, P. et al., "Putative mechanisms of action of antidepressant drugs in affective and anxiety disorders and pain," Journal of Psychiatry and Neuroscience, 26(1):37-43 (2000).
Burger, A. "Isosterism and bioisosterism in drug design," Prog. Drug Res. 37 (1991), pp. 287-371.

(56) References Cited

OTHER PUBLICATIONS

Cameron, N. et al., "The effects of 5-hydroxytryptamine 5-HT 2 receptor antagonists on nerve conduction velocity and endoneurial perfusion in diabetic rats," Naunyn Schmiedeberg's Archive of Pharmacology, 367:607-14 (2003).
Casey, C. et al.,"Constitutively active mutant 5HT2A serotonin receptors: inverse agonist activity of classical 5HT 2A antagonists," Society for Neuroscience, 22: 1778 (1996) Abstract.
Catalan et al., "New Ultraviolet Stabilizers: 3- and 5-(2'-Hydroxyphenyl)pyrazoles," J. Am. Chem. Soc., 114, 5039-5048 (1992).
Cazzola, M. et al., "5-HT modifiers as a potential treatment of asthma," TiPS, 21: 13-6 (2000).
Cecil Textbook of Medicine, 20th edition (1996), vol. 2, pp. 1992-1996.
Cecil Textbook of Medicine, 20th edition (1996), vol. 2, pp. 2050-2057.
Chang et al., "Ipsapirone and ketanserin protects against circulatory shock, intracranial hypertension, and cerebral ischemia durinq heatstroke," Shock 24(4): 336-340 (2005).
Chang, F. A. et al., "Mechanism of ocular hypotensive action of ketanserin," Journal of Ocular Pharmacology, 1(2):137-47 (1985).
Cohen-Mansfield, J. et al., "Agitated behaviors in the elderly I. A conceptual review," JAGS, 34(10):711-21 (1986).
Collier, T. L. et al., "Radiosynthesis and in vivo evaluation of the psuedopeptide o-opioid antagonist [$^{125}$I]-ITIPP($\psi$)," Journal of Labelled Cpd. Radiopharm., 42 (Suool. 1}:S264-6 (1999}.
International Preliminary Report on Patentability for International Application No. PCT/US2005/041726 dated Sep. 21, 2006 by Authorized Officer Stefan Hartinger.
International Search Report for International Application No. PCT/US2005/04 1 726 dated May 18, 2006 by Authorized Officer Stefan Hartinger.
The Written Opinion of the International Searching Authority for International Application No. PCT/US2005/041726.
De Bie, J. J. et al., "Modulation of airway hyperresponsiveness and eosinophilia by selective histamine and 5-HT receptor antagonists in a mouse model of allergic asthma," British Journal of Pharmacology, 124:857-64 (1998).
Deuchar et al., "The role of 5-hydroxytryptamine in the control of pulmonary vascular tone in a rabbit model of pulmonary hypertension secondary to left ventricular dysfunction," Pulm. Pharmacol. Ther. 18(1):23-31 (2005).
Dosa, P.I. et al., "Synthesis and SAR of solubilized pyrazole derivatives as 5-HT 2A inverse-agonists for platelet aggregration," 232th ACS National Meeting, Medi 431.
Elliott et al., "4-0xospiro[benzopyran-2,4'-[piperidines] as Class Ill Antiarrhythmic Agents. Pharmacological Studies on 3,4-Dihydro-1 '42-(benzofurazan-5-yl)-ethyl]-6methanesulfonamidospirol[(2H)-1-benzopyran-2,4'-piperidin]-4-one (L-691, 131)", J. Med. Chem., 35:3973-3976 (1992).
Elphick, G. et al., "The human polyomavirus, JCV, uses serotonin to infect cells," Science, 306: 1380-3 (2004).
FDA mulls drug to slow late-stage Alzheimer's [online], [retrieved on Sep. 23, 2003]. Retrieved from the Internet, URL; http:llwww.cnn.com120031 HEAL TH1conditionsl091241alzheimers.drug.aplindexhtml>.
Fujita et al., "Sarpogrelate treatment reduces restenosis after coronary stenting," Am Heart Journal, 145:16 (2003).
Fujiwara et al., "Augmented responses to 5-HT2-receptor-mediated vasoconstrictions in atherosclerotic rabbit common carotid arteries," Journal of Cardiovascular Pharmacology, 26:503-510, (1995).
Greene et al., Protecting Groups in Organic Synthesis, 3'0 Edition, 1999 (Wiley).
Grunder, G. et al., "Time course of 5-HT 2A receptor occupancy in the human brain after a single dose of the putative antipsychotic drug MDL 100,907 measured by positron emission tomography," Neuropsychopharmacology, 17(3): 175-85 (1997).
Hayashi et al., "Sarpogrelate HCI, a selective 5-HT2A antagonist, retards the progression of atherosclerosis throuah a novel mechanism," Atherosclerosis 168: 23-31 (2003).
Herrick-Davis, K. et al., "Activating mutations of the serotonin 5HT ic receptor," Journal of Neurochemistry, 69(3):1138-44 (1997).
Herrick-Davis, K. et al., "Constitutively active 5HT2C serotonin receptor created by site directed mutagenesis," Society for Neuroscience, 22: 1779 (1996) Abstract.
Higuchi et al., "Pro-Drugs and Novel Delivery Systems", vol. 14 of the ACS Symposium Series; and in Bioreversible Carriers in Drug Design, ed. Edward B. Roche, American Pharmaceutical Association and Pergamon Press, 1987.
Horibe, E., "Sarpogrelate, a 5-HT2 receptor blocker, may have a preconditioning-like effect in patients with coronary artery disease," Circulation Research 68:68-72, 15 (2004).
International Preliminary Report on Patentability for International Application No. PCT/US2007/011810 dated Jul. 16, 2008 by Authorized Officer Bart De Jong.
International Search Report for International Application No. PCT/US2007/011810 dated Oct. 30, 2007 by Authorized Officer Bart De Jong.
International Search Report for International Application No. PCT/US2007/011789, dated Nov. 2, 2007.
International Search Report for International Application No. PCT/US2007/011834, dated Oct. 2, 2007 by Authorized Officer Bart De Jonq.
Kanayama, M. et al., "New treatment oflumbar disc herniation using 5-hydroxytryptamine$_{2A}$ receptor inhibitor: a randomized controlled trial," Journal of Neurosurgery: Spine, 2:441-6 (2005}.
Katz, I. et al., "Comparison of risperidone and placebo for psychosis and behavioral disturbances associated with dementia: a randomized double-blind trial," Journal of Clinical Psychiatry, 60(2): 107-15 (1999).
Kitagawa et al., "Beckman Rearrangement of 0-4 Pentenyl Oxime through N-Bromosuccinimide-Mediated Activating Process," Chem. Pharm. Bull., 45(1) 32-35 (1997).
Koss, E. et al., "Assessing patterns of agitation in Alzheimer's disease patients with the Cohen-Mansfield agitation inventory," Alzheimer's Disease and Associated Disorders, 11{S2):S45-50 (1997).
Krieger et al., "Novel immunosuppressants," Pediatr Transplantation, 8:594-599 (2004).
Landolt, H. et al., "Serotonin-2 receptors and human sleep: effect of a selective antagonist on EEG power spectra," Neuropsychopharmacology, 21(3):455-66 (1999).
Le Bas, M. et al., "Radioiodinated analogs ofEP 00652218 for the exploration of the tachykinin NK1 receptor by spect," Journal of Labelled Cpd. Radiopharm., 44(S 1):S280-2 (2001).
Major et al., "Establishment of a line of human fetal glial cells that supports JC virus multiplication," PNAS USA 82:1257-1261 (1985).
Marcos et al., "Serotonin-induced smooth muscle hyperplasia in various forms of human pulmonary hypertension," Circ. Res. 94(9): 1263-70 (2004).
Mastropasqua, L. et al., "Ocular hypertensive effect ofketanserin in patients with primary open angle glaucoma," Acta Ophthalmologica Scandinavica, 75:24-5 {1997).
Miao et al., "Ketanserin stabilizes blood pressure in conscious spontaneously hypertensive rats," Clin. Exp. Pharmacol. Physio. 30(3):189-193, (2003).
Mueller, "Drug immunosuppression therapy for adult heart transplantation. Part 1: immune response to allograft and mechanism of action of immunosuppressants," Ann Thorac Surg. 77:354-362 (2004).
Muto, T. et al., "Protective effects of sarpogrelate, a 5HT 2A antagonist, against postischemic myocardial dysfunction in guineapig hearts," Molecular and Cellular Biochemistry, 272:119-32 (2005).
National Institutes of Health, "Facts about Insomnia," NIH publication No. 95-3801 (1995).
Nishiyama, T., "Effects of 5HT$_{2A}$ receptor antagonist, sarpogrelate on thermal or inflammatory pain," European Journal of Pharmacology, 516: 18-22 (2005).
Nomura, S. et al., "5HT$_{2A}$ receptor antagonist increases circulating adiponectin in patients with type 2 diabetes," Blood Coagulation and Fibrinolysis, 16(6):423-8 (2005).

(56) References Cited

OTHER PUBLICATIONS

Notice of Allowance dated Sep. 27, 2010 from U.S. Appl. No. 11/602,164.
Office Action dated Jan. 2, 2009 from U.S. Appl. No. 11/602,164.
Office Action dated Jul. 23, 2008 from U.S. Appl. No. 11/602,164.
Office Action dated Jun. 19, 2009 from U.S. Appl. No. 11/602,164.
Pawlak et al., "A potent 5-hydroxytryptamine receptor (5-HT2A) antagonist, DV-7028, delays arterial thrombosis development in rats," Thrombosis Research 90: 259-270 (1998).
Pietraszek, M. H. et al., "Blood serotonergic mechanisms in type 2 (non-insulin dependant) diabetes mellitus," Thrombosis Research, 66:765-74 (1992).
Porte Gies et al., "Guidelines for the diagnosis and management of neurological complications of HIV infection," Eur. J. Neural. 11:297-304 (2004).
Prosser, W. A et al., "Selective serotonin 5HT2A inverse agonists promote sleep consolidation in male Wistar rats during the normal inactive phase," Poster #29.
Querbes et al., "A JC virus-induced signal is required for infection of glial cells by a clathrin- and eps15-dependent pathway," J Viroloqy, 78:250-256 (2004).
Remington, The Science and Practice of Pharmacy, 20th Edition, 2000 (Lippincott Williams & Wilkins).
Restriction Requirement dated Apr. 7, 2008 from U.S. Appl. No. 11/597,306.
Restriction Requirement dated Feb. 14, 2011 from U.S. Appl. No. 12/301,172.
Restriction Requirement dated Feb. 14, 2011 from U.S. Appl. No. 12/301,180.
Restriction Requirement dated Jan. 24, 2008 from U.S. Appl. No. 11/602,164.
Satimura, K. et al., "Sarpogrelate, a specific 5HT2-receptor antagonist, improves the coronary microcirculation in coronary artery disease," Clinical Cardiology, 25:28-32 (2002).
Sawnyok, J. et al., "Antidepressants as analgesics: an overview of central and peripheral mechanisms of action," Journal of Psychiatry and Neuroscience, 26(1):21-9 (2001).
Sharpley, AL. et al., "Slow wave sleep in humans. role of $5HT_{2A}$ and $5HT_{2c}$ receptors," Nauropharmaco/ogy, 33(3/4):467-71 (1994).
Shibata, R. et al., "Adiponectin protects against myocardial ischemiareperfusion injury through AMPK- and COX-2-dependent mechanisms," Nature Medicine, advanced online Publication:1-8.
Silva, A., Chronic treatment with mianserin prevents DOCA-salt hypertension in rats—evidence for the involvement of central 5-HT2 receptors, Eur J. Pharmacol. 518(2-3): 152-172 (2005).
Singh et al., "lmmunosuppressive-associated leukoencephalopathy in organ transplant recipients," Transplantation, 69:467-4 72 (2000).
Smith, G. et al., "Test-retest variability of serotonin 5HT2A receptor binding measured with positron emission tomography and [$^{18}$F]altanserin in the human brain," Synapse, 30:380-92 (1998).
Staley, J. et al., "Comparison of [$^{18}$F]altanserin and [$^{18}$F]deuteroaltanserin for PET imaging of serotonin$_{2A}$ receptors in baboon brain: pharmacological studies," Nuclear Medicine and Biology, 28:271-9 (2001).
Stella, V., "Pro-drugs as Novel Drug Delivery Systems", Higuchi, T. et al., ed. (American Chemical Society, Washinqton), pp. 1-49 (1975).

Stenzel et al., Document No. 94:208858, 1981, retrieved from CAPLUS.
STN Abstract for WO 2003/062206.
Strah-Pleynet, S. et al., "Discovery and SAR of novel $5HT_{2A}$ inverse-agonists," 27th ACS National Meeting , MEDI 270 (2004).
Street, J. et al., "Olanzapine treatment of psychotic and behavioral symptoms in patients with Alzheimer's disease in nursing care facilities," Archive of General Psychiatry, 57:968-76 (2000).
Takahashi, T. et al., "Sarpogrelate hydrochloride, a serotonin 2A receptor antagonist, reduces albuminuria in patients with early-stage diabetic nephropathy," Diabetes Research and Clinical Pratice, 58:123-9 (2002) Takenaka, H. et al., The effect.
Takenaka, H. et al., "The effect of Anplag® (sarpogrelate HCL). Novel selective $5-HT_2$ antagonist of intraocular pressure in glaucoma patients," Investigative Ophthalmology & Visual Science, 36(4):S734 (1995) Abstract.
Talvik-Lofti, M. et al., "High HT2A occupancy in M100907-treated schizophrenic patients," Psychopharmacology, 148:400-3 (2000).
The International Classification of Sleep Disorders, Revised Diagnostic and Coding Manual, American Academy of Sleep Medicine (2001) pp. 1-336 (also includes table of contents and glossary).
Topliss, J.G., "A Manual Method for Applying the Hansch Approach to Drug Design," J. Med. Chem. 1977, 20(4), pp. 463-469.
Turpin, "The next generation of HIV/AIDS drugs: novel and developmental antiHIV drugs and taraets," Expert Rev Anti Infect Ther. Jun; 1 (1):97-128 (2003).
Vacante et al., "Extension of JC virus host range to monkey cells by insertion of a simian virus 40 enhancer into the JC virus regulatory reqion," Viroloqy, 170:353-361, (1989).
Verstraete, M. "Prevention of atherosclerotic complications: controlled trial ofketanserin," British Medical Journal, 298:424-30 (1989).
Vikenes, K. et al., "Serotonin is associated with coronary artery disease and cardiac events," Circulation, 100:483-9 (1999).
Vippagunta, et al. Advanced Drug Delivery Reviews 48 (2001) 3-26.
Wilson, H et al., "LY53857, a HT2 receptor antagonist delays occlusion and inhibits platelet aggression in a rabbit model of carotid artery occlusion," Thrombosis and Haemostasis, 66 (3) 355-60 (1991).
Winokur, A. et al., "Acute effects of Mirtazapine on sleep continuity and sleep architecture in depressed patients: a pilot study," Biological Psychiatry, 48:75-8 (2000).
Written Opinion of the International Searching Authority for International Application No. PCT/US2005/041726.
Written Opinion of the International Searching Authority for International Application No. PCT/US2007/011789.
Written Opinion of the International Searching Authority for International Application No. PCT/US2007/011834.
Yamada et al., "Phase I/II trial of didanosine (2',3'-dideoxyinosine) in hemophiliac patients with AIDS or AIDS-related complex," Clin. Diaq. Viral. 1:245-256 (1993).
Yamashita et al., "Conjunctive effects of the 5HT(2) receptor antagonist, sarpogrelate, on thrombolysis with modified tissue plasminogen activator in different laser-induced thrombosis models," Haemostasis, 30:321-332, (2000).
Zhu, G. et al., "Synthesis and mode of action of 1 ~)1- and 'H-labeled thieno[2,3,-c]pyridine antagonists of cell adhesion molecule expression," Journal of Organic Chemistry, 67:943-8 (2002).

3-PHENYL-PYRAZOLE DERIVATIVES AS MODULATORS OF THE 5-HT$_{2A}$ SEROTONIN RECEPTOR USEFUL FOR THE TREATMENT OF DISORDERS RELATED THERETO

CROSS-REFERENCE TO RELATED APPLICATIONS

This application is a continuation of U.S. patent application Ser. No. 15/137,228, filed Apr. 25, 2016, which is a continuation of U.S. patent application Ser. No. 12/976,887, filed Dec. 22, 2010, which is a continuation of U.S. patent application Ser. No. 11/602,164, filed Nov. 20, 2006, now U.S. Pat. No. 7,884,101, issued on Feb. 8, 2011, which is a continuation of PCT International Application No. PCT/US2005/041726, filed Nov. 17, 2005, which in turn claims priority to U.S. Provisional Application Ser. No. 60/629,774 filed Nov. 19, 2004, and which claims priority to U.S. Provisional Application Ser. No. 60/647,639 filed Jan. 26, 2005, and which claims priority to U.S. Provisional Application Ser. No. 60/658,384 filed Mar. 2, 2005, and which claims priority to U.S. Provisional Application Ser. No. 60/713,384 filed Sep. 1, 2005, and which claims priority to U.S. Provisional Application Ser. No. 60/733,165 filed Nov. 4, 2005, all of which are hereby incorporated by reference in their entirety

FIELD OF THE INVENTION

The present invention relates to certain 3-phenyl-pyrazole derivatives of Formula (Ia) and pharmaceutical compositions thereof that modulate the activity of the 5-HT$_{2A}$ serotonin receptor. Compounds and pharmaceutical compositions thereof are directed to methods useful in the treatment of platelet aggregation, coronary artery disease, myocardial infarction, transient ischemic attack, angina, stroke, atrial fibrillation, reducing the risk of blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy and the like.

The present invention also relates to the methods for the treatment of 5-HT$_{2A}$ serotonin receptor mediated disorders in combination with other pharmaceutical agents administered separately or together.

BACKGROUND OF THE INVENTION

G Protein Coupled Receptors

G Protein coupled receptors share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as, the carboxy terminus, interact with the G protein. Currently, Gq, Gs, Gi and Go are G proteins that have been identified.

Under physiological conditions, G protein coupled receptors exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed "constitutive receptor activation."

Serotonin Receptors

Receptors for serotonin (5-hydroxytryptamine, 5-HT) are an important class of G protein coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive compulsive disorders, schizophrenia, suicide, autism, migraine, emesis, alcoholism, and neurodegenerative disorders. With respect to antipsychotic treatment approaches focused on the serotonin receptors, these types of therapeutics can generally be divided into two classes, the "typical" and the "atypical." Both have anti-psychotic effects, but the typicals also include concomitant motor-related side effects (extra pyramidal syndromes, e.g., lip-smacking, tongue darting, locomotor movement, etc). Such side effects are thought to be associated with the compounds interacting with other receptors, such as the human dopamine D$_2$ receptor in the nigrostriatal pathway. Therefore, an atypical treatment is preferred. Haloperidol is considered a typical anti-psychotic, and clozapine is considered an atypical anti-psychotic.

Serotonin receptors are divided into seven subfamilies, referred to as 5-HT$_1$ through 5-HT$_7$, inclusive. These subfamilies are further divided into subtypes. For example, the 5-HT$_2$ subfamily is divided into three receptor subtypes: 5-HT$_{2A}$, 5-HT$_{2B}$, and 5-HT$_{2C}$. The human 5-HT$_{2C}$ receptor was first isolated and cloned in 1987, and the human 5-HT$_{2A}$ receptor was first isolated and cloned in 1990. These two receptors are thought to be the site of action of hallucinogenic drugs. Additionally, antagonists to the 5-HT$_{2A}$ and 5-HT$_{2C}$ receptors are believed to be useful in treating depression, anxiety, psychosis, and eating disorders.

U.S. Pat. No. 4,985,352 describes the isolation, characterization, and expression of a functional cDNA clone encoding the entire human 5-HT$_{1C}$ receptor (now known as the 5-HT$_{2C}$ receptor). U.S. Pat. Nos. 5,661,024 and 6,541,209 describe the isolation, characterization, and expression of a functional cDNA clone encoding the entire human 5-HT$_{2A}$ receptor.

Mutations of the endogenous forms of the rat 5-HT$_{2A}$ and rat 5-HT$_{2C}$ receptors have been reported to lead to constitutive activation of these receptors (5-HT$_{2A}$: Casey, C. et al. (1996) *Society for Neuroscience Abstracts*, 22:699.10, hereinafter "Casey"; 5-HT$_{2C}$: Herrick-Davis, K., and Teitler, M. (1996) *Society for Neuroscience Abstracts*, 22:699.18, hereinafter "Herrick-Davis 1"; and Herrick-Davis, K. et al. (1997) *J. Neurochemistry* 69(3): 1138, hereinafter "Herrick-Davis-2"). Casey describes a mutation of the cysteine residue at position 322 of the rat 5-$HT_{2A}$ receptor to lysine (C322K), glutamine (C322Q), and arginine (C322R) which reportedly led to constitutive activation. Herrick-Davis 1 and Herrick-Davis 2 describe mutations of the serine residue at position 312 of the rat 5-$HT_{2C}$ receptor to phenylalanine (S312F) and lysine (S312K), which reportedly led to constitutive activation.

SUMMARY OF THE INVENTION

One aspect of the present invention encompasses certain 3-phenyl-pyrazole derivatives as shown in Formula (Ia):

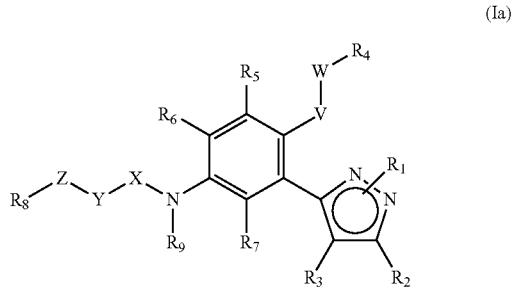

(Ia)

or a pharmaceutically acceptable salt, hydrate or solvate thereof;

wherein:

V is O, S, S(═O), S(═O)$_2$ or $NR_{10}$;

W is $C_{1-4}$ alkylene optionally substituted with 1 to 8 substituents selected independently from the group consisting of $C_{1-3}$ alkyl, $C_{1-4}$ alkoxy, carboxy, cyano, $C_{1-3}$ haloalkyl, halogen and oxo; or W is absent;

X is C(═O), C(═S) or absent;

Y is O, $NR_{11}$ or absent;

Z is $C_{1-4}$ alkylene, or $C_{3-6}$ cycloalkylene, each optionally substituted with 1 to 8 substituents selected independently from the group consisting of $C_{1-3}$ alkyl, $C_{1-4}$ alkoxy, carboxy, cyano, $C_{1-3}$ haloalkyl, halogen, hydroxyl, and oxo; or Z is absent;

$R_1$ is selected from the group consisting of H, $C_{1-6}$ alkyl, $C_{2-6}$ alkenyl, $C_{2-6}$ alkynyl and $C_{3-7}$ cycloalkyl;

$R_2$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is heterobicyclic, heterocyclic, or heteroaryl each optionally substituted with substituents selected independently from the group consisting of $C_{1-6}$ acyl, $C_{1-12}$ acyloxy, $C_{2-6}$ alkenyl, $C_{1-4}$ alkoxy, $C_{1-6}$ alkoxycarbonylamino, $C_{1-6}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{3-7}$ cycloalkylcarbonyl, $C_{2-6}$ dialkylcarboxamide, formyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, hydroxyl, nitro, phenyl and sulfonamide; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy, and heteroaryl are each optionally substituted with substituents selected independently from the group consisting of $C_{1-6}$ alkyl, $C_{1-5}$ acyl, $C_{1-4}$ alkoxy, $C_{1-6}$ alkylamino, $C_{2-8}$ dialkylamino, $C_{1-4}$ alkylcarboxamide, $C_{1-4}$ alkylsulfonyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, hydroxyl, and phenyl;

$R_5$, $R_6$, and $R_7$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl;

$R_8$ is $C_{1-8}$ alkyl, $C_{2-6}$ alkenyl, aryl, $C_{3-7}$ cycloalkyl, or heteroaryl each optionally substituted with substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent substituents together with said aryl or said heteroaryl form a $C_{5-7}$ cycloalkyl optionally comprising 1 to 2 oxygen atoms and optionally substituted with F, Cl or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro; and $R_9$, $R_{10}$, and $R_{11}$ are each independently H or $C_{1-8}$ alkyl;

provided that the compound is other than N-[4-oxiranylmethoxy-3-(2H-pyrazol-3-yl)-phenyl]-acetamide.

One aspect of the present invention encompasses pharmaceutical compositions comprising a compound of the present invention and a pharmaceutically acceptable carrier.

One aspect of the present invention encompasses methods for modulating the activity of a 5-$HT_{2A}$ serotonin receptor by contacting the receptor with a compound according to any of the embodiments described herein or a pharmaceutical composition thereof.

One aspect of the present invention encompasses methods for treating a 5-$HT_{2A}$ mediated disorder in an individual comprising administering to said individual in need thereof a therapeutically effective amount of a compound according to any of the embodiments described herein or a pharmaceutical composition thereof.

One aspect of the present invention encompasses methods for treating platelet aggregation in an individual comprising administering to the individual in need thereof a therapeutically effective amount of a compound according to any of the embodiments described herein or a pharmaceutical composition thereof. It is understood that treatment of platelet aggregation refers to any reduction of platelet aggregation that results in an amelioration of a pathophysiological condition associated with platelet aggregation.

One aspect of the present invention encompasses methods for treating one or more conditions associated with platelet aggregation in an individual comprising administering to the individual in need thereof a therapeutically effective amount of a compound according to any of the embodiments described herein or a pharmaceutical composition thereof.

One aspect of the present invention encompasses methods for treating a 5-$HT_{2A}$ mediated disorder selected from the group consisting of coronary artery disease, myocardial infarction, transient ischemic attack, angina, stroke, and atrial fibrillation in an individual comprising administering to the individual in need thereof a therapeutically effective amount of a compound according to any of the embodiments described herein or a pharmaceutical composition thereof.

One aspect of the present invention encompasses methods for reducing the risk of blood clot formation in an angioplasty or coronary bypass surgery individual comprising administering to the individual in need thereof a therapeutically effective amount of a compound according to any of the embodiments described herein or a pharmaceutical composition thereof.

One aspect of the present invention encompasses methods for reducing the risk of blood clot formation in an individual suffering from atrial fibrillation, comprising administering to the individual in need thereof a therapeutically effective amount of a compound according to any of the embodiments described herein or a pharmaceutical composition thereof.

One aspect of the present invention encompasses methods for treating asthma in an individual comprising administering to the individual in need thereof a therapeutically effective amount of a compound according to any of the embodiments described herein or a pharmaceutical composition thereof.

One aspect of the present invention encompasses methods for treating a symptom of asthma in an individual comprising administering to the individual in need thereof a therapeutically effective amount of a compound according to any of the embodiments described herein or a pharmaceutical composition thereof.

One aspect of the present invention encompasses methods for treating agitation or a symptom thereof in an individual comprising administering to the individual in need thereof a therapeutically effective amount of a compound according to any of the embodiments described herein or a pharmaceutical composition thereof. In some embodiments, the individual is a cognitively intact elderly individual.

One aspect of the present invention encompasses methods for treating agitation or a symptom thereof in an individual suffering from dementia comprising administering to the individual in need thereof a therapeutically effective amount of a compound according to any of the embodiments described herein or a pharmaceutical composition thereof. In some embodiments, the dementia is due to a degenerative disease of the nervous system. In some embodiments, the dementia is Alzheimers disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention encompasses methods for treating an individual suffering from at least one of the indications selected from the group consisting of behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to the individual in need thereof a therapeutically effective amount of a therapeutically effective amount of a dopamine $D_2$ receptor antagonist and a compound according to any of the embodiments described herein or a pharmaceutical composition thereof. In some embodiments, the dopamine $D_2$ receptor antagonist is haloperidol.

One aspect of the present invention encompasses methods for treating an individual with infantile autism, Huntington's chorea or nausea and vomiting from chemotherapy or chemotherapeutic antibodies comprising administering to the individual in need thereof a therapeutically effective amount of a dopamine $D_2$ receptor antagonist and a compound according to any of the embodiments described herein or a pharmaceutical composition thereof. In some embodiments, the dopamine $D_2$ receptor antagonist is haloperidol.

One aspect of the present invention encompasses methods for treating schizophrenia in an individual comprising administering to the individual in need thereof a therapeutically effective amount of a dopamine $D_2$ receptor antagonist and a compound according to any of the embodiments described herein or a pharmaceutical composition thereof. In some embodiments, the dopamine $D_2$ receptor antagonist is haloperidol.

One aspect of the present invention encompasses methods for treating negative symptoms of schizophrenia induced by the administration of haloperidol to an individual suffering from schizophrenia, comprising administering to the individual in need thereof a therapeutically effective amount of a compound according to any of the embodiments described herein or a pharmaceutical composition thereof. In some embodiments, the dopamine $D_2$ receptor antagonist or haloperidol and the compound or pharmaceutical composition are administered in separate dosage forms. In some embodiments, the dopamine $D_2$ receptor antagonist or haloperidol and the compound or pharmaceutical composition are administered in a single dosage form.

One aspect of the present invention encompasses methods for treating a sleep disorder in an individual comprising administering to the individual in need thereof a therapeutically effective amount of a compound according to any of the embodiments described herein or a pharmaceutical composition thereof. In some embodiments, the sleep disorder is a dyssomnia. In some embodiments, the dyssomnia is selected from the group consisting of psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome and non-24-hour sleep-wake disorder. In some embodiments, the sleep disorder is a parasomnia. In some embodiments, the parasomnia is selected from the group consisting of confusional arousals, sleepwalking and sleep terrors, rhythmic movement disorder, sleep starts, sleep talking and nocturnal leg cramps. In some embodiments, the sleep disorder is associated with a medical or psychiatric disorder. In some embodiments, the medical or psychiatric disorder is selected from the group consisting of psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

One aspect of the present invention encompasses methods for treating a diabetic-related disorder in an individual comprising administering to the individual in need thereof a therapeutically effective amount of a compound according to any of the embodiments described herein or a pharmaceutical composition thereof. In some embodiments, the diabetic-related disorder is diabetic peripheral neuropathy. In some embodiments, the diabetic-related disorder is diabetic nephropathy. In some embodiments, the diabetic-related disorder is diabetic retinopathy.

One aspect of the present invention encompasses methods for treating progressive multifocal leukoencephalopathy in an individual comprising administering to the individual in need thereof a therapeutically effective amount of a compound according to any of the embodiments described herein or a pharmaceutical composition thereof. In some embodiments, the individual in need thereof has a lymphoproliferative disorder. In some embodiments, the individual in need thereof has carcinomatosis. In some embodiments, the individual in need thereof is immunocompromised. In some embodiments, the individual in need thereof is infected with HIV. In some embodiments, the HIV-infected individual has a CD4+ cell count of ≤200/mm$^3$. In some embodiments, the HIV-infected individual has AIDS. In some embodiments, the HIV-infected individual has AIDS-related complex (ARC). In some embodiments, the individual in need thereof is undergoing immunosuppressive therapy. In some embodiments, the individual in need thereof is undergoing immunosuppressive therapy after organ transplantation.

One aspect of the present invention encompasses methods for treating hypertension in an individual comprising administering to the individual in need thereof a therapeutically effective amount of a compound according to any of the embodiments described herein or a pharmaceutical composition thereof.

One aspect of the present invention encompasses methods for treating pain in an individual comprising administering to the individual in need thereof a therapeutically effective amount of a compound according to any of the embodiments described herein or a pharmaceutical composition thereof.

One aspect of the present invention encompasses processes for preparing a composition comprising admixing a compound according any embodiments described herein and a pharmaceutically acceptable carrier.

One aspect of the present invention is the use of a compound of the present invention for the production of a medicament for use in the treatment of a 5-HT$_{2A}$ mediated disorder.

One embodiment of the present invention is the use of a compound for the production of a medicament for use in the treatment of a 5-HT$_{2A}$ mediated disorder wherein the disorder is platelet aggregation.

One embodiment of the present invention is the use of a compound for the production of a medicament for use in the treatment of one or more conditions associated with platelet aggregation.

One embodiment of the present invention is the use of a compound for the production of a medicament for use in the treatment of a 5-HT$_{2A}$ mediated disorder wherein the disorder is selected from the group consisting of coronary artery disease, myocardial infarction, transient ischemic attack, angina, stroke, and atrial fibrillation.

One embodiment of the present invention is the use of a compound for the production of a medicament for use in the treatment of a 5-HT$_{2A}$ mediated disorder wherein the disorder is a blood clot formation in an angioplasty or coronary bypass surgery individual.

One embodiment of the present invention is the use of a compound for the production of a medicament for use in the treatment of a 5-HT$_{2A}$ mediated disorder wherein the disorder is a blood clot formation in an individual suffering from atrial fibrillation.

One embodiment of the present invention is the use of a compound for the production of a medicament for use in the treatment of a sleep disorder, such as those disclosed herein.

One embodiment of the present invention is the use of a compound for the production of a medicament for use in the treatment of a dyssomnia.

One embodiment of the present invention is the use of a compound for the production of a medicament for use in the treatment of a parasomnia.

One embodiment of the present invention is the use of a compound for the production of a medicament for use in the treatment of a diabetic-related disorder.

One embodiment of the present invention is the use of a compound for the production of a medicament for use in the treatment of a 5-HT$_{2A}$ mediated disorder wherein the disorder is asthma.

One embodiment of the present invention is the use of a compound for the production of a medicament for use in the treatment of a 5-HT$_{2A}$ mediated disorder wherein the disorder is a symptom of asthma.

One embodiment of the present invention is the use of a compound for the production of a medicament for use in the treatment of a 5-HT$_{2A}$ mediated disorder wherein the disorder is agitation or a symptom thereof in an individual. In some embodiments the individual is a cognitively intact elderly individual.

One embodiment of the present invention is the use of a compound for the production of a medicament for use in the treatment of a 5-HT$_{2A}$ mediated disorder wherein the disorder is agitation or a symptom thereof in an individual suffering from dementia. In some embodiments the dementia is due to a degenerative disease of the nervous system. In some embodiments the dementia is Alzheimers disease, Lewy Body, Parkinson's disease, or Huntington's disease. In some embodiments the dementia is due to diseases that affect blood vessels. In some embodiments the dementia is due to stroke or multi-infract dementia.

One embodiment of the present invention is the use of a compound for the production of a medicament for use in the treatment of a 5-HT$_{2A}$ mediated disorder further comprising a dopamine D$_2$ receptor antagonist wherein the disorder is selected from the group consisting of a behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia. In some embodiments the dopamine D$_2$ receptor antagonist is haloperidol.

One embodiment of the present invention is the use of a compound for the production of a medicament for use in the treatment of a 5-HT$_{2A}$ mediated disorder further comprising a dopamine D$_2$ receptor antagonist wherein the disorder is infantile autism, Huntington's chorea, or nausea and vomiting from chemotherapy or chemotherapeutic antibodies. In some embodiments the dopamine D$_2$ receptor antagonist is haloperidol.

One embodiment of the present invention is the use of a compound for the production of a medicament for use in the treatment of a 5-HT$_{2A}$ mediated disorder further comprising a dopamine D$_2$ receptor antagonist wherein the disorder is schizophrenia. In some embodiments the dopamine D$_2$ receptor antagonist is haloperidol.

One embodiment of the present invention is the use of a compound for the production of a medicament for use in the treatment of a 5-HT$_{2A}$ mediated disorder wherein the disorder is a negative symptom or symptoms of schizophrenia induced by the administration of haloperidol.

One embodiment of the present invention is the use of a compound for the production of a medicament for use in the treatment of a 5-HT$_{2A}$ mediated disorder wherein the haloperidol and the compound or pharmaceutical composition are administered in separate dosage forms.

One embodiment of the present invention is the use of a compound for the production of a medicament for use in the treatment of a 5-HT$_{2A}$ mediated disorder wherein the haloperidol and the compound or pharmaceutical composition are administered in a single dosage form.

One embodiment of the present invention is the use of a compound for the production of a medicament for use in the treatment of a 5-HT$_{2A}$ mediated disorder wherein the disorder is progressive multifocal leukoencephalopathy.

One embodiment of the present invention is the use of a compound for the production of a medicament for use in the treatment of hypertension.

One embodiment of the present invention is the use of a compound for the production of a medicament for use in the treatment of pain.

One aspect of the present invention pertains to compounds according to any of the embodiments described herein for use in a method of treatment of the human or animal body by therapy.

One aspect of the present invention pertains to compounds according to any of the embodiments described herein for use in a method for the treatment of a 5-HT$_{2A}$ mediated disorder, as described herein, in the human or animal body by therapy.

One aspect of the present invention pertains to compounds according to any of the embodiments described herein for use in a method for the treatment of a sleep disorder, as described herein, in the human or animal body by therapy.

One aspect of the present invention pertains to compounds according to any of the embodiments described herein for use in a method for the treatment of platelet aggregation in the human or animal body by therapy.

One aspect of the present invention pertains to compounds according to any of the embodiments described herein for use in a method for the treatment of one of more conditions associated with platelet aggregation in the human or animal body by therapy.

One aspect of the present invention pertains to compounds according to any of the embodiments described herein for use in a method for the treatment of progressive multifocal leukoencephalopathy in the human or animal body by therapy.

One aspect of the present invention pertains to compounds according to any of the embodiments described herein for use in a method of treatment of hypertension in the human or animal body by therapy.

One aspect of the present invention pertains to compounds according to any of the embodiments described herein for use in a method of treatment of pain in the human or animal body by therapy.

These and other aspects of the invention disclosed herein will be set forth in greater detail as the patent disclosure proceeds.

BRIEF DESCRIPTION OF THE DRAWINGS

FIG. 1 shows a general coupling method between a pyrazole boronic acid and an aryl triflate, it is understood that similar coupling methods known in the art can also be used, and a halide, such as, I, Br or Cl, can be used in place of the triflate.

FIG. 2 shows a general coupling method between a pyrazole boronic acid and a phenyl halide using coupling methods known in the art, such as a Suzuki coupling, and the like. FIG. 2 further shows the use of orthogonal protecting groups for the oxygen (V=O) and the nitrogen. After the coupling reaction the phenol protecting group is removed and a variety of —W—R$_4$ groups can be introduced. Subsequently, the alkyl amide protecting group can be hydrolyzed to provide the amine intermediate of the present invention.

FIG. 3 shows a general coupling method between a 2-substituted pyrazol-3-yl-boronic acid and an aryl triflate, it is understood that similar coupling methods known in the art can also be used, and a halide, such as, I, Br or Cl, can be used in place of the triflate.

FIG. 4 shows the general reaction of hydrazines with substituted chromen-4-ones to prepare certain 2-(pyrazol-3-yl)-phenols. Further shown in FIG. 4 are the general alkylation reactions for introducing the W—R$_4$ group.

FIG. 5 illustrates general methods for introducing a variety of halogens to compounds of the invention. It is understood that these halogenation reaction can also be conducted later in the synthesis, for example as the last step.

FIG. 6 shows the general reactions, such as, alkylation and Mitsunobu-like reactions, for introducing the W—R$_4$ group.

FIG. 7 shows the general coupling reactions of the aniline intermediate with a variety of electrophiles, such as, carboxylic acids, acyl halides, isocyanates, isothiocyanates, haloformates, and the like.

FIG. 9 illustrates the coupling of the aniline intermediate with heteroaryl-halo or aryl-halo to give diaryl amines and heteroaryl-aryl amines of the present invention.

FIG. 10 shows the general reactions, such as, alkylation and Mitsunobu-like reactions, for introducing the W—R$_4$ group.

FIG. 11 shows the general reactions, such as, alkylation reactions, for introducing the W—R$_4$ group wherein V is S or NR$_{10}$.

DEFINITIONS

Figure 1:
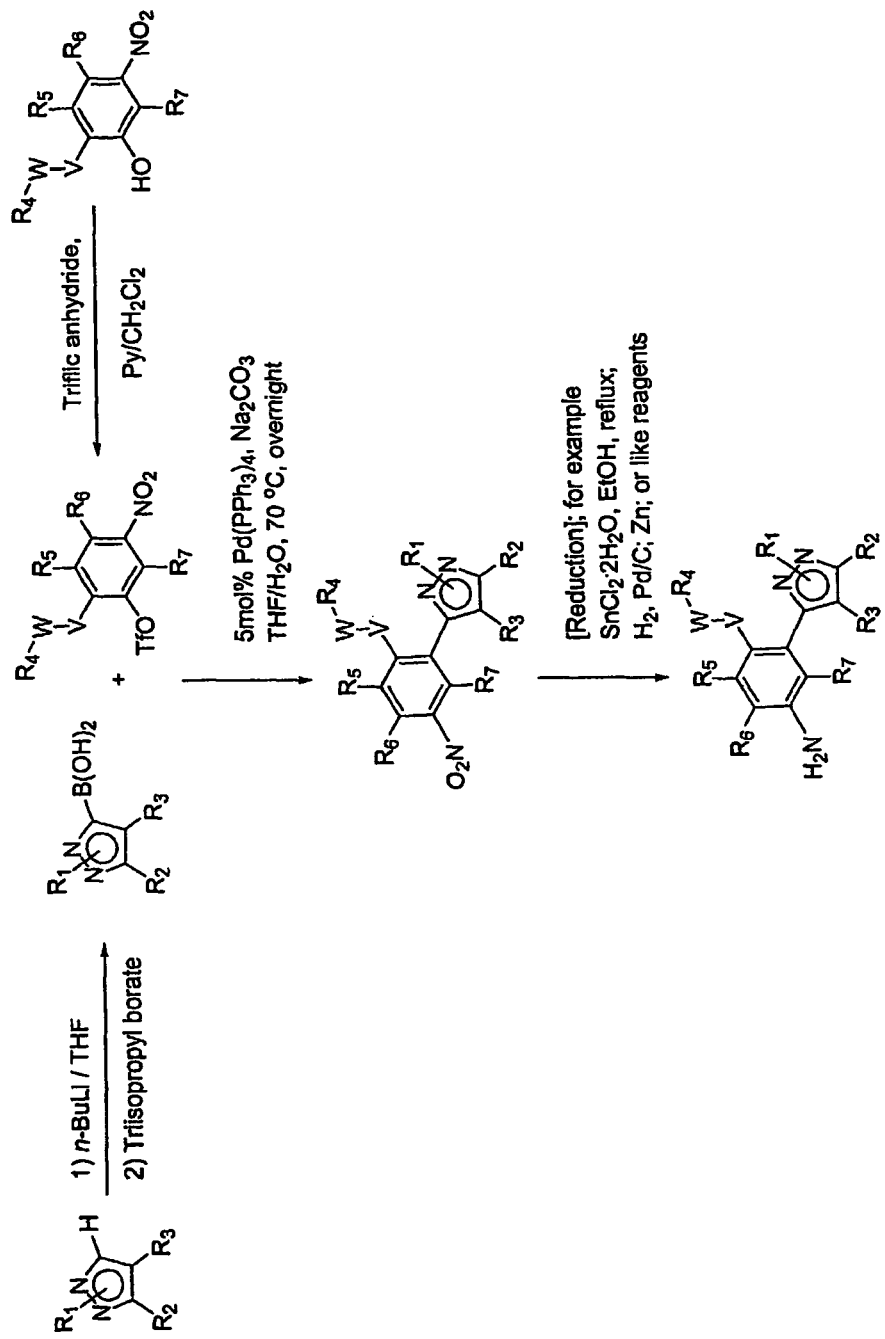
FIG. 1 shows the general synthetic scheme for the preparation of intermediate compounds of the present invention.

The scientific literature that has evolved around receptors has adopted a number of terms to refer to ligands having various effects on receptors. For clarity and consistency, the following definitions will be used throughout this patent document.

AGONISTS shall mean moieties that interact and activate the receptor, such as the 5-HT$_{2A}$ receptor, and initiates a physiological or pharmacological response characteristic of that receptor. For example, when moieties activate the intracellular response upon binding to the receptor, or enhance GTP binding to membranes.

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

The term "C$_{1-6}$ acyl" denotes a C$_{1-6}$ alkyl radical attached to a carbonyl wherein the definition of alkyl has the same definition as described herein; some examples include, but are not limited to, acetyl, propionyl, n-butanoyl, iso-butanoyl, sec-butanoyl, t-butanoyl (i.e., pivaloyl), pentanoyl and the like.

The term "C$_{1-12}$ acyloxy" denotes an acyl radical attached to an oxygen atom wherein acyl has the same definition has described herein; some embodiments are when acyloxy is C$_{1-11}$ acyloxy, some embodiments are when acyloxy is C$_{1-10}$ acyloxy, some embodiments are when acyloxy is C$_{1-8}$ acyloxy, some embodiments are when acyloxy is C$_{1-6}$ acyloxy, some embodiments are when acyloxy is C$_{1-5}$ acyloxy, some embodiments are when acyloxy is C$_{1-4}$ acyloxy, some embodiments are when acyloxy is C$_{10-12}$ acyloxy, some embodiments are when acyloxy is C$_{8-10}$ acyloxy. Some examples include, but are not limited to, acetyloxy, propionyloxy, butanoyloxy, iso-butanoyloxy, sec-butanoyloxy, t-butanoyloxy, pentanoyloxy, hexanoyloxy, heptanoyloxy, octanoyloxy, nonanoyloxy, decanoyloxy, undecanoyloxy, dodecanoyloxy, tridecanoyloxy, and the like.

The term "C$_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "C$_{1-6}$ alkoxy" as used herein denotes an alkyl radical, as defined herein, attached directly to an oxygen atom. Examples include methoxy, ethoxy, n-propoxy, iso-propoxy, n-butoxy, t-butoxy, iso-butoxy, sec-butoxy and the like.

The term "C$_{1-6}$ alkoxycarbonylamino" denotes the group represented by the formula:

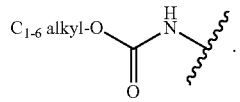

wherein C$_{1-6}$ alkyl has the same definition as found herein. Examples of C$_{1-6}$ alkoxycarbonylamino include methoxycarbonylamino, ethoxycarbonylamino, isopropoxycarbonylamino, propoxycarbonylamino, tert-butoxycarbonylamino, butoxycarbonylamino, and the like.

The term "C$_{1-8}$ alkyl" denotes a straight or branched carbon radical containing 1 to 8 carbons, some embodiments are 1 to 6 carbons, some embodiments are 1 to 4 carbons, some embodiments are 1 to 3 carbons, and some embodiments are 1 or 2 carbons. Examples of an alkyl include, but are not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "C$_{1-6}$ alkylcarboxamido" or "C$_{1-6}$ alkylcarboxamide" denotes a single C$_{1-6}$ alkyl group attached to the nitrogen of an amide group, wherein alkyl has the same definition as found herein. The C$_{1-6}$ alkylcarboxamido may be represented by the following:

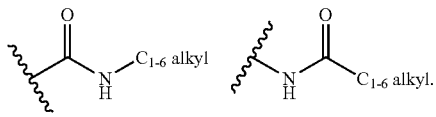

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-4}$ alkylene" refers to a $C_{1-4}$ divalent straight carbon group containing 1 to 4 carbons, some embodiments are 1 to 3 carbons, some embodiments are 1 to 2 carbons. In some embodiments alkylene refers to, for example, —CH$_2$—, —CH$_2$CH$_2$—, —CH$_2$CH$_2$CH$_2$—, —CH$_2$CH$_2$CH$_2$CH$_2$—, and the like.

The term "$C_{1-6}$ alkylsulfinyl" denotes a $C_{1-6}$ alkyl radical attached to a sulfoxide radical of the formula: —S(O)— wherein the alkyl radical has the same definition as described herein. Examples include, but are not limited to, methylsulfinyl, ethylsulfinyl, n-propylsulfinyl, iso-propylsulfinyl, n-butylsulfinyl, sec-butylsulfinyl, iso-butylsulfinyl, t-butylsulfinyl, and the like.

The term "$C_{1-6}$ alkylsulfonamide" refers to the groups shown below:

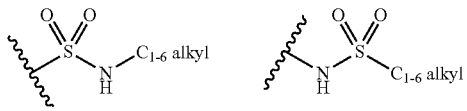

wherein $C_{1-6}$ alkyl has the same definition as described herein.

The term "$C_{1-6}$ alkylsulfonyl" denotes a $C_{1-6}$ alkyl radical attached to a sulfone radical of the formula: —S(O)$_2$— wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical attached to a sulfide of the formula: —S— wherein the alkyl radical has the same definition as described herein. Examples include, but are not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "$C_{1-6}$ alkylthiocarboxamide" denotes a thioamide of the following formulae:

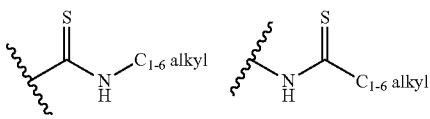

wherein $C_{1-4}$ alkyl has the same definition as described herein.

The term "$C_{1-6}$ alkylureyl" denotes the group of the formula: —NC(O)N— wherein one are both of the nitrogens are substituted with the same or different $C_{1-6}$ alkyl group wherein alkyl has the same definition as described herein. Examples of an alkylureyl include, but are not limited to, CH$_3$NHC(O)NH—, NH$_2$C(O)NCH$_3$—, (CH$_3$)$_2$NC(O)NH—, (CH$_3$)$_2$NC(O)NH—, (CH$_3$)$_2$NC(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —NH$_2$.

The term "$C_{1-6}$ alkylamino" denotes one alkyl radical attached to an amino radical wherein the alkyl radical has the same meaning as described herein. Some examples include, but are not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —CH$_2$—, —CH$_2$CH$_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "bicyclic" refers to two $C_{4-7}$ cycloalkyl groups that share two ring carbons thus forming either a fused or bridged ring. Bicyclic examples include, but not limited to, bicyclo[1.1.1]pentyl, bicyclo[2.1.1]hexyl, bicyclo[2.2.1]heptyl, bicyclo[2.2.2]octyl, bicyclo[3.1.1]heptyl, bicyclo[3.2.1]octyl, and the like.

The term "carbo-$C_{1-6}$-alkoxy" refers to a $C_{1-6}$ alkyl ester of a carboxylic acid, wherein the alkyl group is as defined herein. Examples include, but are not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "$C_{4-7}$ cycloalkenyl" denotes a non-aromatic ring radical containing 4 to 7 ring carbons and at least one double bond; some embodiments contain 4 to 6 carbons; some embodiments contain 4 to 5 carbons; some embodiments contain 4 carbons. Examples include cyclobutenyl, cyclopentenyl, cyclopentenyl, cyclohexenyl, and the like.

The term "$C_{3-7}$ cycloalkyl" denotes a saturated ring radical containing 3 to 7 carbons; some embodiments contain 3 to 6 carbons; some embodiments contain 3 to 5 carbons; some embodiments contain 5 to 7 carbons; some embodiments contain 3 to 4 carbons. Examples include cyclopropyl, cyclobutyl, cyclopentyl, cyclohexyl, cycloheptyl and the like.

The term "$C_{3-7}$ cycloalkylcarbonyl" denotes a $C_{3-7}$ cycloalkyl group, as described herein, bonded to the carbon of a carbonyl group (i.e., —C(═O)—). Examples of the $C_{3-7}$ cycloalkylcarbonyl group include, but not limited to, cyclopropylcarbonyl, cyclobutylcarbonyl, cyclopentylcarbonyl, and the like.

The term "$C_{3-6}$ cycloalkylene" refers to a divalent cycloalkyl radical, where cycloalkyl is as defined herein, containing 3 to 6 carbons; some embodiments contain 3 to 5 carbons; some embodiments contain 3 to 4 carbons. In some embodiments, the $C_{3-6}$ cycloalkylene group has the two bonding groups on the same ring carbon, for example:

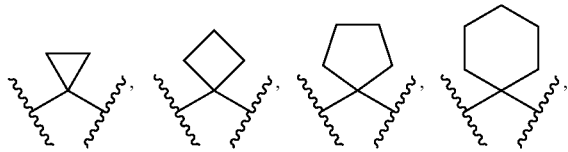

1,1-cyclopropyl

In some embodiments, the $C_{3-6}$ cycloalkylene group has the two bonding groups on different ring carbons. It is understood that when the two groups of the $C_{3-6}$ cycloalkylene group are on different ring carbons they may be cis or trans or mixtures thereof with respect to each other.

The term "$C_{2-8}$ dialkylamino" denotes an amino substituted with two of the same or different $C_{1-4}$ alkyl radicals wherein alkyl radical has the same definition as described herein.

Some examples include, but are not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_{2-4}$ dialkylamino."

The term "$C_{2-8}$ dialkylcarboxamido" or "$C_{2-8}$ dialkylcarboxamide" denotes two alkyl radicals, that are the same or different, attached to an amide group, wherein alkyl has the same definition as described herein. A $C_{2-8}$ dialkylcarboxamido may be represented by the following groups:

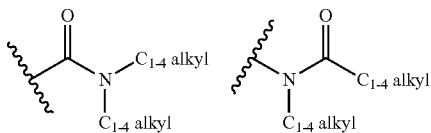

wherein $C_{1-4}$ has the same definition as described herein. Examples of a dialkylcarboxamide include, but are not limited to, N,N-dimethylcarboxamide, N-methyl-N-ethylcarboxamide, N,N-diethylcarboxamide, N-methyl-N-isopropylcarboxamide, and the like.

The term "$C_{2-8}$ dialkylsulfonamide" refers to one of the following groups shown below:

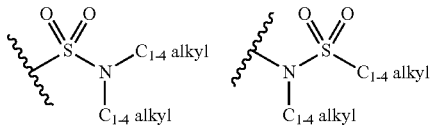

wherein $C_{1-4}$ has the same definition as described herein, for example but are not limited to, methyl, ethyl, n-propyl, isopropyl, and the like.

The term "$C_{2-8}$ dialkylthiocarboxamido" or "$C_{2-8}$ dialkylthiocarbox-amide" denotes two alkyl radicals, that are the same or different, attached to a thioamide group, wherein alkyl has the same definition as described herein. A $C_{2-8}$ dialkylthiocarboxamido or $C_{2-8}$ dialkylthiocarboxamide may be represented by the following groups:

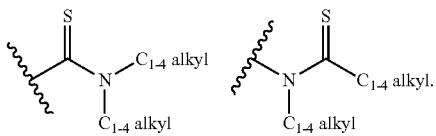

Examples of a dialkylthiocarboxamide include, but are not limited to, N,N-dimethylthiocarboxamide, N-methyl-N-ethylthiocarboxamide and the like.

The term "formyl" refers to the group —CHO.

The term "$C_{1-6}$ haloalkoxy" denotes a $C_{1-6}$ haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_{1-6}$ haloalkyl" denotes an $C_{1-6}$ alkyl group, defined herein, wherein the alkyl is substituted with one halogen up to fully substituted and a fully substituted $C_{1-6}$ haloalkyl can be represented by the formula $C_nL_{2n+1}$ wherein L is a halogen and "n" is 1, 2, 3, 4, 5 or 6; when more than one halogen is present then they may be the same or different and selected from the group consisting of F, Cl, Br and I, preferably F. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "$C_{1-6}$ haloalkylcarboxamide" denotes an $C_{1-6}$ alkylcarboxamide group, defined herein, wherein the alkyl is substituted with one halogen up to fully substituted represented by the formula $C_nL_{2n+1}$ wherein L is a halogen and "n" is 1, 2, 3, 4, 5 or 6. When more than one halogen is present they may be the same or different and selected from the group consisting of F, Cl, Br and I, preferably F.

The term "$C_{1-6}$ haloalkylsulfinyl" denotes a $C_{1-6}$ haloalkyl radical attached to a sulfoxide group of the formula: —S(O)— wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "$C_{1-6}$ haloalkylsulfonyl" denotes a $C_{1-6}$ haloalkyl radical attached to a sulfone group of the formula: —S(O)$_2$— wherein haloalkyl has the same definition as described herein. Examples include, but are not limited to, trifluoromethylsulfonyl, 2,2,2-trifluoroethylsulfonyl, 2,2-difluoroethylsulfonyl and the like.

The term "$C_{1-6}$ haloalkylthio" denotes a $C_{1-6}$ haloalkyl radical directly attached to a sulfur wherein the haloalkyl has the same meaning as described herein. Examples include, but are not limited to, trifluoromethylthio (i.e., CF$_3$S—, also referred to as trifluoromethylsulfanyl), 1,1-difluoroethylthio, 2,2,2-trifluoroethylthio and the like. The term "halogen" or "halo" denotes to a fluoro, chloro, bromo or iodo group.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but are not limited to, pyridyl, benzofuranyl, pyrazinyl, pyridazinyl, pyrimidinyl, triazinyl, quinolinyl, benzoxazolyl, benzothiazolyl, 1H-benzimidazolyl, isoquinolinyl, quinazolinyl, quinoxalinyl and the like. In some embodiments, the heteroatom is selected from, but not limited to, the group consisting of O, S and N, wherein N is substituted with H (i.e., NH), examples include, but are not limited to, pyrrolyl, indolyl, 1H-benzoimidazol-2-yl, and the like. Other examples include, but are not limited to, those in TABLE 1, TABLE 2, and the like.

The term "heterobicyclic" denotes a non-aromatic bicyclic ring, as described herein, wherein 1, 2, or 3 ring carbons are replaced with a heteroatom selected from, but are not limited to, the group consisting of O, S, S(=O), S(=O)$_2$, and NH, wherein the nitrogen can be optionally substituted, and 1 or 2 ring carbons can be optionally substituted with oxo or thiooxo thus together form a carbonyl or thiocarbonyl group respectively. Examples of a heterobicyclic group include, but are not limited to, 2,5-diaza-bicyclo[2.2.1]hept-2-yl, 7-aza-bicyclo[2.2.1]hept-7-yl, and the like.

The term "heterocyclic" denotes a non-aromatic carbon ring (i.e., $C_{3-7}$ cycloalkyl or $C_{4-7}$ cycloalkenyl as defined herein) wherein one, two or three ring carbons are replaced by a heteroatom selected from, but are not limited to, the group consisting of O, S, S(=O), S(=O)$_2$, NH, wherein the N can be optionally substituted as described herein, in some embodiments, the nitrogen is optionally substituted with $C_{1-4}$ acyl or $C_{1-4}$ alkyl, and ring carbon atoms optionally substituted with oxo or a thiooxo thus forming a carbonyl or thiocarbonyl group. The heterocyclic group can be attached/bonded to any available ring atom, for example, ring carbon, ring nitrogen, and the like. The heterocyclic group is a 3-, 4-, 5-, 6- or 7-membered containing ring. Examples of a heterocyclic group include, but are not limited to, aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperzin-1-yl, piperzin-2-yl, piperzin-3-yl, piperzin-4-yl, pyrrolidin-1-yl, pyrrolidin-2-yl, pyrrolidin-3-yl, [1,3]-dioxolan-2-yl, thiomorpholin-4-yl, [1,4]oxazepan-4-yl, 1,1-dioxo-1$\lambda^6$-thiomorpholin-4-yl, azepan-1-yl, azepan-2-yl, azepan-3-yl, azepan-4-yl, and the like.

The term "hydroxyl" refers to the group —OH.

The term "nitro" refers to the group —NO$_2$.

As used herein, the term "oxo" refers to the substituent =O, accordingly, when a carbon is substituted by an oxo group the new group resulting from the carbon and oxo together is a carbonyl group.

The term "phenoxy" refers to the group $C_6H_5O$—.

The term "phenyl" refers to the group $C_6H_5$—.

The term "sulfonic acid" refers to the group —SO$_3$H.

The term "thiol" denotes the group —SH.

COMPOSITION shall mean a material comprising at least two compounds or two components; for example, and without limitation, a Pharmaceutical Composition is a Composition comprising a compound of the present invention and a pharmaceutically acceptable carrier.

CONTACT or CONTACTING shall mean bringing the indicated moieties together, whether in an in vitro system or an in vivo system. Thus, "contacting" a 5-HT$_{2A}$ receptor with a compound of the invention includes the administration of a compound of the present invention to an individual, preferably a human, having a 5-HT$_{2A}$ receptor, as well as, for example, introducing a compound of the invention into a sample containing a cellular or more purified preparation containing a 5-HT$_{2A}$ receptor.

IN NEED OF TREATMENT as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient; including but not limited to, salts, solvates and hydrates of compounds of Formula (Ia); whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Invention:

One aspect of the present invention encompasses certain 3-phenyl-pyrazole derivatives as shown in Formula (Ia):

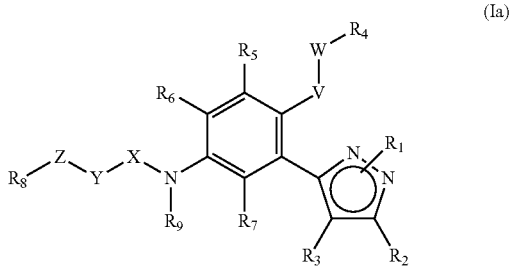

(Ia)

or a pharmaceutically acceptable salt, hydrate or solvate thereof; wherein $R_1$, $R_2$, $R_3$, $R_4$, $R_5$, $R_6$, $R_7$, $R_8$, $R_9$, V, W, X, Y and Z have the same definitions as described herein, supra and infra, provided that the compound is not N-[4-oxiranyl-methoxy-3-(2H-pyrazol-3-yl)-phenyl]-acetamide:

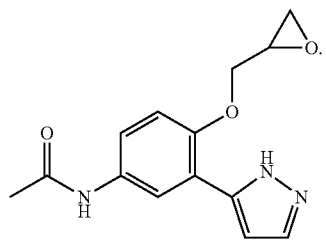 [SMILES: CC(=O)Nc1ccc(OCC2CO2)c(-c2ccn[nH]2)c1]

In some embodiments, the present invention pertains to compounds of Formula (Ia), as described herein, or a pharmaceutically acceptable salt, hydrate, solvate, or N-oxide thereof.

In some embodiments, the present invention pertains to compounds wherein the $R_4$ group contains an N-oxide.

In some embodiments, the present invention pertains to certain 3-phenyl-pyrazole derivatives as shown in Formula (Ia):

or a pharmaceutically acceptable salt thereof;
wherein:

V is O, S, S(=O), S(=O)$_2$ or NR$_{10}$;

W is $C_{1-4}$ alkylene optionally substituted with 1 to 8 substituents selected independently from the group consisting of $C_{1-3}$ alkyl, $C_{1-4}$ alkoxy, carboxy, cyano, $C_{1-3}$ haloalkyl, halogen and oxo; or W is absent;

X is C(=O), C(=S) or absent;

Y is O, NR$_{11}$ or absent;

Z is $C_{1-4}$ alkylene optionally substituted with 1 to 8 substituents selected independently from the group consisting of $C_{1-3}$ alkyl, $C_{1-4}$ alkoxy, carboxy, cyano, $C_{1-3}$ haloalkyl, halogen and oxo; or Z is absent;

$R_1$ is selected from the group consisting of H, $C_{1-6}$ alkyl, $C_{2-6}$ alkenyl, $C_{2-6}$ alkynyl and $C_{3-7}$ cycloalkyl;

$R_2$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of the $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is heterocyclic or heteroaryl each optionally substituted with substituents selected independently from the group consisting of $C_{1-6}$ acyl, $C_{1-12}$ acyloxy, $C_{2-6}$ alkenyl, $C_{1-4}$ alkoxy, $C_{1-6}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide; wherein $C_{1-5}$ acyl, $C_{1-5}$ acyloxy, $C_{1-6}$ alkyl, $C_{1-4}$ alkylcarboxamide, and carbo-$C_{1-6}$-alkoxy are each optionally substituted with substituents selected independently from the group consisting of $C_{1-5}$ acyl, $C_{1-4}$ alkoxy, $C_{1-6}$ alkylamino, $C_{2-8}$ dialkylamino, $C_{1-4}$ alkylcarboxamide, $C_{1-4}$ alkylsulfonyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, hydroxyl, and phenyl;

$R_5$, $R_6$, and $R_7$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl;

$R_8$ is $C_{1-8}$ alkyl, $C_{2-6}$ alkenyl, aryl or heteroaryl each optionally substituted with substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl or two adjacent substituents together with aryl or heteroaryl form a $C_{5-7}$ cycloalkyl optionally comprising 1 to 2 oxygen atoms optionally substituted with F, Cl or Br; and wherein $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$- alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro; and $R_9$, $R_{10}$, and $R_{11}$ are each independently H or $C_{1-8}$ alkyl; provided that the compound is other than N-[4-oxiranyl-methoxy-3-(2H-pyrazol-3-yl)-phenyl]-acetamide.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R_1$, $R_2$, $R_3$, $R_4$, X, Y, Z, etc.) contained within the generic chemical formulae described herein [e.g. (Ia), (Ic), (Ie), etc.] are specifically embraced by the present invention just as if they were explicitly disclosed, to the extent that such combinations embrace compounds that result in stable compounds (ie., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcombination of uses and medical indications were explicitly disclosed herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of the present invention may have one or more chiral centers, and therefore can exist as enantiomers and/or diastereomers. The invention is understood to extend to and embrace all such enantiomers, diastereomers and mixtures thereof, including but not limited, to racemates. Accordingly, some embodiments of the present invention pertain to compounds of the present invention that are R enantiomers. Further, some embodiments of the present invention pertain to compounds of the present invention that are S enantiomers. In examples where more than one chiral center is present, then, some embodiments of the present invention include compounds that are RS or SR enantiomers. In further embodiments, compounds of the present invention are RR or SS enantiomers. It is understood that compounds of the present invention are intended to represent all possible individual enantiomers and mixtures thereof just as if each had been individually named with the structure provided, unless stated or shown otherwise.

Some embodiments of the present invention encompass certain 3-phenyl-pyrazole derivatives as shown in the following Formula (Ic):

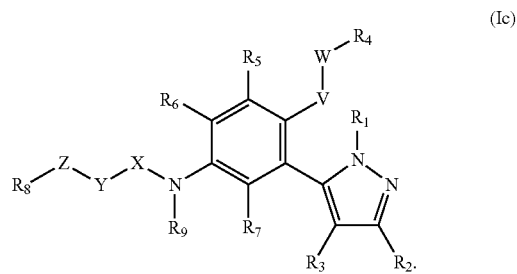

Some embodiments of the present invention encompass certain 3-phenyl-pyrazole derivatives as shown in Formula (Ie):

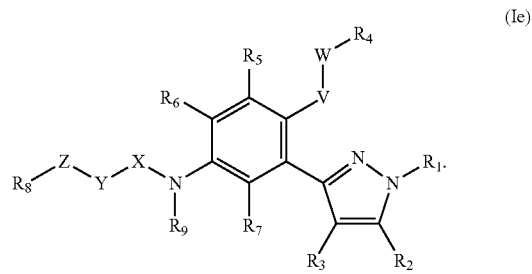

In some embodiments, V is O.

Some embodiments of the present invention encompass certain 3-phenyl-pyrazole derivatives as shown in Formula (Ig):

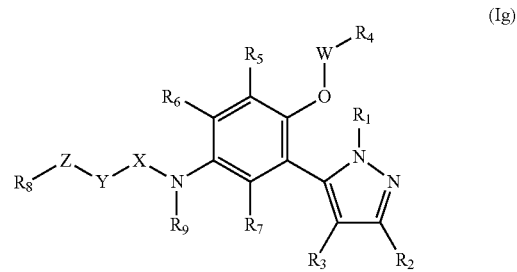

wherein each variable in Formula (Ig) has the same meaning as described herein, supra and infra.

In some embodiments, W is $C_{1-4}$ alkylene optionally substituted with oxo.

In some embodiments, W is —CH$_2$—, —CH$_2$CH$_2$—, —CH$_2$C(=O)—, —CH$_2$CH$_2$CH$_2$—, —C(CH$_3$)$_2$C(=O)—, —CH$_2$CH(C$_3$)—, —CH(CH$_3$)CH$_2$—, —C(CH$_3$)$_2$C$_2$—, or —CH$_2$C(CH$_3$)$_2$—.

In some embodiments, W is —CH$_2$—, —CH$_2$CH$_2$—, —CH$_2$C(=O)— or —CH$_2$CH$_2$CH$_2$—.

In some embodiments, W is —CH$_2$CH$_2$—.

In some embodiments, W is absent.

In some embodiments, X is C(=O).

In some embodiments, X is absent.

In some embodiments, Y is NH, O or absent.

In some embodiments, Y is NH or absent.

In some embodiments, Y is NH.

In some embodiments, Y is O.

In some embodiments, Y is absent.

In some embodiments, Z is C$_{1-4}$ alkylene or C$_{3-6}$ cycloalkylene optionally substituted with 1, 2, 3, or 4 substituents selected independently from the group consisting of C$_{1-3}$ alkyl, halogen, and oxo.

In some embodiments, Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(=O)—.

In some embodiments, Z is absent, —CH$_2$— or —CH(OH)—.

In some embodiments, Z is absent or —CH$_2$—.

In some embodiments, Z is absent.

In some embodiments, R$_1$ is C$_{1-6}$ alkyl.

In some embodiments, R$_1$ is —CH$_3$.

In some embodiments, R$_1$ is H.

It is understood when R$_1$ is H that tautomers are possible. It is well understood and appreciated in the art that pyrazoles can exist in various tautomeric forms. Two possible tautomeric forms are illustrated below:

(Ii)      (Ii')

It is further understood that tautomeric forms can also have corresponding nomenclature for each represented tautomer, for example, the pyrazol-3-yl groups in Formula (Ii) and Formula (Ii') can be represented by the general chemical names 1H-pyrazol-3-yl and 2H-pyrazol-3-yl respectively. Therefore, the present invention includes all tautomers and the various nomenclature designations.

In some embodiments, R$_2$ is H.

In some embodiments, R$_3$ is H or halogen.

In some embodiments, R$_3$ is H, F, Cl or Br.

In some embodiments, R$_3$ is H, Cl or Br.

In some embodiments, R$_3$ is H.

In some embodiments, R$_4$ is a group other than an oxiranyl group.

In some embodiments, R$_4$ is heterobicyclic, heterocyclic, or heteroaryl each optionally substituted with substituents selected independently from the group consisting of C$_{1-6}$ acyl, C$_{1-12}$ acyloxy, C$_{2-6}$ alkenyl, C$_{1-4}$ alkoxy, C$_{1-6}$ alkoxycarbonylamino, C$_{1-6}$ alkyl, C$_{1-6}$ alkylamino, C$_{2-8}$ dialkylamino, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, amino, carbo-C$_{1-6}$-alkoxy, carboxamide, carboxy, cyano, C$_{3-6}$ cycloalkyl, C$_{2-6}$ dialkylcarboxamide, formyl, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heteroaryl, hydroxyl, nitro, phenyl and sulfonamide; wherein said C$_{1-5}$ acyl, C$_{5-8}$ acyloxy, C$_{1-4}$ alkoxy, C$_{1-6}$ alkyl, C$_{1-4}$ alkylcarboxamide, amino, carbo-C$_{1-6}$-alkoxy, and heteroaryl are each optionally substituted with substituents selected independently from the group consisting of C$_{1-6}$ alkyl, C$_{1-5}$ acyl, C$_{1-4}$ alkoxy, C$_{1-6}$ alkylamino, C$_{2-8}$ dialkylamino, C$_{1-4}$ alkylcarboxamide, C$_{1-4}$ alkylsulfonyl, amino, carbo-C$_{1-6}$-alkoxy, carboxamide, carboxy, cyano, C$_{3-6}$ cycloalkyl, halogen, C$_{1-4}$ haloalkoxy, C$_{1-4}$ haloalkyl, hydroxyl, and phenyl.

In some embodiments, R$_4$ is heterobicyclic, heterocyclic or heteroaryl each optionally substituted with substituents selected independently from the group consisting of C$_{1-6}$ acyl, C$_{1-12}$ acyloxy, C$_{1-4}$ alkoxy, C$_{1-6}$ alkoxycarbonylamino, C$_{1-6}$ alkyl, C$_{1-6}$ alkylamino, C$_{2-8}$ dialkylamino, C$_{1-4}$ alkylcarboxamide, C$_{1-4}$ alkylsulfonamide, C$_{1-4}$ alkylsulfonyl, C$_{1-4}$ alkylureyl, amino, carbo-C$_{1-6}$-alkoxy, carboxamide, carboxy, cyano, C$_{3-6}$ cycloalkyl, C$_{2-6}$ dialkylcarboxamide, formyl, halogen, C$_{1-4}$ haloalkoxy, C$_{1-4}$ haloalkyl, heteroaryl, hydroxyl and phenyl; wherein said C$_{1-5}$ acyl, C$_{1-5}$ acyloxy, C$_{1-4}$ alkoxy, C$_{1-6}$ alkyl, C$_{1-4}$ alkylcarboxamide, amino, carbo-C$_{1-6}$-alkoxy and heteroaryl are each optionally substituted with substituents selected independently from the group consisting of C$_{1-6}$ alkyl, C$_{1-5}$ acyl, C$_{1-4}$ alkoxy, C$_{1-6}$ alkylamino, C$_{2-8}$ dialkylamino, C$_{1-4}$ alkylcarboxamide, C$_{1-4}$ alkylsulfonyl, amino, carbo-C$_{1-6}$-alkoxy, carboxamide, carboxy, cyano, C$_{3-6}$ cycloalkyl, halogen, C$_{1-4}$ haloalkoxy, C$_{1-4}$ haloalkyl, hydroxyl, and phenyl In some embodiments, R$_4$ is heterobicyclic, heterocyclic, or heteroaryl each optionally substituted with substituents selected independently from the group consisting of C$_{1-6}$ acyl, C$_{1-12}$ acyloxy, C$_{1-6}$ alkoxycarbonylamino, C$_{1-4}$ alkoxy, C$_{1-6}$ alkyl, C$_{1-4}$ alkylcarboxamide, C$_{1-4}$ alkylsulfonamide, C$_{1-4}$ alkylsulfonyl, C$_{1-4}$ alkylureyl, amino, carbo-C$_{1-6}$-alkoxy, carboxamide, carboxy, C$_{2-6}$ dialkylcarboxamide, formyl, halogen, C$_{1-4}$ haloalkyl, heteroaryl, hydroxyl and phenyl; wherein said C$_{1-5}$ acyl, C$_{1-5}$ acyloxy, C$_{1-4}$ alkoxy, C$_{1-6}$ alkyl, C$_{1-4}$ alkylcarboxamide, amino, carbo-C$_{1-6}$-alkoxy and heteroaryl are each optionally substituted with substituents selected independently from the group consisting of C$_{1-6}$ alkyl, carbo-C$_{1-6}$-alkoxy, carboxy, and phenyl.

In some embodiments, R$_4$ is heterocyclic or heteroaryl each optionally substituted with substituents selected independently from the group consisting of C$_{1-6}$ acyl, C$_{1-12}$ acyloxy, $C_{1-4}$ alkoxy, $C_{1-6}$ alkyl, $C_{1-6}$ alkylamino, $C_{2-8}$ dialkylamino, $C_{1-4}$ alkylcarboxamide, $C_{1-4}$ alkylsulfonyl, $C_{1-4}$ alkylureyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, and hydroxyl; wherein $C_{1-5}$ acyl, $C_{1-5}$ acyloxy, $C_{1-6}$ alkyl, $C_{1-4}$ alkylcarboxamide, and carbo-$C_{1-6}$-alkoxy are each optionally substituted with $C_{1-5}$ acyl, $C_{1-4}$ alkoxy, $C_{1-6}$ alkylamino, $C_{2-8}$ dialkylamino, $C_{1-4}$ alkylcarboxamide, $C_{1-4}$ alkylsulfonyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, hydroxyl, and phenyl.

In some embodiments, $R_4$ is heterocyclic or heteroaryl each optionally substituted with substituents selected independently from the group consisting of $C_{1-6}$ acyl, $C_{1-12}$ acyloxy, $C_{1-4}$ alkoxy, $C_{1-6}$ alkyl, $C_{1-4}$ alkylcarboxamide, $C_{1-4}$ alkylureyl, amino, carbo-$C_{1-6}$-alkoxy, carboxy, and hydroxyl; wherein $C_{1-5}$ acyl, $C_{1-5}$ acyloxy, $C_{1-6}$ alkyl, $C_{1-4}$ alkylcarboxamide, and carbo-$C_{1-6}$-alkoxy are each optionally substituted with carbo-$C_{1-6}$-alkoxy, carboxy, and phenyl.

In some embodiments, heteroaryl is a 5-membered heteroaryl, for example, a 5-membered heteroaryl as shown in TABLE 1:

TABLE 1

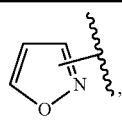

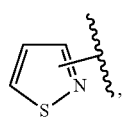

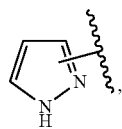

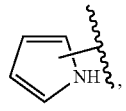

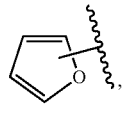

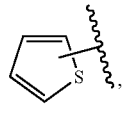

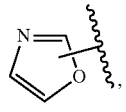

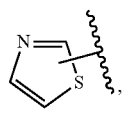

TABLE 1-continued

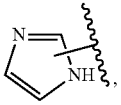

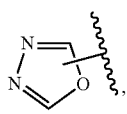

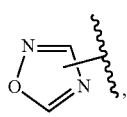

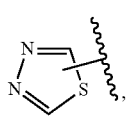

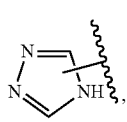

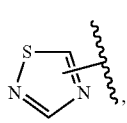

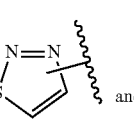

and

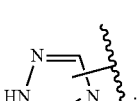

;

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imidazol-5-yl group).

In some embodiments, heteroaryl is a 6-membered heteroaryl, for example, a 6-membered heteroaryl as shown in TABLE 2:

TABLE 2

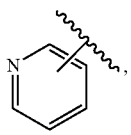

TABLE 2-continued

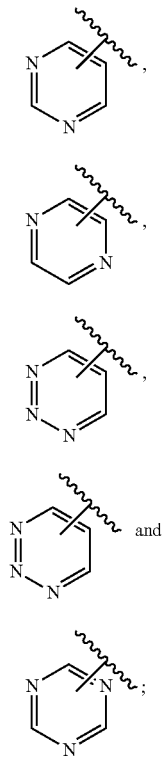

wherein the heteroaryl group is bonded at any ring carbon.

In some embodiments, $R_4$ is selected from the group consisting of pyrrolidinyl, piperidinyl, morpholinyl, piperazinyl, pyridinyl, azetidinyl, thiomorpholinyl 2,5-diaza-bicyclo[2.2.1]heptyl, [1,4]oxazepanyl, 1,1-dioxo-1$\lambda^6$-thiomorpholinyl, azepanyl, and 3-oxo-piperazinyl, aza-bicyclo[2.2.1]heptyl, and imidazolyl each optionally substituted with substituents selected independently from the group consisting of $C_{1-6}$ acyl, $C_{1-12}$ acyloxy, $C_{1-4}$ alkoxy, $C_{1-6}$ alkoxycarbonylamino, $C_{1-6}$ alkyl, $C_{1-4}$ alkylcarboxamide, $C_{1-4}$ alkylsulfonamide, $C_{1-4}$ alkylsulfonyl, $C_{1-4}$ alkylureyl, amino, carbo-$C_{1-6}$-alkoxy, carboxamide, carboxy, $C_{2-6}$ dialkylcarboxamide, formyl, halogen, $C_{1-4}$ haloalkyl, heteroaryl, hydroxyl and phenyl; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy and heteroaryl are each optionally substituted with substituents selected independently from the group consisting of $C_{1-6}$ alkyl, carbo-$C_{1-6}$-alkoxy, carboxy, and phenyl.

In some embodiments, $R_4$ is selected from the group consisting of pyrrolidinyl, piperidinyl, morpholinyl, piperazinyl, pyridinyl, azetidinyl, thiomorpholinyl, 2,5-diaza-bicyclo[2.2.1]heptyl, [1,4]oxazepanyl, 1,1-dioxo-1$\lambda^6$-thiomorpholinyl, azepanyl, 3-oxo-piperazinyl, 7-aza-bicyclo[2.2.1]hept-7-yl, and imidazolyl each optionally substituted with substituents selected independently from the group consisting of $CH_3$, $C(=O)$O-t-butyl, $C(=O)OH$, $C(=O)$OEt, $NHC(=O)$O-t-butyl, OH, $C(=O)NHCH_2C(=O)OCH_3$, $NHC(=O)CH_2C(=O)OCH_3$, $C(=O)NHCH_2C(=O)OH$, $NHC(=O)CH_2C(=O)OH$, $C(=O)OCH_3$, $OC(=O)CH_2CH_2C(=O)OCH_3$, $OC(=O)CH_2CH_2CH_2CH_2CH_3$, $CH_2C(=O)OCH_2CH_3$, $OCH_3$, $CH_2C(=O)OH$, $OC(=O)CH_2CH_2C(=O)OCH_3$, $CH_2CH_2C(=O)OCH_3$, $C(=O)CH_3$, $C(=O)OCH_2$-phenyl, $C(=O)CH_2CH_2C(=O)OCH_3$, $C(=O)CH_2CH_2C(=O)OH$, F, phenyl, $CH_2C(=O)OCH_3$, $S(=O)_2CH_3$, $OCH_2$-phenyl, $CH_2$-phenyl, $C(=O)NH_2$, CHO, $-NH_2$, $NHC(=O)CH_3$, $C(=O)N(CH_3)_2$, $NHS(=O)_2CH_3$, $-CF_3$, 3-methyl-[1,2,4]oxadiazol-5-yl, and $CH(CH_3)_2$.

In some embodiments, $R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl, morpholin-2-yl, 2,5-diaza-bicyclo[2.2.1]hept-2-yl, [1,4]oxazepan-4-yl, 1,1-dioxo-1$\lambda^6$-thiomorpholin-4-yl, piperidin-2-yl, azepan-1-yl, pyrrolidin-3-yl, 3-oxo-piperazin-1-yl, 7-aza-bicyclo[2.2.1]hept-7-yl, and imidazol-1-yl each optionally substituted with substituents selected independently from the group consisting of $CH_3$, $C(=O)$O-t-butyl, $C(=O)OH$, $C(=O)$OEt, $NHC(=O)$O-t-butyl, OH, $C(=O)NHCH_2C(=O)OCH_3$, $NHC(=O)CH_2C(=O)OCH_3$, $C(=O)NHCH_2C(=O)OH$, $NHC(=O)CH_2C(=O)OH$, $C(=O)OCH_3$, $OC(=O)CH_2CH_2C(=O)OCH_3$, $OC(=O)CH_2CH_2CH_2CH_2CH_3$, $CH_2C(=O)OCH_2CH_3$, $OCH_3$, $CH_2C(=O)OH$, $OC(=O)CH_2CH_2C(=O)OCH_3$, $CH_2CH_2C(=O)OCH_3$, $C(=O)CH_3$, and $C(=O)OCH_2$-phenyl, $C(=O)CH_2CH_2C(=O)OCH_3$, $C(=O)CH_2CH_2C(=O)OH$, F, phenyl, $CH_2C(=O)OCH_3$, $S(=O)_2CH_3$, $OCH_2$-phenyl, $CH_2$-phenyl, $C(=O)NH_2$, CHO, $-NH_2$, $NHC(=O)CH_3$, $C(=O)N(CH_3)_2$, $NHS(=O)_2CH_3$, $-CF_3$, 3-methyl-[1,2,4]oxadiazol-5-yl, and $CH(CH_3)_2$.

In some embodiments, $R_4$ is selected from the group consisting of pyrrolidinyl, piperidinyl, morpholinyl, piperazinyl, pyridinyl, azetidinyl, thiomorpholinyl and 2,5-diaza-bicyclo[2.2.1]heptyl optionally substituted with substituents selected independently from the group consisting of $C_{1-5}$ acyl, $C_{1-5}$ acyloxy, $C_{1-4}$ alkoxy, $C_{1-6}$ alkyl, $C_{1-4}$ alkylcarboxamide, $C_{1-4}$ alkylureyl, amino, carbo-$C_{1-6}$-alkoxy, carboxy, and hydroxyl; wherein $C_{1-5}$ acyl, $C_{1-8}$ acyloxy, $C_{1-8}$ alkyl, $C_{1-4}$ alkylcarboxamide, and carbo-$C_{1-6}$-alkoxy are each optionally substituted with carbo-$C_{1-6}$-alkoxy, carboxy, and phenyl.

In some embodiments, $R_4$ is selected from the group consisting of pyrrolidinyl, piperidinyl, morpholinyl, piperazinyl, pyridinyl, azetidinyl, thiomorpholinyl and 2,5-diaza-bicyclo[2.2.1]heptyl optionally substituted with substituents selected independently from the group consisting of $CH_3$, $C(=O)$O-t-butyl, $C(=O)OH$, $C(=O)$OEt, $NHC(=O)$O-t-butyl, OH, $C(=O)NHCH_2C(=O)OCH_3$, $NHC(=O)CH_2C(=O)OCH_3$, $C(=O)NHCH_2C(=O)OH$, $NHC(=O)CH_2C(=O)OH$, $C(=O)OCH_3$, $OC(=O)CH_2CH_2C(=O)OCH_3$, $OC(=O)CH_2CH_2CH_2CH_2CH_3$, $CH_2C(=O)OCH_2CH_3$, $OCH_3$, $CH_2C(=O)OH$, $OC(=O)CH_2CH_2C(=O)OCH_3$, $CH_2CH_2C(=O)OCH_3$, $C(=O)CH_3$, and $C(=O)OCH_2$-phenyl.

In some embodiments, $R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl and 2,5-diaza-bicyclo[2.2.1]heptyl optionally substituted with substituents selected independently from the group consisting of $CH_3$, $C(=O)$O-t-butyl, $C(=O)OH$, $C(=O)$OEt, $NHC(=O)$O-t-butyl, OH, $C(=O)NHCH_2C(=O)OCH_3$, $NHC(=O)CH_2C(=O)OCH_3$, $C(=O)NHCH_2C(=O)OH$, $NHC(=O)CH_2C(=O)OH$, $C(=O)OCH_3$, $OC(=O)CH_2CH_2C(=O)OCH_3$, $OC(=O)CH_2CH_2CH_2CH_2CH_3$, $CH_2C(=O)OCH_2CH_3$, $OCH_3$, $CH_2C(=O)OH$, $OC(=O)CH_2CH_2C(O)OCH_3$, $CH_2CH_2C(=O)OCH_3$, $C(=O)CH_3$, and $C(=O)OCH_2$-phenyl.

In some embodiments, $R_4$ is selected from the group consisting of morpholin-4-yl, piperazin-1-yl, and 7-azabicyclo[2.2.1]hept-7-yl, and the piperazin-1-yl is substituted with either C(=O)CH$_3$ or C(=O)NH$_2$.

In some embodiments, R$_4$ is 4-acetyl-piperazin-1-yl, morpholin-4-yl, piperidin-4-yl or pyrrolidin-1-yl.

In some embodiments, R$_5$, R$_6$, and R$_7$ are all H.

In some embodiments, R$_5$ is H.

In some embodiments, R$_6$ is H.

In some embodiments, R$_7$ is H.

In some embodiments, R$_8$ is C$_{1-8}$ alkyl, C$_{2-6}$ alkenyl, aryl, C$_{3-7}$ cycloalkyl, or heteroaryl each optionally substituted with substituents selected independently from the group consisting of C$_{1-6}$ acyl, C$_{1-6}$ alkoxy, C$_{1-6}$ alkyl, C$_{1-6}$ alkylsulfonyl, amino, C$_{1-6}$ alkylamino, C$_{2-8}$ dialkylamino, carbo-C$_{1-6}$-alkoxy, carboxamide, carboxy, cyano, C$_{3-7}$ cycloalkyl, halogen, C$_{1-6}$ haloalkoxy, C$_{1-6}$ haloalkyl, heterocyclic, hydroxyl, nitro, and phenyl, or two adjacent substituents together with the aryl or heteroaryl form a C$_{5-7}$ cycloalkyl optionally comprising 1 to 2 oxygen atoms and optionally substituted with F.

In some embodiments, R$_8$ is C$_{1-8}$ alkyl, C$_{2-6}$ alkenyl, aryl or heteroaryl each optionally substituted with substituents selected independently from the group consisting of C$_{1-6}$ acyl, C$_{1-6}$ alkoxy, C$_{1-6}$ alkyl, C$_{1-6}$ alkylsulfonyl, amino, C$_{1-6}$ alkylamino, C$_{2-8}$ dialkylamino, C$_{1-6}$ alkylimino, carbo-C$_{1-6}$-alkoxy, carboxamide, carboxy, cyano, C$_{3-7}$ cycloalkyl, halogen, C$_{1-6}$ haloalkoxy, C$_{1-6}$ haloalkyl, heterocyclic, hydroxyl, nitro, and phenyl, or two adjacent substituents together with the aryl or heteroaryl form a C$_{5-7}$ cycloalkyl optionally comprising 1 to 2 oxygen atoms and optionally substituted with F.

In some embodiments, R$_8$ is C$_{1-8}$ alkyl, C$_{2-6}$ alkenyl, aryl, C$_{3-7}$ cycloalkyl, or heteroaryl each optionally substituted with substituents selected independently from the group consisting of C$_{1-6}$ acyl, C$_{1-6}$ alkoxy, C$_{1-6}$ alkyl, cyano, halogen, C$_{1-6}$ haloalkoxy, C$_{1-6}$ haloalkyl, and hydroxyl, or two adjacent substituents together with the aryl or heteroaryl form a C$_{5-7}$ cycloalkyl optionally comprising 1 to 2 oxygen atoms and optionally substituted with F.

In some embodiments, R$_8$ is C$_{1-8}$ alkyl, C$_{2-6}$ alkenyl, aryl or heteroaryl each optionally substituted with substituents selected independently from the group consisting of C$_{1-6}$ acyl, C$_{1-6}$ alkoxy, C$_{1-6}$ alkyl, halogen, C$_{1-6}$ haloalkyl, and hydroxyl, or two adjacent substituents together with the aryl or heteroaryl form a C$_{5-7}$ cycloalkyl optionally comprising 1 to 2 oxygen atoms and optionally substituted with F.

In some embodiments, R$_8$ is C$_{1-8}$ alkyl, C$_{2-6}$ alkenyl, aryl, C$_{3-7}$ cycloalkyl, or heteroaryl each optionally substituted with substituents selected independently from the group consisting of C(=O)CH$_3$, OCH$_3$, CH$_3$, F, Cl, Br, CF$_3$, hydroxyl, OCF$_3$, and CN, or two adjacent substituents together with the aryl or heteroaryl form a C$_{5-7}$ cycloalkyl optionally comprising 1 to 2 oxygen atoms and optionally substituted with F.

In some embodiments, R$_8$ is C$_{1-8}$ alkyl, C$_{2-6}$ alkenyl, aryl or heteroaryl each optionally substituted with substituents selected independently from the group consisting of C(=O) CH$_3$, OCH$_3$, CH$_3$, F, Cl, Br, CF$_3$ and hydroxyl, or two adjacent substituents together with the aryl or heteroaryl form a C$_{5-7}$ cycloalkyl optionally comprising 1 to 2 oxygen atoms and optionally substituted with F.

In some embodiments, R$_8$ is selected from the group consisting of methyl, iso-propyl, iso-butyl, n-propyl, n-butyl, 2-methyl-propenyl, 3-methyl-butyl, phenyl, napthalenyl, cyclopropyl, cyclobutyl, cyclopentyl, pyridinyl, benzoimidazolyl, benzooxazolyl, benzothiazolyl, thienyl, furanyl, benzothienyl, thiazolyl, isoxazolyl, and pyridin-4-yl each optionally substituted with substituents selected independently from the group consisting of C(=O)CH$_3$, OCH$_3$, CH$_3$, F, Cl, Br, CF$_3$, hydroxyl, OCF$_3$, and CN, or two adjacent substituents together with the phenyl form a C$_5$ cycloalkyl comprising 2 oxygen atoms and optionally substituted with F.

In some embodiments, R$_8$ is selected from the group consisting of methyl, iso-propyl, iso-butyl, n-propyl, n-butyl, 2-methyl-propenyl, phenyl, pyridinyl, benzoimidazolyl, benzooxazolyl and benzothiazolyl each optionally substituted with substituents selected independently from the group consisting of C(=O)CH$_3$, OCH$_3$, CH$_3$, F, Cl, Br, CF$_3$ and hydroxyl, or two adjacent substituents together with the phenyl form a C$_5$ cycloalkyl comprising 2 oxygen atoms and optionally substituted with F.

In some embodiments, R$_8$ is selected from the group consisting of methyl, iso-propyl, iso-butyl, n-propyl, n-butyl, 2-methyl-propenyl, phenyl, naphthalen-1-yl, cyclopropyl, cyclobutyl, cyclopentyl, pyridin-2-yl, pyridin-3-yl, 1H-benzoimidazol-2-yl, benzooxazol-2-yl, benzothiazol-2-yl, thiophen-2-yl, furan-2-yl, benzothiophen-2-yl, thiazol-2-yl, isoxazol-3-yl, and pyridin-4-yl each optionally substituted with substituents selected independently from the group consisting of C(=O)CH$_3$, OCH$_3$, CH$_3$, F, Cl, Br, CF$_3$, hydroxyl, OCF$_3$, and CN, or two adjacent substituents together with the phenyl form a C$_5$ cycloalkyl comprising 2 oxygen atoms and optionally substituted with F.

In some embodiments, R$_8$ is selected from the group consisting of methyl, iso-propyl, iso-butyl, n-propyl, n-butyl, 2-methyl-propenyl, phenyl, pyridin-2-yl, pyridin-3-yl, 1H-benzoimidazol-2-yl, benzooxazol-2-yl and benzothiazol-2-yl, each optionally substituted with substituents selected independently from the group consisting of C(=O) CH$_3$, OCH$_3$, CH$_3$, F, Cl, Br, CF$_3$ and hydroxyl, or two adjacent substituents together with the phenyl form a C$_5$ cycloalkyl comprising 2 oxygen atoms and optionally substituted with F.

In some embodiments, R$_8$ is selected from the group consisting of 4-chloro-phenyl, 2,4-difluoro-phenyl, 4-fluoro-phenyl, 3-chloro-phenyl, 2,2-difluoro-benzo[1,3] dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluoro-phenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, and 2,5-dichloro-phenyl.

In some embodiments, R$_8$ is selected from the group consisting of 4-chloro-phenyl, 2,4-difluoro-phenyl, 4-fluoro-phenyl, 3-chloro-phenyl, 2,2-difluoro-benzo[1,3] dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluorophenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, 2,5-dichloro-phenyl, and benzo[1,3]dioxol-5-yl.

In some embodiments, $R_8$ is selected from the group consisting of 4-chloro-phenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl and 3-trifluoromethyl-phenyl.

In some embodiments, $R_8$ is selected from the group consisting of methyl, iso-propyl, iso-butyl, n-propyl, n-butyl, 2-methyl-propenyl, 3-methyl-butyl, cyclopropyl, cyclobutyl, and cyclopentyl.

In some embodiments, $R_8$ is selected from the group consisting of methyl, iso-propyl, iso-butyl, n-propyl, n-butyl, and 2-methyl-propenyl.

In some embodiments, $R_8$ is a 5-membered heteroaryl is selected from the group shown in TABLE 1.

In some embodiments, $R_8$ is a 6-membered heteroaryl is selected from the group shown in TABLE 2.

In some embodiments, $R_8$ is selected from the group consisting of pyridin-3-yl, 6-trifluoromethyl-pyridin-3-yl, 3-hydroxy-pyridin-2-yl, 6-methyl-pyridin-3-yl, 6-hydroxy-pyridin-3-yl, 1H-benzoimidazol-2-yl, benzooxazol-2-yl, benzothiazol-2-yl, thiophen-2-yl, furan-2-yl, 5-chloro-thiophen-2-yl, benzothiophen-2-yl, thiazol-2-yl, 5-methyl-isoxazol-3-yl, and pyridin-4-yl.

In some embodiments, $R_8$ is selected from the group consisting of pyridin-3-yl, 6-trifluoromethyl-pyridin-3-yl, 3-hydroxy-pyridin-2-yl, 6-methyl-pyridin-3-yl, 6-hydroxy-pyridin-3-yl, 1H-benzoimidazol-2-yl, benzooxazol-2-yl and benzothiazol-2-yl.

In some embodiments, $R_9$ is H.
In some embodiments, $R_9$ is $C_{1-8}$ alkyl.
In some embodiments, $R_{10}$ is H.
In some embodiments, $R_{10}$ is $C_{1-8}$ alkyl.
In some embodiments, $R_{11}$ is H.
In some embodiments, $R_{11}$ is $C_{1-8}$ alkyl.

Some embodiments of the present invention encompass certain 3-phenyl-pyrazole derivatives as shown in Formula (Ik):

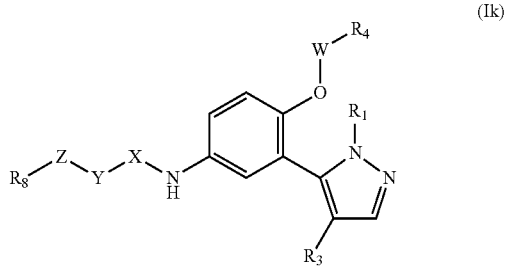

(Ik)

or a pharmaceutically acceptable salt thereof;

wherein:
W is —$CH_2$—, —$CH_2CH_2$—, —$CH_2C(=O)$—, —$CH_2CH_2CH_2$—, —$C(CH_3)_2C(=O)$—, —$CH_2CH(CH_3)$—, —$CH(CH_3)CH_2$—, —$C(CH_3)_2CH_2$—, or —$CH_2C(CH_3)_2$—; or W is absent;
X is C(=O) or absent;
Y is NH, O or absent;
Z is absent, —$CH_2$—, —CH(OH)—, —$CF_2$—, —$C(CH_3)_2$—, 1,1-cyclopropyl, —$CH_2CH_2$—, —$CH_2CH_2CH_2$—, —$CH(CH_3)$—, or —C(=O)—;
$R_1$ is $C_{1-6}$ alkyl;
$R_3$ is H or halogen;
$R_4$ is heterobicyclic, heterocyclic, or heteroaryl, each optionally substituted with substituents selected independently from the group consisting of $C_{1-6}$ acyl, $C_{1-12}$ acyloxy, $C_{1-4}$ alkoxy, $C_{1-6}$ alkoxycarbonylamino, $C_{1-6}$ alkyl, $C_{1-4}$ alkylcarboxamide, $C_{1-4}$ alkylsulfonamide, $C_{1-4}$ alkylsulfonyl, $C_{1-4}$ alkylureyl, amino, carbo-$C_{1-6}$-alkoxy, carboxamide, carboxy, $C_{2-6}$ dialkylcarboxamide, formyl, halogen, $C_{1-4}$ haloalkyl, heteroaryl, hydroxyl and phenyl; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy and heteroaryl are each optionally substituted with substituents selected independently from the group consisting of $C_{1-6}$ alkyl, carbo-$C_{1-6}$-alkoxy, carboxy, and phenyl; and
$R_8$ is $C_{1-8}$ alkyl, $C_{2-6}$ alkenyl, aryl, $C_{3-7}$ cycloalkyl, or heteroaryl, each optionally substituted with substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent substituents together with the aryl or heteroaryl form a $C_{5-7}$ cycloalkyl optionally comprising 1 to 2 oxygen atoms and optionally substituted with F.

Some embodiments of the present invention encompass certain 3-phenyl-pyrazole derivatives as shown in Formula (Ik), supra, or a pharmaceutically acceptable salt thereof; wherein:
W is —$CH_2$—, —$CH_2CH_2$—, —$CH_2C(=O)$—, —$CH_2CH_2CH_2$— or W is absent;
X is C(=O) or absent;
Y is NH, O or absent;
Z is —$CH_2$—, —CH(OH)— or absent;
$R_1$ is $C_{1-6}$ alkyl;
$R_3$ is H or halogen;
$R_4$ is heterocyclic or heteroaryl, each optionally substituted with substituents selected independently from the group consisting of $C_{1-6}$ acyl, $C_{1-12}$ acyloxy, $C_{1-4}$ alkoxy, $C_{1-8}$ alkyl, $C_{1-6}$ alkylamino, $C_{2-8}$ dialkylamino, $C_{1-4}$ alkylcarboxamide, $C_{1-4}$ alkylsulfonyl, $C_{1-4}$ alkylureyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, and hydroxyl; wherein $C_{1-5}$ acyl, $C_{1-5}$ acyloxy, $C_{1-8}$ alkyl, $C_{1-4}$ alkylcarboxamide, and carbo-$C_{1-6}$-alkoxy are each optionally substituted with $C_{1-5}$ acyl, $C_{1-4}$ alkoxy, $C_{1-6}$ alkylamino, $C_{2-8}$ dialkylamino, $C_{1-4}$ alkylcarboxamide, $C_{1-4}$ alkylsulfonyl, amino, carbo-$C_{1-6}$-alkoxy, carboxamide, carboxy, cyano, $C_{3-6}$ cycloalkyl, halogen, $C_{1-4}$ haloalkoxy, $C_{1-4}$ haloalkyl, hydroxyl, and phenyl; and R$_8$ is C$_{1-8}$ alkyl, C$_{2-6}$ alkenyl, aryl or heteroaryl, each optionally substituted with substituents selected independently from the group consisting of C$_{1-6}$ acyl, C$_{1-6}$ alkoxy, C$_{1-6}$ alkyl, C$_{1-6}$ alkylsulfonyl, amino, C$_{1-6}$ alkylamino, C$_{2-8}$ dialkylamino, C$_{1-6}$ alkylimino, carbo-C$_{1-6}$-alkoxy, carboxamide, carboxy, cyano, C$_{3-7}$ cycloalkyl, halogen, C$_{1-6}$ haloalkoxy, C$_{1-6}$ haloalkyl, heterocyclic, hydroxyl, nitro, and phenyl, or two adjacent substituents together with the aryl or heteroaryl form a C$_{5-7}$ cycloalkyl optionally comprising 1 to 2 oxygen atoms and optionally substituted with F.

Some embodiments of the present invention encompass certain 3-phenyl-pyrazole derivatives as shown in Formula (Ik), supra, or a pharmaceutically acceptable salt thereof; wherein:
W is —CH$_2$—, —CH$_2$CH$_2$—, —CH$_2$C(═O)—, —CH$_2$CH$_2$CH$_2$—, —C(CH$_3$)$_2$C(═O)—, —CH$_2$CH (CH$_3$)—, —CH(CH$_3$)CH$_2$—, —C(CH$_3$)$_2$CH$_2$—, or —CH$_2$C(CH$_3$)$_2$—; or W is absent;
X is C(═O) or absent;
Y is NH, O or absent;
Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(═O)—;
R$_1$ is C$_{1-6}$ alkyl;
R$_3$ is H or halogen;
R$_4$ is heterobicyclic, heterocyclic, or heteroaryl, each optionally substituted with substituents selected independently from the group consisting of C$_{1-6}$ acyl, C$_{1-12}$ acyloxy, C$_{1-4}$ alkoxy, C$_{1-6}$ alkoxycarbonylamino, C$_{1-6}$ alkyl, C$_{1-4}$ alkylcarboxamide, C$_{1-4}$ alkylsulfonamide, C$_{1-4}$ alkylsulfonyl, C$_{1-4}$ alkylureyl, amino, carbo-C$_{1-6}$-alkoxy, carboxamide, carboxy, C$_{2-6}$ dialkylcarboxamide, formyl, halogen, C$_{1-4}$ haloalkyl, heteroaryl, hydroxyl and phenyl; wherein said C$_{1-5}$ acyl, C$_{1-5}$ acyloxy, C$_{1-4}$ alkoxy, C$_{1-6}$ alkyl, C$_{1-4}$ alkylcarboxamide, amino, carbo-C$_{1-6}$-alkoxy and heteroaryl are each optionally substituted with substituents selected independently from the group consisting of C$_{1-6}$ alkyl, carbo-C$_{1-6}$-alkoxy, carboxy, and phenyl; and
R$_8$ is selected from the group consisting of 4-chloro-phenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluoro-phenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, 2,5-dichloro-phenyl, and benzo[1,3]dioxol-5-yl.

Some embodiments of the present invention encompass certain 3-phenyl-pyrazole derivatives as shown in Formula (Im):

(Im)

or a pharmaceutically acceptable salt thereof;
wherein:
W is —CH$_2$—, —CH$_2$CH$_2$—, —CH$_2$C(═O)—, —CH$_2$CH$_2$CH$_2$—, —C(CH$_3$)$_2$C(═O)—, —CH$_2$CH (CH$_3$)—, —CH(CH$_3$)CH$_2$—, —C(CH$_3$)$_2$CH$_2$—, or —CH$_2$C(CH$_3$)$_2$—; or W is absent;
Y is NH, O or absent;
Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(═O)—;
R$_1$ is C$_{1-6}$ alkyl;
R$_3$ is H or halogen;
R$_4$ is selected from the group consisting of pyrrolidinyl, piperidinyl, morpholinyl, piperazinyl, pyridinyl, azetidinyl, thiomorpholinyl 2,5-diaza-bicyclo[2.2.1]heptyl, [1,4]oxazepanyl, 1,1-dioxo-1λ$^6$-thiomorpholinyl, azepanyl, and 3-oxo-piperazinyl, aza-bicyclo[2.2.1]heptyl, and imidazolyl, each optionally substituted with substituents selected independently from the group consisting of C$_{1-6}$ acyl, C$_{1-12}$ acyloxy, C$_{1-4}$ alkoxy, C$_{1-6}$ alkyl, C$_{1-4}$ alkylcarboxamide, C$_{1-4}$ alkylsulfonamide, C$_{1-4}$ alkylsulfonyl, C$_{1-4}$ alkylureyl, amino, carbo-C$_{1-6}$-alkoxy, carboxamide, carboxy, C$_{2-6}$ dialkylcarboxamide, formyl, halogen, C$_{1-4}$ haloalkyl, heteroaryl, hydroxyl and phenyl; wherein said C$_{1-5}$ acyl, C$_{1-5}$ acyloxy, C$_{1-4}$ alkoxy, C$_{1-6}$ alkyl, C$_{1-4}$ alkylcarboxamide, amino, carbo-C$_{1-6}$-alkoxy and heteroaryl are each optionally substituted with substituents selected independently from the group consisting of C$_{1-6}$ alkyl, carbo-C$_{1-6}$-alkoxy, carboxy, and phenyl; and
R$_8$ is selected from the group consisting of methyl, iso-propyl, iso-butyl, n-propyl, n-butyl, 2-methyl-propenyl, 3-methyl-butyl, phenyl, napthalenyl, cyclopropyl, cyclobutyl, cyclopentyl, pyridinyl, benzoimidazolyl, benzooxazolyl, benzothiazolyl, thienyl, furanyl, benzothienyl, thiazolyl, isoxazolyl, and pyridin-4-yl, each optionally substituted with substituents selected independently from the group consisting of C(═O)CH$_3$, OCH$_3$, CH$_3$, F, Cl, Br, CF$_3$, hydroxyl, OCF$_3$, and CN, or two adjacent substituents together with the phenyl form a C$_5$ cycloalkyl comprising 2 oxygen atoms and optionally substituted with F.

Some embodiments of the present invention encompass certain 3-phenyl-pyrazole derivatives as shown in Formula (Im), supra, or a pharmaceutically acceptable salt thereof;
wherein:
W is —CH$_2$—, —CH$_2$CH$_2$—, —CH$_2$C(═O)—, —CH$_2$CH$_2$CH$_2$— or W is absent;
Y is NH, O or absent;
Z is absent, —CH$_2$— or —CH(OH)—;
R$_1$ is C$_{1-6}$ alkyl;
R$_3$ is H or halogen;
R$_4$ is selected from the group consisting of pyrrolidinyl, piperidinyl, morpholinyl, piperazinyl, pyridinyl, azetidinyl, thiomorpholinyl and 2,5-diaza-bicyclo[2.2.1]heptyl, optionally substituted with substituents selected independently from the group consisting of $C_{1-8}$ acyl, $C_{1-5}$ acyloxy, $C_{1-4}$ alkoxy, $C_{1-6}$ alkyl, $C_{1-4}$ alkylcarboxamide, $C_{1-4}$ alkylureyl, amino, carbo-$C_{1-6}$-alkoxy, carboxy, and hydroxyl; wherein $C_{1-5}$ acyl, $C_{1-5}$ acyloxy, $C_{1-8}$ alkyl, $C_{1-4}$ alkylcarboxamide, and carbo-$C_{1-6}$-alkoxy are each optionally substituted with carbo-$C_{1-6}$-alkoxy, carboxy, and phenyl; and $R_8$ is selected from the group consisting of methyl, iso-propyl, iso-butyl, n-propyl, n-butyl, 2-methyl-propenyl, phenyl, pyridin-2-yl, pyridin-3-yl, 1H-benzoimidazol-2-yl, benzooxazol-2-yl and benzothiazol-2-yl, each optionally substituted with substituents selected independently from the group consisting of C(=O)CH$_3$, OCH$_3$, CH$_3$, F, Cl, Br, CF$_3$ and hydroxyl, or two adjacent substituents together with the phenyl form a $C_5$ cycloalkyl comprising 2 oxygen atoms and optionally substituted with F.

Some embodiments of the present invention encompass certain 3-phenyl-pyrazole derivatives as shown in Formula (Im), supra, or a pharmaceutically acceptable salt thereof; wherein:

W is —CH$_2$—, —CH$_2$CH$_2$—, —CH$_2$C(=O)—, —CH$_2$CH$_2$CH$_2$—, —C(CH$_3$)$_2$C(=O)—, —CH$_2$CH (CH$_3$)—, —CH(CH$_3$)CH$_2$—, —C(CH$_3$)$_2$CH$_2$—, or —CH$_2$C(CH$_3$)$_2$—; or W is absent;

Y is NH, O or absent;

Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(=O)—;

$R_1$ is $C_{1-6}$ alkyl;

$R_3$ is H or halogen;

$R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl, morpholin-2-yl, 2,5-diaza-bicyclo[2.2.1]hept-2-yl, [1,4]oxazepan-4-yl, 1,1-dioxo-1λ$^6$-thiomorpholin-4-yl, piperidin-2-yl, azepan-1-yl, pyrrolidin-3-yl, 3-oxo-piperazin-1l-yl, 7-aza-bicyclo[2.2.1]hept-7-yl, and imidazol-1-yl, each optionally substituted with substituents selected independently from the group consisting of CH$_3$, C(=O)O-t-butyl, C(=O)OH, C(=O)OEt, NHC(=O)O-t-butyl, OH, C(=O)NHCH$_2$C(=O)OCH$_3$, NHC(=O)CH$_2$C(=O)OCH$_3$, C(=O)NHCH$_2$C(=O)OH, NHC(=O)CH$_2$C(=O)OH, C(=O)OCH$_3$, OC(=O)CH$_2$CH$_2$C(=O)OCH$_3$, OC(=O)CH$_2$CH$_2$CH$_2$CH$_3$, CH$_2$C(=O)OCH$_2$CH$_3$, OCH$_3$, CH$_2$C(=O)OH, OC(=O)CH$_2$CH$_2$C(=O)OCH$_3$, CH$_2$CH$_2$C(=O)OCH$_3$, C(=O)CH$_3$, and C(=O)OCH$_2$-phenyl, C(=O)CH$_2$CH$_2$C(=O)OCH$_3$, C(=O)CH$_2$CH$_2$C(=O)OH, F, phenyl, CH$_2$C(=O)OCH$_3$, S(=O)$_2$CH$_3$, OCH$_2$-phenyl, CH$_2$-phenyl, C(=O)NH$_2$, CHO, —NH$_2$, NHC(=O)CH$_3$, C(=O)N(CH$_3$)$_2$, NHS(=O)$_2$CH$_3$, —CF$_3$, 3-methyl-[1,2,4]oxadiazol-5-yl, and CH(CH$_3$)$_2$; and $R_8$ is selected from the group consisting of 4-chlorophenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxyphenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluoro-phenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, and 2,5-dichloro-phenyl.

Some embodiments of the present invention encompass certain 3-phenyl-pyrazole derivatives as shown in Formula (Im), supra, or a pharmaceutically acceptable salt thereof; wherein:

W is —CH$_2$—, —CH$_2$CH$_2$—, —CH$_2$C(=O)—, —CH$_2$CH$_2$CH$_2$— or W is absent;

Y is NH, O or absent;

Z is absent, —CH$_2$— or —CH(OH)—;

$R_1$ is $C_{1-6}$ alkyl;

$R_3$ is H or halogen;

$R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl and 2,5-diaza-bicyclo[2.2.1]heptyl, each optionally substituted with substituents selected independently from the group consisting of CH$_3$, C(=O)O-t-butyl, C(=O)OH, C(=O)OEt, NHC(=O)O-t-butyl, OH, C(=O)NHCH$_2$C(=O)OCH$_3$, NHC(=O)CH$_2$C(=O)OCH$_3$, C(=O)NHCH$_2$C(=O)OH, NHC(=O)CH$_2$C(=O)OH, C(=O)OCH$_3$, OC(=O)CH$_2$CH$_2$C(=O)OCH$_3$, OC(=O)CH$_2$CH$_2$CH$_2$CH$_3$, CH$_2$C(=O)OCH$_2$CH$_3$, OCH$_3$, CH$_2$C(=O)OH, OC(=O)CH$_2$CH$_2$C(=O)OCH$_3$, CH$_2$CH$_2$C(=O)OCH$_3$, C(=O) CH$_3$, and C(=O)OCH$_2$-phenyl; and $R_8$ is selected from the group consisting of 4-chlorophenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxyphenyl, 3-acetyl-phenyl, 4-methyl-phenyl and 3-trifluoromethyl-phenyl.

Some embodiments of the present invention encompass certain 3-phenyl-pyrazole derivatives as shown in Formula (Im), supra, or a pharmaceutically acceptable salt thereof; wherein:

W is —CH$_2$—, —CH$_2$CH$_2$—, —CH$_2$C(=O)—, —CH$_2$CH$_2$CH$_2$—, —C(CH$_3$)$_2$C(=O)—, —CH$_2$CH (CH$_3$)—, —CH(CH$_3$)CH$_2$—, —C(CH$_3$)$_2$CH$_2$—, or —CH$_2$C(CH$_3$)$_2$—; or W is absent;

Y is NH, O or absent;

Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(=O)—;

$R_1$ is $C_{1-6}$ alkyl;

$R_3$ is H or halogen;

$R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl, morpholin-2-yl, 2,5-diaza-bicyclo[2.2.1]hept-2-yl, [1,4]oxazepan-4-yl, 1,1-dioxo-1λ$^6$-thiomorpholin-4-yl, piperidin-2-yl, azepan-1-yl, pyrrolidin-3-yl, 3-oxo-piperazin-1-yl, 7-aza-bicyclo[2.2.1]hept-7-yl, and imidazol-1-yl, each optionally substituted with substituents selected independently from the group consisting of CH$_3$, C(=O)O-t-butyl, C(=O)OH, C(=O)OEt, NHC(=O)O-t-butyl, OH, C(=O)NHCH$_2$C(=O)OCH$_3$, NHC(=O)CH$_2$C(=O)OCH$_3$, C(=O)NHCH$_2$C(=O)OH, NHC(=O)CH$_2$C(=O)OH, C(=O)OCH$_3$, OC(=O)CH$_2$CH$_2$C(=O)OCH$_3$, OC(=O) CH$_2$CH$_2$CH$_2$CH$_3$, CH$_2$C(=O)OCH$_2$CH$_3$, OCH$_3$, CH₂C(=O)OH, OC(=O)CH₂CH₂C(=O)OCH₃, CH₂CH₂C(=O)OCH₃, C(=O)CH₃, and C(=O)OCH₂-phenyl, C(=O)CH₂CH₂C(=O)OCH₃, C(=O)CH₂CH₂C(=O)OH, F, phenyl, CH₂C(=O)OCH₃, S(=O)₂CH₃, OCH₂-phenyl, CH₂-phenyl, C(=O)NH₂, CHO, —NH₂, NHC(=O)CH₃, C(=O)N(CH₃)₂, NHS(=O)₂CH₃, —CF₃, 3-methyl-[1,2,4]oxadiazol-5-yl, and CH(CH₃)₂; and R₈ is selected from the group consisting of methyl, iso-propyl, iso-butyl, n-propyl, n-butyl, 2-methyl-propenyl, 3-methyl-butyl, cyclopropyl, cyclobutyl, and cyclopentyl.

Some embodiments of the present invention encompass certain 3-phenyl-pyrazole derivatives as shown in Formula (Im), supra, or a pharmaceutically acceptable salt thereof; wherein:

W is —CH₂—, —CH₂CH₂—, —CH₂C(=O)—, —CH₂CH₂CH₂— or W is absent;

Y is NH, O or absent;

Z is absent, —CH₂— or —CH(OH)—;

R₁ is C₁₋₆ alkyl;

R₃ is H or halogen;

R₄ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl and 2,5-diaza-bicyclo[2.2.1]heptyl, each optionally substituted with substituents selected independently from the group consisting of CH₃, C(=O)O-t-butyl, C(=O)OH, C(=O)OEt, NHC(=O)O-t-butyl, OH, C(=O)NHCH₂C(=O)OCH₃, NHC(=O)CH₂C(=O)OCH₃, C(=O)NHCH₂C(=O)OH, NHC(=O)CH₂C(=O)OH, C(=O)OCH₃, OC(=O)CH₂CH₂C(=O)OCH₃, OC(=O)CH₂CH₂CH₂CH₂CH₃, CH₂C(=O)OCH₂CH₃, OCH₃, CH₂C(=O)OH, OC(=O)CH₂CH₂C(=O)OCH₃, CH₂CH₂C(=O)OCH₃, CH₂CH₂C(=O)OCH₃, C(=O)CH₃, and C(=O)OCH₂-phenyl; and R₈ is selected from the group consisting of methyl, iso-propyl, iso-butyl, n-propyl, n-butyl, and 2-methyl-propenyl.

Some embodiments of the present invention encompass certain 3-phenyl-pyrazole derivatives as shown in Formula (Im), supra, or a pharmaceutically acceptable salt thereof; wherein:

W is —CH₂CH₂—; Y is NH or absent; R₁ is CH₃; R₄ is 4-acetyl-piperazin-1-yl, morpholin-4-yl, piperidin-4-yl or pyrrolidin-1-yl; and R₈ is phenyl or C₃₋₇ cycloalkyl, each optionally substituted with 1, 2, or 3 substituents selected independently from the group consisting of C(=O)CH₃, OCH₃, CH₃, F, Cl, Br, CF₃ and hydroxyl.

Some embodiments of the present invention encompass certain 3-phenyl-pyrazole derivatives as shown in Formula (Ik), supra, or a pharmaceutically acceptable salt thereof; wherein:

W is —CH₂—, —CH₂CH₂—, —CH₂C(=O)—, —CH₂CH₂CH₂—, —C(CH₃)₂C(=O)—, —CH₂CH(CH₃)—, —CH(CH₃)CH₂—, —C(CH₃)₂CH₂—, or —CH₂C(CH₃)₂—; or W is absent;

X is C(=O) or absent;

Y is NH, O or absent;

Z is absent, —CH₂—, —CH(OH)—, —CF₂—, —C(CH₃)₂—, 1,1-cyclopropyl, —CH₂CH₂—, —CH₂CH₂CH₂—, —CH(CH₃)—, or —C(=O)—;

R₁ is C₁₋₆ alkyl;

R₃ is H or halogen;

R₄ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl, morpholin-2-yl, 2,5-diaza-bicyclo[2.2.1]hept-2-yl, [1,4]oxazepan-4-yl, 1,1-dioxo-1λ⁶-thiomorpholin-4-yl, piperidin-2-yl, azepan-1-yl, pyrrolidin-3-yl, 3-oxo-piperazin-1-yl, 7-aza-bicyclo[2.2.1]hept-7-yl, and imidazol-1-yl, each optionally substituted with substituents selected independently from the group consisting of CH₃, C(=O)O-t-butyl, C(=O)OH, C(=O)OEt, NHC(=O)O-t-butyl, OH, C(=O)NHCH₂C(=O)OCH₃, NHC(=O)CH₂C(=O)OCH₃, C(=O)NHCH₂C(=O)OH, NHC(=O)CH₂C(=O)OH, C(=O)OCH₃, OC(=O)CH₂CH₂C(=O)OCH₃, OC(=O)CH₂CH₂CH₂CH₂CH₃, CH₂C(=O)OCH₂CH₃, OCH₃, CH₂C(=O)OH, OC(=O)CH₂CH₂C(=O)OCH₃, CH₂CH₂C(=O)OCH₃, C(=O)CH₃, and C(=O)OCH₂-phenyl, C(=O)CH₂CH₂C(=O)OCH₃, C(=O)CH₂CH₂C(=O)OH, F, phenyl, CH₂C(=O)OCH₃, S(=O)₂CH₃, OCH₂-phenyl, CH₂-phenyl, C(=O)NH₂, CHO, —NH₂, NHC(=O)CH₃, C(=O)N(CH₃)₂, NHS(=O)₂CH₃, —CF₃, 3-methyl-[1,2,4]oxadiazol-5-yl, and CH(CH₃)₂; and R₈ is selected from the group consisting of pyridin-3-yl, 6-trifluoromethyl-pyridin-3-yl, 3-hydroxy-pyridin-2-yl, 6-methyl-pyridin-3-yl, 6-hydroxy-pyridin-3-yl, 1H-benzoimidazol-2-yl, benzooxazol-2-yl, benzothiazol-2-yl, thiophen-2-yl, furan-2-yl, 5-chloro-thiophen-2-yl, benzothiophen-2-yl, thiazol-2-yl, 5-methyl-isoxazol-3-yl, and pyridin-4-yl.

Some embodiments of the present invention encompass certain 3-phenyl-pyrazole derivatives as shown in Formula (Ik), supra, or a pharmaceutically acceptable salt thereof; wherein:

W is —CH₂—, —CH₂CH₂—, —CH₂C(=O)—, —CH₂CH₂CH₂— or W is absent;

X is C(=O) or absent;

Y is NH, O or absent;

Z is absent, —CH₂— or —CH(OH)—;

R₁ is C₁₋₆ alkyl;

R₃ is H or halogen;

R₄ is pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl or pyridin-4-yl, each optionally substituted with substituents selected independently from the group consisting of CH₃, C(=O)O-t-butyl, C(=O)OH, C(=O)OEt, NHC(=O)O-t-butyl, OH, C(=O)NHCH₂C(=O)OCH₃, NHC(=O)CH₂C(=O)OCH₃, C(=O)NHCH₂C(=O)OH, NHC(=O)CH₂C(=O)OH, C(=O)OCH₃, OC(=O)CH₂CH₂C(=O)OCH₃, OC(=O)CH₂CH₂CH₂CH₂CH₃, CH₂C(=O)OCH₂CH₃, OCH₃, CH₂C(=O)OH, OC(=O)CH₂CH₂C(=O)OCH₃, CH₂CH₂C(=O)OCH₃, C(=O)CH₃, and C(=O)OCH₂-phenyl; and R₈ is selected from the group consisting of pyridin-3-yl, 6-trifluoromethyl-pyridin-3-yl, 3-hydroxy-pyridin-2-yl, 6-methyl-pyridin-3-yl, 6-hydroxy-pyridin-3-yl, 1H-benzoimidazol-2-yl, benzooxazol-2-yl and benzothiazol-2-yl.

Some embodiments of the present invention encompass certain 3-phenyl-pyrazole derivatives as shown in Formula (Io):

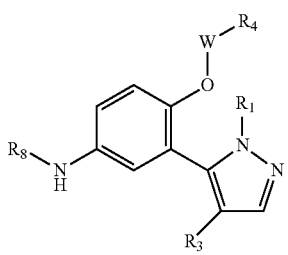

(Io)

or a pharmaceutically acceptable salt thereof;
wherein:

W is —CH$_2$—, —CH$_2$CH$_2$— or —CH$_2$C(=O)—;

R$_1$ is C$_{1-6}$ alkyl;

R$_3$ is H or halogen;

R$_4$ is pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl or pyridin-4-yl, each optionally substituted with substituents selected independently from the group consisting of CH$_3$, C(=O)O-t-butyl, C(=O)OH, C(=O)OEt, NHC(=O)O-t-butyl, OH, C(=O)NHCH$_2$C(=O)OCH$_3$, NHC(=O)CH$_2$C(=O)OCH$_3$, C(=O)NHCH$_2$C(=O)OH, NHC(=O)CH$_2$C(=O)OH, C(=O)OCH$_3$, OC(=O)CH$_2$CH$_2$C(=O)OCH$_3$, OC(=O)CH$_2$CH$_2$CH$_2$CH$_2$CH$_3$, CH$_2$C(=O)OCH$_2$CH$_3$, OCH$_3$, CH$_2$C(=O)OH, OC(=O)CH$_2$CH$_2$C(=O)OCH$_3$, CH$_2$CH$_2$C(=O)OCH$_3$, C(=O)CH$_3$, and C(=O)OCH$_2$-phenyl; and R$_8$ is selected from the group consisting of 1H-benzoimidazol-2-yl, benzooxazol-2-yl and benzothiazol-2-yl.

Some embodiments of the present invention include every combination of one or more compounds selected from the following group, where the number in bold directly preceding the chemical name refers to the Compound Number that is used elsewhere in this disclosure:

1: 1-[3-(4-Bromo-2-methyl-2H-pyrazol-3-yl)-4-(2-pyrrolidin-1-yl-ethoxy)-phenyl]-3-(4-chloro-phenyl)-urea; #2: 1-[3-(4-Bromo-2-methyl-2H-pyrazol-3-yl)-4-(2-piperidin-1-yl-ethoxy)-phenyl]-3-(4-chloro-phenyl)-urea; #3: 1-[3-(4-Bromo-2-methyl-2H-pyrazol-3-yl)-4-(2-morpholin-4-yl-ethoxy)-phenyl]-3-(4-chloro-phenyl)-urea; #4: 1-(4-Chloro-phenyl)-3-[3-(2-methyl-2H-pyrazol-3-yl)-4-(2-pyrrolidin-1-yl-ethoxy)-phenyl]-urea; #5: 1-[3-(4-Bromo-2-methyl-2H-pyrazol-3-yl)-4-(2-pyrrolidin-1-yl-ethoxy)-phenyl]-3-(2,4-difluoro-phenyl)-urea; #6: 1-[3-(4-Bromo-2-methyl-2H-pyrazol-3-yl)-4-(2-piperidin-1-yl-ethoxy)-phenyl]-3-(2,4-difluoro-phenyl)-urea; #7: [3-(4-Bromo-2-methyl-2H-pyrazol-3-yl)-4-(2-pyrrolidin-1-yl-ethoxy)-phenyl]-carbamic acid isopropyl ester; #8: 1-(4-Chloro-phenyl)-3-[3-(2-methyl-2H-pyrazol-3-yl)-4-(2-morpholin-4-yl-ethoxy)-phenyl]-urea; #9: 1-{3-(4-Bromo-2-methyl-2H-pyrazol-3-yl)-4-[2-(4-methyl-piperazin-1-yl)-ethoxy]-phenyl}-3-(4-chloro-phenyl)-urea; #10: 1-[3-(4-Bromo-2-methyl-2H-pyrazol-3-yl)-4-(piperidin-4-ylmethoxy)-phenyl]-3-(4-chloro-phenyl)-urea; #11: 1-[3-(4-Bromo-2-methyl-2H-pyrazol-3-yl)-4-(2-morpholin-4-yl-ethoxy)-phenyl]-3-(2,4-difluoro-phenyl)-urea; #12: [3-(4-Bromo-2-methyl-2H-pyrazol-3-yl)-4-(2-piperidin-1-yl-ethoxy)-phenyl]-carbamic acid isopropyl ester; #13: 1-[3-(4-Chloro-2-methyl-2H-pyrazol-3-yl)-4-(2-pyrrolidin-1-yl-ethoxy)-phenyl]-3-(2,4-difluoro-phenyl)-urea; #14: 1-[3-(4-Chloro-2-methyl-2H-pyrazol-3-yl)-4-(2-piperidin-1-yl-ethoxy)-phenyl]-3-(2,4-difluoro-phenyl)-urea; #15: 1-{3-(4-Chloro-2-methyl-2H-pyrazol-3-yl)-4-[2-(4-methyl-piperazin-1-yl)-ethoxy]-phenyl}-3-(2,4-difluoro-phenyl)-urea; #16: 1-[3-(4-Chloro-2-methyl-2H-pyrazol-3-yl)-4-(2-morpholin-4-yl-ethoxy)-phenyl]-3-(2,4-difluoro-phenyl)-urea; #17: 1-[3-(4-Chloro-2-methyl-2H-pyrazol-3-yl)-4-(2-pyrrolidin-1-yl-ethoxy)-phenyl]-3-(4-chloro-phenyl)-urea; #18: 1-[3-(4-Chloro-2-methyl-2H-pyrazol-3-yl)-4-(2-morpholin-4-yl-ethoxy)-phenyl]-3-(4-chloro-phenyl)-urea; #19: 1-[3-(4-Chloro-2-methyl-2H-pyrazol-3-yl)-4-(2-piperidin-1-yl-ethoxy)-phenyl]-3-(4-chloro-phenyl)-urea; #20: N-[3-(2-Methyl-2H-pyrazol-3-yl)-4-(2-pyrrolidin-1-yl-ethoxy)-phenyl]-acetamide; #21: 1-[3-(4-Bromo-2-methyl-2H-pyrazol-3-yl)-4-(2-pyrrolidin-1-yl-ethoxy)-phenyl]-3-(4-fluoro-phenyl)-urea; #22: 1-[3-(4-Bromo-2-methyl-2H-pyrazol-3-yl)-4-(2-pyrrolidin-1-yl-ethoxy)-phenyl]-3-(3-chloro-phenyl)-urea; #23: [3-(4-Bromo-2-methyl-2H-pyrazol-3-yl)-4-(2-pyrrolidin-1-yl-ethoxy)-phenyl]-carbamic acid isobutyl ester; #24: 1-[3-(4-Bromo-2-methyl-2H-pyrazol-3-yl)-4-(2-pyrrolidin-1-yl-ethoxy)-phenyl]-3-(2,2-difluoro-benzo[1,3]dioxol-5-yl)-urea; #25: 1-[3-(4-Bromo-2-methyl-2H-pyrazol-3-yl)-4-(2-pyrrolidin-1-yl-ethoxy)-phenyl]-3-(4-hydroxy-phenyl)-urea; #26: 1-[3-(4-Bromo-2-methyl-2H-pyrazol-3-yl)-4-(2-pyrrolidin-1-yl-ethoxy)-phenyl]-3-(4-chloro-2-hydroxy-phenyl)-urea; #27: 1-(2,4-Difluoro-phenyl)-3-[3-(2-methyl-2H-pyrazol-3-yl)-4-(2-pyrrolidin-1-yl-ethoxy)-phenyl]-urea; #28: 1-(2,4-Difluoro-phenyl)-3-[3-(2-methyl-2H-pyrazol-3-yl)-4-(pyridin-2-ylmethoxy)-phenyl]-urea; #29: 1-(2,4-Difluoro-phenyl)-3-[3-(2-methyl-2H-pyrazol-3-yl)-4-(pyridin-3-ylmethoxy)-phenyl]-urea; #30: [3-(2-Methyl-2H-pyrazol-3-yl)-4-(pyridin-3-ylmethoxy)-phenyl]-carbamic acid isopropyl ester; #31: (R)-3-[4-[3-(2,4-Difluoro-phenyl)-ureido]-2-(2-methyl-2H-pyrazol-3-yl)-phenoxy]-pyrrolidine-1-carboxylic acid tert-butyl ester; #32: N-[3-(2-Methyl-2H-pyrazol-3-yl)-4-(2-piperidin-1-yl-ethoxy)-phenyl]-acetamide; #33: [3-(2-Methyl-2H-pyrazol-3-yl)-4-(2-piperidin-1-yl-ethoxy)-phenyl]-carbamic acid isopropyl ester; #34: [3-(2-Methyl-2H-pyrazol-3-yl)-4-(2-piperidin-1-yl-ethoxy)-phenyl]-carbamic acid isobutyl ester; #35: N-[3-(2-Methyl-2H-pyrazol-3-yl)-4-(2-piperidin-1-yl-ethoxy)-phenyl]-2-phenyl-acetamide; #36: 4-[4-Acetylamino-2-(2-methyl-2H-pyrazol-3-yl)-phenoxymethyl]-piperidine-1-carboxylic acid tert-butyl ester; #37: (R)-3-[4-Isopropoxycarbonylamino-2-(2-methyl-2H-pyrazol-3-yl)-phenoxy]-pyrrolidine-1-carboxylic acid tert-butyl ester; #38: (S)-3-[4-(4-Fluoro-phenyl)-ureido]-2-(2-methyl-2H-pyrazol-3-yl)-phenoxy]-pyrrolidine-1-carboxylic acid tert-butyl ester; #39: (S)-3-[4-[3-(4-Chloro-phenyl)-ureido]-2-(2-methyl-2H-pyrazol-3-yl)-phenoxy]-pyrrolidine-1-carboxylic acid tert-butyl ester; #40: (S)-2-[4-[3-(2,4-Difluoro-phenyl)-ureido]-2-(2-methyl-2H-pyrazol-3-yl)-phenoxymethyl]-pyrrolidine-1-carboxylic acid tert-butyl ester; #41: (S)-2-[4-[3-(4-Fluoro-phenyl)-ureido]-2-(2-methyl-2H-pyrazol-3-yl)-phenoxymethyl]-pyrrolidine-1-carboxylic acid tert-butyl ester; #42: (R)-2-[4-[3-(4-Chloro-phenyl)-ureido]-2-(2-methyl-2H-pyrazol-3-yl)-phenoxymethyl]-pyrrolidine-1-carboxylic acid tert-butyl ester; #43: 2-(4-Chloro-phenyl)-N-[3-(2-methyl-2H-pyrazol-3-yl)-4-(2-piperidin-1-yl-ethoxy)-phenyl]-acetamide; #44: 1-Benzyl-3-[3-(2-methyl-2H-pyrazol-3-yl)-4-(2-piperidin-1-yl-ethoxy)-phenyl]-urea; #45: 1-(4-Chloro-benzyl)-3-[3-(2-methyl-2H-pyrazol-3-yl)-4-(2-piperidin-1-yl-ethoxy)-phenyl]-urea; #46: 1-(4-Fluoro-phenyl)-3-[3-(2-methyl-2H-pyrazol-3-yl)-4-(2-piperidin-1-yl-ethoxy)-phenyl]-urea; #47: 1-(3-Fluoro-phenyl)-3-[3-(2-methyl-2H-pyrazol-3-yl)-4-(2-piperidin-1-yl-ethoxy)-phenyl]-urea; #48: 4-[4-[3-(4-Chloro-phenyl)-ureido]-2-(2-methyl-2H-pyrazol-3-yl)-phenoxymethyl]-piperidine-1-carboxylic acid tert-butyl ester; #49: 4-[4-[3-(4-Fluorophenyl)-ureido]-2-(2-methyl-2H-pyrazol-3-yl)-phenoxymethyl]-piperidine-1-carboxylic acid tert-butyl ester; #50: 4-[4-[3-(2,4-Difluoro-phenyl)-ureido]-2-(2-methyl-2H-pyrazol-3-yl)-phenoxymethyl]-piperidine-1-carboxylic acid tert-butyl ester; #51: 1-(2,4-Difluoro-phenyl)-3-[3-(2-methyl-2H-pyrazol-3-yl)-4-(pyridin-4-ylmethoxy)-phenyl]-urea; #52: 1-(4-Chloro-phenyl)-3-[3-(2-methyl-2H-pyrazol-3-yl)-4-(piperidin-4-ylmethoxy)-phenyl]-urea; #53: 1-(4-Fluoro-phenyl)-3-[3-(2-methyl-2H-pyrazol-3-yl)-4-(piperidin-4-ylmethoxy)-phenyl]-urea; #54: 1-(2,4-Difluoro-phenyl)-3-[3-(2-methyl-2H-pyrazol-3-yl)-4-(piperidin-4-ylmethoxy)-phenyl]-urea; #55: 1-(2,4-Difluoro-phenyl)-3-[3-(2-methyl-2H-pyrazol-3-yl)-4-((S)-pyrrolidin-3-yloxy)-phenyl]-urea; #56: 1-(4-Fluoro-phenyl)-3-[3-(2-methyl-2H-pyrazol-3-yl)-4-((S)-pyrrolidin-3-yloxy)-phenyl]-urea; #57: 1-(4-Chloro-phenyl)-3-[3-(2-methyl-2H-pyrazol-3-yl)-4-((S)-pyrrolidin-3-yloxy)-phenyl]-urea; #58: 1-(2,4-Difluoro-phenyl)-3-[3-(2-methyl-2H-pyrazol-3-yl)-4-((S)-1-pyrrolidin-2-ylmethoxy)-phenyl]-urea; #59: 1-(4-Fluoro-phenyl)-3-[3-(2-methyl-2H-pyrazol-3-yl)-4-((S)-1-pyrrolidin-2-ylmethoxy)-phenyl]-urea; #60: 1-(4-Chloro-phenyl)-3-[3-(2-methyl-2H-pyrazol-3-yl)-4-((R)-1-pyrrolidin-2-ylmethoxy)-phenyl]-urea; #61: (2R,4R)-4-[4-[3-(2,4-Difluoro-phenyl)-ureido]-2-(2-methyl-2H-pyrazol-3-yl)-phenoxy]-pyrrolidine-1,2-dicarboxylic acid 1-tert-butyl ester; #62: (2R,4R)-4-[4-[3-(4-Chloro-phenyl)-ureido]-2-(2-methyl-2H-pyrazol-3-yl)-phenoxy]-pyrrolidine-1,2-dicarboxylic acid 1-tert-butyl ester; #63: (2R,4R)-4-[4-[3-(2,4-Difluoro-phenyl)-ureido]-2-(2-methyl-2H-pyrazol-3-yl)-phenoxy]-pyrrolidine-2-carboxylic acid; #64: (2R,4R)-4-[4-[3-(4-Chloro-phenyl)-ureido]-2-(2-methyl-2H-pyrazol-3-yl)-phenoxy]-pyrrolidine-2-carboxylic acid; #65: 1-(2-Fluoro-phenyl)-3-[3-(2-methyl-2H-pyrazol-3-yl)-4-(2-piperidin-1-yl-ethoxy)-phenyl]-urea; #66: 1-(3-Chloro-phenyl)-3-[3-(2-methyl-2H-pyrazol-3-yl)-4-(2-piperidin-1-yl-ethoxy)-phenyl]-urea; #67: 1-(2-Chloro-phenyl)-3-[3-(2-methyl-2H-pyrazol-3-yl)-4-(2-piperidin-1-yl-ethoxy)-phenyl]-urea; #68: 1-[3-(2-Methyl-2H-pyrazol-3-yl)-4-(2-piperidin-1-yl-ethoxy)-phenyl]-3-phenyl-urea; #69: 1-(4-Bromo-phenyl)-3-[3-(2-methyl-2H-pyrazol-3-yl)-4-(2-piperidin-1-yl-ethoxy)-phenyl]-urea; #70: 1-(3,5-Difluoro-phenyl)-3-[3-(2-methyl-2H-pyrazol-3-yl)-4-(2-piperidin-1-yl-ethoxy)-phenyl]-urea; #71: 1-(4-Methoxy-phenyl)-3-[3-(2-methyl-2H-pyrazol-3-yl)-4-(2-piperidin-1-yl-ethoxy)-phenyl]-urea; #72: 1-[3-(2-Methyl-2H-pyrazol-3-yl)-4-(2-piperidin-1-yl-ethoxy)-phenyl]-3-(4-trifluoromethyl-phenyl)-urea; #73: 1-(3,5-Bis-trifluoromethyl-phenyl)-3-[3-(2-methyl-2H-pyrazol-3-yl)-4-(2-piperidin-1-yl-ethoxy)-phenyl]-urea; #74: 1-(2-Fluoro-5-methyl-phenyl)-3-[3-(2-methyl-2H-pyrazol-3-yl)-4-(2-piperidin-1-yl-ethoxy)-phenyl]-urea; #75: 1-(3-Methoxy-phenyl)-3-[3-(2-methyl-2H-pyrazol-3-yl)-4-(2-piperidin-1-yl-ethoxy)-phenyl]-urea; #76: 1-(3-Acetyl-phenyl)-3-[3-(2-methyl-2H-pyrazol-3-yl)-4-(2-piperidin-1-yl-ethoxy)-phenyl]-urea; #77: (2S,4S)-4-[4-[3-(2,4-Difluoro-phenyl)-ureido]-2-(2-methyl-2H-pyrazol-3-yl)-phenoxy]-pyrrolidine-1,2-dicarboxylic acid 1-tert-butyl ester; #78: (2S,4S)-4-[4-[3-(4-Chloro-phenyl)-ureido]-2-(2-methyl-2H-pyrazol-3-yl)-phenoxy]-pyrrolidine-1,2-dicarboxylic acid 1-tert-butyl ester; #79: (2S,4S)-4-[4-[3-(2,4-Difluoro-phenyl)-ureido]-2-(2-methyl-2H-pyrazol-3-yl)-phenoxy]-pyrrolidine-2-carboxylic acid; #80: 1-[3-(2-Methyl-2H-pyrazol-3-yl)-4-(2-piperidin-1-yl-ethoxy)-phenyl]-3-p-tolyl-urea; #81: 1-[3-(2-Methyl-2H-pyrazol-3-yl)-4-(2-piperidin-1-yl-ethoxy)-phenyl]-3-(3-trifluoromethyl-phenyl)-urea; #82: (2S,4S)-4-[4-[3-(4-Chloro-phenyl)-ureido]-2-(2-methyl-2H-pyrazol-3-yl)-phenoxy]-pyrrolidine-2-carboxylic acid; #83: 1-[4-(2-Azetidin-1-yl-ethoxy)-3-(2-methyl-2H-pyrazol-3-yl)-phenyl]-3-(4-fluoro-phenyl)-urea; #84: 1-[4-(2-Azetidin-1-yl-ethoxy)-3-(2-methyl-2H-pyrazol-3-yl)-phenyl]-3-(4-chloro-phenyl)-urea; #85: 1-(4-Chloro-phenyl)-3-[4-(1-methyl-piperidin-4-yloxy)-3-(2-methyl-2H-pyrazol-3-yl)-phenyl]-urea; #86: 1-[4-(2-Azetidin-1-yl-ethoxy)-3-(2-methyl-2H-pyrazol-3-yl)-phenyl]-3-(2,4-difluoro-phenyl)-urea; #87: 1-[4-(2-Azetidin-1-yl-ethoxy)-3-(2-methyl-2H-pyrazol-3-yl)-phenyl]-3-(2,2-difluoro-benzo[1,3]dioxol-5-yl)-urea; #88: 1-(4-Chloro-phenyl)-3-[4-[2-(4-methyl-piperazin-1-yl)-2-oxo-ethoxy]-3-(2-methyl-2H-pyrazol-3-yl)-phenyl]-urea; #89: 4-[4-[2-(4-Chloro-phenyl)-acetylamino]-2-(2-methyl-2H-pyrazol-3-yl)-phenoxymethyl]-piperidine-1-carboxylic acid tert-butyl ester; #90: 4-[4-Isobutoxycarbonylamino-2-(2-methyl-2H-pyrazol-3-yl)-phenoxymethyl]-piperidine-1-carboxylic acid tert-butyl ester; #91: 4-[4-Isopropoxycarbonylamino-2-(2-methyl-2H-pyrazol-3-yl)-phenoxymethyl]-piperidine-1-carboxylic acid tert-butyl ester; #92: [3-(2-Methyl-2H-pyrazol-3-yl)-4-(piperidin-4-ylmethoxy)-phenyl]-carbamic acid isopropyl ester; #93: 2-(4-Chloro-phenyl)-N-[3-(2-methyl-2H-pyrazol-3-yl)-4-(piperidin-4-ylmethoxy)-phenyl]-acetamide; #94: [3-(2-Methyl-2H-pyrazol-3-yl)-4-(piperidin-4-ylmethoxy)-phenyl]-carbamic acid isobutyl ester; #95: 2-(4-Chloro-phenyl)-N-hydroxy-N-[3-(2-methyl-2H-pyrazol-3-yl)-4-(2-pyrrolidin-1-yl-ethoxy)-phenyl]-acetamide; #96: 3-Methyl-N-[3-(2-methyl-2H-pyrazol-3-yl)-4-(2-pyrrolidin-1-yl-ethoxy)-phenyl]-butyramide; #97: 1-(4-Chloro-phenyl)-3-[3-(2-methyl-2H-pyrazol-3-yl)-4-(2-piperidin-1-yl-ethoxy)-phenyl]-urea; #98: 1-{2-[4-[3-(4-Chloro-phenyl)-ureido]-2-(2-methyl-2H-pyrazol-3-yl)-phenoxy]-ethyl}-piperidine-4-carboxylic acid ethyl ester; #99: (1-{2-[4-[3-(4-Chloro-phenyl)-ureido]-2-(2-methyl-2H-pyrazol-3-yl)-phenoxy]-ethyl}-piperidin-4-yl)-carbamic acid tert-butyl ester; #100: 1-(4-Chloro-phenyl)-3-[4-[2-((S)-3-hydroxy-piperidin-1-yl)-ethoxy]-3-(2-methyl-2H-pyrazol-3-yl)-phenyl]-urea; #101: 1-(2,4-Difluoro-phenyl)-3-[3-(2-methyl-2H-pyrazol-3-yl)-4-(2-morpholin-4-yl-ethoxy)-phenyl]-urea; #102: 1-(4-Fluoro-phenyl)-3-[3-(2-methyl-2H-pyrazol-3-yl)-4-(2-morpholin-4-yl-ethoxy)-phenyl]-urea; #103: 1-{2-[4-[3-(4-Chloro-phenyl)-ureido]-2-(2-methyl-2H-pyrazol-3-yl)-phenoxy]-ethyl}-piperidine-4-carboxylic acid; #104: 1-[4-[2-(4-Amino-piperidin-1-yl)-ethoxy]-3-(2-methyl-2H-pyrazol-3-yl)-phenyl]-3-(4-chloro-phenyl)-urea; #105: N-[3-(4-Chloro-2-methyl-2H-pyrazol-3-yl)-4-(2-morpholin-4-yl-ethoxy)-phenyl]-acetamide; #106: 3-Methyl-but-2-enoic acid [3-(4-bromo-2-methyl-2H-pyrazol-3-yl)-4-(2-pyrrolidin-1-yl-ethoxy)-phenyl]-amide; #107: [(1-{2-[4-[3-(4-Chloro-phenyl)-ureido]-2-(2-methyl-2H-pyrazol-3-yl)-phenoxy]-ethyl}-piperidine-4-carbonyl)-amino]-acetic acid methyl ester; #108: N-(1-{2-[4-[3-(4-Chloro-phenyl)-ureido]-2-(2-methyl-2H-pyrazol-3-yl)-phenoxy]-ethyl}-piperidin-4-yl)-malonamic acid methyl ester; #109: [(1-{2-[4-[3-(4-Chloro-phenyl)-ureido]-2-(2-methyl-2H-pyrazol-3-yl)-phenoxy]-ethyl}-piperidine-4-carbonyl)-amino]-acetic acid; #110: N-(1-{2-[4-[3-(4-Chloro-phenyl)-ureido]-2-(2-methyl-2H-pyrazol-3-yl)-phenoxy]-ethyl}-piperidin-4-yl)-malonamic acid; #111: (S)-1-{2-[4-[3-(4-Chloro-phenyl)-ureido]-2-(2-methyl-2H-pyrazol-3-yl)-phenoxy]-ethyl}-piperidine-3-carboxylic acid methyl ester; #112: 1-[3-(2-Methyl-2H-pyrazol-3-yl)-4-(2-morpholin-4-yl-ethoxy)-phenyl]-3-(3-trifluoromethyl-phenyl)-urea; #113: [3-(2-Methyl-2H-pyrazol-3-yl)-4-(2-morpholin-4-yl-ethoxy)-phenyl]-carbamic acid isopropyl ester; #114: (S)-1-{2-[4-[3-(4-Chloro-phenyl)-ureido]-2-(2-methyl-2H-pyrazol-3-yl)-phenoxy]-ethyl}-piperidine-3-carboxylic acid; #115:

1-(3-Chloro-phenyl)-3-[3-(2-methyl-2H-pyrazol-3-yl)-4-(2-morpholin-4-yl-ethoxy)-phenyl]-urea; #116: 1-(3-Fluoro-phenyl)-3-[3-(2-methyl-2H-pyrazol-3-yl)-4-(2-morpholin-4-yl-ethoxy)-phenyl]-urea; #117: 2-(4-Chloro-phenyl)-N-[3-(2-methyl-2H-pyrazol-3-yl)-4-(2-morpholin-4-yl-ethoxy)-phenyl]-acetamide; #118: [((S)-1-{2-[4-[3-(4-Chloro-phenyl)-ureido]-2-(2-methyl-2H-pyrazol-3-yl)-phenoxy]-ethyl}-piperidine-3-carbonyl)-amino]-acetic acid methyl ester; #119: [((S)-1-{2-[4-[3-(4-Chloro-phenyl)-ureido]-2-(2-methyl-2H-pyrazol-3-yl)-phenoxy]-ethyl}-piperidine-3-carbonyl)-amino]-acetic acid; #120: 1-(4-Chloro-phenyl)-3-[4-[2-(4-hydroxy-piperidin-1-yl)-ethoxy]-3-(2-methyl-2H-pyrazol-3-yl)-phenyl]-urea; #121: 1-(2-{2-(2-Methyl-2H-pyrazol-3-yl)-4-[(pyridine-3-carbonyl)-amino]-phenoxy}-ethyl)-piperidine-4-carboxylic acid ethyl ester; #122: 1-{2-[4-(3-Methyl-butyrylamino)-2-(2-methyl-2H-pyrazol-3-yl)-phenoxy]-ethyl}-piperidine-4-carboxylic acid ethyl ester; #123: 1-{2-[4-Butyrylamino-2-(2-methyl-2H-pyrazol-3-yl)-phenoxy]-ethyl}-piperidine-4-carboxylic acid ethyl ester; #124: 1-{2-[2-(2-Methyl-2H-pyrazol-3-yl)-4-pentanoylamino-phenoxy]-ethyl}-piperidine-4-carboxylic acid ethyl ester; #125: 1-{2-[4-[3-(2,4-Difluoro-phenyl)-ureido]-2-(2-methyl-2H-pyrazol-3-yl)-phenoxy]-ethyl}-pyrrolidine-2-carboxylic acid methyl ester; #126: 1-{2-[4-[3-(2,4-Difluoro-phenyl)-ureido]-2-(2-methyl-2H-pyrazol-3-yl)-phenoxy]-ethyl}-piperidine-2-carboxylic acid ethyl ester; #127: 4-[4-[3-(2,2-Difluoro-benzo[1,3]dioxol-5-yl)-ureido]-2-(2-methyl-2H-pyrazol-3-yl)-phenoxymethyl]-piperidine-1-carboxylic acid tert-butyl ester; #128: 1-(4-Chloro-phenyl)-3-[4-[2-(4-methyl-piperazin-1-yl)-ethoxy]-3-(2-methyl-2H-pyrazol-3-yl)-phenyl]-urea; #129: 1-(2,4-Difluoro-phenyl)-3-[4-[2-(4-methyl-piperazin-1-yl)-ethoxy]-3-(2-methyl-2H-pyrazol-3-yl)-phenyl]-urea; #130: 1-(4-Fluoro-phenyl)-3-[4-[2-(4-methyl-piperazin-1-yl)-ethoxy]-3-(2-methyl-2H-pyrazol-3-yl)-phenyl]-urea; #131: 1-(4-Chloro-benzyl)-3-[4-[2-(4-methyl-piperazin-1-yl)-ethoxy]-3-(2-methyl-2H-pyrazol-3-yl)-phenyl]-urea; #132: 1-(2,4-Difluoro-phenyl)-3-[3-(2-methyl-2H-pyrazol-3-yl)-4-(2-thiomorpholin-4-yl-ethoxy)-phenyl]-urea; #133: 1-(4-Chloro-phenyl)-3-[3-(2-methyl-2H-pyrazol-3-yl)-4-(2-thiomorpholin-4-yl-ethoxy)-phenyl]-urea; #134: 1-(2-{2-(2-Methyl-2H-pyrazol-3-yl)-4-[(6-trifluoromethyl-pyridine-3-carbonyl)-amino]-phenoxy}-ethyl)-piperidine-4-carboxylic acid ethyl ester; #135: Succinic acid 1-{2-[4-[3-(4-chloro-phenyl)-ureido]-2-(2-methyl-2H-pyrazol-3-yl)-phenoxy]-ethyl}-piperidin-4-yl ester methyl ester; #136: Hexanoic acid 1-{2-[4-[3-(4-chloro-phenyl)-ureido]-2-(2-methyl-2H-pyrazol-3-yl)-phenoxy]-ethyl}-piperidin-4-yl ester; #137: 1-(2,4-Difluoro-phenyl)-3-[3-(4-fluoro-2-methyl-2H-pyrazol-3-yl)-4-(2-morpholin-4-yl-ethoxy)-phenyl]-urea; #138: (1-{2-[4-[3-(4-Chloro-phenyl)-ureido]-2-(2-methyl-2H-pyrazol-3-yl)-phenoxy]-ethyl}-piperidin-4-yl)-acetic acid ethyl ester; #139: 1-(2,2-Difluoro-benzo[1,3]dioxol-5-yl)-3-[3-(2-methyl-2H-pyrazol-3-yl)-4-(piperidin-4-ylmethoxy)-phenyl]-urea; #140: 1-(2,4-Difluoro-phenyl)-3-[4-[2-(4-methoxy-piperidin-1-yl)-ethoxy]-3-(2-methyl-2H-pyrazol-3-yl)-phenyl]-urea; #141: 1-(4-Chloro-phenyl)-3-[4-[2-(4-methoxy-piperidin-1-yl)-ethoxy]-3-(2-methyl-2H-pyrazol-3-yl)-phenyl]-urea; #142: (1-{2-[4-[3-(4-Chloro-phenyl)-ureido]-2-(2-methyl-2H-pyrazol-3-yl)-phenoxy]-ethyl}-piperidin-4-yl)-acetic acid; #143: 1-(4-Chloro-phenyl)-3-[4-[2-(3-hydroxy-azetidin-1-yl)-ethoxy]-3-(2-methyl-2H-pyrazol-3-yl)-phenyl]-urea; #144: N-[3-(4-Bromo-2-methyl-2H-pyrazol-3-yl)-4-(2-morpholin-4-yl-ethoxy)-phenyl]-3-methyl-butyramide; #145: 1-[3-(4-Bromo-2-methyl-2H-pyrazol-3-yl)-4-(2-pyridin-4-yl-ethoxy)-phenyl]-3-(4-chloro-phenyl)-urea; #146: 1-[3-(4-Bromo-2-methyl-2H-pyrazol-3-yl)-4-(2-piperidin-4-yl-ethoxy)-phenyl]-3-(4-chloro-phenyl)-urea; #147: [3-(4-Chloro-2-methyl-2H-pyrazol-3-yl)-4-(2-morpholin-4-yl-ethoxy)-phenyl]-carbamic acid isobutyl ester; #148: Succinic acid (S)-1-{2-[4-[3-(4-chloro-phenyl)-ureido]-2-(2-methyl-2H-pyrazol-3-yl)-phenoxy]-ethyl}-piperidin-3-yl ester methyl ester; #149: 1-(2,4-Difluoro-phenyl)-3-[4-[2-(3-hydroxy-azetidin-1-yl)-ethoxy]-3-(2-methyl-2H-pyrazol-3-yl)-phenyl]-urea; #150: N-[3-(4-Chloro-2-methyl-2H-pyrazol-3-yl)-4-(2-morpholin-4-yl-ethoxy)-phenyl]-3-methyl-butyramide; #151: 3-(1-{2-[4-[3-(4-Chloro-phenyl)-ureido]-2-(2-methyl-2H-pyrazol-3-yl)-phenoxy]-ethyl}-piperidin-4-yl)-propionic acid methyl ester; #152: 1-(2,4-Difluoro-phenyl)-3-[3-(2-methyl-2H-pyrazol-3-yl)-4-(3-morpholin-4-yl-propoxy)-phenyl]-urea; #153: 1-(4-Chloro-phenyl)-3-[3-(2-methyl-2H-pyrazol-3-yl)-4-(3-morpholin-4-yl-propoxy)-phenyl]-urea; #154: [3-(2-Methyl-2H-pyrazol-3-yl)-4-(3-morpholin-4-yl-propoxy)-phenyl]-carbamic acid isopropyl ester; #155: [3-(2-Methyl-2H-pyrazol-3-yl)-4-(3-morpholin-4-yl-propoxy)-phenyl]-carbamic acid isobutyl ester; #156: 1-(4-Chloro-phenyl)-3-[4-[2-(3-hydroxy-pyrrolidin-1-yl)-ethoxy]-3-(2-methyl-2H-pyrazol-3-yl)-phenyl]-urea; #157: (1-{2-[4-[3-(4-Chloro-phenyl)-ureido]-2-(2-methyl-2H-pyrazol-3-yl)-phenoxy]-ethyl}-piperidin-3-yl)-acetic acid ethyl ester; #158: 4-{2-[4-[3-(4-Chloro-phenyl)-ureido]-2-(2-methyl-2H-pyrazol-3-yl)-phenoxy]-ethyl}-piperazine-1-carboxylic acid tert-butyl ester; #159: 1-(4-Chloro-phenyl)-3-[4-[2-((S)-3-methoxy-piperidin-1-yl)-ethoxy]-3-(2-methyl-2H-pyrazol-3-yl)-phenyl]-urea; #160: 2-(4-Fluoro-phenyl)-N-[3-(2-methyl-2H-pyrazol-3-yl)-4-(2-morpholin-4-yl-ethoxy)-phenyl]-acetamide; #161: 2-(4-Methoxy-phenyl)-N-[3-(2-methyl-2H-pyrazol-3-yl)-4-(2-morpholin-4-yl-ethoxy)-phenyl]-acetamide; #162: 1-(2,4-Difluoro-phenyl)-3-[4-[2-(4-methyl-piperidin-1-yl)-ethoxy]-3-(2-methyl-2H-pyrazol-3-yl)-phenyl]-urea; #163: 1-(2,4-Difluoro-phenyl)-3-[4-[2-(3-methyl-piperidin-1-yl)-ethoxy]-3-(2-methyl-2H-pyrazol-3-yl)-phenyl]-urea; #164: 1-(4-Chloro-phenyl)-3-[4-[2-((R)-3-methoxy-piperidin-1-yl)-ethoxy]-3-(2-methyl-2H-pyrazol-3-yl)-phenyl]-urea; #165: 2-(2,4-Difluoro-phenyl)-N-[3-(2-methyl-2H-pyrazol-3-yl)-4-(2-morpholin-4-yl-ethoxy)-phenyl]-acetamide; #166: N-[4-[2-((2S,6R)-2,6-Dimethyl-morpholin-4-yl)-ethoxy]-3-(2-methyl-2H-pyrazol-3-yl)-phenyl]-acetamide; #167: 1-[4-[2-(4-Acetyl-piperazin-1-yl)-ethoxy]-3-(2-methyl-2H-pyrazol-3-yl)-phenyl]-3-(4-chloro-phenyl)-urea; #168: Pentanoic acid [3-(4-chloro-2-methyl-2H-pyrazol-3-yl)-4-(2-morpholin-4-yl-ethoxy)-phenyl]-amide; #169: 3-Hydroxy-pyridine-2-carboxylic acid [3-(4-chloro-2-methyl-2H-pyrazol-3-yl)-4-(2-morpholin-4-yl-ethoxy)-phenyl]-amide; #170: N-[3-(4-Chloro-2-methyl-2H-pyrazol-3-yl)-4-(2-morpholin-4-yl-ethoxy)-phenyl]-6-trifluoromethyl-nicotinamide; #171: N-[3-(4-Chloro-2-methyl-2H-pyrazol-3-yl)-4-(2-morpholin-4-yl-ethoxy)-phenyl]-6-methyl-nicotinamide; #172: 5-{2-[4-[3-(4-Chloro-phenyl)-ureido]-2-(2-methyl-2H-pyrazol-3-yl)-phenoxy]-ethyl}-2,5-diaza-bicyclo[2.2.1]heptane-2-carboxylic acid tert-butyl ester; #173: 2-[4-[3-(4-Chloro-phenyl)-ureido]-2-(2-methyl-2H-pyrazol-3-yl)-phenoxymethyl]-morpholine-4-carboxylic acid benzyl ester; #174: 1-[3-(2-Methyl-2H-pyrazol-3-yl)-4-(morpholin-2-yl-methoxy)-phenyl]-3-phenyl-urea; #175: (1-{2-[4-[3-(4-Chloro-phenyl)-ureido]-2-(2-methyl-2H-pyrazol-3-yl)-phenoxy]-ethyl}-piperidin-3-yl)-acetic acid; #176: 4-(4-{2-[4-[3-(4-Chloro-phenyl)-ureido]-2-(2-methyl-2H-pyrazol-3-yl)-phenoxy]-ethyl}-piperazin-1-yl)-4-oxo-butyric acid methyl ester; #177: 1-(4-Chloro-phenyl)-3-[4-[2-(2,5-diazabicyclo[2.2.1]hept-2-yl)-ethoxy]-3-(2-methyl-2H-pyrazol-3-yl)-phenyl]-urea; #178: N-[3-(4-Chloro-2-methyl-2H-pyrazol-3-yl)-4-(2-morpholin-4-yl-ethoxy)-phenyl]-6-hydroxy-nicotinamide; #179: Pentanoic acid {3-(4-bromo-2-methyl-2H-pyrazol-3-yl)-4-[2-(4-hydroxy-piperidin-1-yl)-ethoxy]-phenyl}-amide; #180: Pentanoic acid {3-(4-chloro-2-methyl-2H-pyrazol-3-yl)-4-[2-(4-hydroxy-piperidin-1-yl)-ethoxy]-phenyl}-amide; #181: N-{3-(4-Chloro-2-methyl-2H-pyrazol-3-yl)-4-[2-(4-hydroxy-piperidin-1-yl)-ethoxy]-phenyl}-6-methyl-nicotinamide; #182: 1-(2,4-Difluoro-phenyl)-3-[4-[2-((2R,6S)-2,6-dimethyl-morpholin-4-yl)-ethoxy]-3-(2-methyl-2H-pyrazol-3-yl)-phenyl]-urea; #183: 1-[4-[2-((2R,6S)-2,6-Dimethyl-morpholin-4-yl)-ethoxy]-3-(2-methyl-2H-pyrazol-3-yl)-phenyl]-3-(4-fluoro-phenyl)-urea; #184: 1-(4-Chloro-phenyl)-3-[4-[2-((2R,6S)-2,6-dimethyl-morpholin-4-yl)-ethoxy]-3-(2-methyl-2H-pyrazol-3-yl)-phenyl]-urea; #185: 1-{2-[2-(2-Methyl-2H-pyrazol-3-yl)-4-pentanoylamino-phenoxy]-ethyl}-piperidine-4-carboxylic acid; #186: 4-Chloro-N-[3-(4-chloro-2-methyl-2H-pyrazol-3-yl)-4-(2-morpholin-4-yl-ethoxy)-phenyl]-benzamide; #187: 4-(5-{2-[4-[3-(4-Chloro-phenyl)-ureido]-2-(2-methyl-2H-pyrazol-3-yl)-phenoxy]-ethyl}-2,5-diaza-bicyclo[2.2.1]hept-2-yl)-4-oxo-butyric acid methyl ester; #188: 1-(4-Chloro-phenyl)-3-[3-(2-methyl-2H-pyrazol-3-yl)-4-(2-piperazin-1-yl-ethoxy)-phenyl]-urea; #189: 1-[4-[2-((2R,6S)-2,6-Dimethyl-morpholin-4-yl)-ethoxy]-3-(2-methyl-2H-pyrazol-3-yl)-phenyl]-3-(3-fluoro-phenyl)-urea; #190: 2-(4-Chloro-phenyl)-N-[4-[2-((2R,6S)-2,6-dimethyl-morpholin-4-yl)-ethoxy]-3-(2-methyl-2H-pyrazol-3-yl)-phenyl]-acetamide; #191: 4-(4-{2-[4-[3-(4-Chloro-phenyl)-ureido]-2-(2-methyl-2H-pyrazol-3-yl)-phenoxy]-ethyl}-piperazin-1-yl)-4-oxo-butyric acid; #192: 1-(2,4-Difluoro-phenyl)-3-[4-(1-methyl-piperidin-4-yloxy)-3-(2-methyl-2H-pyrazol-3-yl)-phenyl]-urea; #193: [4-[2-((2S,6R)-2,6-Dimethyl-morpholin-4-yl)-ethoxy]-3-(2-methyl-2H-pyrazol-3-yl)-phenyl]-carbamic acid isopropyl ester; #194: [(1-{2-[2-(2-Methyl-2H-pyrazol-3-yl)-4-pentanoylamino-phenoxy]-ethyl}-piperidine-4-carbonyl)-amino]-acetic acid methyl ester; #195: [(1-{2-[2-(2-Methyl-2H-pyrazol-3-yl)-4-pentanoylamino-phenoxy]-ethyl}-piperidine-4-carbonyl)-amino]-acetic acid; #196: (1H-Benzoimidazol-2-yl)-[3-(4-bromo-2-methyl-2H-pyrazol-3-yl)-4-(2-piperidin-1-yl-ethoxy)-phenyl]-amine; #197: 1-{2-[4-(Benzooxazol-2-ylamino)-2-(2-methyl-2H-pyrazol-3-yl)-phenoxy]-ethyl}-piperidine-4-carboxylic acid; #198: Benzothiazol-2-yl-[3-(4-bromo-2-methyl-2H-pyrazol-3-yl)-4-(2-piperidin-1-yl-ethoxy)-phenyl]-amine; #199: Benzooxazol-2-yl-[3-(4-bromo-2-methyl-2H-pyrazol-3-yl)-4-(2-piperidin-1-yl-ethoxy)-phenyl]-amine; #200: [(1-{2-[4-(Benzooxazol-2-ylamino)-2-(2-methyl-2H-pyrazol-3-yl)-phenoxy]-ethyl}-piperidine-4-carbonyl)-amino]-acetic acid methyl ester; #201: 1-{2-[4-(Benzooxazol-2-ylamino)-2-(2-methyl-2H-pyrazol-3-yl)-phenoxy]-ethyl}-piperidine-4-carboxylic acid ethyl ester; #202: [(1-{2-[4-(Benzooxazol-2-ylamino)-2-(2-methyl-2H-pyrazol-3-yl)-phenoxy]-ethyl}-piperidine-4-carbonyl)-amino]-acetic acid; #203: Pentanoic acid [4-[2-(4-hydroxy-piperidin-1-yl)-ethoxy]-3-(2-methyl-2H-pyrazol-3-yl)-phenyl]-amide; #204: 3-(4-{2-[2-(2-Methyl-2H-pyrazol-3-yl)-4-pentanoylamino-phenoxy]-ethyl}-piperazin-1-yl)-propionic acid ethyl ester; #205: 1-(2,4-Difluoro-phenyl)-3-[3-(2-methyl-2H-pyrazol-3-yl)-4-(pyrrolidin-2-ylmethoxy)-phenyl]-urea; #206: (4-{2-[2-(2-Methyl-2H-pyrazol-3-yl)-4-pentanoylamino-phenoxy]-ethyl}-piperazin-1-yl)-acetic acid; #207: 3-(4-{2-[2-(2-Methyl-2H-pyrazol-3-yl)-4-pentanoylamino-phenoxy]-ethyl}-piperazin-1-yl)-propionic acid; #208: N-[4-[2-(4-Hydroxy-piperidin-1-yl)-ethoxy]-3-(2-methyl-2H-pyrazol-3-yl)-phenyl]-6-trifluoromethyl-nicotinamide; #209: (4-{2-[4-[3-(4-Chloro-phenyl)-ureido]-2-(2-methyl-2H-pyrazol-3-yl)-phenoxy]-ethyl}-piperazin-1-yl)-acetic acid methyl ester; #210: 4-(5-{2-[4-[3-(4-Chloro-phenyl)-ureido]-2-(2-methyl-2H-pyrazol-3-yl)-phenoxy]-ethyl}-2,5-diaza-bicyclo[2.2.1]hept-2-yl)-4-oxo-butyric acid; #211: 3-(1-{2-[4-[3-(4-Chloro-phenyl)-ureido]-2-(2-methyl-2H-pyrazol-3-yl)-phenoxy]-ethyl}-piperidin-4-yl)-propionic acid; #212: (4-{2-[4-[3-(4-Chloro-phenyl)-ureido]-2-(2-methyl-2H-pyrazol-3-yl)-phenoxy]-ethyl}-piperazin-1-yl)-acetic acid; #213: Pentanoic acid [4-[2-(3-methanesulfonyl-pyrrolidin-1-yl)-ethoxy]-3-(2-methyl-2H-pyrazol-3-yl)-phenyl]-amide; #214: [3-(2-Methyl-2H-pyrazol-3-yl)-4-(2-thiomorpholin-4-yl-ethoxy)-phenyl]-carbamic acid isopropyl ester; #215: [3-(2-Methyl-2H-pyrazol-3-yl)-4-(2-[1,4]oxazepan-4-yl-ethoxy)-phenyl]-carbamic acid isopropyl ester; #216: 1-(4-Chloro-phenyl)-3-[3-(2-methyl-2H-pyrazol-3-yl)-4-(2-[1,4]oxazepan-4-yl-ethoxy)-phenyl]-urea; #217: 1-(2,4-Difluoro-phenyl)-3-[3-(2-methyl-2H-pyrazol-3-yl)-4-(2-[1,4]oxazepan-4-yl-ethoxy)-phenyl]-urea; #218: 1-(4-Chloro-phenyl)-3-[4-(2-imidazol-1-yl-ethoxy)-3-(2-methyl-2H-pyrazol-3-yl)-phenyl]-urea; #219: 1-(2,4-Difluoro-phenyl)-3-[4-(2-imidazol-1-yl-ethoxy)-3-(2-methyl-2H-pyrazol-3-yl)-phenyl]-urea; #220: 1-(2,4-Difluoro-phenyl)-3-[4-[2-(1,1-dioxo-1λ$^6$-thiomorpholin-4-yl)-ethoxy]-3-(2-methyl-2H-pyrazol-3-yl)-phenyl]-urea; #221: 3-Methyl-N-[3-(2-methyl-2H-pyrazol-3-yl)-4-(2-morpholin-4-yl-ethoxy)-phenyl]-butyramide; #222: N-[4-[2-(3-Methoxy-azetidin-1-yl)-ethoxy]-3-(2-methyl-2H-pyrazol-3-yl)-phenyl]-acetamide; #223: 4-Methyl-pentanoic acid {3-(4-bromo-2-methyl-2H-pyrazol-3-yl)-4-[2-(4-hydroxy-piperidin-1-yl)-ethoxy]-phenyl}-amide; #224: 1-(4-Chloro-phenyl)-3-[4-[2-(3-methoxy-azetidin-1-yl)-ethoxy]-3-(2-methyl-2H-pyrazol-3-yl)-phenyl]-urea; #225: N-{3-(4-Chloro-2-methyl-2H-pyrazol-3-yl)-4-[2-(4,4-difluoro-piperidin-1-yl)-ethoxy]-phenyl}-3-trifluoromethyl-benzamide; #226: N-{3-(4-Chloro-2-methyl-2H-pyrazol-3-yl)-4-[2-(4-phenyl-piperidin-1-yl)-ethoxy]-phenyl}-3-trifluoromethyl-benzamide; #227: 1-(2,4-Difluoro-phenyl)-3-[4-[2-(3-methoxy-azetidin-1-yl)-ethoxy]-3-(2-methyl-2H-pyrazol-3-yl)-phenyl]-urea; #228: 2-(4-Chloro-phenyl)-N-[4-[2-(3-methoxy-azetidin-1-yl)-ethoxy]-3-(2-methyl-2H-pyrazol-3-yl)-phenyl]-acetamide; #229: 1-[3-(4-Chloro-2-methyl-2H-pyrazol-3-yl)-4-(2-morpholin-4-yl-ethoxy)-phenyl]-3-(3-fluoro-phenyl)-urea; #230: 1-[3-(4-Chloro-2-methyl-2H-pyrazol-3-yl)-4-(2-morpholin-4-yl-ethoxy)-phenyl]-3-(2-fluoro-phenyl)-urea; #231: 1-[3-(4-Chloro-2-methyl-2H-pyrazol-3-yl)-4-(2-morpholin-4-yl-ethoxy)-phenyl]-3-(3-chloro-phenyl)-urea; #232: 1-[3-(4-Chloro-2-methyl-2H-pyrazol-3-yl)-4-(2-morpholin-4-yl-ethoxy)-phenyl]-3-phenyl-urea; #233: 1-[3-(4-Chloro-2-methyl-2H-pyrazol-3-yl)-4-(2-morpholin-4-yl-ethoxy)-phenyl]-3-(3,5-difluoro-phenyl)-urea; #234: 1-[3-(4-Chloro-2-methyl-2H-pyrazol-3-yl)-4-(2-morpholin-4-yl-ethoxy)-phenyl]-3-(2,4-dichloro-phenyl)-urea; #235: 1-[3-(4-Chloro-2-methyl-2H-pyrazol-3-yl)-4-(2-morpholin-4-yl-ethoxy)-phenyl]-3-(4-chloro-2-trifluoromethyl-phenyl)-urea; #236: 1-[3-(4-Chloro-2-methyl-2H-pyrazol-3-yl)-4-(2-morpholin-4-yl-ethoxy)-phenyl]-3-p-tolyl-urea; #237: 1-[3-(4-Chloro-2-methyl-2H-pyrazol-3-yl)-4-(2-morpholin-4-yl-ethoxy)-phenyl]-3-(4-methoxy-phenyl)-urea; #238: (1-{2-[2-(2-Methyl-2H-pyrazol-3-yl)-4-pentanoylamino-phenoxy]-ethyl}-piperidin-4-yl)-acetic acid methyl ester; #239: N-{3-(4-Chloro-2-methyl-2H-pyrazol-3-yl)-4-[2-(4-methanesulfonyl-piperazin-1-yl)-ethoxy]-phenyl}-3-trifluoromethyl-benzamide; #240: (1-{2-[2-(2-Methyl-2H- pyrazol-3-yl)-4-pentanoylamino-phenoxy]-ethyl}-piperidin-4-yl)-acetic acid; #241: N-[3-(4-Bromo-2-methyl-2H-pyrazol-3-yl)-4-(2-piperidin-1-yl-ethoxy)-phenyl]-acetamide; #242: N-[3-(4-Chloro-2-methyl-2H-pyrazol-3-yl)-4-(2-piperidin-1-yl-ethoxy)-phenyl]-acetamide; #243: [4-[2-(4-Methyl-piperazin-1-yl)-ethoxy]-3-(2-methyl-2H-pyrazol-3-yl)-phenyl]-carbamic acid isopropyl ester; #244: [4-[2-(4-Methyl-piperazin-1-yl)-ethoxy]-3-(2-methyl-2H-pyrazol-3-yl)-phenyl]-carbamic acid butyl ester; #245: 1-(3-Fluoro-phenyl)-3-[4-(1-methyl-piperidin-4-yloxy)-3-(2-methyl-2H-pyrazol-3-yl)-phenyl]-urea; #246: 1-(2-Fluoro-phenyl)-3-[4-(1-methyl-piperidin-4-yloxy)-3-(2-methyl-2H-pyrazol-3-yl)-phenyl]-urea; #247: 1-(4-Methoxy-phenyl)-3-[4-(1-methyl-piperidin-4-yloxy)-3-(2-methyl-2H-pyrazol-3-yl)-phenyl]-urea; #248: 1-(3-Chloro-phenyl)-3-[4-(1-methyl-piperidin-4-yloxy)-3-(2-methyl-2H-pyrazol-3-yl)-phenyl]-urea; #249: N-[3-(2-Methyl-2H-pyrazol-3-yl)-4-(2-[1,4]oxazepan-4-yl-ethoxy)-phenyl]-acetamide; #250: 1-(4-Chloro-phenyl)-3-[4-[2-(1,1-dioxo-1$\lambda^6$-thiomorpholin-4-yl)-ethoxy]-3-(2-methyl-2H-pyrazol-3-yl)-phenyl]-urea; #251: 1-[4-[2-(1,1-Dioxo-1$\lambda^6$-thiomorpholin-4-yl)-ethoxy]-3-(2-methyl-2H-pyrazol-3-yl)-phenyl]-3-(4-fluoro-phenyl)-urea; #252: 1-[3-(4-Bromo-2-methyl-2H-pyrazol-3-yl)-4-(2-thiomorpholin-4-yl-ethoxy)-phenyl]-3-(4-chloro-phenyl)-urea; #253: 1-[3-(4-Bromo-2-methyl-2H-pyrazol-3-yl)-4-(2-thiomorpholin-4-yl-ethoxy)-phenyl]-3-(2,4-difluoro-phenyl)-urea; #254: 1-{3-(4-Bromo-2-methyl-2H-pyrazol-3-yl)-4-[2-(1,1-dioxo-1$\lambda^6$-thiomorpholin-4-yl)-ethoxy]-phenyl}-3-(4-chloro-phenyl)-urea; #255: 1-{3-(4-Bromo-2-methyl-2H-pyrazol-3-yl)-4-[2-(1,1-dioxo-1$\lambda^6$-thiomorpholin-4-yl)-ethoxy]-phenyl}-3-(2,4-difluoro-phenyl)-urea; #256: 1-[3-(4-Bromo-2-methyl-2H-pyrazol-3-yl)-4-(2-[1,4]oxazepan-4-yl-ethoxy)-phenyl]-3-(4-chloro-phenyl)-urea; #257: 1-[3-(4-Bromo-2-methyl-2H-pyrazol-3-yl)-4-(2-[1,4]oxazepan-4-yl-ethoxy)-phenyl]-3-(2,4-difluoro-phenyl)-urea; #258: 1-[3-(4-Chloro-2-methyl-2H-pyrazol-3-yl)-4-(2-morpholin-4-yl-ethoxy)-phenyl]-3-(3,4-difluoro-phenyl)-urea; #259: 1-[3-(4-Chloro-2-methyl-2H-pyrazol-3-yl)-4-(2-morpholin-4-yl-ethoxy)-phenyl]-3-(3-trifluoromethyl-phenyl)-urea; #260: 1-[3-(4-Chloro-2-methyl-2H-pyrazol-3-yl)-4-(2-morpholin-4-yl-ethoxy)-phenyl]-3-(3-methoxy-phenyl)-urea; #261: 1-(3-Acetyl-phenyl)-3-[3-(4-chloro-2-methyl-2H-pyrazol-3-yl)-4-(2-morpholin-4-yl-ethoxy)-phenyl]-urea; #262: 1-[3-(4-Chloro-2-methyl-2H-pyrazol-3-yl)-4-(2-morpholin-4-yl-ethoxy)-phenyl]-3-(2,5-difluoro-phenyl)-urea; #263: 1-[3-(4-Chloro-2-methyl-2H-pyrazol-3-yl)-4-(2-morpholin-4-yl-ethoxy)-phenyl]-3-(2,6-difluoro-phenyl)-urea; #264: 1-(3,5-Bis-trifluoromethyl-phenyl)-3-[3-(4-chloro-2-methyl-2H-pyrazol-3-yl)-4-(2-morpholin-4-yl-ethoxy)-phenyl]-urea; #265: 1-[3-(4-Chloro-2-methyl-2H-pyrazol-3-yl)-4-(2-morpholin-4-yl-ethoxy)-phenyl]-3-naphthalen-1-yl-urea; #266: N-{3-(4-Bromo-2-methyl-2H-pyrazol-3-yl)-4-[2-(3-methoxy-azetidin-1-yl)-ethoxy]-phenyl}-acetamide; #267: 1-{3-(4-Bromo-2-methyl-2H-pyrazol-3-yl)-4-[2-(3-methoxy-azetidin-1-yl)-ethoxy]-phenyl}-3-(4-chloro-phenyl)-urea; #268: 1-{3-(4-Bromo-2-methyl-2H-pyrazol-3-yl)-4-[2-(3-methoxy-azetidin-1-yl)-ethoxy]-phenyl}-3-(2,4-difluoro-phenyl)-urea; #269: N-{3-(4-Bromo-2-methyl-2H-pyrazol-3-yl)-4-[2-(3-methoxy-azetidin-1-yl)-ethoxy]-phenyl}-2-(4-chloro-phenyl)-acetamide; #270: 1-{3-(4-Bromo-2-methyl-2H-pyrazol-3-yl)-4-[2-(3-methoxy-azetidin-1-yl)-ethoxy]-phenyl}-3-(4-fluoro-phenyl)-urea; #271: Cyclopropanecarboxylic acid [3-(4-chloro-2-methyl-2H-pyrazol-3-yl)-4-(2-morpholin-4-yl-ethoxy)-phenyl]-amide; #272: Thiophene-2-carboxylic acid [3-(4-chloro-2-methyl-2H-pyrazol-3-yl)-4-(2-morpholin-4-yl-ethoxy)-phenyl]-amide; #273: N-[3-(4-Chloro-2-methyl-2H-pyrazol-3-yl)-4-(2-morpholin-4-yl-ethoxy)-phenyl]-4-fluoro-benzamide; #274: N-[3-(4-Chloro-2-methyl-2H-pyrazol-3-yl)-4-(2-morpholin-4-yl-ethoxy)-phenyl]-2-(4-chloro-phenyl)-acetamide; #275: N-[3-(4-Bromo-2-methyl-2H-pyrazol-3-yl)-4-(2-pyrrolidin-1-yl-ethoxy)-phenyl]-3-methyl-butyramide; #276: N-[4-[2-(4-Acetyl-piperazin-1-yl)-ethoxy]-3-(4-bromo-2-methyl-2H-pyrazol-3-yl)-phenyl]-3-methyl-butyramide; #277: N-{3-(4-Bromo-2-methyl-2H-pyrazol-3-yl)-4-[2-(4-hydroxy-piperidin-1-yl)-ethoxy]-phenyl}-3-methyl-butyramide; #278: N-{3-(4-Bromo-2-methyl-2H-pyrazol-3-yl)-4-[2-(3-hydroxy-azetidin-1-yl)-ethoxy]-phenyl}-acetamide; #279: 1-{3-(4-Bromo-2-methyl-2H-pyrazol-3-yl)-4-[2-(3-hydroxy-azetidin-1-yl)-ethoxy]-phenyl}-3-(4-chloro-phenyl)-urea; #280: 4-Fluoro-N-[3-(2-methyl-2H-pyrazol-3-yl)-4-(2-morpholin-4-yl-ethoxy)-phenyl]-benzamide; #281: 2,4-Difluoro-N-[3-(2-methyl-2H-pyrazol-3-yl)-4-(2-morpholin-4-yl-ethoxy)-phenyl]-benzamide; #282: N-[3-(2-Methyl-2H-pyrazol-3-yl)-4-(2-morpholin-4-yl-ethoxy)-phenyl]-4-trifluoromethyl-benzamide; #283: N-[3-(2-Methyl-2H-pyrazol-3-yl)-4-(2-morpholin-4-yl-ethoxy)-phenyl]-4-trifluoromethoxy-benzamide; #284: 1-{3-(4-Bromo-2-methyl-2H-pyrazol-3-yl)-4-[2-(3-hydroxy-azetidin-1-yl)-ethoxy]-phenyl}-3-(2,4-difluoro-phenyl)-urea; #285: 1-{3-(4-Bromo-2-methyl-2H-pyrazol-3-yl)-4-[2-(3-hydroxy-azetidin-1-yl)-ethoxy]-phenyl}-3-(4-fluoro-phenyl)-urea; #286: 1-{3-(4-Bromo-2-methyl-2H-pyrazol-3-yl)-4-[2-(3-hydroxy-azetidin-1-yl)-ethoxy]-phenyl}-3-(2-fluoro-phenyl)-urea; #287: Furan-2-carboxylic acid [3-(4-chloro-2-methyl-2H-pyrazol-3-yl)-4-(2-morpholin-4-yl-ethoxy)-phenyl]-amide; #288: N-[3-(4-Chloro-2-methyl-2H-pyrazol-3-yl)-4-(2-morpholin-4-yl-ethoxy)-phenyl]-2-fluoro-benzamide; #289: N-[3-(4-Chloro-2-methyl-2H-pyrazol-3-yl)-4-(2-morpholin-4-yl-ethoxy)-phenyl]-3-fluoro-benzamide; #290: 1-[4-(1-Methyl-piperidin-4-yloxy)-3-(2-methyl-2H-pyrazol-3-yl)-phenyl]-3-p-tolyl-urea; #291: 1-(3-Cyano-phenyl)-3-[4-(1-methyl-piperidin-4-yloxy)-3-(2-methyl-2H-pyrazol-3-yl)-phenyl]-urea; #292: 1-(2-Fluoro-5-methyl-phenyl)-3-[4-(1-methyl-piperidin-4-yloxy)-3-(2-methyl-2H-pyrazol-3-yl)-phenyl]-urea; #293: N-[4-[2-((2R,6S)-2,6-Dimethyl-piperidin-1-yl)-ethoxy]-3-(2-methyl-2H-pyrazol-3-yl)-phenyl]-acetamide; #294: Cyclopropanecarboxylic acid [3-(2-methyl-2H-pyrazol-3-yl)-4-(2-piperidin-1-yl-ethoxy)-phenyl]-amide; #295: Thiophene-2-carboxylic acid [3-(2-methyl-2H-pyrazol-3-yl)-4-(2-piperidin-1-yl-ethoxy)-phenyl]-amide; #296: Furan-2-carboxylic acid [3-(2-methyl-2H-pyrazol-3-yl)-4-(2-piperidin-1-yl-ethoxy)-phenyl]-amide; #297: 4-Fluoro-N-[3-(2-methyl-2H-pyrazol-3-yl)-4-(2-piperidin-1-yl-ethoxy)-phenyl]-benzamide; #298: 1-{3-(4-Chloro-2-methyl-2H-pyrazol-3-yl)-4-[2-(3-hydroxy-azetidin-1-yl)-ethoxy]-phenyl}-3-(4-chloro-phenyl)-urea; #299: 1-{3-(4-Chloro-2-methyl-2H-pyrazol-3-yl)-4-[2-(3-hydroxy-azetidin-1-yl)-ethoxy]-phenyl}-3-(2,4-difluoro-phenyl)-urea; #300: [1-(2-{2-(2-Methyl-2H-pyrazol-3-yl)-4-[(6-trifluoromethyl-pyridine-3-carbonyl)-amino]-phenoxy}-ethyl)-piperidin-4-yl]-acetic acid methyl ester; #301: [1-(2-{2-(2-Methyl-2H-pyrazol-3-yl)-4-[(6-trifluoromethyl-pyridine-3-carbonyl)-amino]-phenoxy}-ethyl)-piperidin-4-yl]-acetic acid; #302: 3-Fluoro-N-[3-(2-methyl-2H-pyrazol-3-yl)-4-(2-piperidin-1-yl-ethoxy)-phenyl]-benzamide; #303: 2-Fluoro-N-[3-(2-methyl-2H-pyrazol-3-yl)-4-(2-piperidin-1-yl-ethoxy)-phenyl]-benzamide; #304: 1-(2,4-Difluoro-phenyl)-3-[3-(2-methyl-2H-pyrazol-3-yl)-4-(2-piperidin-1-yl-ethoxy)-phenyl]-urea; #305: [3-(4-Chloro-2-methyl-2H-pyrazol-3-yl)-4-(2-morpholin-4-yl-ethoxy)-phenyl]-(4-chlorophenyl)-amine; #306: N-[3-(4-Bromo-2-methyl-2H-pyrazol-3-yl)-4-(2-morpholin-4-yl-ethoxy)-phenyl]-2-cyclopropyl-acetamide; #307: N-[3-(4-Bromo-2-methyl-2H-pyrazol-3-yl)-4-(2-morpholin-4-yl-ethoxy)-phenyl]-2-cyclopentyl-acetamide; #308: Cyclopropanecarboxylic acid [3-(4-bromo-2-methyl-2H-pyrazol-3-yl)-4-(2-morpholin-4-yl-ethoxy)-phenyl]-amide; #309: Cyclobutanecarboxylic acid [3-(4-bromo-2-methyl-2H-pyrazol-3-yl)-4-(2-morpholin-4-yl-ethoxy)-phenyl]-amide; #310: Cyclopentanecarboxylic acid [3-(4-bromo-2-methyl-2H-pyrazol-3-yl)-4-(2-morpholin-4-yl-ethoxy)-phenyl]-amide; #311: 1-(4-Chloro-phenyl)-3-[3-(2-methyl-2H-pyrazol-3-yl)-4-(2-morpholin-4-yl-ethylamino)-phenyl]-urea; #312: 1-(2,4-Difluoro-phenyl)-3-[3-(2-methyl-2H-pyrazol-3-yl)-4-(2-morpholin-4-yl-ethylamino)-phenyl]-urea; #313: 2-(4-Chloro-phenyl)-2,2-difluoro-N-[3-(2-methyl-2H-pyrazol-3-yl)-4-(2-morpholin-4-yl-ethoxy)-phenyl]-acetamide; #314: 1-[3-(4-Chloro-2-methyl-2H-pyrazol-3-yl)-4-(2-piperidin-1-yl-ethoxy)-phenyl]-3-(4-fluoro-phenyl)-urea; #315: 1-[3-(4-Chloro-2-methyl-2H-pyrazol-3-yl)-4-(2-piperidin-1-yl-ethoxy)-phenyl]-3-(4-methoxy-phenyl)-urea; #316: 1-(4-Bromo-phenyl)-3-[4-(1-methyl-piperidin-4-yloxy)-3-(2-methyl-2H-pyrazol-3-yl)-phenyl]-urea; #317: 1-[4-(1-Methyl-piperidin-4-yloxy)-3-(2-methyl-2H-pyrazol-3-yl)-phenyl]-3-(2-trifluoromethoxy-phenyl)-urea; #318: 1-[4-(1-Methyl-piperidin-4-yloxy)-3-(2-methyl-2H-pyrazol-3-yl)-phenyl]-3-(4-trifluoromethyl-phenyl)-urea; #319: 1-(4-Chloro-phenyl)-3-[4-[2-((2S,6R)-2,6-dimethyl-piperidin-1-yl)-ethoxy]-3-(2-methyl-2H-pyrazol-3-yl)-phenyl]-urea; #320: 1-(2,4-Difluoro-phenyl)-3-[4-[2-((2S,6R)-2,6-dimethyl-piperidin-1-yl)-ethoxy]-3-(2-methyl-2H-pyrazol-3-yl)-phenyl]-urea; #321: 1-[4-[2-((2S,6R)-2,6-Dimethyl-piperidin-1-yl)-ethoxy]-3-(2-methyl-2H-pyrazol-3-yl)-phenyl]-3-(4-fluoro-phenyl)-urea; #322: 4-(2-{2-(4-Bromo-2-methyl-2H-pyrazol-3-yl)-4-[3-(4-chloro-phenyl)-ureido]-phenoxy}-ethyl)-piperidine-1-carboxylic acid tert-butyl ester; #323: 4-{2-(4-Bromo-2-methyl-2H-pyrazol-3-yl)-4-[3-(4-chloro-phenyl)-ureido]-phenoxymethyl}-piperidine-1-carboxylic acid tert-butyl ester; #324: 1-[4-[2-((2R,6S)-2,6-Dimethyl-piperidin-1-yl)-ethoxy]-3-(2-methyl-2H-pyrazol-3-yl)-phenyl]-3-(4-methoxy-phenyl)-urea; #325: 2-(4-Chloro-phenyl)-N-[4-[2-((2S,6R)-2,6-dimethyl-piperidin-1-yl)-ethoxy]-3-(2-methyl-2H-pyrazol-3-yl)-phenyl]-acetamide; #326: N-{3-(4-Bromo-2-methyl-2H-pyrazol-3-yl)-4-[2-(3-methoxy-azetidin-1-yl)-ethoxy]-phenyl}-3-methyl-butyramide; #327: Thiophene-2-carboxylic acid [3-(2-methyl-2H-pyrazol-3-yl)-4-(2-[1,4]oxazepan-4-yl-ethoxy)-phenyl]-amide; #328: 2-(4-Chloro-phenyl)-2,2-difluoro-N-[3-(2-methyl-2H-pyrazol-3-yl)-4-(2-[1,4]oxazepan-4-yl-ethoxy)-phenyl]-acetamide; #329: 1-(4-Chloro-phenyl)-3-{3-(2-methyl-2H-pyrazol-3-yl)-4-[2-(1-methyl-pyrrolidin-2-yl)-ethoxy]-phenyl}-urea; #330: 3-Methyl-N-{3-(2-methyl-2H-pyrazol-3-yl)-4-[2-(1-methyl-pyrrolidin-2-yl)-ethoxy]-phenyl}-butyramide; #331: (R)-2-{2-[4-[3-(4-Chloro-phenyl)-ureido]-2-(2-methyl-2H-pyrazol-3-yl)-phenoxy]-ethyl}-piperidine-1-carboxylic acid tert-butyl ester; #332: 4-{2-(2-Methyl-2H-pyrazol-3-yl)-4-[(thiophene-2-carbonyl)-amino]-phenoxymethyl}-piperidine-1-carboxylic acid tert-butyl ester; #333: 5-Chloro-thiophene-2-carboxylic acid [3-(4-chloro-2-methyl-2H-pyrazol-3-yl)-4-(2-morpholin-4-yl-ethoxy)-phenyl]-amide; #334: 1-[4-(1-Acetyl-piperidin-4-ylmethoxy)-3-(4-bromo-2-methyl-2H-pyrazol-3-yl)-phenyl]-3-(4-chloro-phenyl)-urea; #335: 1-[3-(4-Bromo-2-methyl-2H-pyrazol-3-yl)-4-(1-methyl-piperidin-4-ylmethoxy)-phenyl]-3-(4-chloro-phenyl)-urea; #336: Thiophene-2-carboxylic acid [3-(2-methyl-2H-pyrazol-3-yl)-4-(2-pyrrolidin-1-yl-ethoxy)-phenyl]-amide; #337: Thiophene-2-carboxylic acid [4-[2-(4-methoxy-piperidin-1-yl)-ethoxy]-3-(2-methyl-2H-pyrazol-3-yl)-phenyl]-amide; #338: Thiophene-2-carboxylic acid [3-(2-methyl-2H-pyrazol-3-yl)-4-(2-morpholin-4-yl-ethoxy)-phenyl]-amide; #339: 1-(4-Chloro-phenyl)-3-[3-(2-methyl-2H-pyrazol-3-yl)-4-((R)-2-piperidin-2-yl-ethoxy)-phenyl]-urea; #340: 1-(4-Chloro-phenyl)-3-[4-(1,1-dimethyl-2-oxo-2-pyrrolidin-1-yl-ethoxy)-3-(2-methyl-2H-pyrazol-3-yl)-phenyl]-urea; #341: N-{3-(4-Bromo-2-methyl-2H-pyrazol-3-yl)-4-[2-(3-hydroxy-azetidin-1-yl)-ethoxy]-phenyl}-2-(4-chloro-phenyl)-acetamide; #342: N-[3-(4-Chloro-2-methyl-2H-pyrazol-3-yl)-4-(2-pyrrolidin-1-yl-ethoxy)-phenyl]-2-(4-chloro-phenyl)-2,2-difluoro-acetamide; #343: N-[3-(2-Methyl-2H-pyrazol-3-yl)-4-(2-pyrrolidin-1-yl-ethoxy)-phenyl]-4-trifluoromethyl-benzamide; #344: Thiophene-2-carboxylic acid [3-(2-methyl-2H-pyrazol-3-yl)-4-(piperidin-4-ylmethoxy)-phenyl]-amide; #345: Thiophene-2-carboxylic acid [3-(4-chloro-2-methyl-2H-pyrazol-3-yl)-4-(2-pyrrolidin-1-yl-ethoxy)-phenyl]-amide; #346: 1-[3-(4-Chloro-2-methyl-2H-pyrazol-3-yl)-4-(2-pyrrolidin-1-yl-ethoxy)-phenyl]-3-(2,5-difluoro-phenyl)-urea; #347: Thiophene-2-carboxylic acid [3-(2-methyl-2H-pyrazol-3-yl)-4-(3-morpholin-4-yl-propoxy)-phenyl]-amide; #348: Thiophene-2-carboxylic acid [3-(4-chloro-2-methyl-2H-pyrazol-3-yl)-4-(2-piperidin-1-yl-ethoxy)-phenyl]-amide; #349: (R)-4-Benzyloxy-2-{2-[4-[3-(4-fluoro-phenyl)-ureido]-2-(2-methyl-2H-pyrazol-3-yl)-phenoxy]-ethyl}-pyrrolidine-1-carboxylic acid ethyl ester; #350: 1-[4-(2-Azepan-1-yl-ethoxy)-3-(4-bromo-2-methyl-2H-pyrazol-3-yl)-phenyl]-3-(4-chloro-phenyl)-urea; #351: 1-[4-(2-Azepan-1-yl-ethoxy)-3-(4-bromo-2-methyl-2H-pyrazol-3-yl)-phenyl]-3-(2,4-difluoro-phenyl)-urea; #352: [4-(2-Azepan-1-yl-ethoxy)-3-(4-bromo-2-methyl-2H-pyrazol-3-yl)-phenyl]-carbamic acid isopropyl ester; #353: 1-(4-Chloro-phenyl)-3-[4-[2-((R)-1-methyl-piperidin-2-yl)-ethoxy]-3-(2-methyl-2H-pyrazol-3-yl)-phenyl]-urea; #354: N-{3-(4-Bromo-2-methyl-2H-pyrazol-3-yl)-4-[2-(3-methoxy-azetidin-1-yl)-ethoxy]-phenyl}-2-(4-chloro-phenyl)-2,2-difluoro-acetamide; #355: 1-(4-Chloro-phenyl)-3-[3-(2-methyl-2H-pyrazol-3-yl)-4-(2-morpholin-4-yl-propoxy)-phenyl]-urea; #356: 1-(4-Chloro-2-fluoro-phenyl)-3-[3-(4-chloro-2-methyl-2H-pyrazol-3-yl)-4-(2-pyrrolidin-1-yl-ethoxy)-phenyl]-urea; #357: Thiophene-2-carboxylic acid [4-(1-methyl-piperidin-4-ylmethoxy)-3-(2-methyl-2H-pyrazol-3-yl)-phenyl]-amide; #358: 1-(2,4-Difluoro-phenyl)-3-[3-(2-methyl-2H-pyrazol-3-yl)-4-(2-morpholin-4-yl-propoxy)-phenyl]-urea; #359: 1-(4-Fluoro-phenyl)-3-[3-(2-methyl-2H-pyrazol-3-yl)-4-(2-morpholin-4-yl-propoxy)-phenyl]-urea; #360: N-[3-(4-Bromo-2-methyl-2H-pyrazol-3-yl)-4-(2-pyrrolidin-1-yl-ethoxy)-phenyl]-4-fluoro-benzamide; #361: N-[3-(4-Bromo-2-methyl-2H-pyrazol-3-yl)-4-(2-pyrrolidin-1-yl-ethoxy)-phenyl]-2-(4-chloro-phenyl)-acetamide; #362: N-[3-(4-Bromo-2-methyl-2H-pyrazol-3-yl)-4-(2-pyrrolidin-1-yl-ethoxy)-phenyl]-2-cyclopentyl-acetamide; #363: 1-(4-Chloro-phenyl)-3-[4-(1-methyl-piperidin-4-ylmethoxy)-3-(2-methyl-2H-pyrazol-3-yl)-phenyl]-urea; #364: (R)-3-[4-[2-(4-Chloro-phenyl)-2-hydroxy-acetylamino]-2-(2-methyl-2H-pyrazol-3-yl)-phenoxy]-pyrrolidine-1-carboxylic acid tert-butyl ester; #365: (R)-3-[4-[3-(4-Fluoro-phenyl)-ureido]-2-(2-methyl-2H-pyrazol-3-yl)-phenoxy]-pyrrolidine-1-carboxylic acid tert-butyl ester; #366: (R)-3-[2-(2-Methyl-2H-pyrazol-3-yl)-4-(4-trifluoromethyl-benzoylamino)-phenoxy]-pyrrolidine-1-carboxylic acid tert-butyl ester; #367: 2-(4-Chloro-phenyl)-N-[3-(2-methyl-2H-pyrazol-3-yl)-4-(2-morpholin-4-yl-propoxy)-phenyl]-acetamide; #368: 2-(4-Chloro-phenyl)-2,2-difluoro-N-[3-

(2-methyl-2H-pyrazol-3-yl)-4-(2-morpholin-4-yl-propoxy)-phenyl]-acetamide; #369: 2-(4-Chloro-phenyl)-N-[4-(1-methyl-piperidin-4-ylmethoxy)-3-(2-methyl-2H-pyrazol-3-yl)-phenyl]-acetamide; #370: 1-(4-Chloro-phenyl)-3-[4-(1-methyl-2-morpholin-4-yl-ethoxy)-3-(2-methyl-2H-pyrazol-3-yl)-phenyl]-urea; #371: 2-(4-Chloro-phenyl)-2-hydroxy-N-[3-(2-methyl-2H-pyrazol-3-yl)-4-((R)-pyrrolidin-3-yloxy)-phenyl]-acetamide; #372: 1-(4-Fluoro-phenyl)-3-[3-(2-methyl-2H-pyrazol-3-yl)-4-((R)-pyrrolidin-3-yloxy)-phenyl]-urea; #373: N-[3-(2-Methyl-2H-pyrazol-3-yl)-4-((R)-pyrrolidin-3-yloxy)-phenyl]-4-trifluoromethyl-benzamide; #374: 4-[4-Acetylamino-2-(4-bromo-2-methyl-2H-pyrazol-3-yl)-phenoxymethyl]-piperidine-1-carboxylic acid tert-butyl ester; #375: 1-(2,4-Difluoro-phenyl)-3-[4-(1-methyl-2-morpholin-4-yl-ethoxy)-3-(2-methyl-2H-pyrazol-3-yl)-phenyl]-urea; #376: 2-(4-Chloro-phenyl)-N-[4-(1-methyl-2-morpholin-4-yl-ethoxy)-3-(2-methyl-2H-pyrazol-3-yl)-phenyl]-acetamide; #377: N-[3-(4-Chloro-2-methyl-2H-pyrazol-3-yl)-4-(2-pyrrolidin-1-yl-ethoxy)-phenyl]-2-(4-chloro-phenyl)-acetamide; #378: 1-[3-(4-Bromo-2-methyl-2H-pyrazol-3-yl)-4-(piperidin-3-yloxy)-phenyl]-3-(4-chloro-phenyl)-urea; #379: 1-[3-(4-Chloro-2-methyl-2H-pyrazol-3-yl)-4-(2-pyrrolidin-1-yl-ethoxy)-phenyl]-3-(2,3-difluoro-phenyl)-urea; #380: Thiophene-2-carboxylic acid [3-(4-bromo-2-methyl-2H-pyrazol-3-yl)-4-(piperidin-4-yl-methoxy)-phenyl]-amide; #381: N-[3-(4-Bromo-2-methyl-2H-pyrazol-3-yl)-4-(piperidin-4-ylmethoxy)-phenyl]-2-(4-chloro-phenyl)-acetamide; #382: Thiophene-2-carboxylic acid [3-(4-bromo-2-methyl-2H-pyrazol-3-yl)-4-(1-methyl-piperidin-4-ylmethoxy)-phenyl]-amide; #383: N-[3-(4-Bromo-2-methyl-2H-pyrazol-3-yl)-4-(1-methyl-piperidin-4-ylmethoxy)-phenyl]-2-(4-chloro-phenyl)-acetamide; #384: 1-[3-(4-Chloro-2-methyl-2H-pyrazol-3-yl)-4-(2-pyrrolidin-1-yl-ethoxy)-phenyl]-3-(2,4,5-trifluoro-phenyl)-urea; #385: 1-[3-(4-Chloro-2-methyl-2H-pyrazol-3-yl)-4-(2-pyrrolidin-1-yl-ethoxy)-phenyl]-3-(2,3,4-trifluoro-phenyl)-urea; #386: N-[3-(4-Bromo-2-methyl-2H-pyrazol-3-yl)-4-((R)-pyrrolidin-3-yloxy)-phenyl]-4-trifluoromethyl-benzamide; #387: N-[3-(4-Bromo-2-methyl-2H-pyrazol-3-yl)-4-((R)-pyrrolidin-3-yloxy)-phenyl]-4-chloro-benzamide; #388: N-[3-(4-Bromo-2-methyl-2H-pyrazol-3-yl)-4-((R)-pyrrolidin-3-yloxy)-phenyl]-4-fluoro-benzamide; #389: N-[3-(4-Bromo-2-methyl-2H-pyrazol-3-yl)-4-((R)-pyrrolidin-3-yloxy)-phenyl]-2,4-difluoro-benzamide; #390: 4-Chloro-N-[3-(4-chloro-2-methyl-2H-pyrazol-3-yl)-4-(2-pyrrolidin-1-yl-ethoxy)-phenyl]-benzamide; #391: 1-[3-(4-Bromo-2-methyl-2H-pyrazol-3-yl)-4-((R)-pyrrolidin-3-yloxy)-phenyl]-3-(4-chloro-phenyl)-urea; #392: 1-[3-(4-Bromo-2-methyl-2H-pyrazol-3-yl)-4-((R)-pyrrolidin-3-yloxy)-phenyl]-3-(2,4-difluoro-phenyl)-urea; #393: 1-(4-Chloro-phenyl)-3-[3-(2-methyl-2H-pyrazol-3-yl)-4-(piperidin-3-yloxy)-phenyl]-urea; #394: 1-[3-(4-Bromo-2-methyl-2H-pyrazol-3-yl)-4-(piperidin-3-yloxy)-phenyl]-3-(4-fluoro-phenyl)-urea; #395: N-[3-(4-Bromo-2-methyl-2H-pyrazol-3-yl)-4-(piperidin-3-yloxy)-phenyl]-4-chloro-benzamide; #396: N-[3-(4-Bromo-2-methyl-2H-pyrazol-3-yl)-4-(piperidin-3-yloxy)-phenyl]-4-fluoro-benzamide; #397: N-[3-(4-Bromo-2-methyl-2H-pyrazol-3-yl)-4-(piperidin-3-yloxy)-phenyl]-2,4-difluoro-benzamide; #398: N-[3-(4-Bromo-2-methyl-2H-pyrazol-3-yl)-4-(piperidin-3-yloxy)-phenyl]-2-(4-fluoro-phenyl)-2-hydroxy-acetamide; #399: 4-Fluoro-N-[3-(4-fluoro-2-methyl-2H-pyrazol-3-yl)-4-(2-morpholin-4-yl-ethoxy)-phenyl]-benzamide; #400: 2-(4-Chloro-phenyl)-N-[3-(4-fluoro-2-methyl-2H-pyrazol-3-yl)-4-(2-morpholin-4-yl-ethoxy)-phenyl]-acetamide; #401: 1-(4-Chloro-phenyl)-3-[4-(1,1-dimethyl-2-pyrrolidin-1-yl-ethoxy)-3-(2-methyl-2H-pyrazol-3-yl)-phenyl]-urea; #402: N-[3-(2-Methyl-2H-pyrazol-3-yl)-4-(piperidin-3-yloxy)-phenyl]-4-trifluoromethyl-benzamide; #403: 1-[4-(1,1-Dimethyl-2-pyrrolidin-1-yl-ethoxy)-3-(2-methyl-2H-pyrazol-3-yl)-phenyl]-3-(4-fluoro-phenyl)-urea; #404: 2-(4-Chloro-phenyl)-N-[4-(1,1-dimethyl-2-pyrrolidin-1-yl-ethoxy)-3-(2-methyl-2H-pyrazol-3-yl)-phenyl]-acetamide; #405: 1-[4-[2-(7-Aza-bicyclo[2.2.1]hept-7-yl)-ethoxy]-3-(2-methyl-2H-pyrazol-3-yl)-phenyl]-3-(4-chloro-phenyl)-urea; #406: 1-[4-[2-(7-Aza-bicyclo[2.2.1]hept-7-yl)-ethoxy]-3-(2-methyl-2H-pyrazol-3-yl)-phenyl]-3-(4-fluoro-phenyl)-urea; #407: 1-(2,4-Difluoro-phenyl)-3-[4-(1,1-dimethyl-2-pyrrolidin-1-yl-ethoxy)-3-(2-methyl-2H-pyrazol-3-yl)-phenyl]-urea; #408: 3,4-Difluoro-N-[3-(2-methyl-2H-pyrazol-3-yl)-4-(2-piperidin-1-yl-ethoxy)-phenyl]-benzamide; #409: 2,4-Dichloro-N-[3-(2-methyl-2H-pyrazol-3-yl)-4-(2-piperidin-1-yl-ethoxy)-phenyl]-benzamide; #410: 3,4-Dichloro-N-[3-(2-methyl-2H-pyrazol-3-yl)-4-(2-piperidin-1-yl-ethoxy)-phenyl]-benzamide; #411: 3-Fluoro-N-[3-(2-methyl-2H-pyrazol-3-yl)-4-(2-piperidin-1-yl-ethoxy)-phenyl]-4-trifluoromethyl-benzamide; #412: 5-Fluoro-N-[3-(2-methyl-2H-pyrazol-3-yl)-4-(2-piperidin-1-yl-ethoxy)-phenyl]-2-trifluoromethyl-benzamide; #413: 3,5-Difluoro-N-[3-(2-methyl-2H-pyrazol-3-yl)-4-(2-piperidin-1-yl-ethoxy)-phenyl]-benzamide; #414: N-[3-(2-Methyl-2H-pyrazol-3-yl)-4-(2-piperidin-1-yl-ethoxy)-phenyl]-4-trifluoromethyl-benzamide; #415: 2-(4-Chloro-phenyl)-N-[3-(2-methyl-2H-pyrazol-3-yl)-4-(2-piperidin-1-yl-ethoxy)-phenyl]-isobutyramide; #416: 1-(4-Chloro-phenyl)-cyclopropanecarboxylic acid [3-(2-methyl-2H-pyrazol-3-yl)-4-(2-piperidin-1-yl-ethoxy)-phenyl]-amide; #417: N-[3-(4-Bromo-2-methyl-2H-pyrazol-3-yl)-4-(2-pyrrolidin-1-yl-ethoxy)-phenyl]-2-(4-chloro-phenyl)-isobutyramide; #418: 1-(4-Chloro-phenyl)-cyclopropanecarboxylic acid [3-(4-bromo-2-methyl-2H-pyrazol-3-yl)-4-(2-pyrrolidin-1-yl-ethoxy)-phenyl]-amide; #419: N-[3-(4-Bromo-2-methyl-2H-pyrazol-3-yl)-4-(2-pyrrolidin-1-yl-ethoxy)-phenyl]-2-(4-chloro-phenyl)-2-hydroxy-acetamide; #420: 1-[4-((R)-1-Benzyl-pyrrolidin-3-yloxy)-3-(2-methyl-2H-pyrazol-3-yl)-phenyl]-3-(4-chloro-phenyl)-urea; #421: 1-(4-Chloro-phenyl)-3-[4-[2-((S)-3-fluoro-pyrrolidin-1-yl)-ethoxy]-3-(2-methyl-2H-pyrazol-3-yl)-phenyl]-urea; #422: 1-(4-Chloro-phenyl)-3-[3-(2-methyl-2H-pyrazol-3-yl)-4-((R)-piperidin-3-yloxy)-phenyl]-urea; #423: 2-(4-Chloro-phenyl)-N-[3-(2-methyl-2H-pyrazol-3-yl)-4-((R)-piperidin-3-yloxy)-phenyl]-acetamide; #424: 2,4-Difluoro-N-[3-(2-methyl-2H-pyrazol-3-yl)-4-(2-piperidin-1-yl-ethoxy)-phenyl]-benzamide; #425: N-[3-(2-Methyl-2H-pyrazol-3-yl)-4-(2-piperidin-1-yl-ethoxy)-phenyl]-3-trifluoromethyl-benzamide; #426: N-[3-(2-Methyl-2H-pyrazol-3-yl)-4-(2-piperidin-1-yl-ethoxy)-phenyl]-2-trifluoromethyl-benzamide; #427: N-[4-[2-(7-Aza-bicyclo[2.2.1]hept-7-yl)-ethoxy]-3-(2-methyl-2H-pyrazol-3-yl)-phenyl]-2-(4-chloro-phenyl)-acetamide; #428: 1-[4-[2-(7-Aza-bicyclo[2.2.1]hept-7-yl)-ethoxy]-3-(2-methyl-2H-pyrazol-3-yl)-phenyl]-3-(2,4-difluoro-phenyl)-urea; #429: 1-[4-[2-(7-Aza-bicyclo[2.2.1]hept-7-yl)-ethoxy]-3-(2-methyl-2H-pyrazol-3-yl)-phenyl]-3-(2,5-difluoro-phenyl)-urea; #430: N-[4-[2-(7-Aza-bicyclo[2.2.1]hept-7-yl)-ethoxy]-3-(2-methyl-2H-pyrazol-3-yl)-phenyl]-4-chloro-benzamide; #431: N-[4-[2-(7-Aza-bicyclo[2.2.1]hept-7-yl)-ethoxy]-3-(2-methyl-2H-pyrazol-3-yl)-phenyl]-4-fluoro-benzamide; #432: Benzo[b]thiophene-2-carboxylic acid [3-(2-methyl-2H-pyrazol-3-yl)-4-(2-piperidin-1-yl-ethoxy)-phenyl]-amide; #433: 2-(4-Chloro-phenyl)-N-[3-(2-methyl-2H-pyrazol-3-yl)-4-((S)-piperidin-3-yloxy)-phenyl]-acetamide; #434: 2-(4-Chloro-phenyl)-2-hydroxy-N-[3-(2-methyl-2H-pyrazol-3-yl)-4-

((S)-piperidin-3-yloxy)-phenyl]-acetamide; #435: N-[3-(2-Methyl-2H-pyrazol-3-yl)-4-(2-pyrrolidin-1-yl-ethoxy)-phenyl]-3-trifluoromethyl-benzamide; #436: N-[3-(2-Methyl-2H-pyrazol-3-yl)-4-(2-piperidin-1-yl-ethoxy)-phenyl]-2-thiophen-2-yl-acetamide; #437: N-[3-(4-Bromo-2-methyl-2H-pyrazol-3-yl)-4-(2-piperidin-1-yl-ethoxy)-phenyl]-3-(4-fluoro-phenyl)-propionamide; #438: 1-(2,4-Difluoro-phenyl)-3-[3-(2-methyl-2H-pyrazol-3-yl)-4-(piperidin-4-yloxy)-phenyl]-urea; #439: 1-(4-Chloro-phenyl)-3-[3-(2-methyl-2H-pyrazol-3-yl)-4-(piperidin-4-yloxy)-phenyl]-urea; #440: N-[3-(4-Chloro-2-methyl-2H-pyrazol-3-yl)-4-(2-morpholin-4-yl-ethoxy)-phenyl]-4-trifluoromethyl-benzamide; #441: N-[3-(4-Chloro-2-methyl-2H-pyrazol-3-yl)-4-(2-morpholin-4-yl-ethoxy)-phenyl]-3,4-difluoro-benzamide; #442: 1-(4-Chloro-phenyl)-3-[3-(2-methyl-2H-pyrazol-3-yl)-4-(2-methyl-2-pyrrolidin-1-yl-propoxy)-phenyl]-urea; #443: 2-(4-Chloro-phenyl)-N-[3-(2-methyl-2H-pyrazol-3-yl)-4-(2-methyl-2-pyrrolidin-1-yl-propoxy)-phenyl]-acetamide; #444: 3,4-Difluoro-N-[3-(2-methyl-2H-pyrazol-3-yl)-4-(piperidin-4-yloxy)-phenyl]-benzamide; #445: N-[3-(2-Methyl-2H-pyrazol-3-yl)-4-(piperidin-4-yloxy)-phenyl]-4-trifluoromethyl-benzamide; #446: N-[3-(2-Methyl-2H-pyrazol-3-yl)-4-(2-methyl-2-pyrrolidin-1-yl-propoxy)-phenyl]-4-trifluoromethyl-benzamide; #447: N-[3-(4-Bromo-2-methyl-2H-pyrazol-3-yl)-4-(2-piperidin-1-yl-ethoxy)-phenyl]-2-(4-fluoro-phenyl)-2-hydroxy-acetamide; #448: N-[3-(4-Bromo-2-methyl-2H-pyrazol-3-yl)-4-(2-piperidin-1-yl-ethoxy)-phenyl]-2-(2-chloro-phenyl)-2-hydroxy-acetamide; #449: N-[3-(4-Bromo-2-methyl-2H-pyrazol-3-yl)-4-(2-piperidin-1-yl-ethoxy)-phenyl]-4-fluoro-benzamide; #450: N-[3-(4-Bromo-2-methyl-2H-pyrazol-3-yl)-4-(2-piperidin-1-yl-ethoxy)-phenyl]-3-fluoro-benzamide; #451: N-[4-[2-(7-Aza-bicyclo[2.2.1]hept-7-yl)-ethoxy]-3-(2-methyl-2H-pyrazol-3-yl)-phenyl]-4-trifluoromethyl-benzamide; #452: N-[3-(4-Bromo-2-methyl-2H-pyrazol-3-yl)-4-(2-piperidin-1-yl-ethoxy)-phenyl]-4-trifluoromethyl-benzamide; #453: N-[3-(4-Bromo-2-methyl-2H-pyrazol-3-yl)-4-(2-piperidin-1-yl-ethoxy)-phenyl]-3,4-difluoro-benzamide; #454: N-[3-(4-Bromo-2-methyl-2H-pyrazol-3-yl)-4-(2-pyrrolidin-1-yl-ethoxy)-phenyl]-4-trifluoromethyl-benzamide; #455: N-[3-(4-Bromo-2-methyl-2H-pyrazol-3-yl)-4-(2-pyrrolidin-1-yl-ethoxy)-phenyl]-3-fluoro-benzamide; #456: N-[3-(4-Bromo-2-methyl-2H-pyrazol-3-yl)-4-(2-pyrrolidin-1-yl-ethoxy)-phenyl]-3,4-difluoro-benzamide; #457: N-[4-[2-(2-Methyl-piperidin-1-yl)-ethoxy]-3-(2-methyl-2H-pyrazol-3-yl)-phenyl]-4-trifluoromethyl-benzamide; #458: 3-Fluoro-N-[4-[2-(2-methyl-piperidin-1-yl)-ethoxy]-3-(2-methyl-2H-pyrazol-3-yl)-phenyl]-benzamide; #459: 3,4-Difluoro-N-[4-[2-(2-methyl-piperidin-1-yl)-ethoxy]-3-(2-methyl-2H-pyrazol-3-yl)-phenyl]-benzamide; #460: 1-(4-Chloro-phenyl)-3-[4-[2-(2-methyl-piperidin-1-yl)-ethoxy]-3-(2-methyl-2H-pyrazol-3-yl)-phenyl]-urea; #461: N-[3-(4-Bromo-2-methyl-2H-pyrazol-3-yl)-4-(2-pyrrolidin-1-yl-ethoxy)-phenyl]-3-(4-chloro-phenyl)-propionamide; #462: N-[3-(4-Bromo-2-methyl-2H-pyrazol-3-yl)-4-(2-pyrrolidin-1-yl-ethoxy)-phenyl]-3-(2,4-dichloro-phenyl)-propionamide; #463: N-[3-(4-Bromo-2-methyl-2H-pyrazol-3-yl)-4-(2-pyrrolidin-1-yl-ethoxy)-phenyl]-3-thiazol-2-yl-propionamide; #464: N-[3-(4-Bromo-2-methyl-2H-pyrazol-3-yl)-4-(2-pyrrolidin-1-yl-ethoxy)-phenyl]-3-pyridin-3-yl-propionamide; #465: N-[3-(4-Bromo-2-methyl-2H-pyrazol-3-yl)-4-(2-pyrrolidin-1-yl-ethoxy)-phenyl]-3-(4-hydroxy-phenyl)-propionamide; #466: N-[3-(4-Bromo-2-methyl-2H-pyrazol-3-yl)-4-(2-pyrrolidin-1-yl-ethoxy)-phenyl]-3-(4-methoxy-phenyl)-propionamide; #467: 2-(4-Chloro-phenyl)-N-[3-(2-methyl-2H-pyrazol-3-yl)-4-(piperidin-4-yloxy)-phenyl]-acetamide; #468: 2,4-Difluoro-N-[3-(2-methyl-2H-pyrazol-3-yl)-4-(2-pyrrolidin-1-yl-ethoxy)-phenyl]-benzamide; #469: 3,4-Dichloro-N-[3-(2-methyl-2H-pyrazol-3-yl)-4-(2-pyrrolidin-1-yl-ethoxy)-phenyl]-benzamide; #470: N-[4-[2-((S)-3-Fluoro-pyrrolidin-1-yl)-ethoxy]-3-(2-methyl-2H-pyrazol-3-yl)-phenyl]-4-trifluoromethyl-benzamide; #471: N-[4-[2-((S)-3-Fluoro-pyrrolidin-1-yl)-ethoxy]-3-(2-methyl-2H-pyrazol-3-yl)-phenyl]-3-trifluoromethyl-benzamide; #472: N-[4-[2-((S)-3-Fluoro-pyrrolidin-1-yl)-ethoxy]-3-(2-methyl-2H-pyrazol-3-yl)-phenyl]-3-methyl-benzamide; #473: 3-Fluoro-N-[4-[2-((S)-3-fluoro-pyrrolidin-1-yl)-ethoxy]-3-(2-methyl-2H-pyrazol-3-yl)-phenyl]-benzamide; #474: N-{3-(4-Bromo-2-methyl-2H-pyrazol-3-yl)-4-[2-((S)-3-fluoro-pyrrolidin-1-yl)-ethoxy]-phenyl}-4-fluoro-benzamide; #475: N-{3-(4-Bromo-2-methyl-2H-pyrazol-3-yl)-4-[2-((S)-3-fluoro-pyrrolidin-1-yl)-ethoxy]-phenyl}-3-fluoro-benzamide; #476: 4-Chloro-N-[3-(2-methyl-2H-pyrazol-3-yl)-4-(2-methyl-2-pyrrolidin-1-yl-propoxy)-phenyl]-benzamide; #477: 2-Fluoro-N-[3-(2-methyl-2H-pyrazol-3-yl)-4-(2-morpholin-4-yl-ethoxy)-phenyl]-4-trifluoromethyl-benzamide; #478: 1-[3-(2-Methyl-2H-pyrazol-3-yl)-4-(2-morpholin-4-yl-ethoxy)-phenyl]-3-(4-trifluoromethyl-phenyl)-urea; #479: 4-Chloro-N-[3-(2-methyl-2H-pyrazol-3-yl)-4-(2-morpholin-4-yl-ethoxy)-phenyl]-benzamide; #480: N-[3-(2-Methyl-2H-pyrazol-3-yl)-4-(2-morpholin-4-yl-ethoxy)-phenyl]-3-trifluoromethyl-benzamide; #481: N-[4-[2-(4-Fluoro-piperidin-1-yl)-ethoxy]-3-(2-methyl-2H-pyrazol-3-yl)-phenyl]-4-trifluoromethyl-benzamide; #482: N-[4-[2-(4-Fluoro-piperidin-1-yl)-ethoxy]-3-(2-methyl-2H-pyrazol-3-yl)-phenyl]-3-trifluoromethyl-benzamide; #483: 3,4-Difluoro-N-[3-(2-methyl-2H-pyrazol-3-yl)-4-(2-pyrrolidin-1-yl-ethoxy)-phenyl]-benzamide; #484: 3-Chloro-4-fluoro-N-[3-(2-methyl-2H-pyrazol-3-yl)-4-(2-pyrrolidin-1-yl-ethoxy)-phenyl]-benzamide; #485: 4-Fluoro-N-[3-(2-methyl-2H-pyrazol-3-yl)-4-(2-pyrrolidin-1-yl-ethoxy)-phenyl]-3-trifluoromethyl-benzamide; #486: 4-Fluoro-3-methyl-N-[3-(2-methyl-2H-pyrazol-3-yl)-4-(2-pyrrolidin-1-yl-ethoxy)-phenyl]-benzamide; #487: 3-Fluoro-N-[3-(2-methyl-2H-pyrazol-3-yl)-4-(2-pyrrolidin-1-yl-ethoxy)-phenyl]-4-trifluoromethyl-benzamide; #488: 3-Fluoro-4-methyl-N-[3-(2-methyl-2H-pyrazol-3-yl)-4-(2-pyrrolidin-1-yl-ethoxy)-phenyl]-benzamide; #489: 4-Chloro-N-[3-(2-methyl-2H-pyrazol-3-yl)-4-(2-pyrrolidin-1-yl-ethoxy)-phenyl]-benzamide; #490: 3,4-Dichloro-N-[3-(2-methyl-2H-pyrazol-3-yl)-4-(2-morpholin-4-yl-ethoxy)-phenyl]-benzamide; #491: 4-Fluoro-N-[3-(2-methyl-2H-pyrazol-3-yl)-4-(2-morpholin-4-yl-ethoxy)-phenyl]-3-trifluoromethyl-benzamide; #492: N-[4-[2-(7-Aza-bicyclo[2.2.1]hept-7-yl)-ethoxy]-3-(2-methyl-2H-pyrazol-3-yl)-phenyl]-3-trifluoromethyl-benzamide; #493: 3-Chloro-4-fluoro-N-[3-(2-methyl-2H-pyrazol-3-yl)-4-(2-piperidin-1-yl-ethoxy)-phenyl]-benzamide; #494: 4-Fluoro-N-[3-(2-methyl-2H-pyrazol-3-yl)-4-(2-piperidin-1-yl-ethoxy)-phenyl]-3-trifluoromethyl-benzamide; #495: 3-Fluoro-4-methyl-N-[3-(2-methyl-2H-pyrazol-3-yl)-4-(2-piperidin-1-yl-ethoxy)-phenyl]-benzamide; #496: 4-Fluoro-3-methyl-N-[3-(2-methyl-2H-pyrazol-3-yl)-4-(2-piperidin-1-yl-ethoxy)-phenyl]-benzamide; #497: N-[3-(4-Bromo-2-methyl-2H-pyrazol-3-yl)-4-(2-pyrrolidin-1-yl-ethoxy)-phenyl]-2,4-difluoro-benzamide; #498: N-[3-(4-Bromo-2-methyl-2H-pyrazol-3-yl)-4-(2-pyrrolidin-1-yl-ethoxy)-phenyl]-4-chloro-benzamide; #499: N-[3-(4-Bromo-2-methyl-2H-pyrazol-3-yl)-4-(2-pyrrolidin-1-yl-ethoxy)-phenyl]-4-methyl-benzamide; #500: N-[3-(4-Bromo-2-methyl-2H-pyrazol-3-yl)-4-(2-pyrrolidin-1-yl-ethoxy)-phenyl]-3- trifluoromethyl-benzamide; #501: N-[3-(4-Bromo-2-methyl-2H-pyrazol-3-yl)-4-(2-pyrrolidin-1-yl-ethoxy)-phenyl]-3-chloro-benzamide; #502: N-[3-(4-Bromo-2-methyl-2H-pyrazol-3-yl)-4-(2-pyrrolidin-1-yl-ethoxy)-phenyl]-benzamide; #503: N-[3-(4-Bromo-2-methyl-2H-pyrazol-3-yl)-4-(2-piperidin-1-yl-ethoxy)-phenyl]-2,4-difluoro-benzamide; #504: N-[3-(4-Bromo-2-methyl-2H-pyrazol-3-yl)-4-(2-piperidin-1-yl-ethoxy)-phenyl]-4-chloro-benzamide; #505: N-[3-(4-Bromo-2-methyl-2H-pyrazol-3-yl)-4-(2-piperidin-1-yl-ethoxy)-phenyl]-4-methyl-benzamide; #506: N-[3-(4-Bromo-2-methyl-2H-pyrazol-3-yl)-4-(2-piperidin-1-yl-ethoxy)-phenyl]-3-trifluoromethyl-benzamide; #507: N-[3-(4-Bromo-2-methyl-2H-pyrazol-3-yl)-4-(2-piperidin-1-yl-ethoxy)-phenyl]-3-chloro-benzamide; #508: N-[3-(4-Bromo-2-methyl-2H-pyrazol-3-yl)-4-(2-piperidin-1-yl-ethoxy)-phenyl]-benzamide; #509: 4-Fluoro-N-[3-(2-methyl-2H-pyrazol-3-yl)-4-(2-pyrrolidin-1-yl-ethoxy)-phenyl]-benzamide; #510: 4-Methyl-N-[3-(2-methyl-2H-pyrazol-3-yl)-4-(2-pyrrolidin-1-yl-ethoxy)-phenyl]-benzamide; #511: N-[3-(2-Methyl-2H-pyrazol-3-yl)-4-(2-pyrrolidin-1-yl-ethoxy)-phenyl]-4-trifluoromethoxy-benzamide; #512: 3-Chloro-N-[3-(2-methyl-2H-pyrazol-3-yl)-4-(2-pyrrolidin-1-yl-ethoxy)-phenyl]-benzamide; #513: 3-Fluoro-N-[3-(2-methyl-2H-pyrazol-3-yl)-4-(2-pyrrolidin-1-yl-ethoxy)-phenyl]-benzamide; #514: 1-(4-Chloro-phenyl)-3-[4-(2-methyl-2-morpholin-4-yl-propoxy)-3-(2-methyl-2H-pyrazol-3-yl)-phenyl]-urea; #515: N-[4-(2-Methyl-2-morpholin-4-yl-propoxy)-3-(2-methyl-2H-pyrazol-3-yl)-phenyl]-3-trifluoromethyl-benzamide; #516: N-[3-(4-Bromo-2-methyl-2H-pyrazol-3-yl)-4-(2-morpholin-4-yl-ethoxy)-phenyl]-3-fluoro-benzamide; #517: N-[3-(4-Bromo-2-methyl-2H-pyrazol-3-yl)-4-(2-morpholin-4-yl-ethoxy)-phenyl]-4-fluoro-benzamide; #518: N-[4-(2-Methyl-2-morpholin-4-yl-propoxy)-3-(2-methyl-2H-pyrazol-3-yl)-phenyl]-4-trifluoromethyl-benzamide; #519: 4-Chloro-3-fluoro-N-[3-(2-methyl-2H-pyrazol-3-yl)-4-(2-piperidin-1-yl-ethoxy)-phenyl]-benzamide; #520: 4-Chloro-N-[3-(4-chloro-2-methyl-2H-pyrazol-3-yl)-4-(2-morpholin-4-yl-ethoxy)-phenyl]-3-fluoro-benzamide; #521: N-[3-(4-Chloro-2-methyl-2H-pyrazol-3-yl)-4-(2-morpholin-4-yl-ethoxy)-phenyl]-3-(4-fluoro-phenyl)-propionamide; #522: N-[3-(4-Chloro-2-methyl-2H-pyrazol-3-yl)-4-(2-morpholin-4-yl-ethoxy)-phenyl]-3-(3-fluoro-phenyl)-propionamide; #523: N-[3-(4-Chloro-2-methyl-2H-pyrazol-3-yl)-4-(2-morpholin-4-yl-ethoxy)-phenyl]-3-(4-chloro-phenyl)-propionamide; #524: N-[3-(4-Chloro-2-methyl-2H-pyrazol-3-yl)-4-(2-morpholin-4-yl-ethoxy)-phenyl]-2,4-difluoro-benzamide; #525: 3,4-Dichloro-N-[3-(4-chloro-2-methyl-2H-pyrazol-3-yl)-4-(2-morpholin-4-yl-ethoxy)-phenyl]-benzamide; #526: 3-Chloro-N-[3-(4-chloro-2-methyl-2H-pyrazol-3-yl)-4-(2-morpholin-4-yl-ethoxy)-phenyl]-4-fluoro-benzamide; #527: N-[3-(4-Chloro-2-methyl-2H-pyrazol-3-yl)-4-(2-morpholin-4-yl-ethoxy)-phenyl]-3-trifluoromethyl-benzamide; #528: 3-Chloro-N-[3-(4-chloro-2-methyl-2H-pyrazol-3-yl)-4-(2-morpholin-4-yl-ethoxy)-phenyl]-benzamide; #529: N-[3-(4-Chloro-2-methyl-2H-pyrazol-3-yl)-4-(2-morpholin-4-yl-ethoxy)-phenyl]-3-methyl-benzamide; #530: N-[3-(4-Chloro-2-methyl-2H-pyrazol-3-yl)-4-(2-morpholin-4-yl-ethoxy)-phenyl]-4-trifluoromethoxy-benzamide; #531: N-[3-(4-Chloro-2-methyl-2H-pyrazol-3-yl)-4-(2-morpholin-4-yl-ethoxy)-phenyl]-4-methoxy-benzamide; #532: N-[3-(4-Chloro-2-methyl-2H-pyrazol-3-yl)-4-(2-morpholin-4-yl-ethoxy)-phenyl]-4-methyl-benzamide; #533: N-{3-(2-Methyl-2H-pyrazol-3-yl)-4-[2-(1-methyl-pyrrolidin-2-yl)-ethoxy]-phenyl}-3-trifluoromethyl-benzamide; #534: 2,4-Difluoro-N-{3-(2-methyl-2H-pyrazol-3-yl)-4-[2-(1-methyl-pyrrolidin-2-yl)-ethoxy]-phenyl}-benzamide; #535: 3-Chloro-4-fluoro-N-{3-(2-methyl-2H-pyrazol-3-yl)-4-[2-(1-methyl-pyrrolidin-2-yl)-ethoxy]-phenyl}-benzamide; #536: N-[4-[2-(3,3-Difluoro-pyrrolidin-1-yl)-ethoxy]-3-(2-methyl-2H-pyrazol-3-yl)-phenyl]-3-trifluoromethyl-benzamide; #537: 4-Fluoro-N-[4-[2-(4-fluoro-piperidin-1-yl)-ethoxy]-3-(2-methyl-2H-pyrazol-3-yl)-phenyl]-3-methyl-benzamide; #538: 3-Chloro-4-fluoro-N-[4-[2-(4-fluoro-piperidin-1-yl)-ethoxy]-3-(2-methyl-2H-pyrazol-3-yl)-phenyl]-benzamide; #539: N-[3-(2-Methyl-2H-pyrazol-3-yl)-4-((S)-1-methyl-pyrrolidin-2-ylmethoxy)-phenyl]-3-trifluoromethyl-benzamide; #540: 3-Chloro-4-fluoro-N-[3-(2-methyl-2H-pyrazol-3-yl)-4-((S)-1-methyl-pyrrolidin-2-ylmethoxy)-phenyl]-benzamide; #541: 4-Chloro-3-fluoro-N-[3-(2-methyl-2H-pyrazol-3-yl)-4-(2-pyrrolidin-1-yl-ethoxy)-phenyl]-benzamide; #542: N-[3-(4-Chloro-2-methyl-2H-pyrazol-3-yl)-4-(2-morpholin-4-yl-ethoxy)-phenyl]-3-pyridin-3-yl-propionamide; #543: N-[3-(4-Chloro-2-methyl-2H-pyrazol-3-yl)-4-(2-morpholin-4-yl-ethoxy)-phenyl]-3-thiophen-2-yl-propionamide; #544: N-[3-(4-Chloro-2-methyl-2H-pyrazol-3-yl)-4-(2-morpholin-4-yl-ethoxy)-phenyl]-3-thiazol-2-yl-propionamide; #545: 3-Chloro-N-[4-[2-(3,3-difluoro-pyrrolidin-1-yl)-ethoxy]-3-(2-methyl-2H-pyrazol-3-yl)-phenyl]-4-fluoro-benzamide; #546: N-[4-[2-(3,3-Difluoro-pyrrolidin-1-yl)-ethoxy]-3-(2-methyl-2H-pyrazol-3-yl)-phenyl]-4-fluoro-3-methyl-benzamide; #547: 4-Fluoro-3-methyl-N-[3-(2-methyl-2H-pyrazol-3-yl)-4-((S)-1-methyl-pyrrolidin-2-ylmethoxy)-phenyl]-benzamide; #548: N-[3-(4-Bromo-2-methyl-2H-pyrazol-3-yl)-4-(2-morpholin-4-yl-ethoxy)-phenyl]-2,4-difluoro-benzamide; #549: 5-Methyl-isoxazole-3-carboxylic acid [3-(4-bromo-2-methyl-2H-pyrazol-3-yl)-4-(2-morpholin-4-yl-ethoxy)-phenyl]-amide; #550: N-[3-(4-Chloro-2-methyl-2H-pyrazol-3-yl)-4-(2-morpholin-4-yl-ethoxy)-phenyl]-3-(2,4-dichloro-phenyl)-propionamide; #551: N-[3-(4-Chloro-2-methyl-2H-pyrazol-3-yl)-4-(2-morpholin-4-yl-ethoxy)-phenyl]-3-(2-chloro-phenyl)-propionamide; #552: N-[3-(4-Chloro-2-methyl-2H-pyrazol-3-yl)-4-(2-morpholin-4-yl-ethoxy)-phenyl]-3-(2,6-dichloro-phenyl)-propionamide; #553: N-[3-(4-Chloro-2-methyl-2H-pyrazol-3-yl)-4-(2-morpholin-4-yl-ethoxy)-phenyl]-3-(4-methoxy-phenyl)-propionamide; #554: N-[3-(4-Chloro-2-methyl-2H-pyrazol-3-yl)-4-(2-morpholin-4-yl-ethoxy)-phenyl]-3-(4-hydroxy-phenyl)-propionamide; #555: N-[3-(2-Methyl-2H-pyrazol-3-yl)-4-((R)-1-methyl-pyrrolidin-3-yloxy)-phenyl]-3-trifluoromethyl-benzamide; #556: 3-Chloro-4-fluoro-N-[3-(2-methyl-2H-pyrazol-3-yl)-4-((R)-1-methyl-pyrrolidin-3-yloxy)-phenyl]-benzamide; #557: 5-Methyl-isoxazole-3-carboxylic acid [3-(2-methyl-2H-pyrazol-3-yl)-4-((R)-1-methyl-pyrrolidin-3-yloxy)-phenyl]-amide; #558: N-[3-(4-Chloro-2-methyl-2H-pyrazol-3-yl)-4-(2-morpholin-4-yl-ethoxy)-phenyl]-3-fluoro-4-trifluoromethyl-benzamide; #559: N-[3-(4-Chloro-2-methyl-2H-pyrazol-3-yl)-4-(2-morpholin-4-yl-ethoxy)-phenyl]-3-fluoro-4-methyl-benzamide; #560: N-[3-(4-Chloro-2-methyl-2H-pyrazol-3-yl)-4-(2-morpholin-4-yl-ethoxy)-phenyl]-4-fluoro-3-trifluoromethyl-benzamide; #561: N-[3-(4-Chloro-2-methyl-2H-pyrazol-3-yl)-4-(2-morpholin-4-yl-ethoxy)-phenyl]-4-fluoro-3-methyl-benzamide; #562: N-[3-(4-Chloro-2-methyl-2H-pyrazol-3-yl)-4-(2-morpholin-4-yl-ethoxy)-phenyl]-isonicotinamide; #563: N-[3-(4-Chloro-2-methyl-2H-pyrazol-3-yl)-4-(2-morpholin-4-yl-ethoxy)-phenyl]-nicotinamide; #564: N-[3-(4-Chloro-2-methyl-2H-pyrazol-3-yl)-4-(2-morpholin-4-yl-ethoxy)-phenyl]-benzamide; #565: N-[3-(4-Chloro-2-methyl-2H-pyrazol-3-yl)-4-(2-morpholin-4-yl-ethoxy)-phenyl]-4-cyano-benzamide; #566: N-[3-(2-Methyl-2H-pyrazol-3-yl)-

4-(2-[1,4]oxazepan-4-yl-ethoxy)-phenyl]-4-trifluoromethyl-benzamide; #567: N-[3-(2-Methyl-2H-pyrazol-3-yl)-4-(2-[1,4]oxazepan-4-yl-ethoxy)-phenyl]-4-trifluoromethoxy-benzamide; #568: N-[3-(2-Methyl-2H-pyrazol-3-yl)-4-(2-[1,4]oxazepan-4-yl-ethoxy)-phenyl]-3-trifluoromethyl-benzamide; #569: 3,4-Difluoro-N-[3-(2-methyl-2H-pyrazol-3-yl)-4-(2-[1,4]oxazepan-4-yl-ethoxy)-phenyl]-benzamide; #570: 4-Fluoro-N-[3-(2-methyl-2H-pyrazol-3-yl)-4-(2-[1,4]oxazepan-4-yl-ethoxy)-phenyl]-benzamide; #571: 4-Fluoro-3-methyl-N-[3-(2-methyl-2H-pyrazol-3-yl)-4-(2-[1,4]oxazepan-4-yl-ethoxy)-phenyl]-benzamide; #572: N-{3-(2-Methyl-2H-pyrazol-3-yl)-4-[2-(2-methyl-pyrrolidin-1-yl)-ethoxy]-phenyl}-3-trifluoromethyl-benzamide; #573: N-[3-(4-Chloro-2-methyl-2H-pyrazol-3-yl)-4-(2-morpholin-4-yl-ethoxy)-phenyl]-2-fluoro-4-trifluoromethyl-benzamide; #574: N-[3-(4-Chloro-2-methyl-2H-pyrazol-3-yl)-4-(2-morpholin-4-yl-ethoxy)-phenyl]-3-(4-trifluoromethyl-phenyl)-propionamide; #575: N-[4-[2-((S)-3-Hydroxy-pyrrolidin-1-yl)-ethoxy]-3-(2-methyl-2H-pyrazol-3-yl)-phenyl]-3-trifluoromethyl-benzamide; #576: 3-Chloro-4-fluoro-N-[4-[2-((S)-3-hydroxy-pyrrolidin-1-yl)-ethoxy]-3-(2-methyl-2H-pyrazol-3-yl)-phenyl]-benzamide; #577: N-{3-(4-Bromo-2-methyl-2H-pyrazol-3-yl)-4-[2-((S)-3-fluoro-pyrrolidin-1-yl)-ethoxy]-phenyl}-2,4-difluoro-benzamide; #578: 3-Chloro-4-fluoro-N-{3-(2-methyl-2H-pyrazol-3-yl)-4-[2-(2-methyl-pyrrolidin-1-yl)-ethoxy]-phenyl}-benzamide; #579: N-{3-(4-Bromo-2-methyl-2H-pyrazol-3-yl)-4-[2-(2-methyl-pyrrolidin-1-yl)-ethoxy]-phenyl}-3,4-difluoro-benzamide; #580: N-{3-(4-Bromo-2-methyl-2H-pyrazol-3-yl)-4-[2-(2-methyl-pyrrolidin-1-yl)-ethoxy]-phenyl}-2,4-difluoro-benzamide; #581: N-[3-(2-Methyl-2H-pyrazol-3-yl)-4-(2-morpholin-4-yl-ethoxy)-phenyl]-acetamide; #582: 4-Fluoro-N-[4-[2-(4-methoxy-piperidin-1-yl)-ethoxy]-3-(2-methyl-2H-pyrazol-3-yl)-phenyl]-3-trifluoromethyl-benzamide; #583: N-[3-(4-Bromo-2-methyl-2H-pyrazol-3-yl)-4-((R)-1-methyl-pyrrolidin-3-yloxy)-phenyl]-2,4-difluoro-benzamide; #584: N-[4-[2-((R)-3-Hydroxy-pyrrolidin-1-yl)-ethoxy]-3-(2-methyl-2H-pyrazol-3-yl)-phenyl]-3-trifluoromethyl-benzamide; #585: N-[3-(4-Bromo-2-methyl-2H-pyrazol-3-yl)-4-((R)-1-methyl-pyrrolidin-3-yloxy)-phenyl]-3,4-difluoro-benzamide; #586: N-[4-[2-((S)-3-Hydroxy-pyrrolidin-1-yl)-ethoxy]-3-(2-methyl-2H-pyrazol-3-yl)-phenyl]-4-trifluoromethyl-benzamide; #587: N-[4-((S)-4-Benzyl-morpholin-3-ylmethoxy)-3-(2-methyl-2H-pyrazol-3-yl)-phenyl]-3-trifluoromethyl-benzamide; #588: N-[4-[2-(7-Aza-bicyclo[2.2.1]hept-7-yl)-ethoxy]-3-(4-bromo-2-methyl-2H-pyrazol-3-yl)-phenyl]-3-trifluoromethyl-benzamide; #589: N-[4-[2-(7-Aza-bicyclo[2.2.1]hept-7-yl)-ethoxy]-3-(4-bromo-2-methyl-2H-pyrazol-3-yl)-phenyl]-4-trifluoromethyl-benzamide; #590: 1-[4-[2-(2-Methyl-piperidin-1-yl)-ethoxy]-3-(2-methyl-2H-pyrazol-3-yl)-phenyl]-3-(4-trifluoromethyl-phenyl)-urea; #591: 1-[4-[2-(2-Methyl-piperidin-1-yl)-ethoxy]-3-(2-methyl-2H-pyrazol-3-yl)-phenyl]-3-(3-trifluoromethyl-phenyl)-urea; #592: N-[3-(2-Methyl-2H-pyrazol-3-yl)-4-((S)-1-morpholin-3-yl-methoxy)-phenyl]-3-trifluoromethyl-benzamide; #593: N-[3-(2-Methyl-2H-pyrazol-3-yl)-4-((R)-1-morpholin-3-yl-methoxy)-phenyl]-3-trifluoromethyl-benzamide; #594: N-[4-((R)-4-Benzyl-morpholin-3-ylmethoxy)-3-(2-methyl-2H-pyrazol-3-yl)-phenyl]-3-trifluoromethyl-benzamide; #595: N-[4-[2-(7-Aza-bicyclo[2.2.1]hept-7-yl)-ethoxy]-3-(4-bromo-2-methyl-2H-pyrazol-3-yl)-phenyl]-4-fluoro-benzamide; #596: N-[4-[2-(7-Aza-bicyclo[2.2.1]hept-7-yl)-ethoxy]-3-(4-bromo-2-methyl-2H-pyrazol-3-yl)-phenyl]-2-fluoro-benzamide; #597: 3-Fluoro-N-[4-[2-(4-methoxy-piperidin-1-yl)-ethoxy]-3-(2-methyl-2H-pyrazol-3-yl)-phenyl]-4-trifluoromethyl-benzamide; #598: 3,4-Difluoro-N-[4-[2-(4-methoxy-piperidin-1-yl)-ethoxy]-3-(2-methyl-2H-pyrazol-3-yl)-phenyl]-benzamide; #599: N-[4-[2-(7-Aza-bicyclo[2.2.1]hept-7-yl)-ethoxy]-3-(4-bromo-2-methyl-2H-pyrazol-3-yl)-phenyl]-2-(4-chloro-phenyl)-acetamide; #600: N-[4-[2-(4-Methoxy-piperidin-1-yl)-ethoxy]-3-(2-methyl-2H-pyrazol-3-yl)-phenyl]-4-trifluoromethyl-benzamide; #601: N-[4-[2-(7-Aza-bicyclo[2.2.1]hept-7-yl)-ethoxy]-3-(4-bromo-2-methyl-2H-pyrazol-3-yl)-phenyl]-4-chloro-benzamide; #602: N-[4-[2-(4-Methoxy-piperidin-1-yl)-ethoxy]-3-(2-methyl-2H-pyrazol-3-yl)-phenyl]-3-trifluoromethyl-benzamide; #603: N-[4-[2-(7-Aza-bicyclo[2.2.1]hept-7-yl)-ethoxy]-3-(4-bromo-2-methyl-2H-pyrazol-3-yl)-phenyl]-3-chloro-benzamide; #604: N-[3-(4-Bromo-2-methyl-2H-pyrazol-3-yl)-4-(2-[1,4]oxazepan-4-yl-ethoxy)-phenyl]-4-trifluoromethyl-benzamide; #605: N-[3-(4-Bromo-2-methyl-2H-pyrazol-3-yl)-4-(2-[1,4]oxazepan-4-yl-ethoxy)-phenyl]-3-trifluoromethyl-benzamide; #606: N-[3-(4-Bromo-2-methyl-2H-pyrazol-3-yl)-4-(2-[1,4]oxazepan-4-yl-ethoxy)-phenyl]-3-fluoro-4-trifluoromethyl-benzamide; #607: N-[3-(4-Bromo-2-methyl-2H-pyrazol-3-yl)-4-(2-[1,4]oxazepan-4-yl-ethoxy)-phenyl]-4-fluoro-3-methyl-benzamide; #608: N-[3-(4-Bromo-2-methyl-2H-pyrazol-3-yl)-4-(2-[1,4]oxazepan-4-yl-ethoxy)-phenyl]-4-fluoro-3-trifluoromethyl-benzamide; #609: N-[3-(4-Bromo-2-methyl-2H-pyrazol-3-yl)-4-(2-thiomorpholin-4-yl-ethoxy)-phenyl]-4-trifluoromethyl-benzamide; #610: N-[3-(4-Bromo-2-methyl-2H-pyrazol-3-yl)-4-(2-thiomorpholin-4-yl-ethoxy)-phenyl]-3-trifluoromethyl-benzamide; #611: 1-[4-[2-(4-Methoxy-piperidin-1-yl)-ethoxy]-3-(2-methyl-2H-pyrazol-3-yl)-phenyl]-3-(4-trifluoromethyl-phenyl)-urea; #612: N-[3-(4-Bromo-2-methyl-2H-pyrazol-3-yl)-4-(2-thiomorpholin-4-yl-ethoxy)-phenyl]-3-fluoro-4-trifluoromethyl-benzamide; #613: 1-[4-[2-(4-Methoxy-piperidin-1-yl)-ethoxy]-3-(2-methyl-2H-pyrazol-3-yl)-phenyl]-3-(3-trifluoromethyl-phenyl)-urea; #614: N-[3-(4-Bromo-2-methyl-2H-pyrazol-3-yl)-4-(2-thiomorpholin-4-yl-ethoxy)-phenyl]-4-fluoro-3-trifluoromethyl-benzamide; #615: N-{3-(4-Bromo-2-methyl-2H-pyrazol-3-yl)-4-[2-((S)-3-hydroxy-pyrrolidin-1-yl)-ethoxy]-phenyl}-2,4-difluoro-benzamide; #616: N-{3-(4-Bromo-2-methyl-2H-pyrazol-3-yl)-4-[2-((S)-3-hydroxy-pyrrolidin-1-yl)-ethoxy]-phenyl}-4-chloro-benzamide; #617: 1-[4-((R)-4-Benzyl-morpholin-3-yl-methoxy)-3-(2-methyl-2H-pyrazol-3-yl)-phenyl]-3-(4-chloro-phenyl)-urea; #618: 4-Chloro-N-[4-[2-((R)-3-hydroxy-pyrrolidin-1-yl)-ethoxy]-3-(2-methyl-2H-pyrazol-3-yl)-phenyl]-benzamide; #619: 2-(4-Chloro-phenyl)-N-[4-[2-((R)-3-hydroxy-pyrrolidin-1-yl)-ethoxy]-3-(2-methyl-2H-pyrazol-3-yl)-phenyl]-acetamide; #620: N-[4-[2-(7-Aza-bicyclo[2.2.1]hept-7-yl)-ethoxy]-3-(4-bromo-2-methyl-2H-pyrazol-3-yl)-phenyl]-3-fluoro-4-trifluoromethyl-benzamide; #621: N-[4-[2-(7-Aza-bicyclo[2.2.1]hept-7-yl)-ethoxy]-3-(4-bromo-2-methyl-2H-pyrazol-3-yl)-phenyl]-4-fluoro-3-trifluoromethyl-benzamide; #622: N-{3-(2-Methyl-2H-pyrazol-3-yl)-4-[2-(3-oxo-piperazin-1-yl)-ethoxy]-phenyl}-3-trifluoromethyl-benzamide; #623: 2-(4-Chloro-phenyl)-N-{3-(2-methyl-2H-pyrazol-3-yl)-4-[2-(3-oxo-piperazin-1-yl)-ethoxy]-phenyl}-acetamide; #624: 4-Fluoro-3-methyl-N-{3-(2-methyl-2H-pyrazol-3-yl)-4-[2-(3-oxo-piperazin-1-yl)-ethoxy]-phenyl}-benzamide; #625: N-[4-[2-(4-Hydroxy-piperidin-1-yl)-ethoxy]-3-(2-methyl-2H-pyrazol-3-yl)-phenyl]-3-trifluoromethyl-benzamide; #626: N-[4-[2-(4-Hydroxy-piperidin-1-yl)-ethoxy]-3-(2-methyl-2H-pyrazol-3-yl)-phenyl]-4-trifluoromethyl-benzamide; #627: N-[4-{2-[4-(3-

Methyl-[1,2,4]oxadiazol-5-yl)-piperidin-1-yl]-ethoxy}-3-(2-methyl-2H-pyrazol-3-yl)-phenyl]-4-trifluoromethyl-benzamide; #628: 2-(4-Chloro-phenyl)-N-[4-{2-[4-(3-methyl-[1,2,4]oxadiazol-5-yl)-piperidin-1-yl]-ethoxy}-3-(2-methyl-2H-pyrazol-3-yl)-phenyl]-acetamide; #629: 4-Fluoro-3-methyl-N-[4-{2-[4-(3-methyl-[1,2,4]oxadiazol-5-yl)-piperidin-1-yl]-ethoxy}-3-(2-methyl-2H-pyrazol-3-yl)-phenyl]-benzamide; #630: 2-(4-Chloro-phenyl)-N-[4-[2-(4-methoxy-piperidin-1-yl)-ethoxy]-3-(2-methyl-2H-pyrazol-3-yl)-phenyl]-acetamide; #631: 1-(4-Chloro-benzyl)-3-[4-[2-(4-methoxy-piperidin-1-yl)-ethoxy]-3-(2-methyl-2H-pyrazol-3-yl)-phenyl]-urea; #632: 1-(4-Fluoro-benzyl)-3-[4-[2-(4-methoxy-piperidin-1-yl)-ethoxy]-3-(2-methyl-2H-pyrazol-3-yl)-phenyl]-urea; #633: N-{3-(4-Chloro-2-methyl-2H-pyrazol-3-yl)-4-[2-(4-methoxy-piperidin-1-yl)-ethoxy]-phenyl}-4-trifluoromethyl-benzamide; #634: N-{3-(4-Chloro-2-methyl-2H-pyrazol-3-yl)-4-[2-(4-methoxy-piperidin-1-yl)-ethoxy]-phenyl}-3-trifluoromethyl-benzamide; #635: N-{3-(4-Chloro-2-methyl-2H-pyrazol-3-yl)-4-[2-(4-methoxy-piperidin-1-yl)-ethoxy]-phenyl}-3,4-difluoro-benzamide; #636: N-{3-(4-Bromo-2-methyl-2H-pyrazol-3-yl)-4-[2-(4-methoxy-piperidin-1-yl)-ethoxy]-phenyl}-4-fluoro-benzamide; #637: N-{3-(4-Bromo-2-methyl-2H-pyrazol-3-yl)-4-[2-(4-methoxy-piperidin-1-yl)-ethoxy]-phenyl}-3-fluoro-benzamide; #638: N-[4-[2-(7-Aza-bicyclo[2.2.1]hept-7-yl)-ethoxy]-3-(4-bromo-2-methyl-2H-pyrazol-3-yl)-phenyl]-2,4-difluoro-benzamide; #639: N-[4-[2-(7-Aza-bicyclo[2.2.1]hept-7-yl)-ethoxy]-3-(4-bromo-2-methyl-2H-pyrazol-3-yl)-phenyl]-3,4-dichloro-benzamide; #640: N-{3-(4-Chloro-2-methyl-2H-pyrazol-3-yl)-4-[2-(2-methyl-piperidin-1-yl)-ethoxy]-phenyl}-4-trifluoromethyl-benzamide; #641: N-{3-(4-Chloro-2-methyl-2H-pyrazol-3-yl)-4-[2-(2-methyl-piperidin-1-yl)-ethoxy]-phenyl}-3,4-difluoro-benzamide; #642: 1-(4-Chloro-benzyl)-3-{3-(4-chloro-2-methyl-2H-pyrazol-3-yl)-4-[2-(2-methyl-piperidin-1-yl)-ethoxy]-phenyl}-urea; #643: 1-{3-(4-Chloro-2-methyl-2H-pyrazol-3-yl)-4-[2-(2-methyl-piperidin-1-yl)-ethoxy]-phenyl}-3-(4-fluoro-benzyl)-urea; #644: N-{3-(4-Bromo-2-methyl-2H-pyrazol-3-yl)-4-[2-(2-methyl-piperidin-1-yl)-ethoxy]-phenyl}-4-trifluoromethyl-benzamide; #645: N-{3-(4-Bromo-2-methyl-2H-pyrazol-3-yl)-4-[2-(2-methyl-piperidin-1-yl)-ethoxy]-phenyl}-3,4-difluoro-benzamide; #646: 1-{3-(4-Bromo-2-methyl-2H-pyrazol-3-yl)-4-[2-(2-methyl-piperidin-1-yl)-ethoxy]-phenyl}-3-(4-fluoro-benzyl)-urea; #647: 4-Chloro-N-{3-(4-chloro-2-methyl-2H-pyrazol-3-yl)-4-[2-(3-oxo-piperazin-1-yl)-ethoxy]-phenyl}-benzamide; #648: 1-(4-Chloro-benzyl)-3-[3-(4-chloro-2-methyl-2H-pyrazol-3-yl)-4-(2-morpholin-4-yl-ethoxy)-phenyl]-urea; #649: 1-[3-(4-Chloro-2-methyl-2H-pyrazol-3-yl)-4-(2-morpholin-4-yl-ethoxy)-phenyl]-3-(4-fluoro-benzyl)-urea; #650: 1-[3-(4-Chloro-2-methyl-2H-pyrazol-3-yl)-4-(2-morpholin-4-yl-ethoxy)-phenyl]-3-(3-fluoro-benzyl)-urea; #651: 4-{2-[2-(2-Methyl-2H-pyrazol-3-yl)-4-(4-trifluoromethyl-benzoylamino)-phenoxy]-ethyl}-piperazine-1-carboxylic acid ethyl ester; #652: N-{3-(4-Chloro-2-methyl-2H-pyrazol-3-yl)-4-[2-(3-oxo-piperazin-1-yl)-ethoxy]-phenyl}-4-fluoro-benzamide; #653: 4-{2-[4-(3-Fluoro-benzoylamino)-2-(2-methyl-2H-pyrazol-3-yl)-phenoxy]-ethyl}-piperazine-1-carboxylic acid ethyl ester; #654: 4-{2-[4-[3-(4-Chloro-phenyl)-ureido]-2-(2-methyl-2H-pyrazol-3-yl)-phenoxy]-ethyl}-piperazine-1-carboxylic acid ethyl ester; #655: (1-{2-[4-(3-Fluoro-benzoylamino)-2-(2-methyl-2H-pyrazol-3-yl)-phenoxy]-ethyl}-piperidin-4-yl)-carbamic acid tert-butyl ester; #656: (1-{2-[2-(2-Methyl-2H-pyrazol-3-yl)-4-(3-trifluoromethyl-benzoylamino)-phenoxy]-ethyl}-piperidin-4-yl)-carbamic acid tert-butyl ester; #657: (1-{2-[4-[2-(4-Chloro-phenyl)-acetylamino]-2-(2-methyl-2H-pyrazol-3-yl)-phenoxy]-ethyl}-piperidin-4-yl)-carbamic acid tert-butyl ester; #658: 1-[4-[2-(7-Aza-bicyclo[2.2.1]hept-7-yl)-ethoxy]-3-(4-bromo-2-methyl-2H-pyrazol-3-yl)-phenyl]-3-benzyl-urea; #659: N-[4-[2-(4-Acetyl-piperazin-1-yl)-ethoxy]-3-(2-methyl-2H-pyrazol-3-yl)-phenyl]-3-trifluoromethyl-benzamide; #660: N-[4-[2-(4-Acetyl-piperazin-1-yl)-ethoxy]-3-(2-methyl-2H-pyrazol-3-yl)-phenyl]-3-fluoro-benzamide; #661: N-[4-[2-(4-Acetyl-piperazin-1-yl)-ethoxy]-3-(2-methyl-2H-pyrazol-3-yl)-phenyl]-2-(4-chloro-phenyl)-acetamide; #662: (1-{2-[4-(3-Fluoro-benzoylamino)-2-(2-methyl-2H-pyrazol-3-yl)-phenoxy]-ethyl}-piperidin-4-yl)-carbamic acid ethyl ester; #663: (1-{2-[2-(2-Methyl-2H-pyrazol-3-yl)-4-(3-trifluoromethyl-benzoylamino)-phenoxy]-ethyl}-piperidin-4-yl)-carbamic acid ethyl ester; #664: 1-[3-(2-Methyl-2H-pyrazol-3-yl)-4-(3-morpholin-4-yl-propoxy)-phenyl]-3-(4-trifluoromethyl-phenyl)-urea; #665: 1-[3-(2-Methyl-2H-pyrazol-3-yl)-4-(3-morpholin-4-yl-propoxy)-phenyl]-3-(3-trifluoromethyl-phenyl)-urea; #666: 1-(4-Chloro-benzyl)-3-[3-(2-methyl-2H-pyrazol-3-yl)-4-(3-morpholin-4-yl-propoxy)-phenyl]-urea; #667: 2-(4-Chloro-phenyl)-N-[3-(2-methyl-2H-pyrazol-3-yl)-4-(3-morpholin-4-yl-propoxy)-phenyl]-acetamide; #668: N-[3-(2-Methyl-2H-pyrazol-3-yl)-4-(3-morpholin-4-yl-propoxy)-phenyl]-4-trifluoromethyl-benzamide; #669: N-[3-(2-Methyl-2H-pyrazol-3-yl)-4-(3-morpholin-4-yl-propoxy)-phenyl]-3-trifluoromethyl-benzamide; #670: N-{3-(4-Bromo-2-methyl-2H-pyrazol-3-yl)-4-[2-(3-oxo-piperazin-1-yl)-ethoxy]-phenyl}-3-chloro-benzamide; #671: 1-(3-Fluoro-benzyl)-3-[3-(2-methyl-2H-pyrazol-3-yl)-4-(3-morpholin-4-yl-propoxy)-phenyl]-urea; #672: 4-Chloro-N-[3-(2-methyl-2H-pyrazol-3-yl)-4-(3-morpholin-4-yl-propoxy)-phenyl]-benzamide; #673: 3,4-Difluoro-N-[3-(2-methyl-2H-pyrazol-3-yl)-4-(3-morpholin-4-yl-propoxy)-phenyl]-benzamide; #674: N-{3-(4-Bromo-2-methyl-2H-pyrazol-3-yl)-4-[2-(3-oxo-piperazin-1-yl)-ethoxy]-phenyl}-3-trifluoromethyl-benzamide; #675: 1-{3-(4-Bromo-2-methyl-2H-pyrazol-3-yl)-4-[2-(3-oxo-piperazin-1-yl)-ethoxy]-phenyl}-3-(4-chloro-phenyl)-urea; #676: 1-(4-Fluoro-benzyl)-3-[3-(2-methyl-2H-pyrazol-3-yl)-4-(3-morpholin-4-yl-propoxy)-phenyl]-urea; #677: N-{3-(4-Bromo-2-methyl-2H-pyrazol-3-yl)-4-[2-(3-oxo-piperazin-1-yl)-ethoxy]-phenyl}-3-fluoro-benzamide; #678: N-{3-(4-Chloro-2-methyl-2H-pyrazol-3-yl)-4-[2-(4-methyl-3-oxo-piperazin-1-yl)-ethoxy]-phenyl}-3-trifluoromethyl-benzamide; #679: N-[3-(2-Methyl-2H-pyrazol-3-yl)-4-(3-pyrrolidin-1-yl-propoxy)-phenyl]-4-trifluoromethyl-benzamide; #680: N-[3-(2-Methyl-2H-pyrazol-3-yl)-4-(3-pyrrolidin-1-yl-propoxy)-phenyl]-3-trifluoromethyl-benzamide; #681: 4-Chloro-N-[3-(2-methyl-2H-pyrazol-3-yl)-4-(3-pyrrolidin-1-yl-propoxy)-phenyl]-benzamide; #682: 3,4-Difluoro-N-[3-(2-methyl-2H-pyrazol-3-yl)-4-(3-pyrrolidin-1-yl-propoxy)-phenyl]-benzamide; #683: 2-(4-Chloro-phenyl)-N-[3-(2-methyl-2H-pyrazol-3-yl)-4-(3-pyrrolidin-1-yl-propoxy)-phenyl]-acetamide; #684: 1-(2,4-Difluoro-phenyl)-3-[3-(2-methyl-2H-pyrazol-3-yl)-4-(3-pyrrolidin-1-yl-propoxy)-phenyl]-urea; #685: 1-(4-Chloro-phenyl)-3-[3-(2-methyl-2H-pyrazol-3-yl)-4-(3-pyrrolidin-1-yl-propoxy)-phenyl]-urea; #686: 1-(4-Chloro-benzyl)-3-[3-(2-methyl-2H-pyrazol-3-yl)-4-(3-pyrrolidin-1-yl-propoxy)-phenyl]-urea; #687: N-{3-(4-Chloro-2-methyl-2H-pyrazol-3-yl)-4-[2-(3-oxo-piperazin-1-yl)-ethoxy]-phenyl}-3-trifluoromethyl-benzamide; #688: N-[4-(3-Imidazol-1-yl-propoxy)-3-(2-methyl-2H-pyrazol-3-yl)-phenyl]-4-trifluoromethyl-benzamide; #689: N-[4-(3-Imidazol-1-yl-propoxy)-3-(2-methyl-2H-pyrazol-3-yl)-phenyl]-3- trifluoromethyl-benzamide; #690: 2-(4-Chloro-phenyl)-N-[4-(3-imidazol-1-yl-propoxy)-3-(2-methyl-2H-pyrazol-3-yl)-phenyl]-acetamide; #691: 1-(4-Chloro-phenyl)-3-[4-(3-imidazol-1-yl-propoxy)-3-(2-methyl-2H-pyrazol-3-yl)-phenyl]-urea; #692: 1-[4-((S)-4-Benzyl-morpholin-3-ylmethoxy)-3-(4-chloro-2-methyl-2H-pyrazol-3-yl)-phenyl]-3-(4-fluoro-phenyl)-urea; #693: 1-[3-(4-Chloro-2-methyl-2H-pyrazol-3-yl)-4-((S)-1-morpholin-3-ylmethoxy)-phenyl]-3-(4-fluoro-phenyl)-urea; #694: N-[4-((S)-4-Benzyl-morpholin-3-ylmethoxy)-3-(4-chloro-2-methyl-2H-pyrazol-3-yl)-phenyl]-3-trifluoromethyl-benzamide; #695: 3-Chloro-N-{3-(4-chloro-2-methyl-2H-pyrazol-3-yl)-4-[2-(4-methyl-3-oxo-piperazin-1-yl)-ethoxy]-phenyl}-benzamide; #696: N-[3-(4-Chloro-2-methyl-2H-pyrazol-3-yl)-4-((S)-1-morpholin-3-ylmethoxy)-phenyl]-3-trifluoromethyl-benzamide; #697: 4-{2-[2-(4-Chloro-2-methyl-2H-pyrazol-3-yl)-4-(3-trifluoromethyl-benzoylamino)-phenoxy]-ethyl}-4-methyl-morpholin-4-ium; #698: 1-[4-[2-(7-Aza-bicyclo[2.2.1]hept-7-yl)-ethoxy]-3-(4-bromo-2-methyl-2H-pyrazol-3-yl)-phenyl]-3-(2-fluoro-benzyl)-urea; #699: 1-[4-[2-(7-Aza-bicyclo[2.2.1]hept-7-yl)-ethoxy]-3-(4-bromo-2-methyl-2H-pyrazol-3-yl)-phenyl]-3-(3-fluoro-benzyl)-urea; #700: 1-[4-[2-(7-Aza-bicyclo[2.2.1]hept-7-yl)-ethoxy]-3-(4-bromo-2-methyl-2H-pyrazol-3-yl)-phenyl]-3-(4-fluoro-benzyl)-urea; #701: 1-[4-[2-(7-Aza-bicyclo[2.2.1]hept-7-yl)-ethoxy]-3-(4-bromo-2-methyl-2H-pyrazol-3-yl)-phenyl]-3-(2,4-di-chloro-benzyl)-urea; #702: 1-[4-[2-(7-Aza-bicyclo[2.2.1]hept-7-yl)-ethoxy]-3-(4-bromo-2-methyl-2H-pyrazol-3-yl)-phenyl]-3-(1-phenyl-ethyl)-urea; #703: N-[4-[2-(4-Acetyl-piperazin-1-yl)-ethoxy]-3-(4-chloro-2-methyl-2H-pyrazol-3-yl)-phenyl]-3-trifluoromethyl-benzamide; #704: N-[4-[2-(4-Acetyl-piperazin-1-yl)-ethoxy]-3-(4-chloro-2-methyl-2H-pyrazol-3-yl)-phenyl]-3-fluoro-benzamide; #705: N-[4-[2-(4-Acetyl-piperazin-1-yl)-ethoxy]-3-(4-chloro-2-methyl-2H-pyrazol-3-yl)-phenyl]-3-chloro-benzamide; #706: N-[4-[2-(4-Acetyl-piperazin-1-yl)-ethoxy]-3-(2-methyl-2H-pyrazol-3-yl)-phenyl]-3-chloro-4-fluoro-benzamide; #707: N-[4-[2-(4-Acetyl-piperazin-1-yl)-ethoxy]-3-(2-methyl-2H-pyrazol-3-yl)-phenyl]-4-trifluoromethyl-benzamide; #708: N-[4-[2-(4-Acetyl-piperazin-1-yl)-ethoxy]-3-(2-methyl-2H-pyrazol-3-yl)-phenyl]-3-chloro-benzamide; #709: 1-[4-[2-(7-Aza-bicyclo[2.2.1]hept-7-yl)-ethoxy]-3-(4-bromo-2-methyl-2H-pyrazol-3-yl)-phenyl]-3-(4-trifluoromethyl-benzyl)-urea; #710: 1-[4-[2-(7-Aza-bicyclo[2.2.1]hept-7-yl)-ethoxy]-3-(4-bromo-2-methyl-2H-pyrazol-3-yl)-phenyl]-3-(3-trifluoromethyl-benzyl)-urea; #711: 1-[4-[2-(4-Acetyl-piperazin-1-yl)-ethoxy]-3-(2-methyl-2H-pyrazol-3-yl)-phenyl]-3-(4-fluoro-phenyl)-urea; #712: 1-[4-[2-(7-Aza-bicyclo[2.2.1]hept-7-yl)-ethoxy]-3-(4-bromo-2-methyl-2H-pyrazol-3-yl)-phenyl]-3-(4-chloro-benzyl)-urea; #713: (S)-1-{2-[2-(4-Chloro-2-methyl-2H-pyrazol-3-yl)-4-(3-trifluoromethyl-benzoylamino)-phenoxy]-ethyl}-pyrrolidine-2-carboxylic acid amide; #714: N-{3-(4-Chloro-2-methyl-2H-pyrazol-3-yl)-4-[2-(4-formyl-piperazin-1-yl)-ethoxy]-phenyl}-3-trifluoromethyl-benzamide; #715: 1-{2-[2-(4-Chloro-2-methyl-2H-pyrazol-3-yl)-4-(3-trifluoromethyl-benzoylamino)-phenoxy]-ethyl}-piperidine-4-carboxylic acid amide; #716: 4-{2-[2-(4-Chloro-2-methyl-2H-pyrazol-3-yl)-4-(3-trifluoromethyl-benzoylamino)-phenoxy]-ethyl}-piperazine-1-carboxylic acid amide; #717: N-[3-(4-Chloro-2-methyl-2H-pyrazol-3-yl)-4-(1-methyl-piperidin-4-yloxy)-phenyl]-acetamide; #718: (1-{2-[2-(4-Chloro-2-methyl-2H-pyrazol-3-yl)-4-(3-trifluoromethyl-benzoylamino)-phenoxy]-ethyl}-piperidin-4-yl)-carbamic acid tert-butyl ester; #719: N-[4-[2-(4-Amino-piperidin-1-yl)-ethoxy]-3-(4-chloro-2-methyl-2H-pyrazol-3-yl)-phenyl]-3-trifluoromethyl-benzamide; #720: N-[4-[2-(4-Acetylamino-piperidin-1-yl)-ethoxy]-3-(4-chloro-2-methyl-2H-pyrazol-3-yl)-phenyl]-3-trifluoromethyl-benzamide; #721: 1-[4-[2-(7-Aza-bicyclo[2.2.1]hept-7-yl)-ethoxy]-3-(4-bromo-2-methyl-2H-pyrazol-3-yl)-phenyl]-3-(2-chloro-benzyl)-urea; #722: 1-[4-[2-(7-Aza-bicyclo[2.2.1]hept-7-yl)-ethoxy]-3-(2-methyl-2H-pyrazol-3-yl)-phenyl]-3-(2-fluoro-benzyl)-urea; #723: 4-{2-[2-(4-Chloro-2-methyl-2H-pyrazol-3-yl)-4-(3-trifluoromethyl-benzoylamino)-phenoxy]-ethyl)}-piperazine-1-carboxylic acid dimethylamide; #724: N-{3-(4-Chloro-2-methyl-2H-pyrazol-3-yl)-4-[2-(4-isopropyl-piperazin-1-yl)-ethoxy]-phenyl}-3-trifluoromethyl-benzamide; #725: N-{3-(4-Chloro-2-methyl-2H-pyrazol-3-yl)-4-[2-(3,3-difluoro-pyrrolidin-1-yl)-ethoxy]-phenyl})-3-trifluoromethyl-benzamide; #726: N-[3-(4-Chloro-2-methyl-2H-pyrazol-3-yl)-4-(1-methyl-piperidin-4-yloxy)-phenyl]-3-trifluoromethyl-benzamide; #727: 3-Chloro-N-[3-(2-methyl-2H-pyrazol-3-yl)-4-(2-morpholin-4-yl-ethoxy)-phenyl]-benzamide; #728: N-[3-(4-Chloro-2-methyl-2H-pyrazol-3-yl)-4-(1-methyl-piperidin-4-ylmethoxy)-phenyl]-3-trifluoromethyl-benzamide; #729: 3-Fluoro-N-[3-(2-methyl-2H-pyrazol-3-yl)-4-(2-morpholin-4-yl-ethoxy)-phenyl]-benzamide; #730: 3,4-Difluoro-N-[3-(2-methyl-2H-pyrazol-3-yl)-4-(2-morpholin-4-yl-ethoxy)-phenyl]-benzamide; #731: N-[4-[2-(4-Acetyl-piperazin-1-yl)-ethoxy]-3-(2-methyl-2H-pyrazol-3-yl)-phenyl]-2,4-difluoro-benzamide; #732: 3-Fluoro-4-methyl-N-[3-(2-methyl-2H-pyrazol-3-yl)-4-(2-morpholin-4-yl-ethoxy)-phenyl]-benzamide; #733: 3-Methoxy-N-[3-(2-methyl-2H-pyrazol-3-yl)-4-(2-morpholin-4-yl-ethoxy)-phenyl]-benzamide; #734: 1-[4-[2-(7-Aza-bicyclo[2.2.1]hept-7-yl)-ethoxy]-3-(4-bromo-2-methyl-2H-pyrazol-3-yl)-phenyl]-3-(2,4-difluoro-benzyl)-urea; #735: N-{3-(4-Chloro-2-methyl-2H-pyrazol-3-yl)-4-[2-(3,3-difluoro-azetidin-1-yl)-ethoxy]-phenyl}-3-trifluoromethyl-benzamide; #736: 1-[4-[2-(7-Aza-bicyclo[2.2.1]hept-7-yl)-ethoxy]-3-(4-chloro-2-methyl-2H-pyrazol-3-yl)-phenyl]-3-(3-fluoro-benzyl)-urea; #737: 1-[4-[2-(7-Aza-bicyclo[2.2.1]hept-7-yl)-ethoxy]-3-(4-chloro-2-methyl-2H-pyrazol-3-yl)-phenyl]-3-(2-fluoro-benzyl)-urea; #738: 1-[4-[2-(7-Aza-bicyclo[2.2.1]hept-7-yl)-ethoxy]-3-(4-chloro-2-methyl-2H-pyrazol-3-yl)-phenyl]-3-(4-fluoro-benzyl)-urea; #739: N-[3-(4-Chloro-2-methyl-2H-pyrazol-3-yl)-4-(1-methyl-piperidin-4-yloxy)-phenyl]-4-fluoro-benzamide; #740: N-[3-(4-Chloro-2-methyl-2H-pyrazol-3-yl)-4-(1-methyl-piperidin-4-yloxy)-phenyl]-3-fluoro-benzamide; #741: N-[3-(4-Chloro-2-methyl-2H-pyrazol-3-yl)-4-(1-methyl-piperidin-4-yloxy)-phenyl]-2-fluoro-benzamide; #742: N-[3-(4-Chloro-2-methyl-2H-pyrazol-3-yl)-4-(1-methyl-piperidin-4-yloxy)-phenyl]-3-methoxy-benzamide; #743: N-[3-(4-Chloro-2-methyl-2H-pyrazol-3-yl)-4-(1-methyl-piperidin-4-yloxy)-phenyl]-4-methyl-benzamide; #744: N-[3-(4-Chloro-2-methyl-2H-pyrazol-3-yl)-4-(1-methyl-piperidin-4-yloxy)-phenyl]-3-fluoro-4-methyl-benzamide; #745: N-[3-(4-Chloro-2-methyl-2H-pyrazol-3-yl)-4-(1-methyl-piperidin-4-yloxy)-phenyl]-4-fluoro-3-methyl-benzamide; #746: 1-[4-[2-(7-Aza-bicyclo[2.2.1]hept-7-yl)-ethoxy]-3-(4-chloro-2-methyl-2H-pyrazol-3-yl)-phenyl]-3-benzyl-urea; #747: 1-{2-[4-(3-Fluoro-benzoylamino)-2-(2-methyl-2H-pyrazol-3-yl)-phenoxy]-ethyl}-piperidine-4-carboxylic acid amide; #748: 4-{2-[4-(3-Fluoro-benzoylamino)-2-(2-methyl-2H-pyrazol-3-yl)-phenoxy]-ethyl}-piperazine-1-carboxylic acid amide; #749: 1-[4-[2-(7-Aza-bicyclo[2.2.1]hept-7-yl)-ethoxy]-3-(4-chloro-2-methyl-2H-pyrazol-3-yl)-phenyl]-3-benzoyl-urea; #750: N-[4-[2-(7-Aza-bicyclo[2.2.1]hept-7-yl)-ethoxy]-3-(4-chloro-2-methyl-2H-pyrazol-3-yl)- phenyl]-benzamide; #751: N-{3-(4-Chloro-2-methyl-2H-pyrazol-3-yl)-4-[2-(4-methyl-piperazin-1-yl)-2-oxo-ethoxy]-phenyl}-3-trifluoromethyl-benzamide; #752: 3-Fluoro-N-[4-[2-(4-formyl-piperazin-1-yl)-ethoxy]-3-(2-methyl-2H-pyrazol-3-yl)-phenyl]-benzamide; #753: 3-Fluoro-N-[4-[2-(4-methanesulfonyl-piperazin-1-yl)-ethoxy]-3-(2-methyl-2H-pyrazol-3-yl)-phenyl]-benzamide; #754: 3-Fluoro-N-{3-(2-methyl-2H-pyrazol-3-yl)-4-[2-(4-trifluoromethyl-piperidin-1-yl)-ethoxy]-phenyl}-benzamide; #755: N-[4-[2-(4-Acetyl-piperazin-1-yl)-ethoxy]-3-(2-methyl-2H-pyrazol-3-yl)-phenyl]-3-methoxy-benzamide; #756: N-[3-(4-Chloro-2-methyl-2H-pyrazol-3-yl)-4-(2-oxo-2-piperazin-1-yl-ethoxy)-phenyl]-3-trifluoromethyl-benzamide; #757: N-{3-(4-Chloro-2-methyl-2H-pyrazol-3-yl)-4-[2-(4-methanesulfonylamino-piperidin-1-yl)-ethoxy]-phenyl}-3-trifluoromethyl-benzamide; #758: N-[4-[2-(4-Acetyl-[1,4]diazepan-1-yl)-ethoxy]-3-(4-chloro-2-methyl-2H-pyrazol-3-yl)-phenyl]-2,4-difluoro-benzamide; #759: 2,5-Difluoro-N-[3-(2-methyl-2H-pyrazol-3-yl)-4-(2-morpholin-4-yl-ethoxy)-phenyl]-benzamide; #760: 3,5-Dimethoxy-N-[3-(2-methyl-2H-pyrazol-3-yl)-4-(2-morpholin-4-yl-ethoxy)-phenyl]-benzamide; #761: 3,5-Difluoro-N-[3-(2-methyl-2H-pyrazol-3-yl)-4-(2-morpholin-4-yl-ethoxy)-phenyl]-benzamide; #762: N-[3-(2-Methyl-2H-pyrazol-3-yl)-4-(2-morpholin-4-yl-ethoxy)-phenyl]-2-phenyl-acetamide; #763: 2-(2-Chloro-phenyl)-N-[3-(2-methyl-2H-pyrazol-3-yl)-4-(2-morpholin-4-yl-ethoxy)-phenyl]-acetamide; #764: N-[3-(2-Methyl-2H-pyrazol-3-yl)-4-(2-morpholin-4-yl-ethoxy)-phenyl]-2-(2-trifluoromethyl-phenyl)-acetamide; #765: 2-(2-Methoxy-phenyl)-N-[3-(2-methyl-2H-pyrazol-3-yl)-4-(2-morpholin-4-yl-ethoxy)-phenyl]-acetamide; #766: 2-(3-Fluoro-phenyl)-N-[3-(2-methyl-2H-pyrazol-3-yl)-4-(2-morpholin-4-yl-ethoxy)-phenyl]-acetamide; #767: 2-(3-Chloro-phenyl)-N-[3-(2-methyl-2H-pyrazol-3-yl)-4-(2-morpholin-4-yl-ethoxy)-phenyl]-acetamide; #768: N-[3-(2-Methyl-2H-pyrazol-3-yl)-4-(2-morpholin-4-yl-ethoxy)-phenyl]-2-(3-trifluoromethyl-phenyl)-acetamide; #769: 2-(3-Methoxy-phenyl)-N-[3-(2-methyl-2H-pyrazol-3-yl)-4-(2-morpholin-4-yl-ethoxy)-phenyl]-acetamide; #770: N-[3-(2-Methyl-2H-pyrazol-3-yl)-4-(2-morpholin-4-yl-ethoxy)-phenyl]-2-m-tolyl-acetamide; #771: N-[3-(2-Methyl-2H-pyrazol-3-yl)-4-(2-morpholin-4-yl-ethoxy)-phenyl]-2-p-tolyl-acetamide; #772: 2-Benzo[1,3]dioxol-5-yl-N-[3-(2-methyl-2H-pyrazol-3-yl)-4-(2-morpholin-4-yl-ethoxy)-phenyl]-acetamide; #773: N-[3-(2-Methyl-2H-pyrazol-3-yl)-4-(2-morpholin-4-yl-ethoxy)-phenyl]-2-o-tolyl-acetamide; #774: N-[3-(4-Chloro-2-methyl-2H-pyrazol-3-yl)-4-(2-[1,4]diazepan-1-yl-ethoxy)-phenyl]-2,4-difluoro-benzamide; #775: N-{3-(4-Chloro-2-methyl-2H-pyrazol-3-yl)-4-[2-(4-methyl-[1,4]diazepan-1-yl)-ethoxy]-phenyl}-2,4-difluoro-benzamide; #776: N-[4-[2-(4-Acetyl-piperazin-1-yl)-ethoxy]-3-(4-chloro-2-methyl-2H-pyrazol-3-yl)-phenyl]-2,4-difluoro-benzamide; #777: 1-[3-(4-Bromo-2-methyl-2H-pyrazol-3-yl)-4-(2-morpholin-4-yl-ethoxy)-phenyl]-3-(3-fluoro-benzyl)-urea; #778: N-[4-[2-(4,4-Difluoro-piperidin-1-yl)-ethoxy]-3-(2-methyl-2H-pyrazol-3-yl)-phenyl]-3-fluoro-benzamide; #779: Cyclobutanecarboxylic acid [3-(4-chloro-2-methyl-2H-pyrazol-3-yl)-4-(2-morpholin-4-yl-ethoxy)-phenyl]-amide; #780: Cyclopentanecarboxylic acid [3-(4-chloro-2-methyl-2H-pyrazol-3-yl)-4-(2-morpholin-4-yl-ethoxy)-phenyl]-amide; #781: Cyclohexanecarboxylic acid [3-(4-chloro-2-methyl-2H-pyrazol-3-yl)-4-(2-morpholin-4-yl-ethoxy)-phenyl]-amide; #782: N-{3-(4-Chloro-2-methyl-2H-pyrazol-3-yl)-4-[2-(4-formyl-[1,4]diazepan-1-yl)-ethoxy]-phenyl}-2,4-difluoro-benzamide; #783: 1-[4-[2-(4-Acetyl-piperazin-1-yl)-ethoxy]-3-(4-bromo-2-methyl-2H-pyrazol-3-yl)-phenyl]-3-(3-fluoro-benzyl)-urea; #784: N-[3-(4-Chloro-2-methyl-2H-pyrazol-3-yl)-4-(1-methyl-piperidin-4-yloxy)-phenyl]-2,4-difluoro-benzamide; #785: N-[3-(4-Chloro-2-methyl-2H-pyrazol-3-yl)-4-(1-methyl-piperidin-4-yloxy)-phenyl]-3-methyl-benzamide; #786: 4-{2-[4-(2,4-Difluoro-benzoylamino)-2-(2-methyl-2H-pyrazol-3-yl)-phenoxy]-ethyl}-piperazine-1-carboxylic acid amide; #787: N-[4-[2-(4-Acetyl-piperazin-1-yl)-ethoxy]-3-(4-chloro-2-methyl-2H-pyrazol-3-yl)-phenyl]-2-fluoro-benzamide; #788: 1-{2-[2-(4-Chloro-2-methyl-2H-pyrazol-3-yl)-4-(2-fluoro-benzoylamino)-phenoxy]-ethyl}-piperidine-4-carboxylic acid amide; #789: 3-Methoxy-N-{3-(2-methyl-2H-pyrazol-3-yl)-4-[2-(4-trifluoromethyl-piperidin-1-yl)-ethoxy]-phenyl}-benzamide; #790: N-[3-(4-Chloro-2-methyl-2H-pyrazol-3-yl)-4-(2-piperazin-1-yl-ethoxy)-phenyl]-2,4-difluoro-benzamide; #791: 4-{2-[4-(3-Methoxy-benzoylamino)-2-(2-methyl-2H-pyrazol-3-yl)-phenoxy]-ethyl}-piperazine-1-carboxylic acid amide; #792: N-[3-(2-Methyl-2H-pyrazol-3-yl)-4-(2-morpholin-4-yl-ethoxy)-phenyl]-2-pyridin-3-yl-acetamide; #793: 2-(2-Fluoro-phenyl)-N-[3-(2-methyl-2H-pyrazol-3-yl)-4-(2-morpholin-4-yl-ethoxy)-phenyl]-acetamide; #794: N-[3-(2-Methyl-2H-pyrazol-3-yl)-4-(2-morpholin-4-yl-ethoxy)-phenyl]-2-(4-trifluoromethyl-phenyl)-acetamide; #795: N-[3-(2-Methyl-2H-pyrazol-3-yl)-4-(2-morpholin-4-yl-ethoxy)-phenyl]-2-thiophen-2-yl-acetamide; #796: 3-Fluoro-N-[3-(2-methyl-2H-pyrazol-3-yl)-4-(2-piperazin-1-yl-ethoxy)-phenyl]-benzamide; #797: N-[4-[2-(4-Cyclopropanecarbonyl-piperazin-1-yl)-ethoxy]-3-(2-methyl-2H-pyrazol-3-yl)-phenyl]-3-fluoro-benzamide; #798: 3-Fluoro-N-[4-[2-(4-isobutyryl-piperazin-1-yl)-ethoxy]-3-(2-methyl-2H-pyrazol-3-yl)-phenyl]-benzamide; #799: N-[3-(2-Methyl-2H-pyrazol-3-yl)-4-(2-morpholin-4-yl-ethoxy)-phenyl]-2-pyridin-2-yl-acetamide; #800: (R)-1-{2-[2-(2-Methyl-2H-pyrazol-3-yl)-4-(3-trifluoromethyl-benzoylamino)-phenoxy]-ethyl}-pyrrolidine-2-carboxylic acid amide; #801: (R)-1-{2-[4-(3-Chloro-4-fluoro-benzoylamino)-2-(2-methyl-2H-pyrazol-3-yl)-phenoxy]-ethyl}-pyrrolidine-2-carboxylic acid amide; #802: (S)-1-{2-[2-(2-Methyl-2H-pyrazol-3-yl)-4-(4-trifluoromethyl-benzoylamino)-phenoxy]-ethyl}-pyrrolidine-2-carboxylic acid amide; #803: (S)-1-{2-[4-(3-Chloro-4-fluoro-benzoylamino)-2-(2-methyl-2H-pyrazol-3-yl)-phenoxy]-ethyl}-pyrrolidine-2-carboxylic acid amide; #804: (S)-1-{2-[2-(2-Methyl-2H-pyrazol-3-yl)-4-(3-trifluoromethyl-benzoylamino)-phenoxy]-ethyl}-pyrrolidine-2-carboxylic acid amide; #805: N-[4-[2-(4-Amino-piperidin-1-yl)-ethoxy]-3-(2-methyl-2H-pyrazol-3-yl)-phenyl]-3-fluoro-benzamide; #806: N-[4-[2-(4-Amino-piperidin-1-yl)-ethoxy]-3-(2-methyl-2H-pyrazol-3-yl)-phenyl]-3-trifluoromethyl-benzamide; #807: N-[4-[2-(4-Amino-piperidin-1-yl)-ethoxy]-3-(2-methyl-2H-pyrazol-3-yl)-phenyl]-2-(4-chloro-phenyl)-acetamide; #808: [3-(4-Bromo-2-methyl-2H-pyrazol-3-yl)-4-(2-pyrrolidin-1-yl-ethoxy)-phenyl]-(4-trifluoromethyl-phenyl)-amine; #809: [3-(4-Bromo-2-methyl-2H-pyrazol-3-yl)-4-(2-pyrrolidin-1-yl-ethoxy)-phenyl]-(4-chloro-phenyl)-amine; #810: [3-(4-Bromo-2-methyl-2H-pyrazol-3-yl)-4-(2-pyrrolidin-1-yl-ethoxy)-phenyl]-(4-fluoro-phenyl)-amine; #811: [3-(4-Bromo-2-methyl-2H-pyrazol-3-yl)-4-(2-pyrrolidin-1-yl-ethoxy)-phenyl]-(3-fluoro-phenyl)-amine; #812: [3-(4-Chloro-2-methyl-2H-pyrazol-3-yl)-4-(2-morpholin-4-yl-ethoxy)-phenyl]-(4-trifluoromethyl-phenyl)-amine; #813: [3-(4-Chloro-2-methyl-2H-pyrazol-3-yl)-4-(2-morpholin-4-yl-ethoxy)-phenyl]-(4-fluoro-phenyl)-amine; #814: [3-(4-Chloro-2-methyl-2H-pyrazol-3-yl)-4-(2-morpholin-4-yl-ethoxy)-phenyl]-(3-chloro-phenyl)-amine; #815: [3-(4-

Chloro-2-methyl-2H-pyrazol-3-yl)-4-(2-morpholin-4-yl-ethoxy)-phenyl]-(3-fluoro-phenyl)-amine; #816: [3-(4-Chloro-2-methyl-2H-pyrazol-3-yl)-4-(2-morpholin-4-yl-ethoxy)-phenyl]-(3,4-difluoro-phenyl)-amine; #817: [3-(4-Chloro-2-methyl-2H-pyrazol-3-yl)-4-(2-morpholin-4-yl-ethoxy)-phenyl]-(4-trifluoromethoxy-phenyl)-amine; #818: [3-(4-Chloro-2-methyl-2H-pyrazol-3-yl)-4-(2-morpholin-4-yl-ethoxy)-phenyl]-pyridin-3-yl-amine; #819: 1-{3-(4-Bromo-2-methyl-2H-pyrazol-3-yl)-4-[2-(1-methyl-piperidin-4-yl)-ethoxy]-phenyl}-3-(4-chloro-phenyl)-urea; #820: Thiophene-2-carboxylic acid [3-(4-bromo-2-methyl-2H-pyrazol-3-yl)-4-(2-pyrrolidin-1-yl-ethoxy)-phenyl]-amide; #821: N-[3-(4-Bromo-2-methyl-2H-pyrazol-3-yl)-4-(2-pyrrolidin-1-yl-ethoxy)-phenyl]-4-fluoro-benzamide; #822: N-[3-(4-Bromo-2-methyl-2H-pyrazol-3-yl)-4-(2-pyrrolidin-1-yl-ethoxy)-phenyl]-2-(4-chloro-phenyl)-acetamide; #823: 3,4-Dichloro-N-[3-(2-methyl-2H-pyrazol-3-yl)-4-(2-piperidin-1-yl-ethoxy)-phenyl]-benzamide; #824: N-[3-(2-Methyl-2H-pyrazol-3-yl)-4-(2-piperidin-1-yl-ethoxy)-phenyl]-4-trifluoromethyl-benzamide; #825: N-[3-(4-Bromo-2-methyl-2H-pyrazol-3-yl)-4-(2-piperidin-1-yl-ethoxy)-phenyl]-3-fluoro-benzamide; #826: 4-Fluoro-N-[4-[2-(4-methoxy-piperidin-1-yl)-ethoxy]-3-(2-methyl-2H-pyrazol-3-yl)-phenyl]-3-trifluoromethyl-benzamide; #827: N-[4-[2-(8-Acetyl-3,8-diaza-bicyclo[3.2.1]oct-3-yl)-ethoxy]-3-(2-methyl-2H-pyrazol-3-yl)-phenyl]-3-fluoro-benzamide; #828: N-[4-[2-(3-Acetyl-3,8-diaza-bicyclo[3.2.1]oct-8-yl)-ethoxy]-3-(2-methyl-2H-pyrazol-3-yl)-phenyl]-3-fluoro-benzamide; #829: N-[4-[2-(8-Acetyl-3,8-diaza-bicyclo[3.2.1]oct-3-yl)-ethoxy]-3-(2-methyl-2H-pyrazol-3-yl)-phenyl]-3-methoxy-benzamide; #830: N-[4-[2-(3-Acetyl-3,8-diaza-bicyclo[3.2.1]oct-8-yl)-ethoxy]-3-(2-methyl-2H-pyrazol-3-yl)-phenyl]-3-methoxy-benzamide; #831: (S)-3-[4-[3-(2,4-Difluoro-phenyl)-ureido]-2-(2-methyl-2H-pyrazol-3-yl)-phenoxy]-pyrrolidine-1-carboxylic acid tert-butyl ester; #832: (R)-3-[4-[3-(4-Chloro-phenyl)-ureido]-2-(2-methyl-2H-pyrazol-3-yl)-phenoxy]-pyrrolidine-1-carboxylic acid tert-butyl ester; #833: (R)-2-[4-[3-(2,4-Difluoro-phenyl)-ureido]-2-(2-methyl-2H-pyrazol-3-yl)-phenoxymethyl]-pyrrolidine-1-carboxylic acid tert-butyl ester; #834: (R)-2-[4-[3-(4-Fluoro-phenyl)-ureido]-2-(2-methyl-2H-pyrazol-3-yl)-phenoxymethyl]-pyrrolidine-1-carboxylic acid tert-butyl ester; #835: 1-(4-Chloro-phenyl)-3-[3-(2-methyl-2H-pyrazol-3-yl)-4-((R)-pyrrolidin-3-yloxy)-phenyl]-urea; and #836: 1-(4-Fluoro-phenyl)-3-[3-(2-methyl-2H-pyrazol-3-yl)-4-((S)-1-pyrrolidin-2-ylmethoxy)-phenyl]-urea.

Additionally, individual compounds and chemical genera of the present invention, such as Formula (Ia) and related Formulae therefrom, encompass all pharmaceutically acceptable salts, solvates, and particularly hydrates, thereof.

It is understood that the present invention embraces each diastereomer, each enantiomer and mixtures thereof of each compound and generic Formulae disclosed herein just as if they were each individually disclosed with the specific stereochemical designation for each chiral atom, for example carbon.

Figure 2:
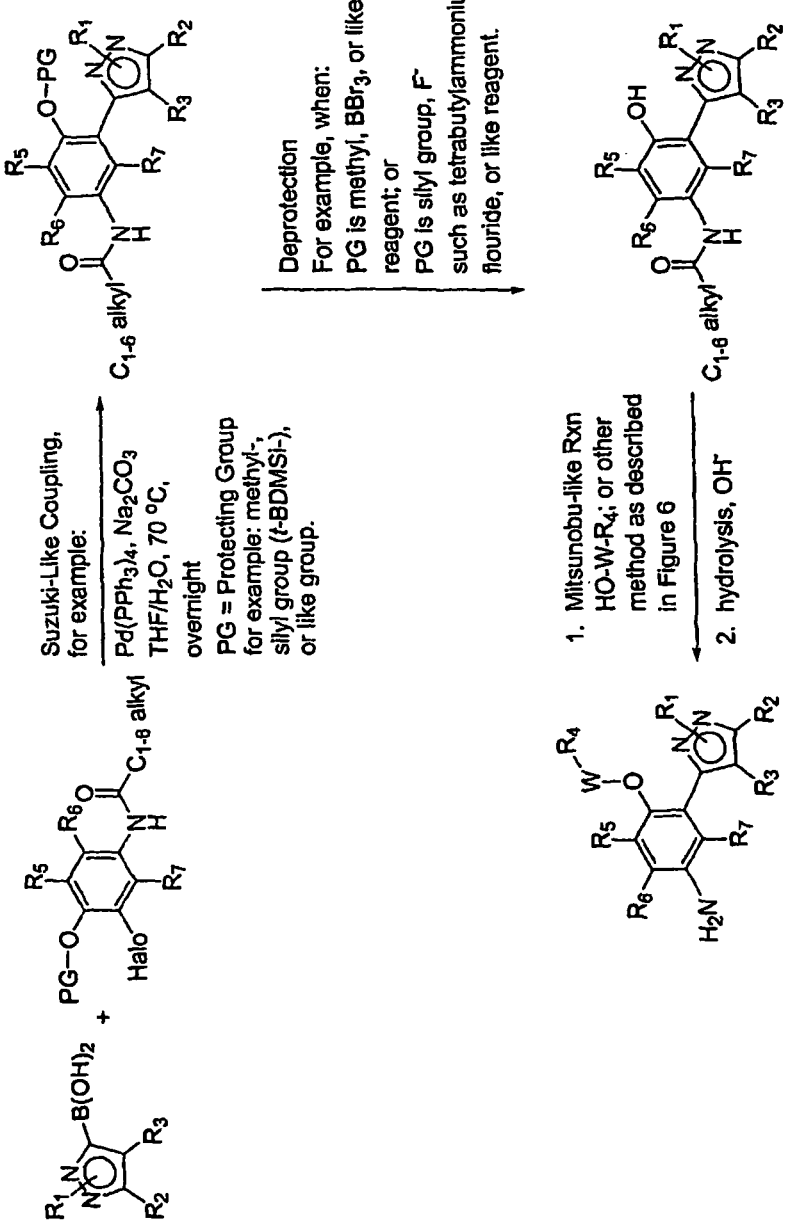
FIG. 2 shows the general synthetic scheme for the preparation of intermediate compounds of the present invention wherein "V" is oxygen.
Figure 3:
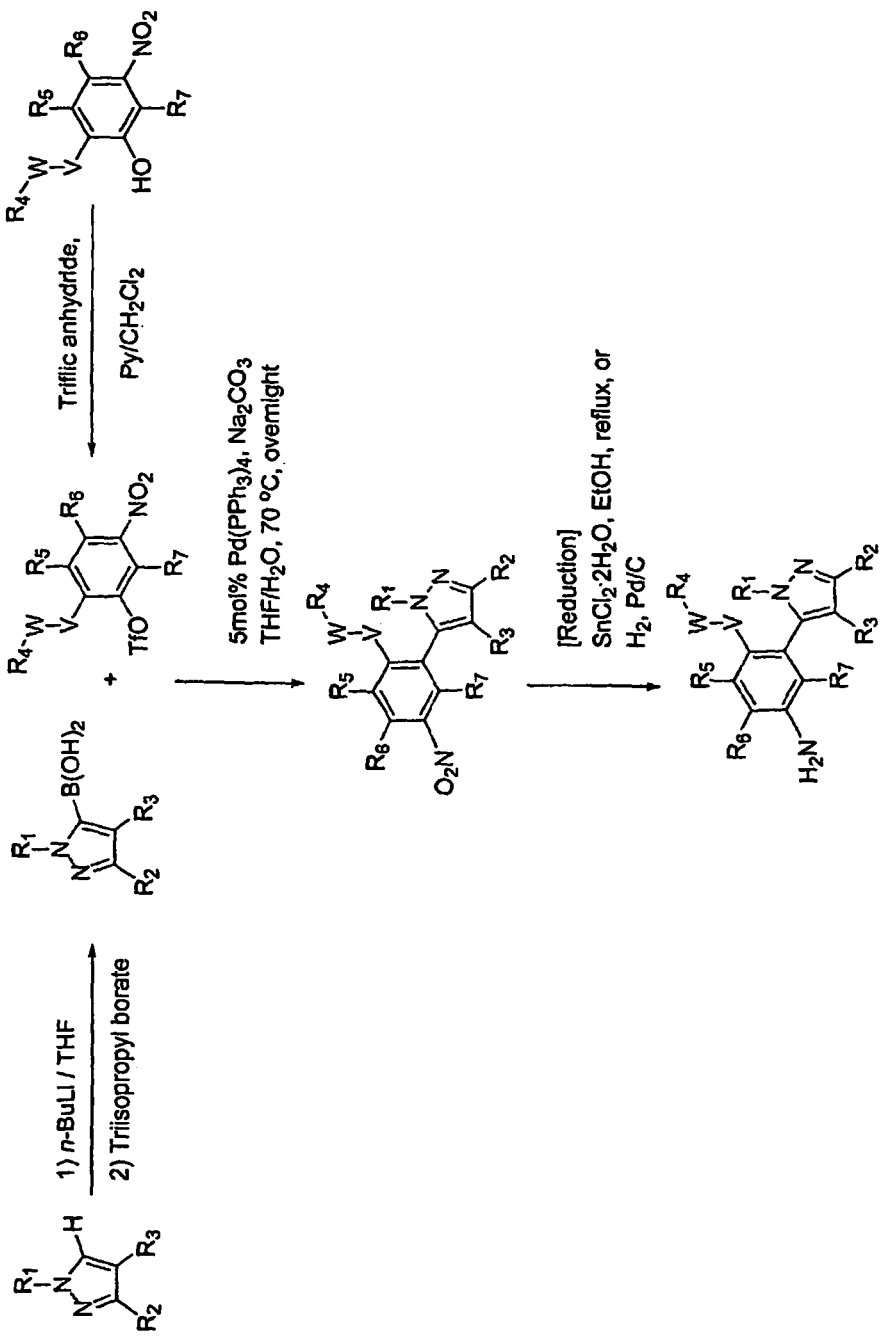
FIG. 3 shows the general synthetic scheme for the preparation of intermediate compounds of the present invention.
Figure 4:
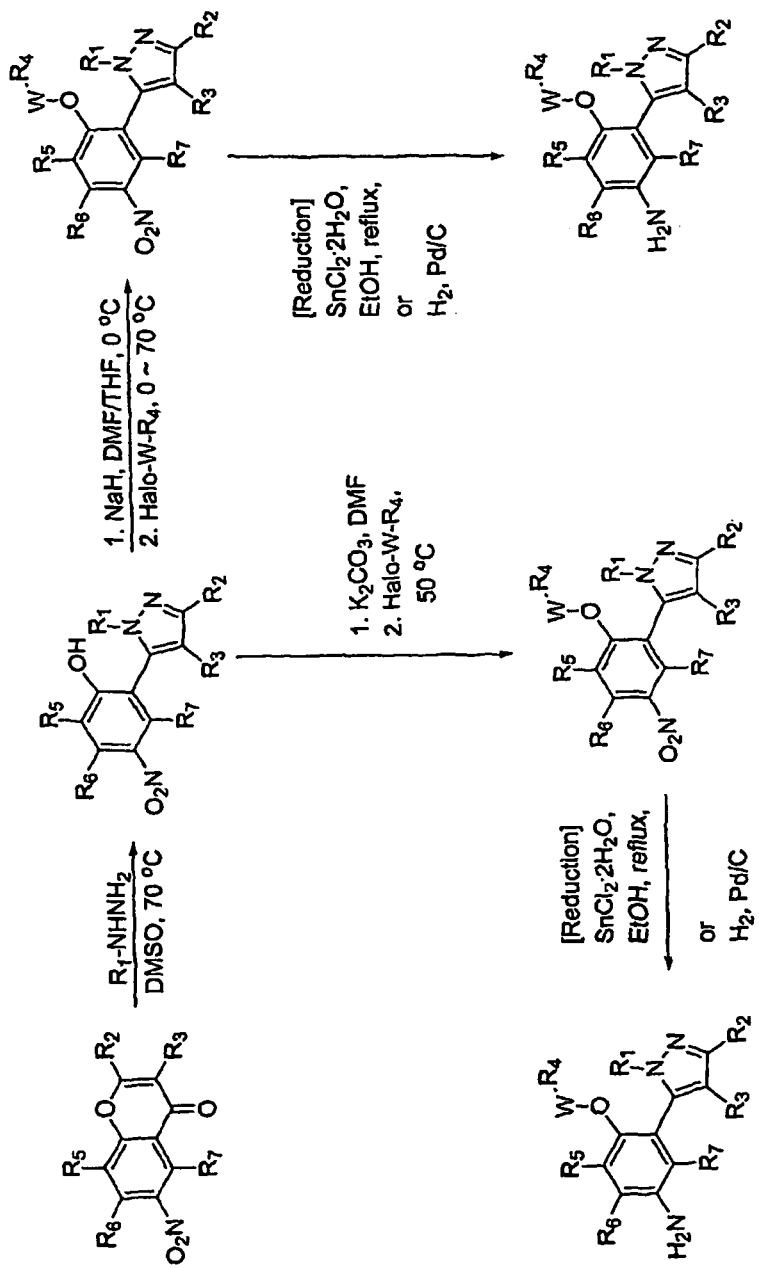
FIG. 4 shows the general synthetic scheme for the preparation of intermediate compounds of the present invention.
Figure 5:
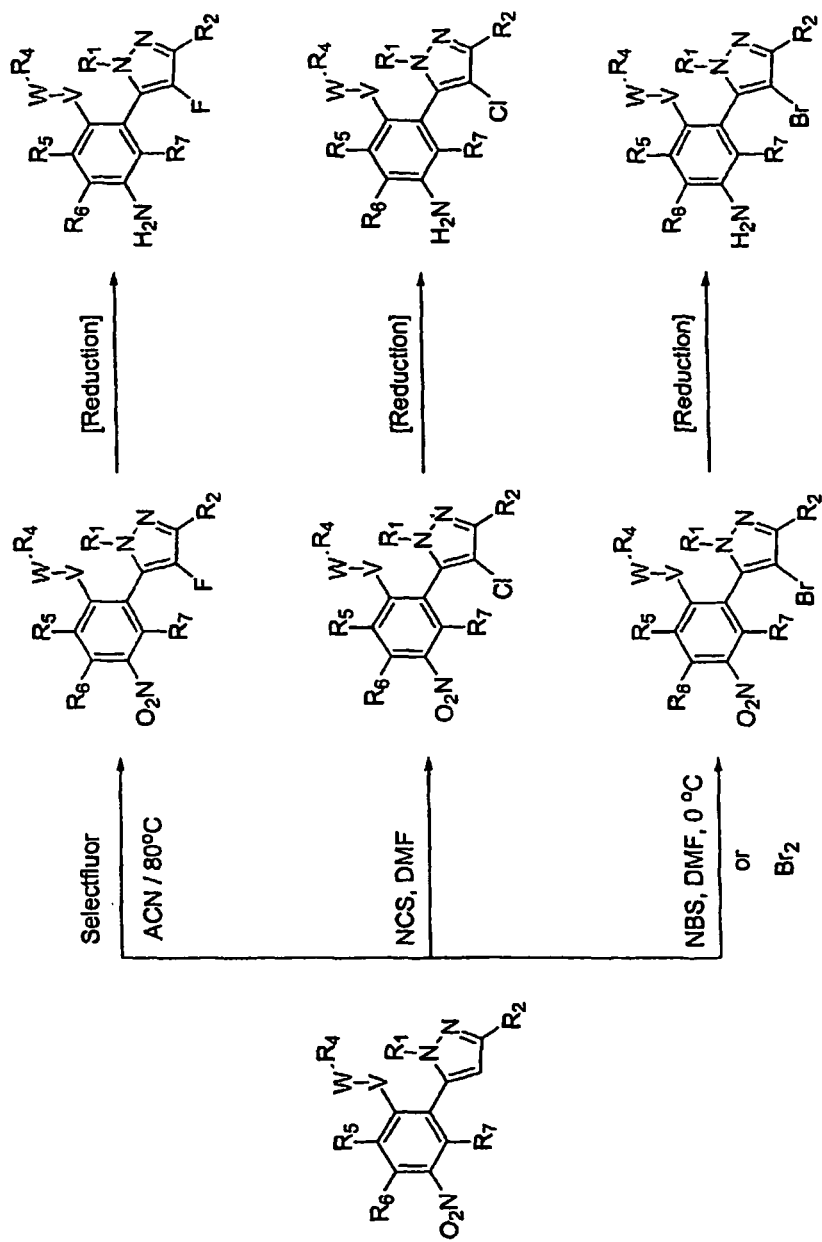
FIG. 5 shows the general synthetic scheme for the preparation of intermediate compounds of the present invention.
Figure 6:
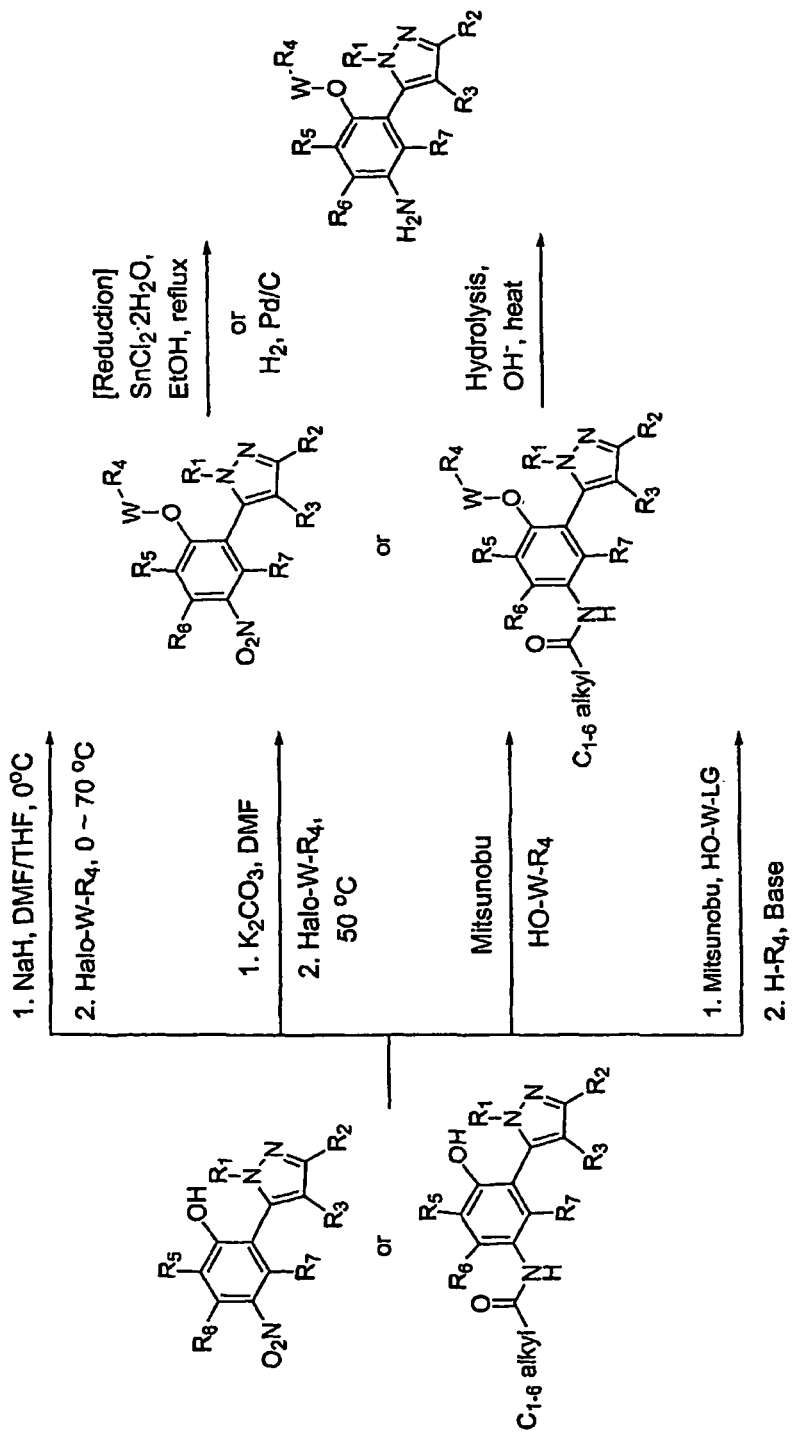
FIG. 6 shows the general synthetic scheme for the preparation of intermediate compounds of the present invention.
Figure 7:
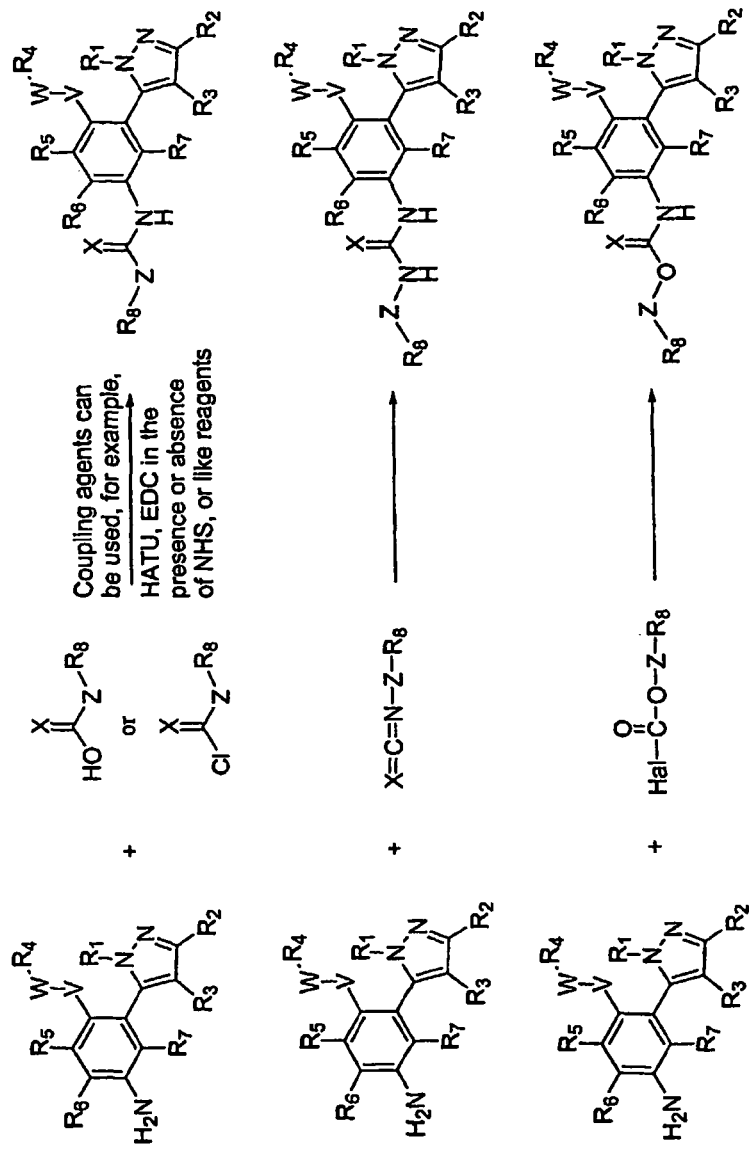
FIG. 7 shows the general synthetic scheme for the preparation of compounds of the present invention.
Figure 8:
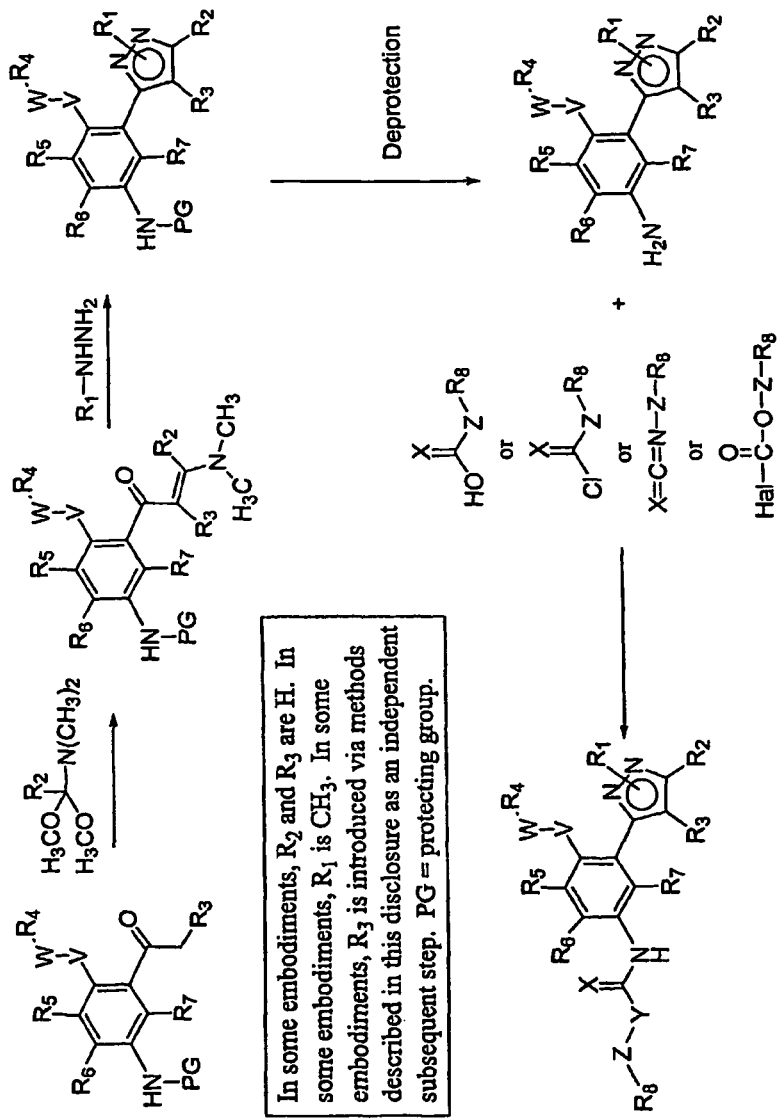
FIG. 8 shows the general synthetic scheme for the preparation of intermediates and compounds of the present invention.
Figure 9:
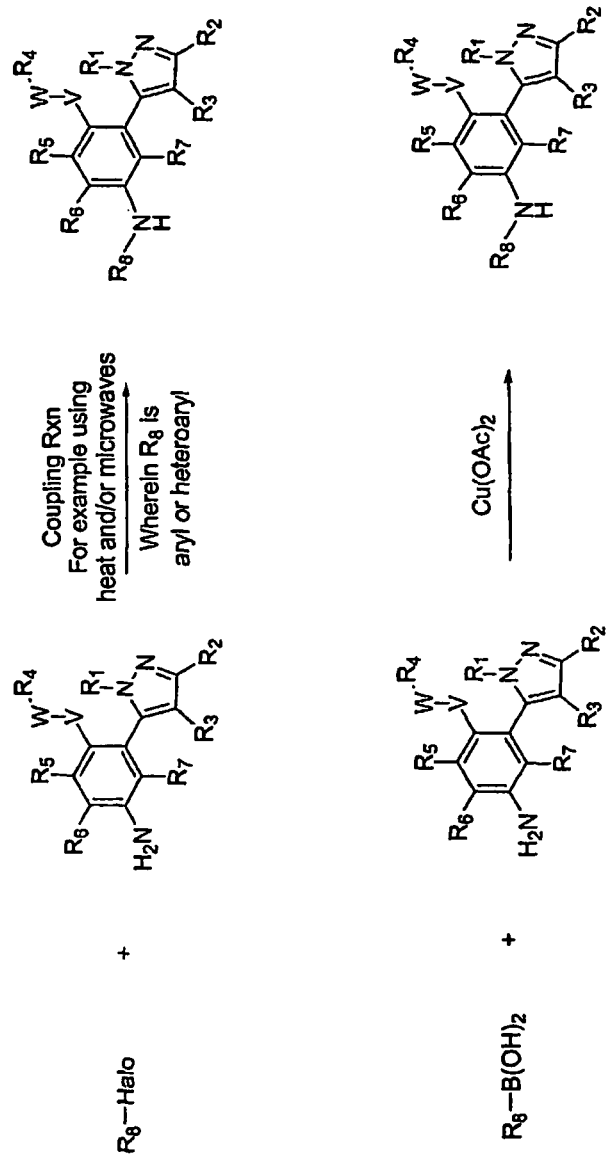
FIG. 9 shows the general reaction for the preparation of diaryl amines and heteroaryl-aryl amines.
Figure 10:
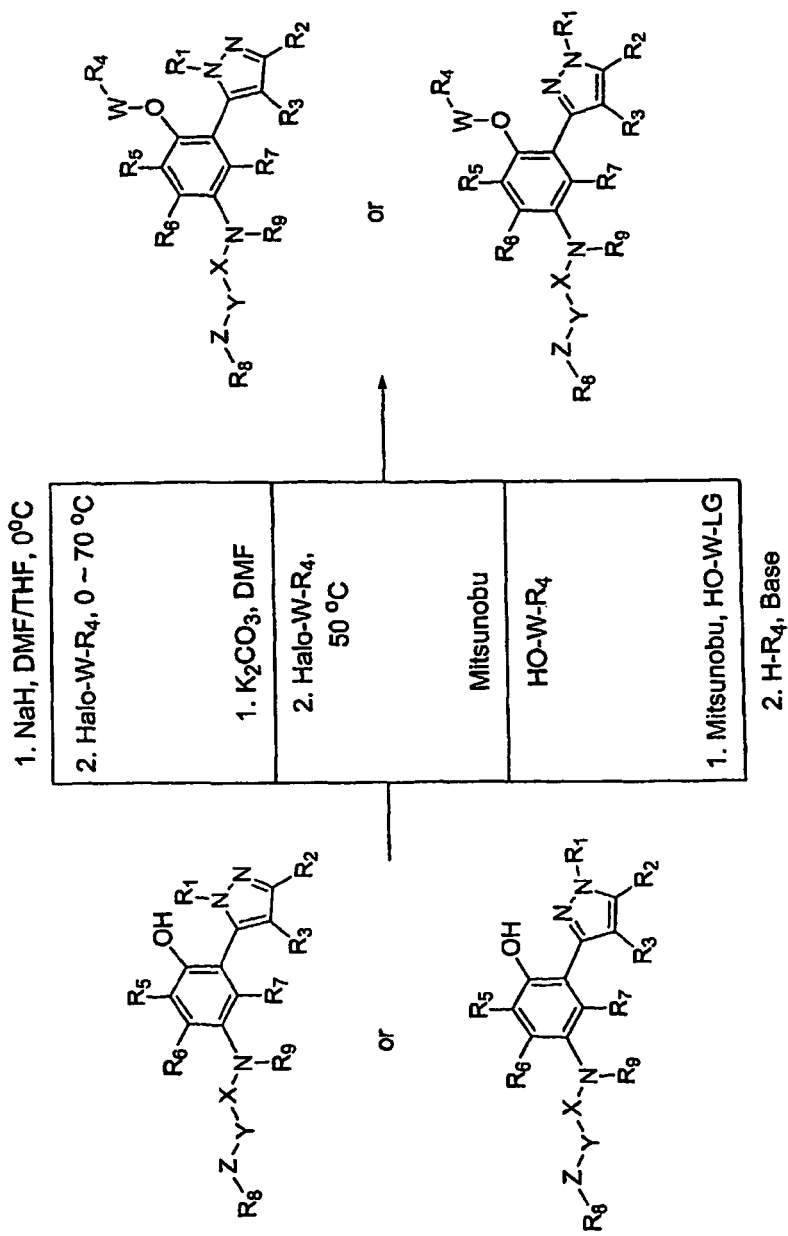
FIG. 10 shows the general synthetic scheme for the preparation of compounds of the invention wherein the W—R$_4$ group is introduced in the last step(s).
Figure 11:
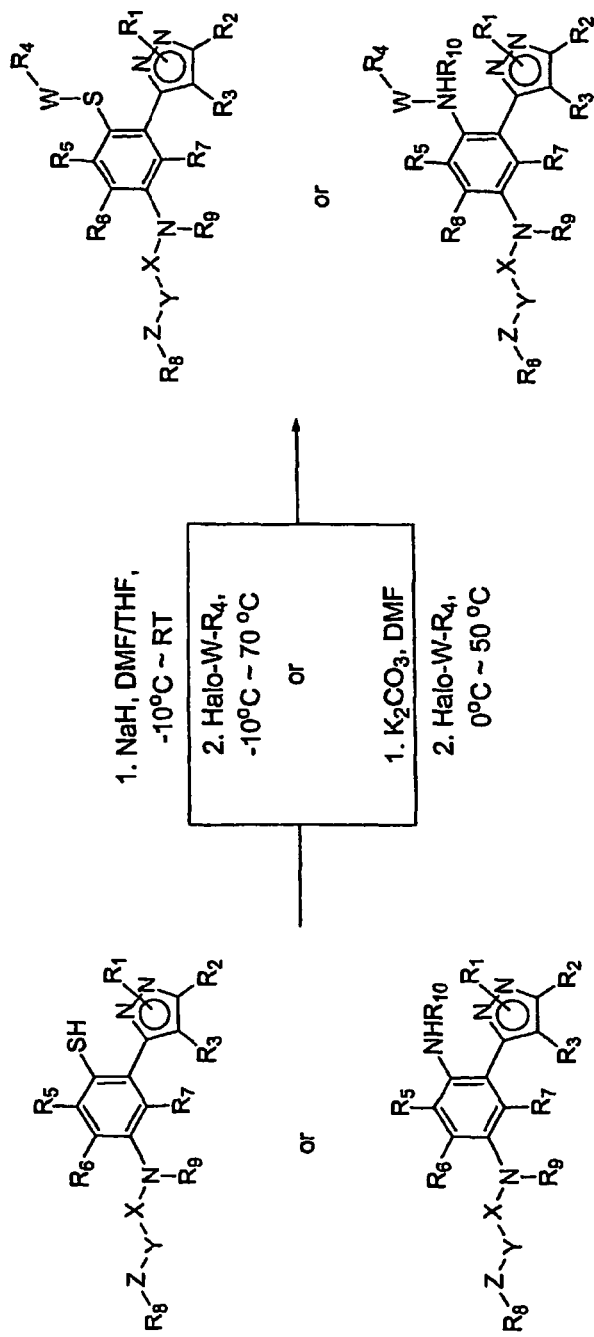
FIG. 11 shows the general synthetic scheme for the preparation of compounds of the invention wherein V is S or NR$_{10}$ and the W—R$_4$ group is introduced in the last step(s).
Figure 12:
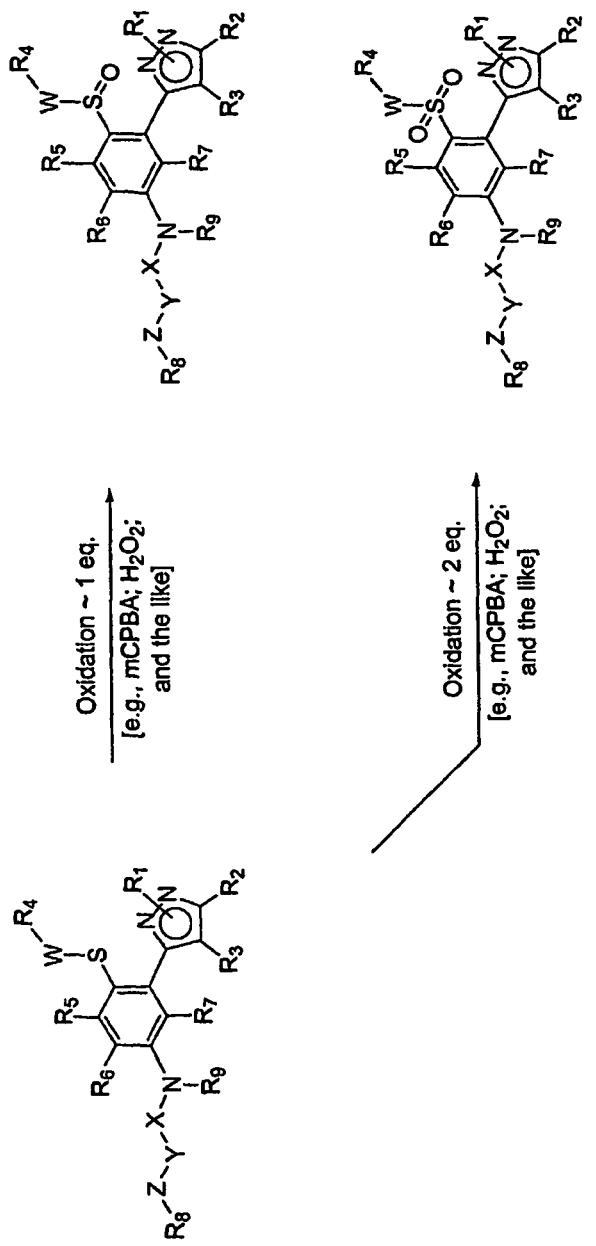
FIG. 12 shows the general synthetic scheme for the preparation of compounds of the invention wherein V is S(O) or S(O)$_2$.

The compounds of the Formula (Ia) of the present invention can be prepared according to the general synthetic schemes in FIGS. 1 through 12 as well as relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., Protecting Groups in Organic Synthesis, 3$^{rd}$ Edition, 1999 [Wiley]; incorporated herein by reference in its entirety).

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers (such as, chiral HPLC, recrystallization of diastereomeric mixture, and the like) or selective synthesis (such as, enantiomeric selective synthesis, and the like) of the individual isomers is accomplished by application of various methods which are well known to practitioners in the art.

Indications and Methods of Treatment

In addition to the foregoing beneficial uses for the modulators of 5-HT$_{2A}$ receptor activity disclosed herein, the compounds disclosed herein are believed to be useful in the treatment of several additional diseases and disorders, and in the amelioration of symptoms thereof. Without limitation, these include the following:

1. Antiplatelet Therapies (Conditions Related to Platelet Aggregation):

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood as a result of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-HT$_{2A}$ receptors are expressed on smooth muscle of blood vessels and 5-HT secreted by activated platelets causes vasoconstriction as well as activation of additional platelets during clotting. There is evidence that a 5-HT$_{2A}$ inverse agonist will inhibit platelet aggregation and thus be a potential treatment as an antiplatelet therapy (see Satimura, K, et al., Clin Cardiol 2002 Jan. 25 (1):28-32; and Wilson, H. C et al., Thromb Haemost 1991 Sep. 2; 66(3):355-60).

5-HT$_{2A}$ inverse agonists can be used to treat, for example, claudication or peripheral artery disease as well as cardiovascular complications (see Br. Med. J. 298: 424-430, 1989), Arterial thrombosis (see, Pawlak, D. et al. Thrombosis Research 90: 259-270, 1998), atherosclerosis (see, Hayashi, T. et al. Atherosclerosis 168: 23-31, 2003), vasoconstriction, caused by serotonin (see, Fujiwara, T. and Chiba, S. Journal of Cardiovascular Pharmacology 26: 503-510, 1995), restenosis of arteries following angioplasty or stent placement (see, Fujita, M. et al. Am Heart J. 145:e16 2003). It can also be used alone or in combination with thrombolytic therapy, for example, tPA (see, Yamashita, T. et al. Haemostasis 30:321-332, 2000), to provide cardioprotection following MI or postischemic myocardial dysfunction (see, Muto, T. et al. Mol. Cell. Biochem. 272: 119-132, 2005) or protection from ischemic injury during percutaneous coronary intervention (see, Horibe, E. Circulation Research 68: 68-72, 2004), and the like, including complications resulting therefrom.

5-HT$_{2A}$ inverse antagonists can increase circulating adiponectin in patients, suggesting that they would also be useful in protecting patients against indications that are linked to adiponectin, for example, myocardial ischemia reperfusion injury and arteriosclerosis (see Nomura, Shosaku, et al. Blood Coagulation and Fibrinolysis 2005, 16, 423-428).

The 5-HT$_{2A}$ inverse agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof comprising administering to the patient a composition comprising a 5-HT$_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a 5-HT$_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a 5-HT$_{2A}$ inverse agonist disclosed herein at a time where such risk exists.

2. Asthma

5-HT (5-hydroxytryptamine) has been linked to the pathophysiology of acute asthma (see Cazzola, M. and Matera, M. G., TIPS, 2000, 21, 13; and De Bie, J. J. et al., British J. Pharm., 1998, 124, 857-864). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a 5-HT$_{2A}$ inverse agonist disclosed herein. In further embodiments, methods are provided for treating a symptom of asthma in a patient in need of the treatment, comprising administering to the patient a composition comprising a 5-HT$_{2A}$ inverse agonist disclosed herein.

3. Agitation

Agitation is a well-recognized behavioral syndrome with a range of symptoms, including hostility, extreme excitement, poor impulse control, tension and uncooperativeness (See Cohen-Mansfield J, and Billig, N., (1986), Agitated Behaviors in the Elderly. I. A Conceptual Review. J Am Geriatr Soc 34(10): 711-721).

Agitation is a common occurrence in the elderly and often associated with dementia such as those caused by Alzheimer's disease, Lewy Body, Parkinson's, and Huntington's, which are degenerative diseases of the nervous system and by diseases that affect blood vessels, such as stroke, or multi-infarct dementia, which is caused by multiple strokes in the brain can also induce dementia. Alzheimer's disease accounts for approximately 50 to 70% of all dementias (See Koss E, et al., (1997), Assessing patterns of agitation in Alzheimer's disease patients with the Cohen-Mansfield Agitation Inventory. The Alzheimer's Disease Cooperative Study. Alzheimer Dis Assoc Disord 11(suppl 2):S45-S50).

An estimated five percent of people aged 65 and older and up to 20 percent of those aged 80 and older are affected by dementia; of these sufferers, nearly half exhibit behavioral disturbances, such as agitation, wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the 5-HT$_{2A}$ receptors in the brain have the effects of reducing agitation in patients, including Alzheimer's dementia (See Katz, I. R., et al., J Clin Psychiatry 1999 February, 60(2): 107-115; and Street, J. S., et al., Arch Gen Psychiatry 2000 October, 57(10):968-976).

The compounds of the invention disclosed herein are useful for treating agitation and symptoms thereof. Thus, in some embodiments, the present invention provides methods for treating agitation in a patient in need of such treatment comprising administering to the patient a composition comprising a 5-HT$_{2A}$ inverse agonist disclosed herein. In some embodiments, the agitation is due to a psychiatric disorder other than dementia. In some embodiments, the present invention provides methods for treatment of agitation or a symptom thereof in a patient suffering from dementia comprising administering to the patient a composition comprising a 5-HT$_{2A}$ inverse agonist disclosed herein. In some embodiments of such methods, the dementia is due to a degenerative disease of the nervous system, for example and without limitation, Alzheimers disease, Lewy Body, Parkinson's disease, and Huntington's disease, or dementia due to diseases that affect blood vessels, including, without limitation, stroke and multi-infarct dementia. In some embodiments, methods are provided for treating agitation or a symptom thereof in a patient in need of such treatment, where the patient is a cognitively intact elderly patient, comprising administering to the patient a composition comprising a 5-HT$_{2A}$ inverse agonist disclosed herein.

4. Add-on Therapy to Haloperidol in the Treatment of Schizophrenia and Other Disorders:

Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of interhuman relationships, and finally psychomotoric disorders (such as catatonia). Other symptoms are also associated with this disorder. (See, American Statistical and Diagnostic Handbook).

Haloperidol (Haldol) is a potent dopamine $D_2$ receptor antagonist. It is widely prescribed for acute schizophrenic symptoms, and is very effective for the positive symptoms of schizophrenia. However, Haldol is not effective for the negative symptoms of schizophrenia and may actually induce negative symptoms as well as cognitive dysfunction. In accordance with some methods of the invention, adding a 5-$HT_{2A}$ inverse agonist concomitantly with Haldol will provide benefits including the ability to use a lower dose of Haldol without losing its effects on positive symptoms, while reducing or eliminating its inductive effects on negative symptoms, and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, huntington's chorea, and nausea and vomiting from chemotherapy and chemotherapeutic antibodies. Administration of 5-$HT_{2A}$ inverse agonists disclosed herein with haloperidol also will provide benefits in these indications.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient a dopamine $D_2$ receptor antagonist and a 5-$HT_{2A}$ inverse agonist disclosed herein.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient haloperidol and a 5-$HT_{2A}$ inverse agonist disclosed herein.

In some embodiments, the present invention provides methods for treating infantile autism, huntington's chorea, or nausea and vomiting from chemotherapy or chemotherapeutic antibodies comprising administering to the patient a dopamine $D_2$ receptor antagonist and a 5-$HT_{2A}$ inverse agonist disclosed herein.

In some embodiments, the present invention provides methods for treating infantile autism, huntington's chorea, or nausea and vomiting from chemotherapy or chemotherapeutic antibodies comprising administering to the patient haloperidol and a 5-$HT_{2A}$ inverse agonist disclosed herein.

In further embodiments, the present invention provides methods for treating schizophrenia in a patient in need of the treatment comprising administering to the patient a dopamine $D_2$ receptor antagonist and a 5-$HT_{2A}$ inverse agonist disclosed herein. Preferably, the dopamine $D_2$ receptor antagonist is haloperidol.

The administration of the dopamine $D_2$ receptor antagonist can be concomitant with administration of the 5-$HT_{2A}$ inverse agonist, or they can be administered at different times. Those of skill in the art will easily be able to determine appropriate dosing regimes for the most efficacious reduction or elimination of deleterious haloperidol effects. In some embodiments, haloperidol and the 5-$HT_{2A}$ inverse agonist are administered in a single dosage form, and in other embodiments, they are administered in separate dosage forms.

The present invention further provides methods of alleviating negative symptoms of schizophrenia induced by the administration of haloperidol to a patient suffering from schizophrenia, comprising administering to the patient a 5-$HT_{2A}$ inverse agonist as disclosed herein.

5. Sleep Disorders

It is reported in the National Sleep Foundation's 2002 Sleep In America Poll, more than one-half of the adults surveyed (58%) report having experienced one or more symptoms of insomnia at least a few nights a week in the past year. Additionally, about three in ten (35%) say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, compounds of the present invention are effective, for example, in any one or more of the following sleep disorders (ICSD—International Classification of Sleep Disorders: Diagnostic and Coding Manual. *Diagnostic Classification Steering Committee*, American Sleep Disorders Association, 1990):

A. Dyssomnias a. Intrinsic Sleep Disorders:

Psychophysiological insomnia, Sleep state misperception, Idiopathic insomnia, Obstructive sleep apnea syndrome, Central sleep apnea syndrome, Central alveolar hypoventilation syndrome, Periodic limb movement disorder, Restless leg syndrome and Intrinsic sleep disorder NOS.

b. Extrinsic Sleep Disorders:

Inadequate sleep hygiene, Environmental sleep disorder, Altitude insomnia, Adjustment sleep disorder, Insufficient sleep syndrome, Limit-setting sleep disorder, SleepOnset association disorder, Nocturnal eating (drinking) syndrome, Hypnotic dependent sleep disorder, Stimulant-dependent sleep disorder, Alcohol-dependent sleep disorder, Toxin-induced sleep disorder and Extrinsic sleep disorder NOS.

c. Circadian Rhythm Sleep Disorders:

Time zone change (jet lag) syndrome, Shift work sleep disorder, Irregular sleep-wake pattern, Delayed sleep phase syndrome, Advanced sleep phase syndrome, Non-24-hour sleep-wake disorder and Circadian rhythm sleep disorder NOS.

B. Parasomnias a. Arousal Disorders:

Confusional arousals, Sleepwalking and Sleep terrors.

b. Sleep-Wake Transition Disorders:

Rhythmic movement disorder, Sleep starts, Sleep talking and Nocturnal leg cramps.

C. Sleep Disorders Associated with Medical/Psychiatric Disorders a. Associated with Mental Disorders:

Psychoses, Mood disorders, Anxiety disorders, Panic disorders and Alcoholism.

b. Associated with Neurological Disorders:

Cerebral degenerative disorders, Dementia, Parkinsonism, Fatal familial insomnia, Sleep-related epilepsy, Electrical status epilepticus of sleep and Sleep-related headaches.

c. Associated with Other Medical Disorders:

Sleeping sickness, Nocturnal cardiac ischemia, Chronic obstructive pulmonary disease, Sleep-related asthma, Sleep-related gastroesophageal reflux, Peptic ulcer disease, Fibrositis syndrome, Osteoarthritis, Rheumatoid arthritis, Fibromyalgia and Post-surgical.

The effects of sleep deprivation are more than excessive daytime sleepiness. Chronic insomniacs report elevated levels of stress, anxiety, depression and medical illnesses (National Institutes of Health, National Heart, Lung, and Blood Institute, *Insomnia Facts Sheet*, October 1995). Preliminary evidence suggests that having a sleep disorder that causes significant loss of sleep may contribute to increased susceptibility to infections due to immunosuppression, cardiovascular complications such as hypertension, cardiac arrhythmias, stroke, and myocardial infarction, compromised glucose tolerance, increased obesity and metabolic syndrome. Compounds of the present invention are useful to prevent or alleviate these complications by improving sleep quality.

The most common class of medications for the majority of sleep disorders are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as are compounds of the present invention have demonstrated significant improvements on objective and subjective sleep parameters in normal, healthy volunteers as well as patients with sleep disorders and mood disorders [Sharpley A L, et al. Slow Wave Sleep in Humans: Role of 5-$HT_{2A}$ and $5HT_{2C}$ Receptors. *Neuropharmacology*, 1994, Vol. 33(3/4):467-71; Winokur A, et al. Acute Effects of Mirtazapine on Sleep Continuity and Sleep Architecture in Depressed Patients: A Pilot Study. *Soc of Biol Psych*, 2000, Vol. 48:75-78; and Landolt H P, et al. Serotonin-2 Receptors and Human Sleep: Effect of Selective Antagonist on EEG Power Spectra. *Neuropsychopharmacology*, 1999, Vol. 21(3):455-66].

Some sleep disorders are sometimes found in conjunction with other conditions and accordingly those conditions are treatable by compounds of Formula (Ia). For example, but not limited to, patients suffering from mood disorders typically suffer from a sleep disorder that can be treatable by compounds of Formula (Ia). Having one pharmacological agent which treats two or more existing or potential conditions, as does the present invention, is more cost effective, leads to better compliance and has fewer side effects than taking two or more agents.

It is an object of the present invention to provide a therapeutic agent for the use in treating Sleep Disorders. It is another object of the present invention to provide one pharmaceutical agent, which may be useful in treating two or more conditions wherein one of the conditions is a sleep disorder. Compounds of the present invention described herein may be used alone or in combination with a mild sleep inducer (i.e. antihistamine).

Sleep Architecture:

Sleep comprises two physiological states: Non rapid eye movement (NREM) and rapid eye movement (REM) sleep. NREM sleep consists of four stages, each of which is characterized by progressively slower brain wave patterns, with the slower patterns indicating deeper sleep. So called delta sleep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning the patient spends a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a Waking state by limited external stimuli. As a result, the individual cycles through frequent bouts of light sleep interrupted by frequent awakenings throughout the sleep period. Many sleep disorders are characterized by a fragmented sleep architecture. For example, many elderly patients with sleep complaints have difficulty achieving long bouts of deep refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly Stages 3 and 4, and the length of those sleep bouts are increased, while the number and length of waking bouts are decreased. In essence, the architecture of the sleep disorder patient is consolidated to a sleeping state with increased periods of sleep and fewer awakenings during the night and more time is spent in slow wave sleep (Stages 3 and 4) with fewer oscillation Stage 1 and 2 sleep. Compounds of the present invention can be effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall, and muscles relax. In normal sleep architecture, NREM sleep makes up about 75% of total sleep time; stage 1 accounting for 5-10% of total sleep time, stage 2 for about 45-50%, stage 3 approximately 12%, and stage 4 13-15%. About 90 minutes after sleep onset, NREM sleep gives way to the first REM sleep episode of the night. REM makes up approximately 25% of total sleep time. In contrast to NREM sleep, REM sleep is characterized by high pulse, respiration, and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable; a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep, and thus have a large build-up of Process S with limited ability to discharge this buildup during sleep. 5-$HT_{2A}$ agonists tested preclinically and clinically mimic the effect of sleep deprivation on delta power, suggesting that subjects with sleep disorders treated with a 5-$HT_{2A}$ inverse agonist or antagonist will be able to achieve deeper more refreshing sleep. These same effects have not been observed with currently marketed pharmacotherapies. In addition, currently marketed pharmacotherapies for sleep have side effects such as hangover effects or addiction that are associated with the GABA receptor. 5-$HT_{2A}$ inverse agonists do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the compounds of the invention can be useful for the treatment of the sleep disorders characterized by excessive daytime sleepiness such as narcolepsy. Inverse agonists at the serotonin 5-$HT_{2A}$ receptor improve the quality of sleep at nighttime which can decrease excessive daytime sleepiness.

Accordingly, another aspect of the present invention relates to the therapeutic use of compounds of the present invention for the treatment of Sleep Disorders. Compounds of the present invention are potent inverse agonists at the serotonin 5-$HT_{2A}$ receptor and can be effective in the treatment of Sleep Disorders by promoting one or more of the following: reducing the sleep onset latency period (measure of sleep induction), reducing the number of nighttime awakenings, and prolonging the amount of time in delta-wave sleep (measure of sleep quality enhancement and sleep consolidation) without effecting REM sleep. In addition, compounds of the present invention can be effective either as a monotherapy or in combination with sleep inducing agents, for example but not limited to, antihistamines.

6. Diabetic-Related Pathologies:

Although hyperglycemia is the major cause for the pathogenesis of diabetic complications such as diabetic peripheral neuropathy (DPN), diabetic nephropathy (DN) and diabetic retinopathy (DR), increased plasma serotonin concentration in diabetic patients has also been implicated to play a role in disease progression (Pietraszek, M. H., et al. *Thrombosis Res*. 1992, 66(6), 765-74; and Andrzejewska-Buczko J, et al., *Klin Oczna*. 1996; 98(2), 101-4). Scrotonin is believed to play a role in vasospasm and increased platelet aggregability. Improving microvascular blood flow is able to benefit diabetic complications.

A recent study by Cameron and Cotter in *Naunyn Schmiedebergs Arch Pharmacol*. 2003 June; 367(6):607-14, used a 5-$HT_{2A}$ antagonist experimental drug AT-1015, and other nonspecific 5-$HT_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarogrelate was evaluated for the prevention of the development or progression of diabetic nephropathy (Takahashi, T., et al., *Diabetes Res Clin Pract.* 2002 November; 58(2):123-9). In the trial of 24 months of treatment, sarpogrelate significantly reduced urinary albumin excretion level.

7. Glaucoma

Topical ocular administration of 5-HT2 receptor antagonists result in a decrease in intra ocular pressure (IOP) in monkeys (Chang et al., *J. Ocul Pharmacol* 1:137-147 (1985)) and humans (Mastropasqua et al., *Acta Ophthalmol Scand Suppl* 224:24-25 (1997)) indicating utility for similar compounds such as 5-$HT_{2A}$ inverse agonists in the treatment of ocular hypertension associated with glaucoma. The 5-HT2 receptor antagonist ketanserin (Mastropasqua supra) and sarpogrelate (Takenaka et al., *Investig Ophthalmol Vis Sci* 36:S734 (1995)) have been shown to significantly lower IOP in glaucoma patients.

8. Progressive Multifocal Leukoencephalopathy

Progressive multifocal leukoencephalopathy (PML) is a lethal demyelinating disease caused by an opportunistic viral infection of oligodendrocytes in immunocompromised patients. The causative agent is JC virus, a ubiquitous papovavirus that infects the majority of the population before adulthood and establishes a latent infection in the kidney. In immunocompromised hosts, the virus can reactivate and productively infect oligodendrocytes. This previously rare condition, until 1984 reported primarily in persons with underlying lymphoproliferative disorders, is now more common because it occurs in 4% of patients with AIDS. Patients usually present with relentlessly progressive focal neurologic defects, such as hemiparesis or visual field deficits, or with alterations in mental status. On brain MRI, one or more white matter lesions are present; they are hyperintense on T2-weighted images and hypointense on T1-weighted images. There is no mass effect, and contrast enhancement is rare. Diagnosis can be confirmed by brain biopsy, with demonstration of virus by in situ hybridization or immunocytochemistry. Polymerase chain reaction amplification of JC virus sequences from the CSF can confirm diagnosis without the need for biopsy [see, e.g., Antinori et al., *Neurology* (1997) 48:687-694; Berger and Major, *Seminars in Neurology* (1999) 19:193-200; and Portegies, et al., *Eur. J. Neurol.* (2004) 11:297-304]. Currently, there is no effective therapy. Survival after diagnosis is about 3 to 5 months in AIDS patients.

JC virus enters cells by receptor-mediated clathrin-dependent endocytosis. Binding of JC virus to human glial cells (e.g., oligodendrocytes) induces an intracellular signal that is critical for entry and infection by a ligand-inducible clathrin-dependent mechanism [Querbes et al., *J Virology* (2004) 78:250-256]. Recently, 5-$HT_{2A}$ was shown to be the receptor on human glial cells mediating infectious entry of JC virus by clathrin-dependent endocytosis [Elphick et al., *Science* (2004) 306:1380-1383]. 5-$HT_{2A}$ antagonists, including ketanserin and ritanserin, inhibited JC virus infection of human glial cells. Ketanserin and ritanserin have inverse agonist activity at 5-$HT_{2A}$.

5-$HT_{2A}$ antagonists including inverse agonists have been contemplated to be useful in the treatment of PML [Elphick et al., *Science* (2004) 306:1380-1383]. Prophylactic treatment of HIV-infected patients with 5-$HT_{2A}$ antagonists is envisioned to prevent the spread of JC virus to the central nervous system and the development of PML. Aggressive therapeutic treatment of patients with PML is envisioned to reduce viral spread within the central nervous system and prevent additional episodes of demyelination.

In some embodiments, methods are provided for treating progressive multifocal leukoencephalopathy in a patient in need of such treatment, comprising administering to the patient a composition comprising a 5-$HT_{2A}$ inverse agonist disclosed herein.

9. Hypertension

Serotonin has been observed to play an important role in the regulation of vascular tone, vasoconstriction, and pulmonary hypertension (see, Deuchar, G. et al. Pulm. Pharmacol. Ther. 18(1):23-31. 2005; and Marcos, E. et al. Circ. Res. 94(9):1263-70 2004). Ketanserin, a 5-HT2A inverse agonist, have been demonstrated to protect against circulatory shocks, intracranial hypertension, and cerebral ischemia during heatstroke (see, Chang, C. et al. Shock 24(4): 336-340 2005); and to stabilize blood pressure in spontaneously hypertensive rats (see, Miao, C. Clin. Exp. Pharmacol. Physiol. 30(3): 189-193). Mainserin, a 5-HT2A inverse agonist, has been shown to prevent DOCA-salt induced hypertension in rats (see, Silva, A. Eur, J. Pharmacol. 518(2-3): 152-7 2005).

10. Pain

5-HT2A inverse agonists are also effective for the treatment of pain. Sarpogrelate has been observed to provide a significant analgesic effect both on thermal induced pain in rats after intraperitoneal administration and on inflammatory pain in rats after either intrathecal or intraperitoneal administration (see, Nishiyama, T. Eur. J. Pharmacol. 516:18-22 2005). This same 5-HT2A inverse agonist in humans has been shown to be an effective treatment for lower back pain, leg pain and numbness associated with sciatica brought on by lumbar disc herniation (see, Kanayama, M. et al. J. Neurosurg: Spine 2:441-446 2005).

Representative Methods of the Invention:

One aspect of the present invention encompasses methods for modulating the activity of a 5-$HT_{2A}$ serotonin receptor by contacting the receptor with a compound according to any of the embodiments described herein or a pharmaceutical composition.

One aspect of the present invention encompasses methods for the treatment of platelet aggregation in an individual comprising administering to the individual in need thereof a therapeutically effective amount of a compound according to any of the embodiments described herein or a pharmaceutical composition.

One aspect of the present invention encompasses methods for the treatment of an indication selected from the group consisting of coronary artery disease, myocardial infarction, transient ischemic attack, angina, stroke, and atrial fibrillation in an individual comprising administering to the individual in need thereof a therapeutically effective amount of a compound according to any of the embodiments described herein or a pharmaceutical composition.

One aspect of the present invention encompasses methods for the treatment of reducing the risk of blood clot formation in an angioplasty or coronary bypass surgery individual comprising administering to the individual in need thereof a therapeutically effective amount of a compound according to any of the embodiments described herein or a pharmaceutical composition.

One aspect of the present invention encompasses methods for the treatment of reducing the risk of blood clot formation in an individual suffering from atrial fibrillation, comprising administering to the individual in need thereof a therapeutically effective amount of a compound according to any of the embodiments described herein or a pharmaceutical composition.

One aspect of the present invention encompasses methods for the treatment of asthma in an individual comprising administering to the individual in need thereof a therapeutically effective amount of a compound according to any of the embodiments described herein or a pharmaceutical composition.

One aspect of the present invention encompasses methods for the treatment of a symptom of asthma in an individual comprising administering to the individual in need thereof a therapeutically effective amount of a compound according to any of the embodiments described herein or a pharmaceutical composition.

One aspect of the present invention encompasses methods for the treatment of agitation or a symptom thereof in an individual comprising administering to the individual in need thereof a therapeutically effective amount of a compound according to any of the embodiments described herein or a pharmaceutical composition. In some embodiments, the individual is a cognitively intact elderly individual.

One aspect of the present invention encompasses methods for the treatment of agitation or a symptom thereof in an individual suffering from dementia comprising administering to the individual in need thereof a therapeutically effective amount of a compound according to any of the embodiments described herein or a pharmaceutical composition. In some embodiments, the dementia is due to a degenerative disease of the nervous system. In some embodiments, the dementia is Alzheimers disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention encompasses methods for the treatment of an individual suffering from at least one of the indications selected from the group consisting of behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to the individual in need thereof a therapeutically effective amount of a dopamine $D_2$ receptor antagonist and a compound according to any of the embodiments described herein or a pharmaceutical composition. In some embodiments, the dopamine $D_2$ receptor antagonist is haloperidol.

One aspect of the present invention encompasses methods for the treatment of an individual with infantile autism, Huntington's chorea, or nausea and vomiting from chemotherapy or chemotherapeutic antibodies comprising administering to the individual in need thereof a therapeutically effective amount of a dopamine $D_2$ receptor antagonist and a compound according to any of the embodiments described herein or a pharmaceutical composition. In some embodiments, the dopamine $D_2$ receptor antagonist is haloperidol.

One aspect of the present invention encompasses methods for the treatment of schizophrenia in an individual comprising administering to the individual in need thereof a therapeutically effective amount of a dopamine $D_2$ receptor antagonist and a compound according to any of the embodiments described herein or a pharmaceutical composition. In some embodiments, the dopamine $D_2$ receptor antagonist is haloperidol.

One aspect of the present invention encompasses methods for the treatment of alleviating negative symptoms of schizophrenia induced by the administration of haloperidol to an individual suffering from the schizophrenia, comprising administering to the individual in need thereof a therapeutically effective amount of a compound according to any of the embodiments described herein or a pharmaceutical composition. In some embodiments, the haloperidol and the compound or pharmaceutical composition are administered in separate dosage forms. In some embodiments, the haloperidol and the compound or pharmaceutical composition are administered in a single dosage form.

One aspect of the present invention encompasses methods for the treatment of a sleep disorder in an individual comprising administering to the individual in need thereof a therapeutically effective amount of a compound according to any of the embodiments described herein or a pharmaceutical composition.

In some embodiments, the sleep disorder is a dyssomnia. In some embodiments, the dyssomnia is selected from the group consisting of psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome, and non-24-hour sleep-wake disorder.

In some embodiments, the sleep disorder is a parasomnia. In some embodiments, the parasomnia is selected from the group consisting of confusional arousals, sleepwalking and sleep terrors, rhythmic movement disorder, sleep starts, sleep talking and nocturnal leg cramps. In some embodiments, the sleep disorder is characterized by excessive daytime sleepiness such as narcolepsy.

In some embodiments, the sleep disorder is associated with a medical or psychiatric disorder. In some embodiments, the medical or psychiatric disorder is selected from the group consisting of psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

One aspect of the present invention encompasses methods for the treatment of a diabetic-related disorder in an individual comprising administering to the individual in need thereof a therapeutically effective amount of a compound according to any of the embodiments described herein or a pharmaceutical composition.

In some embodiments, the diabetic-related disorder is diabetic peripheral neuropathy.

In some embodiments, the diabetic-related disorder is diabetic nephropathy.

In some embodiments, the diabetic-related disorder is diabetic retinopathy.

One aspect of the present invention encompasses methods for the treatment of glaucoma or other diseases of the eye with abnormal intraocular pressure.

One aspect of the present invention encompasses methods for the treatment of progressive multifocal leukoencephalopathy in an individual comprising administering to the individual in need thereof a therapeutically effective amount of a compound according to any of the embodiments described herein or a pharmaceutical composition.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a myeloproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of ≤200/mm$^3$. In some embodiments, the HIV-infected individual has AIDS. In some embodiments, the HIV-infected individual has AIDS-related complex (ARC). In certain embodiments, ARC is defined as the presence of two successive CD4+ cell counts below 200/mm$^3$ and at least two of the following signs or symptoms: oral hairy leukoplakia, recurrent oral candidiasis, weight loss of at least 2.5 kg or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn. Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann Thorac Surg* (2004) 77:354-362; and Krieger and Emre, *Pediatr Transplantation* (2004) 8:594-599]. In some embodiments, the immunosuppressive therapy comprises administering an immunosuppressive agent selected from the group consisting of: corticosteroids (for example, prednisone and the like), calcineurin inhibitors (for example, cyclosporine, tacrolimus, and the like), antiproliferative agents (for example, azathioprine, mycophenolate mofetil, sirolimus, everolimus, and the like), T-cell depleting agents (for example, OKT®3 monoclonal antibody (mAb), anti-CD3 immunotoxin FN18-CRM9, Campath-1H (anti-CD52) mAb, anti-CD4 mAb, anti-T cell receptor mAb, and the like), anti-IL-2 receptor (CD25) mAb (for example, basiliximab, daclizumab, and the like), inhibitors of co-stimulation (for example, CTLA4-Ig, anti-CD154 (CD40 ligand) mAb, and the like), deoxyspergualin and analogs thereof (for example, 15-DSG, LF-08-0299, LF14-0195, and the like), leflunomide and analogs thereof (for example, leflunomide, FK778, FK779, and the like), FTY720, anti-alpha-4-integrin monoclonal antibody, and anti-CD45 RB monoclonal antibody. In some embodiments, the immunosuppressive agent and said compound or pharmaceutical composition are administered in separate dosage forms. In some embodiments, the immunosuppressive agent and said compound or pharmaceutical composition are administered in a single dosage form.

In some embodiments, the individual in need thereof is undergoing immunosuppressive therapy after organ transplantation. In some embodiments, the organ is liver, kidney, lung, heart, or the like [see, e.g., Singh et al., *Transplantation* (2000) 69:467-472].

In some embodiments, the individual in need thereof is undergoing treatment for a rheumatic disease. In some embodiments, the rheumatic disease is systemic lupus erythematosus or the like.

In some embodiments, the compound or the pharmaceutical composition inhibits JC virus infection of human glial cells.

One aspect of the present invention encompasses processes for preparing a composition comprising admixing a compound according any embodiments described herein and pharmaceutically acceptable carrier.

One aspect of the present invention is the use of a compound for the production of a medicament for use in the treatment of a 5-HT$_{2A}$ mediated disorder.

One embodiment of the present invention is the use of a compound for the production of a medicament for use in the treatment of a 5-HT$_{2A}$ mediated disorder wherein the disorder is platelet aggregation.

One embodiment of the present invention is the use of a compound for the production of a medicament for use in the treatment of a 5-HT$_{2A}$ mediated disorder wherein the disorder is selected from the group consisting of coronary artery disease, myocardial infarction, transient ischemic attack, angina, stroke, and atrial fibrillation.

One embodiment of the present invention is the use of a compound for the production of a medicament for use in the treatment of a 5-HT$_{2A}$ mediated disorder wherein the disorder is a blood clot formation in an angioplasty or coronary bypass surgery individual.

One embodiment of the present invention is the use of a compound for the production of a medicament for use in the treatment of a 5-HT$_{2A}$ mediated disorder wherein the disorder is a blood clot formation in an individual suffering from atrial fibrillation.

One embodiment of the present invention is the use of a compound for the production of a medicament for use in the treatment of a 5-HT$_{2A}$ mediated disorder wherein the disorder is asthma.

One embodiment of the present invention is the use of a compound for the production of a medicament for use in the treatment of a 5-HT$_{2A}$ mediated disorder wherein the disorder is a symptom of asthma.

One embodiment of the present invention is the use of a compound for the production of a medicament for use in the treatment of a 5-HT$_{2A}$ mediated disorder wherein the disorder is agitation or a symptom thereof in an individual. In some embodiments the individual is a cognitively intact elderly individual.

One embodiment of the present invention is the use of a compound for the production of a medicament for use in the treatment of a 5-HT$_{2A}$ mediated disorder wherein the disorder is agitation or a symptom thereof in an individual suffering from dementia. In some embodiments the dementia is due to a degenerative disease of the nervous system. In some embodiment the dementia is Alzheimers disease, Lewy Body, Parkinson's disease, or Huntington's disease. In some embodiments the dementia is due to diseases that affect blood vessels. In some embodiments the dementia is due to stroke or multi-infract dementia.

One embodiment of the present invention is the use of a compound for the production of a medicament for use in the treatment of a 5-HT$_{2A}$ mediated disorder further comprising a dopamine D$_2$ receptor antagonist wherein the disorder is selected from the group consisting of a behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia. In some embodiments the dopamine $D_2$ receptor antagonist is haloperidol.

One embodiment of the present invention is the use of a compound for the production of a medicament for use in the treatment of a 5-$HT_{2A}$ mediated disorder further comprising a dopamine $D_2$ receptor antagonist wherein the disorder is infantile autism, Huntington's chorea, or nausea and vomiting from chemotherapy or chemotherapeutic antibodies. In some embodiments the dopamine $D_2$ receptor antagonist is haloperidol.

One embodiment of the present invention is the use of a compound for the production of a medicament for use in the treatment of a 5-$HT_{2A}$ mediated disorder further comprising a dopamine $D_2$ receptor antagonist wherein the disorder is schizophrenia. In some embodiments the dopamine $D_2$ receptor antagonist is haloperidol.

One embodiment of the present invention is the use of a compound for the production of a medicament for use in the treatment of a 5-$HT_{2A}$ mediated disorder wherein the disorder is a negative symptom or symptoms of schizophrenia induced by the administration of haloperidol.

One embodiment of the present invention is the use of a compound for the production of a medicament for use in the treatment of a 5-$HT_{2A}$ mediated disorder wherein the haloperidol and the compound or pharmaceutical composition are administered in separate dosage forms.

One embodiment of the present invention is the use of a compound for the production of a medicament for use in the treatment of a 5-$HT_{2A}$ mediated disorder wherein the haloperidol and the compound or pharmaceutical composition are administered in a single dosage form.

One embodiment of the present invention is the use of a compound for the production of a medicament for use in the treatment of a 5-$HT_{2A}$ mediated disorder wherein the disorder is progressive multifocal leukoencephalopathy.

One aspect of the present invention are compounds according to any of the embodiments described herein for use in a method of treatment of the human or animal body by therapy.

One aspect of the present invention are compounds according to any of the embodiments described herein for use in a method for the treatment of a 5-$HT_{2A}$ mediated disorder, as described herein, in the human or animal body by therapy.

One aspect of the present invention are compounds according to any of the embodiments described herein for use in a method for the treatment of a sleep disorder, as described herein, in the human or animal body by therapy.

One aspect of the present invention are compounds according to any of the embodiments described herein for use in a method for the treatment of platelet aggregation in the human or animal body by therapy.

One aspect of the present invention are compounds according to any of the embodiments described herein for use in a method for the treatment of progressive multifocal leukoencephalopathy in the human or animal body by therapy.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as $5\text{-}HT_{2A}$ receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, or whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bio-availability, solubilizers, dispersants and others, and, if appropriate, customary propellants, for example include carbon dioxide, CFC's, such as, dichlorodifluoromethane, trichlorofluoromethane, or dichlorotetrafluoro ethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2A}$ receptor modulators, for the treatment of a 5-$HT_{2A}$ mediated disease or disorder in domestic animals (e.g., cats and dogs) and in other domestic animals (e.g., such as cows, chickens, fish, etc.). Those of ordinary skill in the art are readily credited with understanding the utility of such compounds in such settings.

Combination Therapy:

While the compounds of the present invention can be administered as the sole active pharmaceutical agent (i.e., mono-therapy), they can also be used in combination with other pharmaceutical agents (i.e., combination-therapy) for the treatment of the diseases/conditions/disorders described herein. Accordingly, another aspect of the present invention includes methods of treatment of 5-$HT_{2A}$ serotonin receptor mediated disorders diseases comprising administering to an individual in need of such treatment a therapeutically-effective amount of a compound of the present invention in combination with one or more additional pharmaceutical agent as described herein.

Suitable pharmaceutical agents that can be used in combination with the compounds of the present invention include other antiplatelet, antithrombotic or anticoagulant drugs, anti-arrhythmic agents, Cholesteryl ester transfer protein (CETP) inhibitors, Niacin or niacin analogs, Adenosine or adenosine analogs, Nitroglycerin or nitrates, prothrombolytic agents, and the like. Other pharmaceutical agents, including the agents set forth infra, are well known or will be readily apparent in light of the instant disclosure, to one of ordinary skill in the art.

The compounds of the present invention can also be used in combination with other antiplatelet, antithrombotic or anticoagulant drugs such as thrombin inhibitors, platelet aggregation inhibitors such as aspirin, clopidogrel (Plavix®), ticlopidine or CS-747 {i.e., acetic acid 5-[2-cyclopropyl-1-(2-fluorophenyl)-2-oxo ethyl]-4,5,6,7-tetrahydrothieno [3,2-c]pyridin-2-yl ester and its active metabolite R-99224, (Z)-2-[1-[2-cyclopropyl-1 (S)-(2-fluorophenyl)-2-oxoethyl]-4(R)-sulfanylpiperidin-3-ylidene]acetic acid}, abciximab (ReoPro®), eptifibatide (Integrilin®), tirofiban (Aggrastat®), warfarin, low molecular weight heparins (such as LOVENOX), GPIIb/GPIIIa blockers, PAI-1 inhibitors such as XR-330 [i.e., (3Z,6Z)-3-Benzylidene-6-(4-methoxybenzylidene)-1-methylpiperazine-2,5-dione] and T-686 [i.e., 3(E)-Benzylidene-4(E)-(3, 4,5-trimethoxybenzylidene)pyrrolidine-2,5-dione], inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole (Persantine®) or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, and itavastatin (Nissan/Kowa); microsomal triglyceride transport protein inhibitors (such as disclosed in U.S. Pat. Nos. 5,739,135, 5,712,279 and 5,760,246), anti-hypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel (Plavix®) and the like.

The compound of the present invention can also be used in combination with anti-arrhythmic agents such as for atrial fibrillation, for example, amiodarone or dofetilide.

The compound of the present invention can also be used in combination with Cholesteryl ester transfer protein (CETP) inhibitors for dislipidemia and atherosclerosis, Niacin or niacin analogs for dislipidemia and atherosclerosis, Adenosine or adenosine analogs for vasodilation, Nitroglycerin or nitrates for vasodilation.

The compounds of the present invention can be used in combination with prothrombolytic agents, such as tissue plasminogen activator (natural or recombinant), streptokinase, reteplase, activase, lanoteplase, urokinase, prourokinase, an isolated streptokinase plasminogen activator complex (ASPAC), animal salivary gland plasminogen activators, and the like. The compounds of the present invention may also be used in combination with β-adrenergic agonists such as albuterol, terbutaline, formoterol, salmeterol, bitolterol, pilbuterol, or fenoterol; anticholinergics such as ipratropium bromide; anti-inflammatory corticosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

Suitable pharmaceutical agents that can be used in combination with compounds of the present invention include antiretrovirals [see, e.g., Turpin, *Expert Rev Anti Infect Ther* (2003) 1:97-128]. Some embodiments of the present invention include methods of treatment of progressive multifocal leukoencephalopathy as described herein comprising administering to an individual in need of such treatment a therapeutically effective amount or dose of a compound of the present invention in combination with at least one pharmaceutical agent selected from the group consisting of: nucleoside reverse transcriptase inhibitors (for example, Retrovir®, Epivir®, Combivir®, Hivid®, Videx®, Trizvir®, Zerit®, Ziagen®, Vired®, Emtricitabine, DAPD, and the like), non-nucleoside reverse transcriptase inhibitors (for example, Virammune®, Rescriptor®, Sustiva®, GW687, DPC083, TMC 125, Emivirine, Capravirine, BMS 561390, UC-781 and other oxathiin carboxyanilides, SJ-3366, Alkenyldiarylmethane (ADAM), Tivirapine, Calanolide A, HBY097, Loviride, HEPT Family Derivatives, TIBO Derivatives, and the like), protease inhibitors (for example, Fortovase®, Invirase®, Novir®, Crixivan®, Viracep®, Ageberase®, Kaletra®, Atazanavir, Tipranavir, DMP450, and the like), inhibitors of HIV-cell interaction (for example, soluble CD4, toxin-conjugated CD4, monoclonal antibodies to CD4 or gp120, PRO 542, dextran sulfate, Rersobene, FP-23199, Cyanovirin-N, Zintevir (T30177, AR177), L-chicoric acid and derivatives, and the like), coreceptor inhibitors ligands (for example, R5, X4, modified ligands (R5), modified ligands (X4), and the like), coreceptor inhibitors X4 (for example, T22, T134, ALX40-4C, AMD3100, bycyclam derivatives, and the like), coreceptor inhibitors R5 (for example, TAK-779, SCH-C (SCH-351125), SCH-D (SCH-350634), NSC 651016, ONO Pharmaceutical, Merck, and the like), fusion inhibitors (for example, Fuzeon® (T-20, DP 178, enfuvritide) trimeris, T-1249, TMC 125, and the like), integrase inhibitors (for example, 5CITEP, L731,988, L708,906, L-870,812, S-1360, and the like), NCp7 nucleocapsid Zn finger inhibitors (for example, NOBA, DIBA, dithianes, PD-161374, pyridinioalkanoyl thioesters (PATES), azodicarbonamide (ADA), cyclic 2,2 dithio bisbenzamide, and the like), RNase H inhibitors (for example, BBHN, CPHM PD-26388, and the like), Tat inhibitors (for example, dominant negative mutants, Ro24-7429, Ro5-3335, and the like), Rev inhibitors (for example, dominant negative mutants, Leptomycin B, PKF050-638, and the like), transcriptional inhibitors (for example, Temacrazine, K-12 and K-37, EM2487, and the like), inhibitors of HIV assembly/maturation (for example, CAP-1 and CAP-2, and the like), and pharmaceutical agents directed to cellular anti-HIV targets (for example, LB6-B275 and HRM1275, Cdk9 inhibitors, and the like).

In a certain embodiment, a compound of the invention can be used in conjunction with highly active antiretroviral therapy (HAART). When antiretroviral drugs are used in combinations of three or four drugs, this treatment is called HAART [see, e.g., Portegies, et al., *Eur. J. Neurol.* (2004) 11:297-304].

In accordance with the present invention, the combination of a compound of the present invention and pharmaceutical agent can be prepared by mixing the respective active components either all together or independently with a pharmaceutically acceptable carrier, excipient, binder, diluent, etc. as described herein, and administering the mixture or mixtures either orally or non-orally as a pharmaceutical composition(s). When a compound or a mixture of compounds of Formula (Ia) are administered as a combination therapy with another active compound each can be formulated as separate pharmaceutical compositions given at the same time or at different times. Alternatively, in some embodiments, pharmaceutical compositions of the present invention comprise a compound or a mixture of compounds of Formula (Ia) and the pharmaceutical agent(s) as a single pharmaceutical composition.

Other Utilities

Another object of the present invention relates to radio-labeled compounds of the present invention that would be useful not only in radio-imaging but also in assays, both in vitro and in vivo, for localizing and quantitating the 5-$HT_{2A}$ receptor in tissue samples, including human, and for identifying 5-$HT_{2A}$ receptor ligands by inhibition binding of a radio-labeled compound. It is a further object of this invention to develop novel 5-$HT_{2A}$ receptor assays of which comprise such radio-labeled compounds.

The present invention embraces isotopically-labeled compounds of the present invention. An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include, but are not limited to, $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro 5-$HT_{2A}$ receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (Ia) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]— This procedure is rather inexpensive and requires precursors containing reducible functional groups such as aldehydes, ketones, lactones, esters, and the like.

C. Reduction with Lithium Aluminum Hydride [$^3$H]— This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]— This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in J. Org. Chem. 2002, 67, 943-948.

B. Ortho $^{125}$Iodination of phenols—This procedure allows for the incorporation of $^{125}$I at the ortho position of a phenol as reported by Collier, T. L. and co-workers in J. Labeled Compd Radiopharm. 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)4] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in J. Labeled Compd Radiopharm. 2001, 44, S280-S282.

A radio-labeled 5-HT$_{2A}$ receptor compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the 5-HT$_{2A}$ receptor. Accordingly, the ability of a test compound to compete with the "radio-labeled compound of Formula (Ia)" for the binding to the 5-HT$_{2A}$ receptor directly correlates to its binding affinity.

The labeled compounds of the present invention bind to the 5-HT$_{2A}$ receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM, and in still yet another embodiment the labeled inhibitor has an IC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIGS. 1 through 12 where the symbols have the same definitions as used throughout this disclosure.

The compounds of the invention and their synthesis are further illustrated by the following examples. The following examples are provided to further define the invention without, however, limiting the invention to the particulars of these examples. The compounds described herein, supra and infra, are named according to CS Chem Draw Ultra Version 7.0.1 or AutoNom 2000. In certain instances common names are used and it is understood that these common names would be recognized by those skilled in the art.

Chemistry:

Proton nuclear magnetic resonance ($^1$H NMR) spectra were recorded on a Varian Mercury Vx-400 equipped with a 4 nucleus auto switchable probe and z-gradient or a Bruker Avance-400 or 500 MHz equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublet, dt=doublet of triplet, t=triplet, q=quartet, m=multiplet, br=broad. Microwave irradiations were carried out using the Emrys Synthesizer (Personal Chemistry). Thin-layer chromatography (TLC) was performed on silica gel 60 F$_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. 2) Mac: HPLC-pumps: LC-8A VP, Shimadzu Inc; HPLC system controller: SCL-10A VP, Shimadzu Inc.

UV-Detector: SPD-10A VP, Shimadzu Inc; Autosampler: 215 Liquid Handler, Gilson Inc; Mass spectrometer: API 150EX with Turbo Ion Spray source, AB/MDS Sciex Software: Masschrom 1.5.2.

Example 1.1: Preparation of 1-[3-(4-chloro-2-methyl-2H-pyrazol-3-yl)-4-(2-pyrrolidin-1-yl-ethoxy)-phenyl]-3-(2,4-difluoro-phenyl)-urea (Compound 13)

Step 1.1a: Preparation of the Intermediate 1-[3-(4-chloro-2-methyl-2H-pyrazol-3-yl)-4-hydroxy-phenyl]-3-(2,4-difluoro-phenyl)-urea. Method A

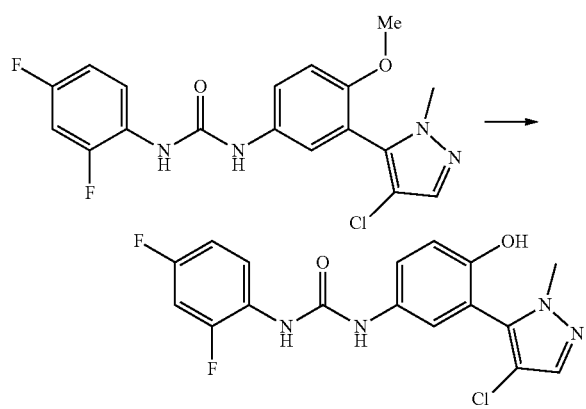

A mixture of 1-[3-(4-chloro-2-methyl-2H-pyrazol-3-yl)-4-methoxy-phenyl]-3-(2,4-difluoro-phenyl)urea (0.270 g, 0.69 mmol) in anhydrous 1,2-dichloroethane (10 mL) was cooled to 0° C. in an ice bath and stirred for 10 minutes. Anhydrous aluminum chloride (0.368 g, 2.76 mmol) was added and the reaction mixture stirred at 0° C. for 20 minutes, then moved to an oil bath and stirred at 80° C. for 1 hour. Ethyl acetate was added and washed with potassium sodium tartrate (10%) twice. The organic layer was separated, dried over anhydrous $Na_2SO_4$, filtered and concentrated to give a crude product that was subjected to purification on HPLC. The proper fractions were collected and lyophilized to afford 1-[3-(4-chloro-2-methyl-2H-pyrazol-3-yl)-4-hydroxy-phenyl]-3-(2,4-difluoro-phenyl)-urea as a white solid in 75.0% yield. LCMS m/z (%)=379 (M+H $^{35}$Cl, 100), 381 (M+H $^{37}$Cl, 40). $^1$H NMR (400 MHz, DMSO-$d_6$) δ 9.81 (s, 1H), 8.92 (s, 1H), 8.45 (s, 1H), 8.12-8.06 (m, 1H), 7.63 (s, 1H), 7.40-7.31 (m, 3H), 7.09-7.04 (m, 1H), 6.99 (d, $J_1$=8.72 Hz, 1H), 3.69 (s, 3H).

Step 1.1b: Preparation of 1-[3-(4-chloro-2-methyl-2H-pyrazol-3-yl)-4-(2-pyrrolidin-1-yl-ethoxy)-phenyl]-3-(2,4-difluoro-phenyl)-urea (Compound 13). Method B

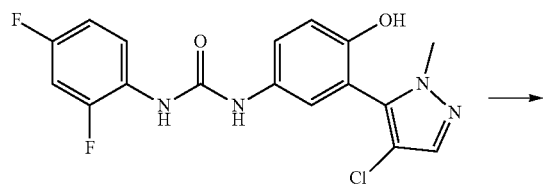

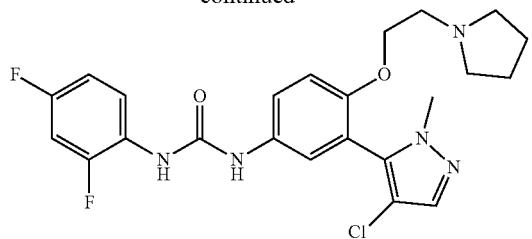

To a solution of 1-[3-(4-chloro-2-methyl-2H-pyrazol-3-yl)-4-hydroxy-phenyl]-3-(2,4-difluoro-phenyl)-urea (0.35 g, 0.09 mmol) in anhydrous THF (2 mL), triphenyl phosphine (70.8 mg, 0.27 mmol) and 1-(2-hydroxyethyl)-pyrrolidine (0.032 mL, 0.27 mmol) were added followed by dropwise addition of diisopropyl azodicarboxylate (DIAD) (0.052 mL, 0.27 mmol). The reaction mixture was stirred at room temperature for 2 hours, concentrated to give a crude product that was subjected to purification by preparative HPLC. The proper fractions were collected, neutralized with 1N NaOH and extracted with EtOAc four times. The solution was evaporated under reduced pressure to afford Compound 13 as an off-white solid in 52.8% yield. LCMS ml/z (%)=476 (M+H $^{35}$Cl, 100), 478 (M+H $^{37}$Cl, 40). $^1$H NMR (400 MHz, DMSO-$d_6$) δ: 9.10 (s, 1H), 8.55 (s, 1H), 8.17-8.09 (m, 1H), 7.69 (s, 1H), 7.61 (dd, J=8.97 and 2.72 Hz, 1H), 7.47 (d, J=2.70 Hz, 1H), 7.43-7.36 (m, 1H), 7.26 (d, J=9.04 Hz, 1H), 7.16-7.09 (m, 1H), 4.25-4.08 (nm, 2H), 3.73 (s, 3H), 2.58-2.45 (m, 2H), 2.45-2.29 (m, 4H), 1.75-1.69 (m, 4H).

Example 1.2: Preparation of the Intermediate 3-(2-methyl-2H-pyrazol-3-yl)-4-(2-piperidin-1-yl-ethoxy)-phenylamine. Method C

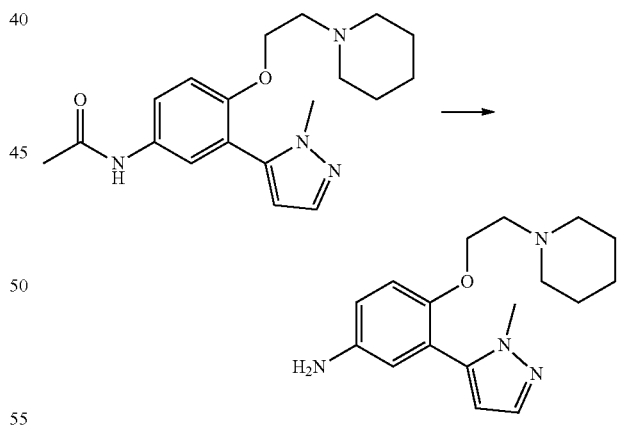

N-[3-(2-methyl-2H-pyrazol-3-yl)-4-(2-piperidin-1-yl-ethoxy)-phenyl]-acetamide (1.0 g, 2.92 mmol) was dissolved in ethanol (15 mL) then aqueous sodium hydroxide (2.5 mL, 50% w/w) was added and the reaction mixture stirred at 80° C. overnight then concentrated. Water and brine were added then extracted with EtOAc three times. The organic layers were combined, dried over anhydrous $Na_2SO_4$ then solvent removed under reduced pressure to afford 3-(2-methyl-2H-pyrazol-3-yl)-4-(2-piperidin-1-yl-ethoxy)-phenylamine as a brown oil in 97.1% yield.
LCMS m/z (%)=301 (M+H, 100).

Example 1.3: Preparation of [3-(2-methyl-2H-pyrazol-3-yl)-4-(2-piperidin-1-yl-ethoxy)-phenyl]-carbamic Acid Isopropyl Ester (Compound 33). Method D

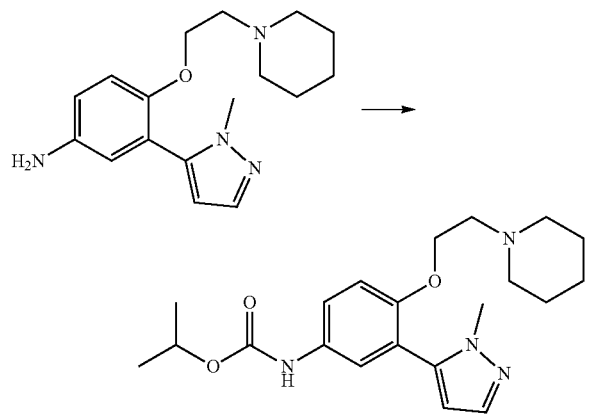

To a solution of 3-(2-methyl-2H-pyrazol-3-yl)-4-(2-piperidin-1-yl-ethoxy)-phenylamine (30.0 mg, 0.1 mmol) in methylene chloride (1 mL) was added pyridine (24.3 µL, 0.3 mmol). The mixture was treated with isopropyl chloroformate (13.3 µL, 0.11 mmol) then the reaction mixture was stirred at room temperature overnight and concentrated to give an oily residue that was subjected to purification by flash chromatography (SiO$_2$, CH$_2$Cl$_2$/MeOH gradient elution) to afford Compound 33 as an off-white waxy solid in 90.6% yield. LCMS m/z (%)=387 (M+H, 100).

Example 1.4: Preparation of N-[3-(2-methyl-2H-pyrazol-3-yl)-4-(2-piperidin-1-yl-ethoxy)-phenyl]-2-phenyl-acetamide (Compound 35). Method E

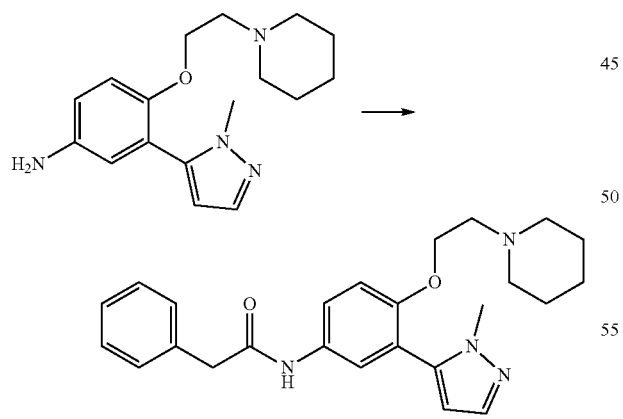

To a solution of 3-(2-methyl-2H-pyrazol-3-yl)-4-(2-piperidin-1-yl-ethoxy)-phenylamine (21.0 mg, 0.07 mmol) in methylene chloride (1 mL) was added pyridine (17.0 µL, 0.3 mmol). The mixture was treated with phenylacetylchloride (10.6 µL, 0.8 mmol) then the reaction mixture was stirred at room temperature overnight and concentrated to give an oily residue that was subjected to purification by flash chromatography (SiO$_2$, CH$_2$Cl$_2$/MeOH gradient elution) to afford Compound 35 as an off-white solid in 81.2% yield. LCMS m/z (%)=419 (M+H, 100).

Example 1.5: Preparation of 1-benzyl-3-[3-(2-methyl-2H-pyrazol-3-yl)-4-(2-piperidin-1-yl-ethoxy)-phenyl]-urea (Compound 44). Method F

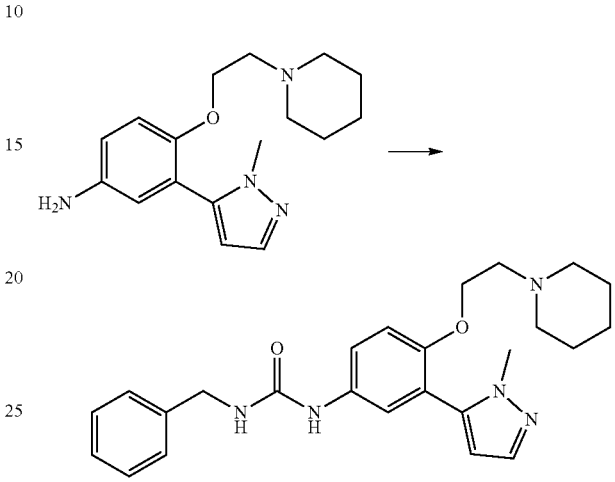

A solution of 3-(2-methyl-2H-pyrazol-3-yl)-4-(2-piperidin-1-yl-ethoxy)-phenylamine (21.0 mg, 0.07 mmol) in methylene chloride (1 mL) was treated with benzyl isocyanate (9.1 µL, 0.074 mmol) then the reaction mixture was stirred at room temperature overnight and concentrated to give an oily residue that was subjected to purification by flash chromatography (SiO$_2$, CH$_2$Cl$_2$/MeOH gradient elution) to afford Compound 44 as an off-white solid in 51.4% yield. LCMS m/z (%)=434 (M+H, 100). $^1$H NMR (400 MHz, Acetone-d$_6$) δ: 8.04 (s, 1H), 7.57 (dd, J=8.88 and 2.70 Hz, 1H), 7.48 (d, J=2.67 Hz, 1H), 7.42-7.27 (m, 6H), 7.07 (d, J=8.91 Hz, 1H), 6.26 (bs, 1H), 6.23 (d, J=1.8 Hz, 1H), 4.45 (d, J=5.85 Hz, 2H), 4.13 (t, J=5.70 Hz, 1H), 3.77 (s, 3H), 2.70-2.64 (m, 2H), 2.52-2.41 (m, 4H), 1.58-1.51 (m, 4H), 1.46-1.38 (m, 2H).

Example 1.6: Preparation of 1-{2-[4-[3-(2,4-difluoro-phenyl)-ureido]-2-(2-methyl-2H-pyrazol-3-yl)-phenoxy]-ethyl}-pyrrolidine-2-carboxylic Acid Methyl Ester (Compound 125)

Step 1.6a: Preparation of 1-{2-[2-(2-methyl-2H-pyrazol-3-yl)-4-nitro-phenoxy]-ethyl}-pyrrolidine-2-carboxylic Acid Methyl Ester. Method G

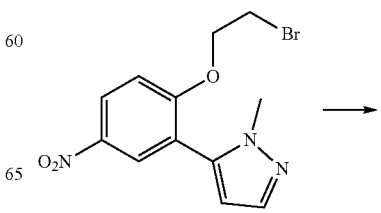

-continued

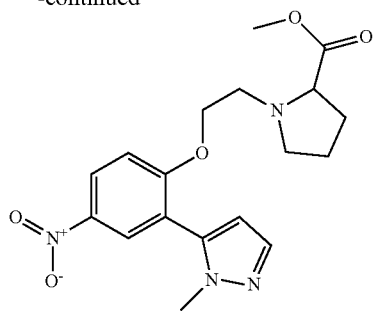

To 5-[2-(2-bromo-ethoxy)-5-nitro-phenyl]-1-methyl-1H-pyrazole (200.0 mg, 0.61 mmol) in acetonitrile (3 mL), was added DIEA followed by addition of the H-DL-Pro-OMe. The reaction mixture was heated with microwaves at 170° C. for 20 min then subjected to purification by prep HPLC. The proper fractions were collected and lyophilized to afford a trifluoroacetic acid salt of 1-{2-[2-(2-methyl-2H-pyrazol-3-yl)-4-nitro-phenoxy]-ethyl}-pyrrolidine-2-carboxylic acid methyl ester as a light brown oil in 84.2% yield. LCMS m/z (%)=375 (M+H, 100).

Step 1.6b: Preparation of 1-{2-[4-amino-2-(2-methyl-2H-pyrazol-3-yl)-phenoxy]-ethyl}-pyrrolidine-2-carboxylic Acid Methyl Ester. Method H

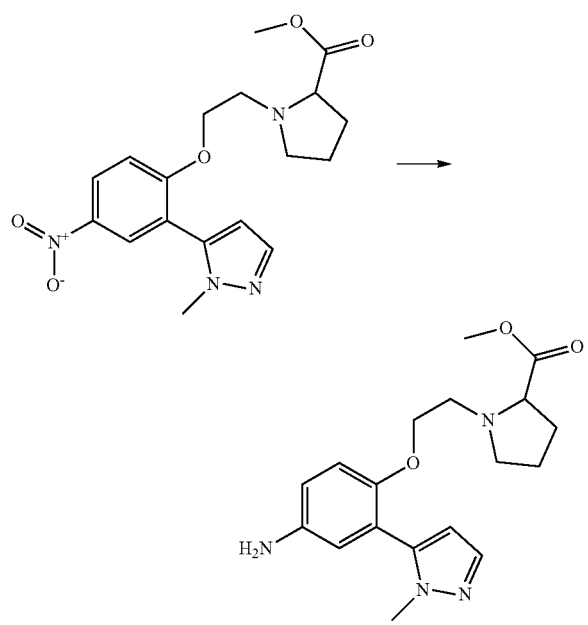

1-{2-[2-(2-Methyl-2H-pyrazol-3-yl)-4-nitro-phenoxy]-ethyl}-pyrrolidine-2-carboxylic acid methyl ester (150.0 mg) in methanol (15 mL) was treated with a catalytic amount of palladium on activated carbon (10 wt %, Degussa), degassed with argon then hydrogen from a balloon was allowed to bubble through the slurry at room temperature overnight. The reaction mixture was filtered through Celite. The filtrate was concentrated under reduced pressure and dried to afford a trifluoroacetic acid salt of 1-{2-[4-amino-2-(2-methyl-2H-pyrazol-3-yl)-phenoxy]-ethyl}-pyrrolidine-2-carboxylic acid methyl ester as a brown oil in 92% yield. LCMS m/z (%)=345 (M+H, 100).

Step 1.6c: Preparation of 1-{2-[4-[3-(2,4-difluoro-phenyl)-ureido]-2-(2-methyl-2H-pyrazol-3-yl)-phenoxy]-ethyl}-pyrrolidine-2-carboxylic Acid Methyl Ester (Compound 125)

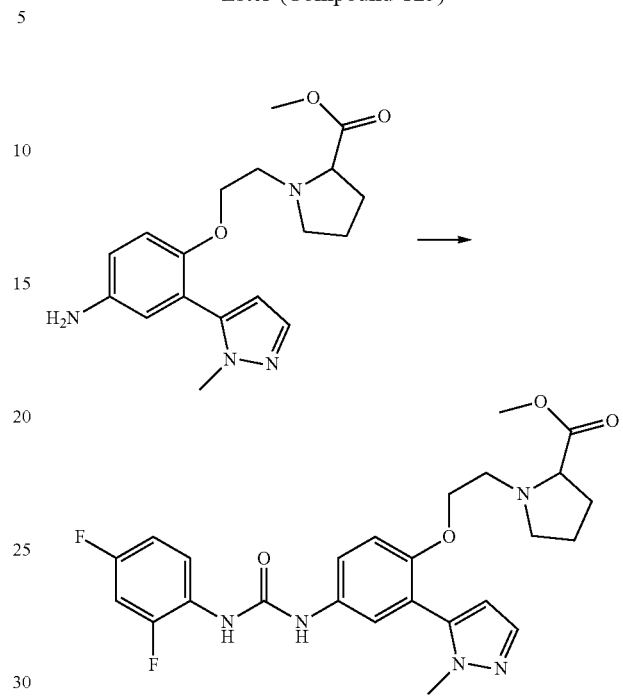

The title compound was prepared in a similar manner as described in Method F to give a colorless oil. LCMS m/z (%)=500 (M+H, 100).

Example 1.7: Preparation of (1H-benzoimidazol-2-yl)-[3-(4-bromo-2-methyl-2H-pyrazol-3-yl)-4-(2-piperidin-1-yl-ethoxy)-phenyl]-amine (Compound 196). Method I

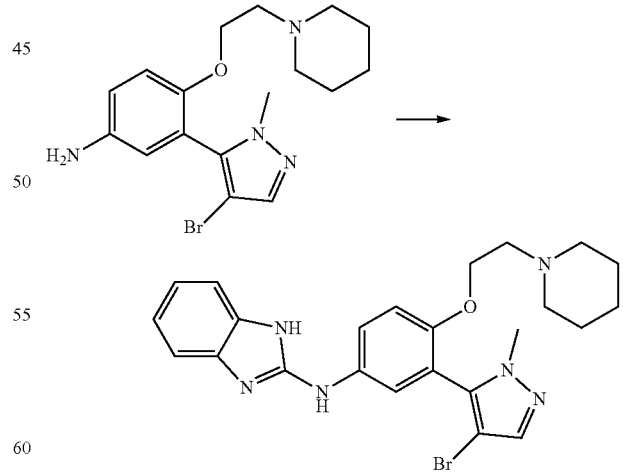

To a mixture of 3-(4-bromo-2-methyl-2H-pyrazol-3-yl)-4-(2-piperidin-1-yl-ethoxy)-phenylamine (0.105 g, 0.28 mmol) and 2-chlorobenzimidazole (0.057 g, 0.33 mmol) in ethanol (1 mL) two drops of 1N HCl were added. The reaction mixture was heated with microwaves at 180° C. for 1 hour, concentrated then subjected to purification by prep HPLC. The proper fractions were collected and lyophilized to afford Compound 196 as an off-white solid in 17.1% yield. LCMS m/z (%)=495 (M+H $^{79}$Br, 100), 497 (M+H $^{81}$Br, 90).

Example 1.8: Preparation of 3-(1-{2-[4-[3-(4-chloro-phenyl)-ureido]-2-(2-methyl-2H-pyrazol-3-yl)-phenoxy]-ethyl}-piperidin-4-yl)-propionic Acid Methyl Ester (Compound 151). Method J

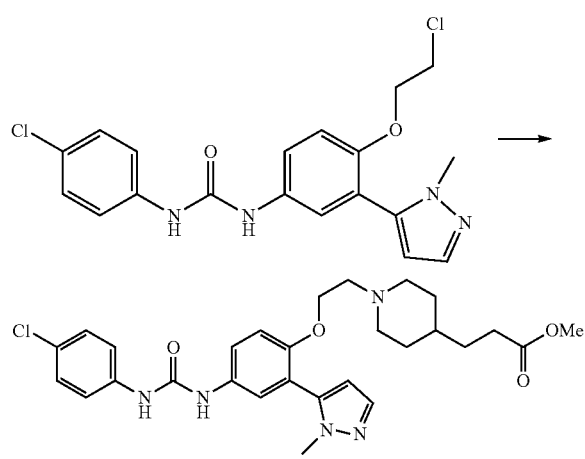

A mixture of 1-[4-(2-chloro-ethoxy)-3-(2-methyl-2H-pyrazol-3-yl)-phenyl]-3-(4-chloro-phenyl)-urea (0.104 g, 0.257 mmol), 3-piperidin-4-yl-propionic acid methyl ester (0.108 g, 0.631 mmol), and potassium carbonate (0.143, 1.03 mmol) in DMA (4.5 mL) was heated with microwave irradiation at 150° C. for 1 hour. The crude mixture was purified by HPLC to afford Compound 151 as an oil (TFA salt, 0.030 g, 18%). Exact mass calculated for $C_{28}H_{34}ClN_5O_4$ 539.23, found 540.4 (MH$^+$). $^1$H NMR (400 MHz, chloroform-d$_6$) δ: 10.70 (s, 1H), 8.24-8.30 (m, 2H), 7.61-7.62 (m, 1H), 7.57 (broad s, 1H), 7.34-7.36 (m, 2H), 7.20-7.22 (m, 2H), 7.14-7.16 (m, 1H), 6.70-6.71 (m, 1H), 6.23 (s, 1H), 4.27 (s, 2H), 3.71 (s, 3H), 3.67 (s, 3H), 3.24-3.31 (m, 2H), 3.51-3.57 (m, 2H), 2.24-2.28 (t, J=7.33 Hz, 2H), 1.40-1.75 (m, 8H).

Example 1.9: Preparation of (1-{2-[4-[3-(4-chloro-phenyl)-ureido]-2-(2-methyl-2H-pyrazol-3-yl)-phenoxy]-ethyl}-piperidin-3-yl)-acetic Acid (Compound 175). Method K

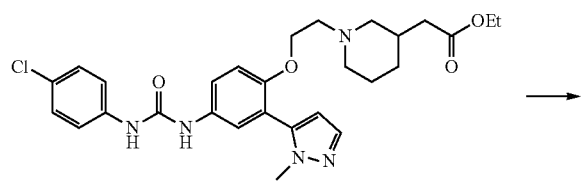

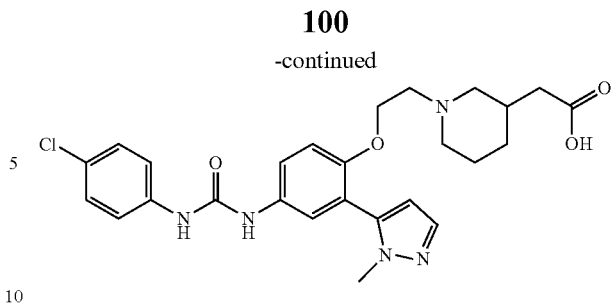

To a stirred solution of (1-{2-[4-[3-(4-chloro-phenyl)-ureido]-2-(2-methyl-2H-pyrazol-3-yl)-phenoxy]-ethyl}-piperidin-3-yl)-acetic acid ethyl ester (TFA salt, 0.038 g, 0.058 mmol) in a mixture of THF (0.9 mL), MeOH (0.3 mL), and H$_2$O (0.3 mL) was added lithium hydroxide, monohydrate (0.044 g, 1.05 mmol) at room temperature, and the mixture was stirred for 45 mins. The crude mixture was purified by HPLC to afford Compound 175 as an oil (TFA salt, 0.024 g, 66%). Exact mass calculated for $C_{26}H_{30}ClN_5O_4$ 511.2, found 512.3 (MH$^+$). $^1$H NMR (400 MHz, methanol-d$_4$) δ: 7.39-7.42 (m, 2H), 7.29-7.32 (m, 3H), 7.13-7.15 (m, 2H), 7.01-7.03 (m, 1H), 6.23 (s, 1H), 4.23-4.24 (m, 2H), 3.36 (s, 2H), 3.30 (s, 1H), 3.18 (s, 3H), 2.58-2.64 (m, 2H), 2.46-2.52 (m, 2H), 2.10-2.15 (m, 2H), 2.03-2.06 (m, 1H), 1.71 (s br, 2H), 1.54-1.57 (m, 1H), 1.01-1.04 (m, 1H).

Example 1.10: Preparation of 4-(4-{2-[4-[3-(4-chloro-phenyl)-ureido]-2-(2-methyl-2H-pyrazol-3-yl)-phenoxy]-ethyl}-piperazin-1-yl)-4-oxo-butyric Acid Methyl Ester (Compound 176). Method L

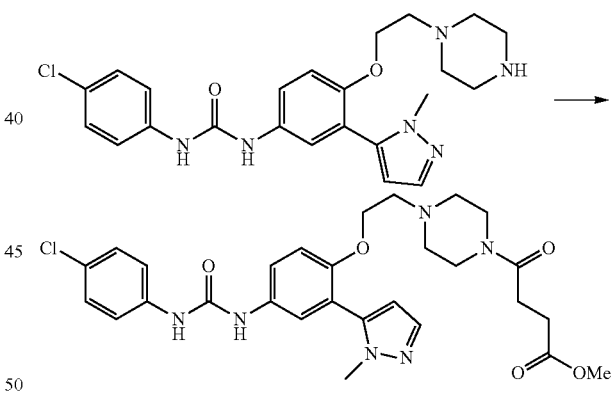

To a stirred solution of 1-(4-chloro-phenyl)-3-[3-(2-methyl-2H-pyrazol-3-yl)-4-(2-piperazin-1-yl-ethoxy)-phenyl]-urea (HCl salt, 0.033 g, 0.067 mmol) and DIEA (0.035 g, 46 μL, 0.266 mmol) in THF (5 mL) was added methyl 4-chloro-4-oxo-butyrate (0.011 g, 46 μL, 1.05 mmol) at 0° C. The mixture was warmed to room temperature and stirred for 45 mins. The crude mixture was purified by HPLC to afford Compound 176 as an oil (TFA salt, 0.024 g, 52%). Exact mass calculated for $C_{28}H_{33}ClN_6O_5$ 568.22, found 569.5 (MH$^+$). $^1$H NMR (400 MHz, methanol-d$_4$) δ: 7.50 (s, 1H), 7.42-7.45 (m, 1H), 7.32-7.36 (m, 3H), 7.15-7.18 (m, 2H), 7.05-7.07 (m, 1H), 6.28 (s, 1H), 4.29-4.30 (m, 2H), 3.64 (s, 5H), 3.46-3.47 (m, 2H), 3.11-3.13 (m, 2H), 3.01-3.13 (m, 4H), 2.58-2.59 (m, 2H), 2.53-2.55 (m, 2H), 1.26-1.28 (m, 5H).

Example 1.11: Preparation of 1-(4-chloro-phenyl)-3-[4-[2-(2,5-diaza-bicyclo[2.2.1]hept-2-yl)-ethoxy]-3-(2-methyl-2H-pyrazol-3-yl)-phenyl]-urea (Compound 177). Method M

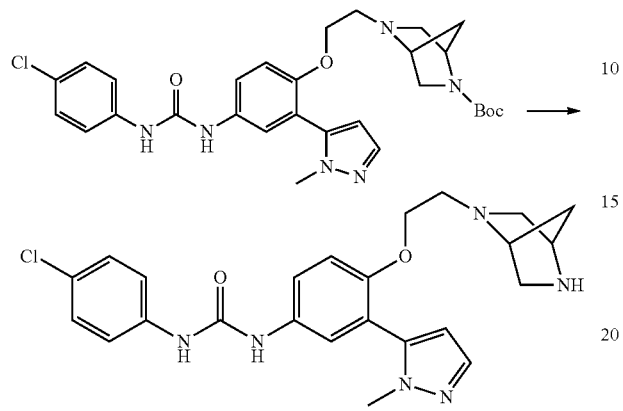

A suspension of 5-{2-[4-[3-(4-chloro-phenyl)-ureido]-2-(2-methyl-2H-pyrazol-3-yl)-phenoxy]-ethyl}-2,5-diaza-bicyclo[2.2.1]heptane-2-carboxylic acid tert-butyl ester (TFA salt, 0.042 g, 0.062 mmol) and 4M HCl in dioxane (2 mL) was stirred at room temperature overnight. The mixture was dried in vacuo to afford Compound 177 as an oil (HCl salt, 0.046 g, 100%). Exact mass calculated for $C_{24}H_{27}ClN_6O_2$ 466.19, found 467.5 (MH$^+$).

Example 1.12: Preparation of (4-{2-[4-[3-(4-chloro-phenyl)-ureido]-2-(2-methyl-2H-pyrazol-3-yl)-phenoxy]-ethyl}-piperazin-1-yl)-acetic Acid Methyl Ester (Compound 209). Method N

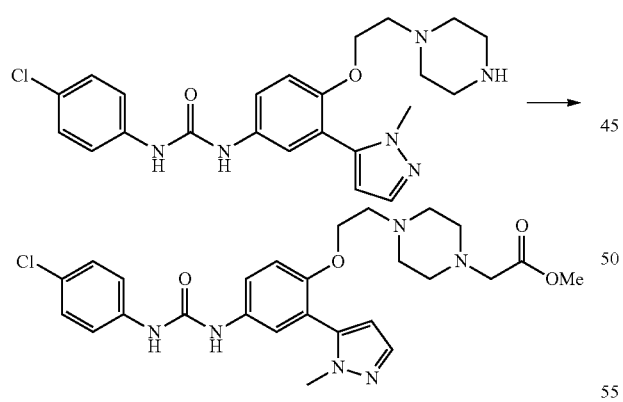

To a stirred solution of 1-(4-chloro-phenyl)-3-[3-(2-methyl-2H-pyrazol-3-yl)-4-(2-piperazin-1-yl-ethoxy)-phenyl]-urea (TFA salt, 0.063 g, 0.11 mmol) and DIEA (0.572 g, 77 μL, 0.44 mmol) in THF (3 mL) was added methyl bromoacetate (0.019 g, 12 μL, 0.121 mmol) at 0° C. The mixture was warmed to room temperature and stirred for 20 hrs. The crude mixture was purified by HPLC to afford Compound 209 as an oil (TFA salt, 0.053 g, 74%). Exact mass calculated for $C_{26}H_{31}ClN_6O_4$ 526.21, found 527.5 (MH$^+$). $^1$H NMR (400 MHz, acetonitrile-d$_3$) δ: 7.78-7.89 (m, 2H), 7.77 (s, 1H), 7.54-7.77 (m, 1H), 7.43-7.48 (m, 3H), 7.25-7.29 (m, 2H), 7.06-7.08 (m, 1H), 6.49 (s, 1H), 4.33-4.35 (t, J=4.55, 4.80 Hz, 2H), 3.84 (s, 2H), 3.80 (s, 3H), 3.75 (s, 3H), 3.46-3.48 (t, J=4.55 Hz, 2H), 3.39-3.41 (m, 8H).

Example 1.13: Preparation of 1-[3-(4-chloro-2-methyl-2H-pyrazol-3-yl)-4-(2-pyrrolidin-1-yl-ethoxy)-phenyl]-3-(4-chloro-phenyl)-urea (Compound 17). Method O—Comprising Steps 1.13a to 1.13c to Give a Phenol Step 1.13a: Preparation of 6-amino-chromen-4-one

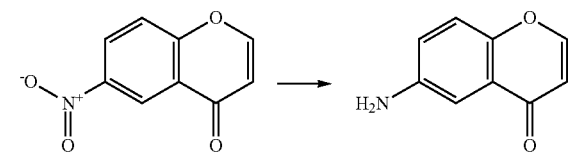

To a solution of 6-nitrochromone (2.0 g, 10.5 mmol) in methanol/ethyl acetate (100 mL/20 mL) purged with argon, was added 5% Pd/C (Degussa-wet, 0.5 g) catalyst. Hydrogen gas was bubbled through the slurry with stirring until (2 hrs.) LCMS and TLC showed complete conversion of starting material to product. The spent palladium catalyst was filtered off through a celite, and the solid was washed with methanol. The combined filtrate and washings were evaporated to produce 6-amino-chromen-4-one (1.58 g, 94%) as a light yellow solid. LCMS m/z (%)=162 (M+H, 100), 1H NMR (400 MHz, CDCl$_3$) δ: 7.79 (d, J=5.96 Hz, 1H), 7.38 (d, J=2.86 Hz, 1H), 7.29 (d, J=8.88 Hz, 1H), 7.01 (dd, J=8.80 Hz, 2.8 Hz, 1H), 6.26 (d, J=5.96 Hz, 1H), 5.29 (s, 2H).

Step 1.13b: Preparation of 1-(4-chloro-phenyl)-3-(4-oxo-4H-chromen-6-yl)-urea

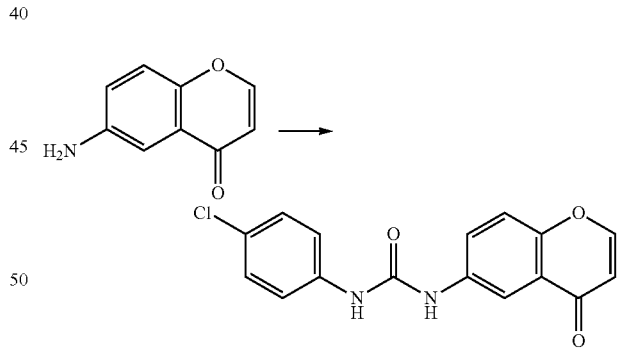

To a stirred and heated (80° C.) slurry of 6-aminochromone (3.0 g, 18.6 mmol) in toluene (200 mL) was added 4-chlorophenyl isocyanate (3.2 g, 20.5 mmol) and the mixture was refluxed further for 18 hours. The reaction mixture was cooled and the precipitate was filtered and washed with methanol. The residue was dried in vacuo to afford 1-(4-chloro-phenyl)-3-(4-oxo-4H-chromen-6-yl)-urea (5.8 g, 99%) as a yellow powder. LCMS m/z (%)=315 (M+H $^{35}$Cl, 100), 317 (M+H $^{37}$Cl, 32.2)$^1$H NMR (400 MHz, DMSO-d$_6$) δ: 9.09 (bs, 1H), 8.94 (bs, 1H), 8.29 (d, J=5.99 Hz, 1H), 8.20 (d, J=2.69 Hz, 1H), 7.81 (dd, J=9.0, 2.75 Hz, 1H), 7.62 (d, J=9.07 Hz, 1H), 7.52 (dd, J=6.84, 2.16 Hz, 2H), 7.35 (dd, J=6.85, 2.11 Hz, 2H), 6.33 (d, J=5.98 Hz, 1H).

Step 1.13c: Preparation of 1-(4-chloro-phenyl)-3-[4-hydroxy-3-(2-methyl-2H-pyrazol-3-yl)-phenyl]-urea

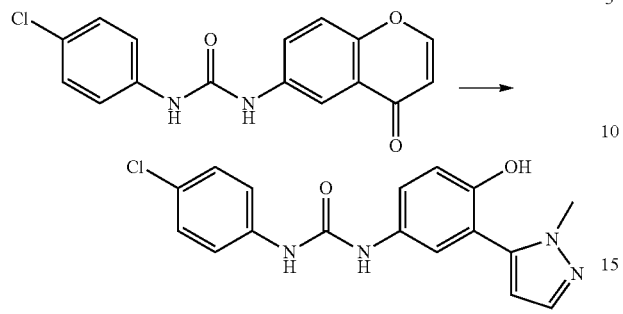

To a stirred and ice-cooled solution of methyl hydrazine (1.46 g, 31.6 mmol) in pyridine was added a slurry of 1-(4-chloro-phenyl)-3-(4-oxo-4H-chromen-6-yl)-urea (2.5 g, 7.9 mmol) in pyridine over a period of 10 mins. The reaction mixture was stirred further at this temperature for 2 hours and then allowed to warm slowly to ambient temperature. After 6 hrs the reaction mixture turned clear. The reaction was stirred at this temperature for 18 hours. Pyridine was evaporated and the resulting dark colored residue was dissolved in DMSO and purified using a Varian Prep. HPLC system (20 mL/min., λ=240, 0.1% TFA/H₂O:0.1% TFA/CH₃CN). The two regio-isomers were separated. The fractions containing the product were concentrated and dried in vacuo to produce (1.78 g, 47%) as a colorless powder. LCMS m/z (%)=343 (M+H ³⁵Cl, 100), 345 (M+H ³⁷Cl, 32.5). ¹H NMR (400 MHz, DMSO-d₆) δ: 9.59 (bs, 1H), 8.72 (bs, 1H), 8.48 (bs, 1H), 7.43 (dd, J=6.8, 2.07 Hz, 2H), 7.41 (d, J=1.83 Hz, 1H), 7.28 (dd, J=7.13, 2.09 Hz, 2H), 7.26 (d, J=2.72 Hz, 1H), 6.89 (d, J=9.36 Hz, 1H), 6.21 (d, J=1.84 Hz, 1H), 3.67 (s, 3H).

Step 1.13d: Preparation of 1-(4-chloro-phenyl)-3-[3-(2-methyl-2H-pyrazol-3-yl)-4-(2-pyrrolidin-1-yl-ethoxy)-phenyl]-urea

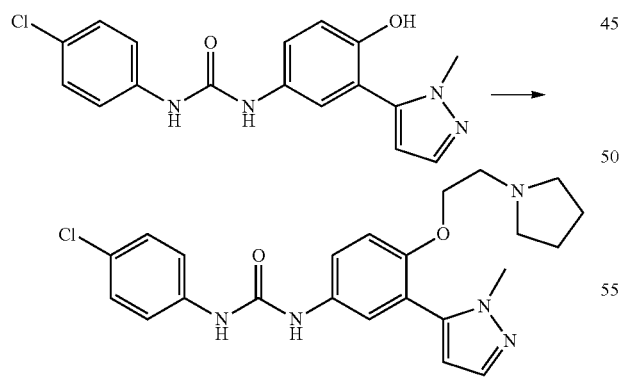

To a stirred and ice-cooled solution of 1-(4-chloro-phenyl)-3-[4-hydroxy-3-(2-methyl-2H-pyrazol-3-yl)-phenyl]-urea (0.1 g, 0.2923 mmol), triphenyl phosphine (0.291 g, 1.1078 mmol) and 1-(2-hydroxy ethyl)-pyrrolidine (0.127 g, 1.099 mmol) in THF (25 mL) was added diisopropyl azodicarboxylate (0.224 g, 1.104 mmol) slowly over 10 minutes. The reaction mixture was allowed to warm to ambient temperature and stirred further for 4 hrs at this temperature. THF was evaporated and the syrup was dissolved in DMSO and purified using a Varian preparative HPLC system (60 mL/min flow and λ=240 0.1% TFA/H₂O:0.1% TFA/CH₃CN). The fractions containing the product were evaporated. The pink colored residue was subjected to 2ⁿᵈ purification using SiO₂ flash chromatography (eluant: 1% methanol in DCM to 15% methanol in DCM). The fractions containing the product were evaporated to give a colorless solid that was used directly in the next step.

Step 1.13e: Preparation of 1-[3-(4-chloro-2-methyl-2H-pyrazol-3-yl)-4-(2-pyrrolidin-1-yl-ethoxy)-phenyl]-3-(4-chloro-phenyl)-urea

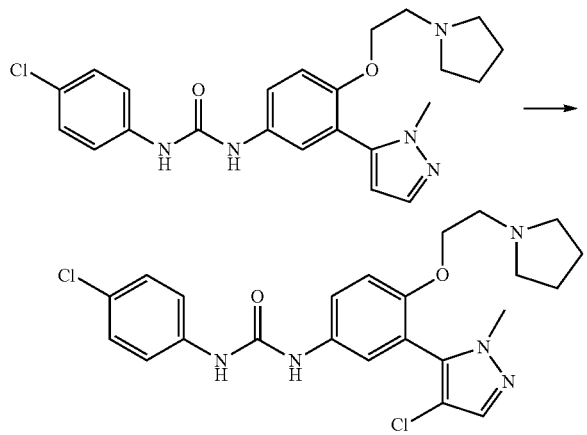

To a solution of 1-(4-chloro-phenyl)-3-[3-(2-methyl-2H-pyrazol-3-yl)-4-(2-pyrrolidin-1-yl-ethoxy)-phenyl]-urea in cold methanol was added a solution of N-chloro succinimide (0.044 g, 0.3215 mmol) in methanol. The reaction mixture was stirred for 60 minutes. Then the methanol was evaporated and the residue was purified using silica flash chromatography with 15% methanol in DCM as eluant. The fractions containing the product were evaporated and dried in vacuo to afford 1-[3-(4-chloro-2-methyl-2H-pyrazol-3-yl)-4-(2-pyrrolidin-1-yl-ethoxy)-phenyl]-3-(4-chloro-phenyl)-urea (Compound 17) (0.05 g, 38%) as an off-white solid. LCMS m/z (%)=474 (M+H ³⁵Cl ³⁵Cl, 100), 476 (M+H ³⁵Cl ³⁷Cl, 81.7), 478 (M+H ³⁷Cl ³⁷Cl, 11.2). ¹H NMR (400 MHz, DMSO-d₆) δ: 8.83 (bs, 1H), 8.73 (bs, 1H), 7.61 (s, 1H), 7.54 (dd, J=2.65, 2.69 Hz, 1H), 7.46 (dd, J=2.06, 2.11 Hz, 2H), 7.37 (d, J=2.7 Hz, 1H), 7.31 (dd, J=2.09, 2.04 Hz, 2H), 7.16 (d, J=9.03 Hz, 1H), 4.2-4.0 (bm, 2H), 3.65 (s, 3H), 2.7-2.5 (bm, 2H), 2.4-2.3 (bm, 4H), 1.7-1.5 (bm, 4H).

Example 1.14: Preparation of 1-(2,4-difluoro-phenyl)-3-[3-(2-methyl-2H-pyrazol-3-yl)-4-(pyridin-2-ylmethoxy)-phenyl]-urea (Compound 28)

Step 1.14a: Preparation of 2-[2-(2-methyl-2H-pyrazol-3-yl)-4-nitro-phenoxymethyl]-pyridine. Method P

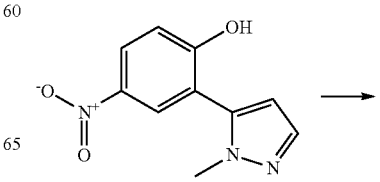

105

-continued

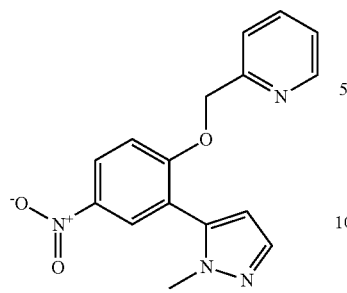

A mixture of 2-(2-methyl-2H-pyrazol-3-yl)-4-nitro-phenol (100 mg, 0.46 mmol), 2-bromomethylpyridine hydrobromide salt (140 mg, 0.55 mmol) and potassium carbonate (158 mg, 1.15 mmol) in DMSO (4 mL) was stirred at 100° C. overnight. The crude was purified by HPLC to provide the title compound as a brown solid (158 mg, 81%). Exact mass calculated for $C_{16}H_{14}N_4O_3$ 310.1, found 311.2 (MH$^+$).

Step 1.14b: Preparation of 3-(2-methyl-2H-pyrazol-3-yl)-4-(pyridin-2-ylmethoxy)-phenylamine. Method Q

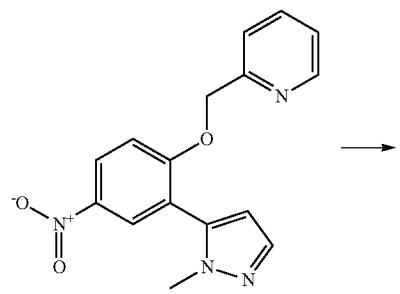

To a solution of 2-[2-(2-methyl-2H-pyrazol-3-yl)-4-nitro-phenoxy-methyl]-pyridine (158 mg, 0.37 mmol) in THF (3 mL) and saturated ammonium chloride (1 mL) was added zinc dust (192 mg, 2.96 mmol) at 0° C. The mixture was stirred at the same temperature for 15 minutes and then filtered through celite. The solution was concentrated in vacuo to give the title compound as a solid (150 mg, 100%). Exact mass calculated for $C_{16}H_{16}N_4O$ 280.1, found 281.4 (MH$^+$).

106

Step 1.14c: Preparation of 1-(2,4-difluoro-phenyl)-3-[3-(2-methyl-2H-pyrazol-3-yl)-4-(pyridin-2-ylmethoxy)-phenyl]-urea (Compound 28)

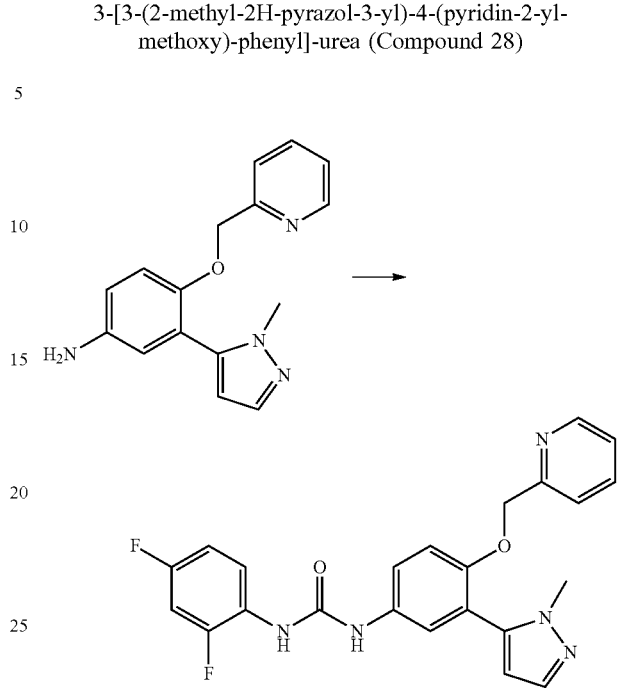

The title compound was prepared in a similar manner as described in Method F to give an off-white solid. H NMR (DMSO-d$_6$, 400 MHz) δ 3.68 (s, 3H), 5.20 (s, 2H), 6.31 (d, J=2.02 Hz, 1H), 7.04-7.06 (m, 1H), 7.18 (d, J=8.34 Hz, 1H), 7.27-7.34 (m, 2H), 7.37-7.47 (m, 4H), 7.87 (dt, J=2.02, 8.08 Hz, 1H), 8.00-8.07 (m, 1H), 8.48 (s, 1H), 8.59-8.60 (m, 1H), 8.98-8.99 (m, 1H). Exact mass calculated for $C_{23}H_{19}F_2N_5O_2$ 435.2, found 436.4 (MH$^+$).

Example 1.15: Preparation of 2-(4-chloro-phenyl)-2-hydroxy-N-[3-(2-methyl-2H-pyrazol-3-yl)-4-(2-pyrrolidin-1-yl-ethoxy)-phenyl]-acetamide (Compound 95). Method R

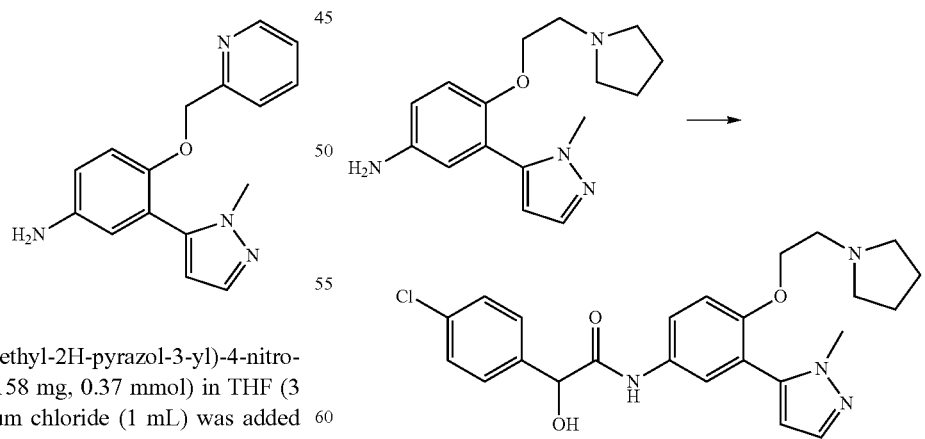

A mixture of 3-(2-methyl-2H-pyrazol-3-yl)-4-(2-pyrrolidin-1-yl-ethoxy)-phenylamine (100 mg, 0.35 mmol), 4-chloromandelic acid (98 mg, 0.525 mmol), HATU (200 mg, 0.525 mmol) and triethylamine (0.5 mL) in DMF (6 mL) was heated at 50° C. overnight. The crude was purified by HPLC to provide the title compound as a semi-solid (24 mg, 15%). $^1$H NMR (DMSO-$d_6$, 400 MHz) δ 1.60-1.73 (m, 2H), 1.84-1.91 (m, 2H), 2.80-2.90 (m, 2H), 3.22-3.30 (m, 4H), 3.65 (s, 3H), 4.25 (t, J=5.05 Hz, 2H), 6.26 (d, J=1.77 Hz, 1H), 7.17 (d, J=9.09 Hz, 1H), 7.39-7.46 (m, 2H), 7.51-7.53 (m, 3H), 7.67 (d, J=2.53 Hz, 1H), 7.80 (dd, J=2.78, 8.84 Hz, 1H), 9.50 (s br, 1H), 10.0 (s, 1H). Exact mass calculated for $C_{24}H_{27}ClN_4O_3$ 454.2, found 455.4 (MH$^+$).

Example 1.16: Preparation of 3-methyl-but-2-enoic acid [3-(4-bromo-2-methyl-2H-pyrazol-3-yl)-4-(2-pyrrolidin-1-yl-ethoxy)-phenyl]-amide (Compound 106). Method S

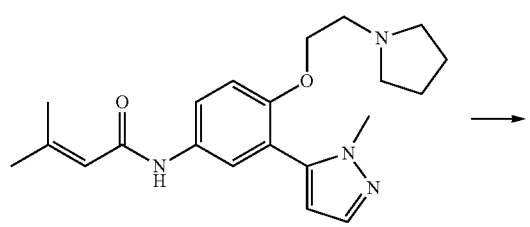

3-Methyl-N-[3-(2-methyl-2H-pyrazol-3-yl)-4-(2-pyrrolidin-1-yl-ethoxy)-phenyl]-butyramide (20 mg, 0.054 mmol) was treated with NBS (10 mg, 0.054 mmol) in DMF (2 mL) at room temperature for 2 hours. The crude was purified by HPLC to provide the title compound as an off-white solid (6 mg, 25%). Exact mass calculated for $C_{21}H_{27}BrN_4O_2$ 446.1, found 447.2 (MH$^+$).

Example 1.17: Preparation of 4-bromo-5-[2-(2-bromo-ethoxy)-5-nitro-phenyl]-1-methyl-1H-pyrazole. Method T

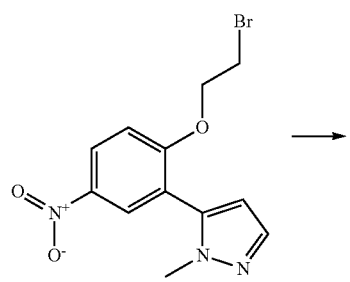

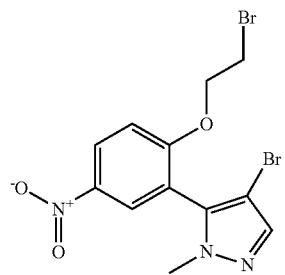

A mixture of 5-[2-(2-bromo-ethoxy)-5-nitro-phenyl]-1-methyl-1H-pyrazole (200 mg, 0.61 mmole), and N-bromosuccinimide (0.61 mmole, 1.0 eq) in 2 mL of DMF was stirred at 100° C. for 10 minutes in the Microwave. The mixture was quenched with water, extract with ethyl acetate, and dried in vacuo give the title compound as a yellow solid (200 mg, 81%). $^1$H NMR (400 MHz, CDCl$_3$) δ 3.53-3.64 (m, 2H), 3.78 (s, 3H), 4.38-4.49 (m, 2H), 7.11 (d, 1H), 7.57 (s, 1H), 8.23 (s, 1H), 8.39 (d, 1H). Exact mass calculated for $C_{12}H_{11}Br_2N_3O_3$ 402.9, found 406.1 (MH$^+$).

Example 1.18: Preparation of Pentanoic Acid {3-(4-bromo-2-methyl-2H-pyrazol-3-yl)-4-[2-(4-hydroxy-piperidin-1-yl)-ethoxy]-phenyl}-amide (Compound 179). Method U

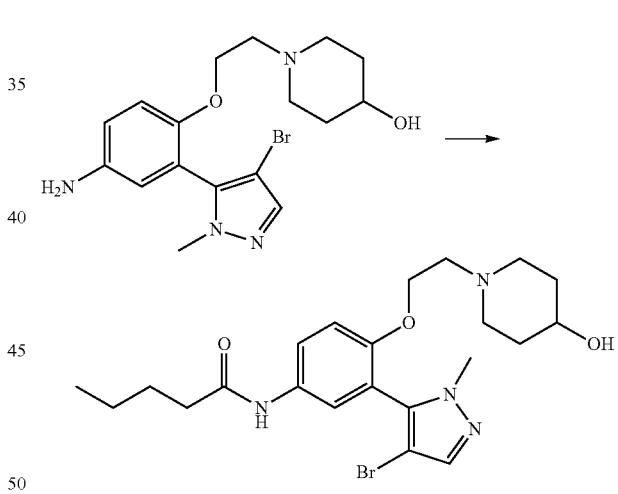

A mixture of 1-{2-[4-amino-2-(4-bromo-2-methyl-2H-pyrazol-3-yl)-phenoxy]-ethyl}-piperidin-4-ol (50 mg, 0.126 mmol), valeric anhydride (28 mg, 0.15 mmol) and triethylamine (0.1 mL) in DMF (1 mL) was heated with microwaves at 80° C. for 10 minutes. The crude was purified by HPLC to provide the title compound as a yellow solid (27 mg, 45%). $^1$H NMR (DMSO-$d_6$, 400 MHz) δ 0.90 (t, J=7.33 Hz, 3H), 1.33 (quar, J=7.58 Hz, 2H), 1.47-1.51 (m, 1H), 1.57 (quin, J=7.58 Hz, 2H), 1.68-1.90 (m, 2H), 2.30 (t, J=7.33 Hz, 2H), 2.75-3.30 (m, 6H), 3.40-3.43 (m, 2H), 3.70-3.71 (m, 3H), 3.85-3.90 (m, 1H), 4.22-4.50 (m, 2H), 7.22 (d, J=9.35 Hz, 1H), 7.53 (d, J=2.53 Hz, 1H), 7.64 (d, J=8.84 Hz, 1H), 7.76 (dd, J=2.53, 9.09 Hz, 1H), 9.37 (s, br, 1H), 9.98 (s, 1H). Exact mass calculated for $C_{22}H_{31}BrN_4O_3$ 478.2, found 479.3 (MH$^+$).

Example 1.19: Preparation of Pentanoic Acid [4-[2-(4-hydroxy-piperidin-1-yl)-ethoxy]-3-(2-methyl-2H-pyrazol-3-yl)-phenyl]-amide (Compound 203)

Step 1.19a: Preparation of 4-(2-chloro-ethoxy)-3-(2-methyl-2H-pyrazol-3-yl)-phenylamine. Method V

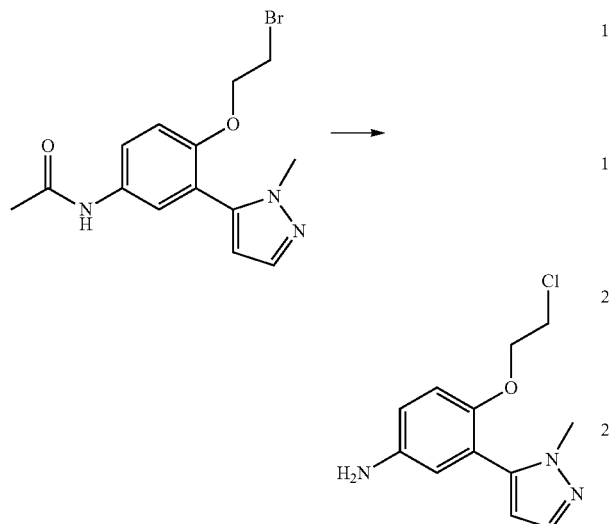

A mixture of N-[4-(2-bromo-ethoxy)-3-(2-methyl-2H-pyrazol-3-yl)-phenyl]-acetamide (450 mg, 1.33 mmol), concentrated HCl (0.9 mL) in THF (4 mL) was heated with microwave irradiation at 150° C. for 30 minutes. The crude was concentrated in vacuo to give the title compound as a brown oil. Exact mass calculated for $C_{12}H_{14}ClN_2O$ 251.1, found 252.0 (MH$^+$). This was used without purification in next step.

Step 1.19b: Preparation of Pentanoic Acid [4-(2-chloro-ethoxy)-3-(2-methyl-2H-pyrazol-3-yl)-phenyl]-amide

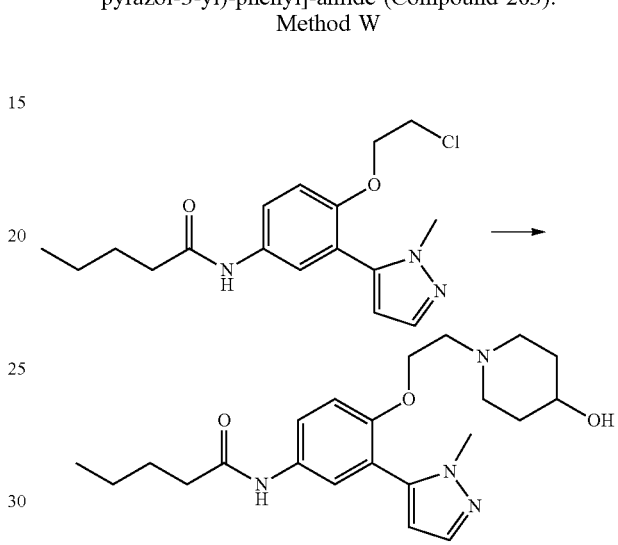

The title compound was prepared in a similar manner as described in Method U to give a white solid. $^1$H NMR (CDCl$_3$, 400 MHz) δ 0.95 (t, J=7.33 Hz, 3H), 1.43 (quar, J=7.58 Hz, 2H), 1.72 (quin, J=7.60 Hz, 2H), 2.40 (t, J=7.58 Hz, 2H), 3.72 (t, J=5.31 Hz, 2H), 4.04 (s, 3H), 4.25 (t, 2H), 6.25 (d, 1H), 6.98-7.00 (m, 1H), 7.44 (s, br, 1H), 7.59-7.60 (m, 1H), 7.64-7.66 (m, 1H), 7.81 (d, J=2.53 Hz, 1H). Exact mass calculated for $C_{17}H_{22}ClN_3O_3$ 335.1, found 336.3 (MH$^+$).

Step 1.19c: Preparation of Pentanoic Acid [4-[2-(4-hydroxy-piperidin-1-yl)-ethoxy]-3-(2-methyl-2H-pyrazol-3-yl)-phenyl]-amide (Compound 203). Method W

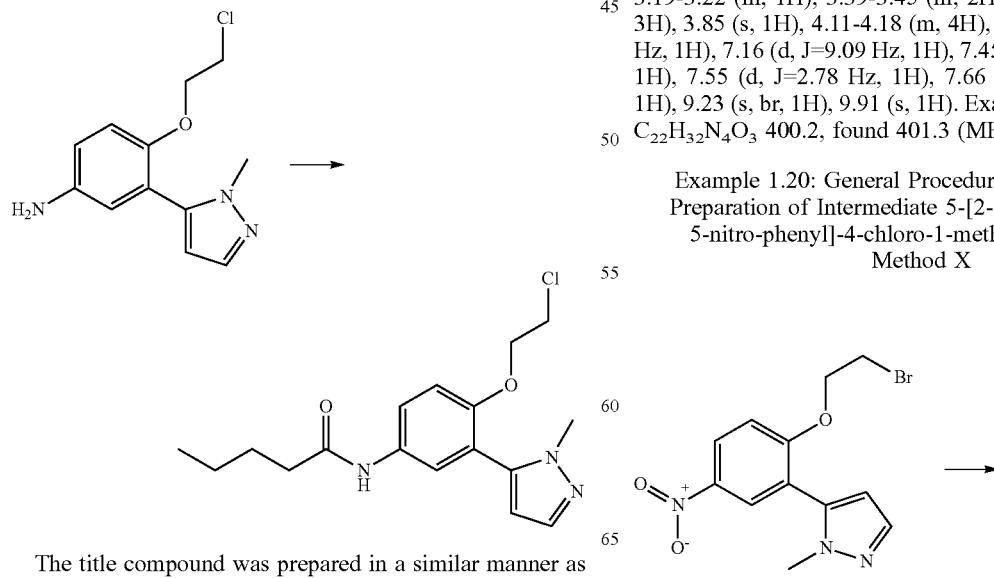

A mixture of pentanoic acid [4-(2-chloro-ethoxy)-3-(2-methyl-2H-pyrazol-3-yl)-phenyl]-amide (50 mg, 0.15 mmol), 4-hydroxypiperidine (18 mg, 0.18 mmol), potassium carbonate (31 mg, 0.225 mmol) and catalytic amount of tetrabutyl ammonium iodide in DMF (1 mL) was heated with microwaves at 100° C. for 2.5 hours. The crude was purified by HPLC to provide the title compound as a sticky solid (51 mg, 85%). $^1$H NMR (DMSO-d$_6$, 400 MHz) δ 0.89 (t, J=7.33 Hz, 3H), 1.30 (quar, J=7.58 Hz, 2H), 1.40-1.48 (m, 1H), 1.54 (quin, J=7.58 Hz, 2H), 1.66-1.82 (m, 2H), 2.28 (t, J=7.33 Hz, 2H), 2.82-2.89 (m, 1H), 3.05-3.09 (m, 2H), 3.19-3.22 (m, 1H), 3.39-3.45 (m, 2H), 3.64 (d, J=2.53 Hz, 3H), 3.85 (s, 1H), 4.11-4.18 (m, 4H), 6.25 (dd, J=2.02, 5.05 Hz, 1H), 7.16 (d, J=9.09 Hz, 1H), 7.45 (dd, J=2.02, 5.31 Hz, 1H), 7.55 (d, J=2.78 Hz, 1H), 7.66 (dd, J=2.53, 9.09 Hz, 1H), 9.23 (s, br, 1H), 9.91 (s, 1H). Exact mass calculated for $C_{22}H_{32}N_4O_3$ 400.2, found 401.3 (MH$^+$).

Example 1.20: General Procedure of Chlorination. Preparation of Intermediate 5-[2-(2-bromo-ethoxy)-5-nitro-phenyl]-4-chloro-1-methyl-1H-pyrazole. Method X -continued

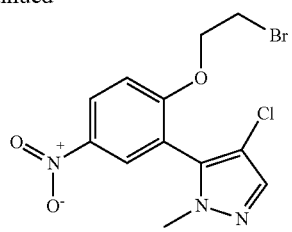

A mixture of 5-[2-(2-bromo-ethoxy)-5-nitro-phenyl]-1-methyl-1H-pyrazole (470 mg, 1.44 mmole), and N-chlorosuccinimide (1.44 mmole, 1.0 eq) in 2 mL of DMF was stirred at 100° C. for 20 minutes in the Microwave. The mixture was quenched with water, extract with ethyl acetate, and dried in vacuo give the title compound as a yellow solid (462 mg, 89%). $^1$H NMR (400 MHz, CDCl$_3$) δ 3.61 (t, 2H), 3.78 (s, 3H), 4.44 (t, 2H), 7.13 (d, 1H), 7.57 (s, 1H), 8.23 (s, 1H), 8.40 (d, 1H). Exact mass calculated for $C_{12}H_{11}{}^{81}BrClN_3O_3$ 359.0, found 362.0 (MH$^+$).

Example 1.21: Preparation of 1-[4-(2-azetidin-1-yl-ethoxy)-3-(2-methyl-2H-pyrazol-3-yl)-phenyl]-3-(2,2-difluoro-benzo[1,3]dioxol-5-yl)-urea (Compound 87). Method Y

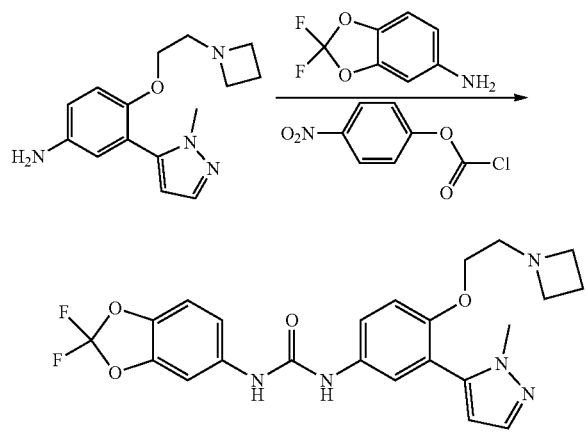

To a solution of 4-nitrophenyl chloroformate (51.5 mg, 0.255 mmol) in 1,2-dichloroethane (4 mL) and pyridine (50 μL) was added 5-amino-2,2-difluoro-1,3-benzodioxole (32 μL, 0.275 mmol). After 1 hour, 4-(2-azetidin-1-yl-ethoxy)-3-(2-methyl-2H-pyrazol-3-yl)-phenylamine (47.4 mg, 0.147 mmol) in 1,2-dichloroethane (5 mL) was added and stirring continued overnight. The resulting material was purified by HPLC. The product was dried in vacuo to afford Compound 87 as a white solid (40.7 mg, 50%). LCMS m/z (%)=472 (M+H, 100), $^1$H NMR (400 MHz, DMSO-d$_6$) δ: 8.96 (bs, 1H), 8.73 (bs, 1H), 7.65 (d, J=2.10 Hz, 1H), 7.47-7.41 (m, 2H), 7.36 (d, J=2.71 Hz, 1H), 7.30 (d, J=8.74 Hz, 1H), 7.10-7.02 (m, 2H), 6.22 (d, J=1.84 Hz, 1H), 3.89 (t, J=5.51 Hz, 2H), 3.67 (s, 3H), 2.98 (t, J=6.92 Hz, 4H), 2.60 (t, J=5.47 Hz, 2H), 1.86 (quintet, J=6.90 Hz, 2H).

Example 1.22: Preparation of 1-[3-(4-bromo-2-methyl-2H-pyrazol-3-yl)-4-(2-pyrrolidin-1-yl-ethoxy)-phenyl]-3-(4-hydroxy-phenyl)-urea (Compound 25). Method Z

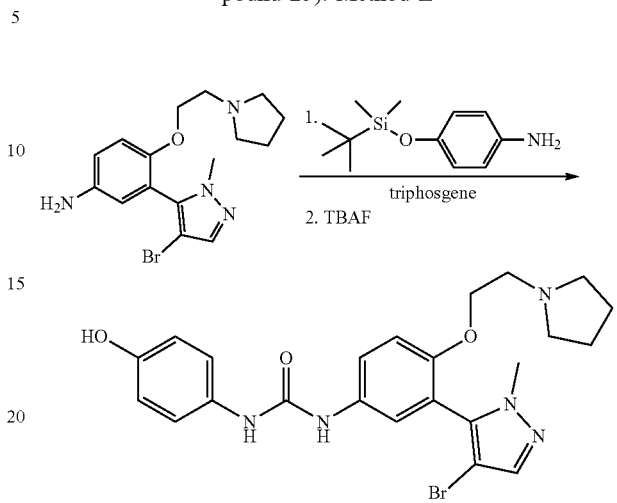

To a solution of triphosgene (19.7 mg, 0.066 mmol) in THF (4 mL) was added 4-(tert-butyl-dimethyl-silanyloxy)-phenylamine (48.4 mg, 0.217 mmol). After 1 hour, 3-(4-bromo-2-methyl-2H-pyrazol-3-yl)-4-(2-pyrrolidin-1-yl-ethoxy)-phenylamine (62.3 mg, 0.171 mmol) in THF (5 mL) was added followed 30 min. later by triethylamine (100 μL) and stirring continued overnight. The resulting material was purified by HPLC. The isolated oil (80 mg) was dissolved in THF (15 mL). To this solution, TBAF (0.165 mL of a 1.0 M in THF solution, 0.165 mmol) was added. The reaction mixture was concentrated, yielding an oil which was purified by SiO$_2$ column chromatography (eluent: 20% methanol/80% dichloromethane) to afford Compound 25 as a white solid (57.2 mg, 67%). LCMS m/z (%)=500 (M+H $^{79}$Br, 100), 502 (M+H $^{81}$Br, 89), $^1$H NMR (400 MHz, DMSO-d$_6$) δ: 9.03 (s, 1H), 8.59 (bs, 1H), 8.35 (bs, 1H), 7.59 (s, 1H), 7.51 (dd, J=8.97, 2.71 Hz, 1H), 7.33 (d, J=2.70 Hz, 1H), 7.20 (d, J=8.86 Hz, 1H), 7.12 (d, J=9.04 Hz, 1H), 6.67 (d, J=8.85 Hz, 1H), 4.13-4.04 (m, 1H), 4.04-3.95 (m, 1H), 3.66 (s, 3H), 2.77-2.66 (m, 1H), 2.66-2.57 (m, 1H), 2.41-2.30 (m, 4H), 1.65-1.55 (m, 4H).

Example 1.23: Preparation of 2-(tert-butyl-diphenyl-silanyloxy)-4-chloro-phenylamine. Method AA

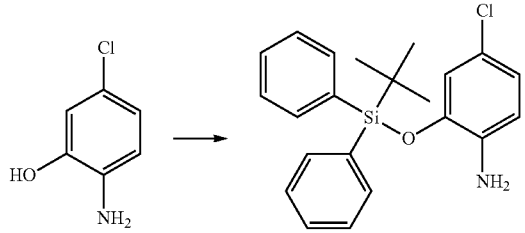 [SMILES: Nc1ccc(Cl)cc1O ; CC(C)(C)[Si](Oc1cc(Cl)ccc1N)(c1ccccc1)c1ccccc1]

2-Amino-5-chlorophenol (0.949 g, 6.61 mmol), tert-butylchlorodiphenylsilane (2.50 mL, 9.61 mmol), and imidazole (1.335 g, 19.6 mmol) were dissolved in THF (50 mL). Several days later, the reaction mixture was concentrated to give an oil which was purified by SiO$_2$ column chromatography (eluent: 45% dichloromethane/55% hexanes). The product was dried in vacuo to afford 2-(tert-butyl-diphenyl-silanyloxy)-4-chloro-phenylamine as a yellow oil (784.2 mg, 31%). ¹H NMR (400 MHz, DMSO-$d_6$) δ: 7.72-7.64 (m, 4H), 7.55-7.43 (m, 6H), 6.71 (d, J=8.45 Hz, 1H), 6.65 (dd, J=8.46, 2.27 Hz, 1H), 6.10 (d, J=2.26 Hz, 1H), 1.05 (s, 9H).

Example 1.24: Preparation of the Intermediate 5-(2-methoxy-5-nitro-phenyl)-1-methyl-1H-pyrazole. Method AB

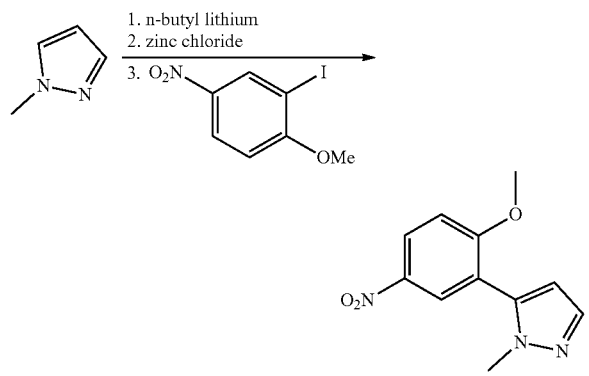

A solution of N-methylpyrazole (5.12 g, 62.4 mmol) in THF (100 mL) was cooled to −78° C. and 2.5M n-butyl-lithium in hexane (27.5 mL, 68.8 mmol) was added. After stirring for 30 minutes at the same temperature, 0.5 M zinc chloride in THF (107 mL, 53.5 mmol) and 1 M zinc chloride in diethyl ether (15.3 mL, 15.2 mmol) were added. The mixture was allowed to warm to room temperature and 2-iodo-4-nitroanisole (17.4 g, 62.4 mmol) followed by tetrakis(triphenylphosphine)palladium (3.6 g, 3.1 mmol) were added. After stirring at 60° C. for 20 hours, the black solution was concentrated on a rotary evaporator, and extracted with ethyl acetate and brine. Combined organic layers were dried over magnesium sulfate, filtered, and partly concentrated until a solid started to precipitate. Hexane was added, precipitate was filtered off, and washed with a cold 3:1 mixture of hexane/ethyl acetate to give 5-(2-methoxy-5-nitro-phenyl)-1-methyl-1H-pyrazole (8.6 g, 36.9 mmol, 59%) as a tan solid. LCMS m/z (%)=234 (M+H, 100). ¹H NMR (400 MHz, CDCl₃) δ: 8.34 (dd, J=2.8, 9.2 Hz, 1H), 8.19 (d, J=2.8 Hz, 1H), 7.56 (d, J=2.0 Hz, 1H), 7.08 (d, J=9.2 Hz, 1H), 6.31 (d, J=1.6 Hz, 1H), 3.96 (s, 3H), 3.74 (s, 3H).

Example 1.25: Preparation of the Intermediate 4-methoxy-3-(2-methyl-2H-pyrazol-3-yl)-phenylamine. Method AC

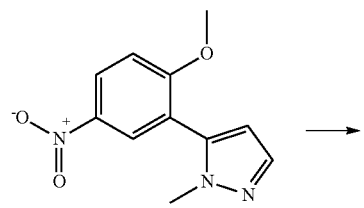

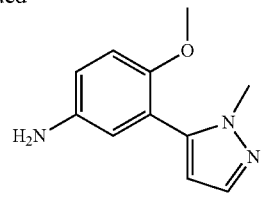

To a solution of 5-(2-methoxy-5-nitro-phenyl)-1-methyl-1H-pyrazole (7.95 g, 34.1 mmol) in acetic acid (250 mL) was added zinc dust (11.7 g, 179 mmol) in portions under cooling in an ice bath over a period of 10 minutes. After stirring for 30 min at room temperature, solids were filtered of through celite. Filtrate was concentrated and residue was purified by SiO₂ column chromatography (Eluent: methylene chloride/methanol 20:1) to give 4-methoxy-3-(2-methyl-2H-pyrazol-3-yl)-phenylamine (4.34 g, 21.4 mmol, 62%) as an oil. LCMS m/z (%)=204 (M+H). ¹H NMR (400 MHz, CDCl₃) δ: 7.51 (d, J=1.8 Hz, 1H), 6.83 (d, J=8.7 Hz, 1H), 6.76 (dd, J=2.8, 8.7 Hz, 1H), 6.62 (d, J=2.8 Hz, 1H), 6.22 (d, J=1.8 Hz, 1H), 3.74 (s, 3H), 3.73 (s, 3H), 3.24-3.55 (broad s, 2H).

Example 1.26: Preparation of the Intermediate 1-[3-(2-methyl-2H-pyrazol-3-yl)-4-hydroxy-phenyl]-3-(4-chloro-phenyl)-urea. Method AD

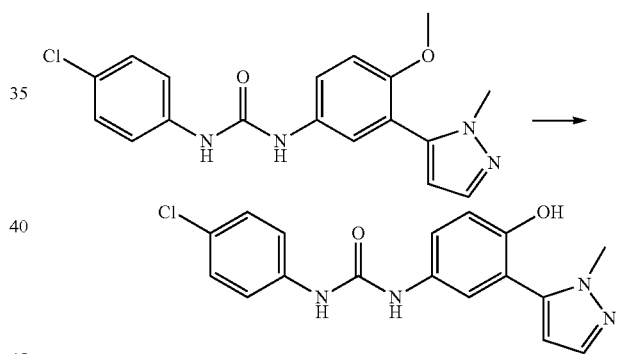

To a mixture of 1-[3-(2-methyl-2H-pyrazol-3-yl)-4-methoxy-phenyl]-3-(4-chloro-phenyl)-urea (6.35 g, 17.8 mmol) and dichloroethane (500 mL), tribromoborane (10 mL, 106 mmol) was added. The mixture was allowed to warm to room temperature. After stirring over the weekend, the mixture was cooled in an ice bath and a mixture of ice cold ammonium hydroxide and water (ca. 100 mL) was added slowly. The mixture was transferred into a separatory funnel and extracted with methylene chloride and water. Solid in the water phase was filtered off and washed with water to give 1-[3-(2-methyl-2H-pyrazol-3-yl)-4-hydroxy-phenyl]-3-(4-chloro-phenyl)-urea as a white solid (4.92 g, 90% pure, 12.7 mmol, 71%). Combined organic phases were dried over MgSO₄, filtered, and concentrated to afford additional 1-[3-(2-methyl-2H-pyrazol-3-yl)-4-hydroxy-phenyl]-3-(4-chloro-phenyl)-urea as a white solid (1.71 g, 4.99 mmol, 28%). Overall yield: 99%. LCMS m/z (%)=343.1 (M+H). ¹H NMR (400 MHz, CDCl₃) δ: 9.60 (br s, 1H), 8.78 (s, 1H), 8.53 (s, 1H), 7.48-7.42 (m, 3H), 7.32-7.27 (m, 4H), 6.91-6.89 (m, 1H), 6.21 (d, J=1.8 Hz, 1H), 3.68 (s, 3H).

Example 1.27: Preparation of 1-[3-(2-methyl-2H-pyrazol-3-yl)-4-(morpholin-2-ylmethoxy)-phenyl]-3-phenyl-urea (Compound 174). Method AE

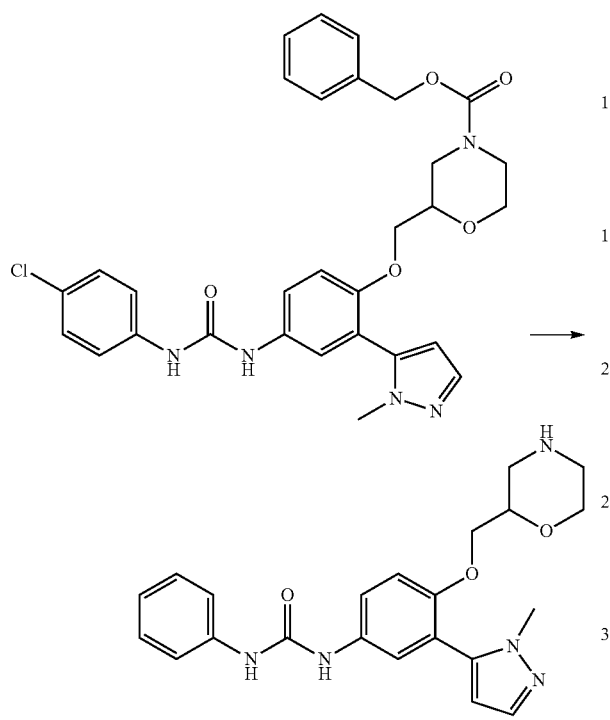

To a solution of 2-[4-[3-(4-chloro-phenyl)-ureido]-2-(2-methyl-2H-pyrazol-3-yl)-phenoxymethyl]-morpholine-4-carboxylic acid benzyl ester (30 mg, 0.052 mmol) in methanol (5 mL), was added Pd on carbon (10%, 50% $H_2O$, 50 mg, 0.024 mmol), and the mixture was stirred under a hydrogen atmosphere (balloon) at room temperature for 2 hours. Solids were filtered off through celite and mixture was purified by HPLC to give Compound 174 as a white solid (TFA salt, 9.8 mg, 0.0176 mmol, 36%). LCMS m/z (%)=408.5 (M+H). $^1$H NMR (400 MHz, MeOH-$d_4$) δ: 7.43-7.38 (m, 2H), 7.32-7.30 (m, 3H), 7.20-7.16 (m, 2H), 7.00 (d, J=8.9 Hz, 1H), 6.99-6.90 (m, 1H), 6.23 (s, 1H), 4.01-3.98 (m, 3H), 3.88-3.85 (m, 1H), 3.72-3.69 (m, 1H), 3.65 (s, 3H), 3.14-3.09 (m, 2H), 2.98-2.92 (m, 1H), 2.79-2.73 (m, 1H).

Example 1.28: Amination with a Boronic Acid and Copper(II) Acetate, Preparation of [3-(4-chloro-2-methyl-2H-pyrazol-3-yl)-4-(2-morpholin-4-yl-ethoxy)-phenyl]-(4-chloro-phenyl)-amine (Compound 305). Method AF

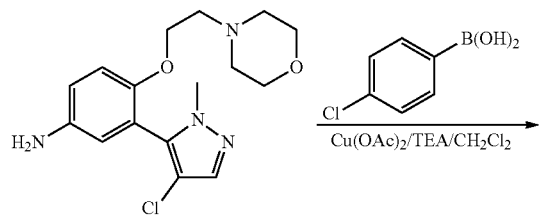

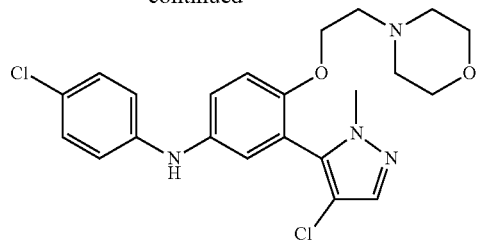

A mixture of 3-(4-chloro-2-methyl-2H-pyrazol-3-yl)-4-(2-morpholin-4-yl-ethoxy)-phenylamine (0.050 g, 0.15 mmol), 4-chlorophenyl boronic acid (0.035 g, 0.23 mmol), copper(II) acetate (0.0273 g, 0.15 mmol) and triethylamine (0.042 mL, 0.3 mmol) in methylene chloride (3 mL) was stirred at room temperature for 48 hours. The reaction mixture was concentrated to give a crude product that was subjected to a purification by prep HPLC. The corresponding fractions were collected and lyophilized to give a TFA-salt of Compound 305 as a gray solid in 21.3% yield. LCMS: Exact mass calculated for $C_{22}H_{24}Cl_2N_4O_2$ is 446.13, found m/z=447.1 (M+H).

Example 1.29: Reductive Amination, Preparation of 1-[3-(4-bromo-2-methyl-2H-pyrazol-3-yl)-4-(1-methyl-piperidin-4-ylmethoxy)-phenyl]-3-(4-chloro-phenyl)-urea (Compound 335). Method AG

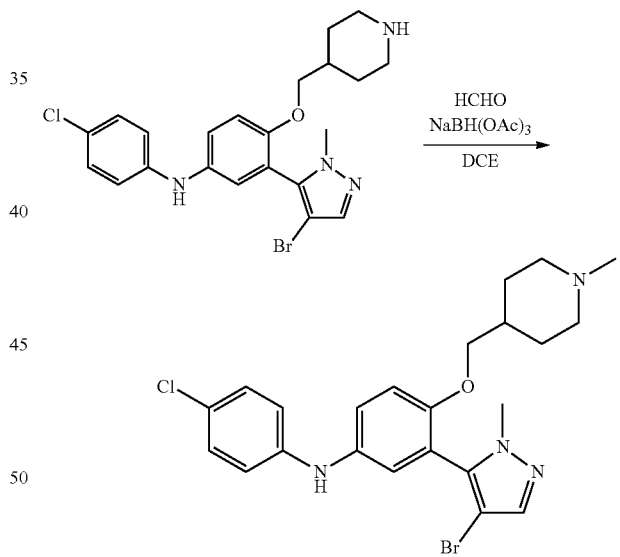

A mixture of 1-[3-(4-bromo-2-methyl-2H-pyrazol-3-yl)-4-(piperidin-4-ylmethoxy)-phenyl]-3-(4-chloro-phenyl)-urea (0.030 g, 0.06 mmol) and formaldehyde (37% aqueous solution, 0.015 mL, 0.18 mmol) in 1,2-dichloroethane (2 mL) was treated with sodium triacetoxyborohydride (0.025 g, 0.12 mmol). The mixture was stirred at room temperature under argon atmosphere overnight, diluted with ethyl acetate and washed with saturated sodium bicarbonate. The organic layer was separated, dried over anhydrous sodium sulfate, filtered and concentrated to give a crude product that was subjected to a purification by prep HPLC. The corresponding fractions were collected and lyophilized to give a TFA-salt of Compound 335 as a white solid in 54.7% yield.

Example 1.30: Preparation of N-{3-(4-chloro-2-methyl-2H-pyrazol-3-yl)-4-[2-(4-methanesulfonylamino-piperidin-1-yl)-ethoxy]-phenyl}-3-trifluoromethyl-benzamide (Compound 757). Method AH

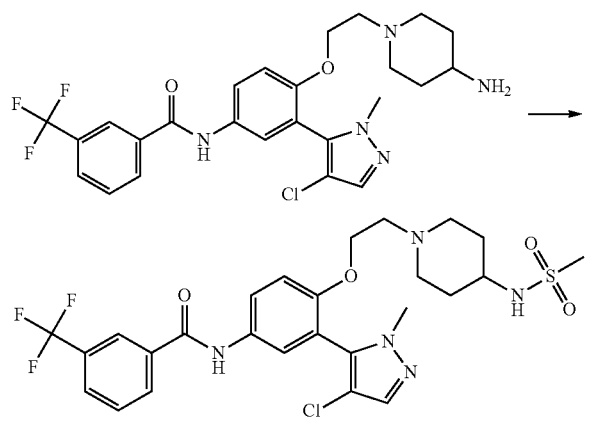

N-[4-[2-(4-Amino-piperidin-11-yl)-ethoxy]-3-(4-chloro-2-methyl-2H-pyrazol-3-yl)-phenyl]-3-trifluoromethyl-benzamide (0.038 g, 0.073 mmol) was dissolved in DMA (2.0 mL) in a vial with stir bar. Methanesulfonyl chloride (0.0085 g, 0.11 mmol) was added and the reaction was stirred at rt overnight. The reaction was concentrated, added to NaHCO₃ (5 mL), and the solution was extracted with EtOAc (2×20 mL). The organic extracts were dried (Na₂SO₄), filtered, coned and purified by prep HPLC to afford the title compound (0.016 g, 0.026 mmol, 35%, TFA salt) as a white solid. LCMS m/z (%)=600 (M+H$^{35}$Cl, 100), 602 (M+H$^{37}$Cl, 36). ¹H NMR (400 MHz, DMSO-d₆) δ: 10.54 (s, 1H), 9.30 (s, 1H), 8.30 (s, 1H), 8.26 (d, J=8.0 Hz, 1H), 7.97 (m, 2H), 7.80 (m, 1H), 7.72 (d, J=2.6 Hz, 1H), 7.68 (s, 1H), 7.31 (m, 1H), 4.40 (m, 1H), 4.32 (m, 1H), 3.69 (s, 3H), 3.50-2.90 (m, 7H), 2.95 (s, 3H), 2.00-1.50 (m, 4H).

Example 1.31: Preparation of 1-(4-Chloro-phenyl)-3-[4-[2-((R)-1-methyl-piperidin-2-yl)-ethoxy]-3-(2-methyl-2H-pyrazol-3-yl)-phenyl]-urea (Compound 353). Method AI

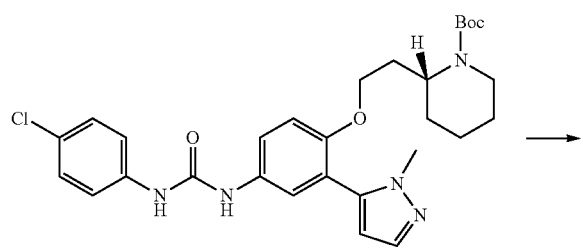

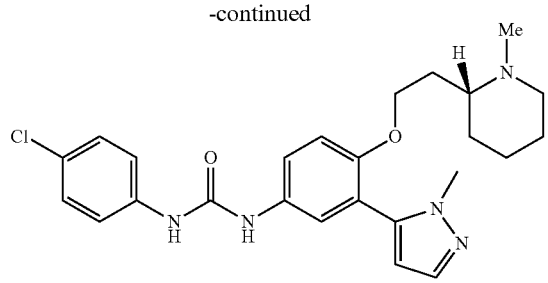

2-{2-[4-[3-(4-Chloro-phenyl)-ureido]-2-(2-methyl-2H-pyrazol-3-yl)-phenoxy]-ethyl}-piperidine-1-carboxylic acid tert-butyl ester (240 mg, 0.434 mmole) was added into solution of 1M LiAlH₄ in THF (3.472 mL, 3.472 mmole) and THF (10 mL) at 0° C. Reaction mixture was heated to reflux at 75° C. for 8 hours. The crude reaction mixture was quenched with water at 0° C. while stirring and Na₂SO₄ was added into crude, and then stirred at room temperature for another 30 minutes. The resulting solid was filtered, washed with ethyl acetate and supernatant was concentrated and dried in vacuo. Crude was purified through HPLC gave the title compound as a pale pink solid as a TFA salt. Exact mass calculated for C₂₅ClH₃₀N₅O₂ 467.2, found 468.5 (MH⁺).

Example 1.32: Preparation of N-{3-(4-bromo-2-methyl-2H-pyrazol-3-yl)-4-[2-(4-methoxy-piperidin-1-yl)-ethoxy]-phenyl}-3-fluoro-benzamide (Compound 637)

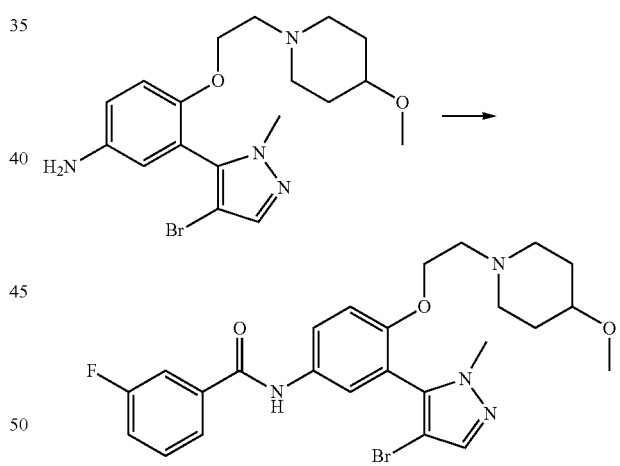

To a solution of 3-(4-bromo-1-methyl-1H-pyrazol-5-yl)-4-(2-(4-methoxypiperidin-1-yl)ethoxy)benzenamine (0.024 g, 0.060 mmol) in CH₂Cl₂ (0.9 mL) was added 3-fluorobenzoyl chloride (0.0086 mL, 0.0714 mmol) and triethylamine (0.011 mL, 0.077 mmol). The reaction was stirred for 1 h, and concentrated and purified by RP-HPLC. Lyophilization afforded a TFA salt as a brown oil (0.027 g, 56%). LCMS m/z (%)=531 (M+H$^{79}$Br, 94), 533 (M+H$^{81}$Br, 100). ¹H NMR (400 MHz, DMSO-d₆) δ: 10.42 (s, 1H), 7.95 (dd, J=2.1, 8.5 Hz, 1H), 7.82 (d, J=7.9 Hz, 1H), 7.79-7.75 (m, 1H), 7.74-7.72 (m, 1H), 7.68 (d, J=8.6 Hz, 1H), 7.63-7.57 (m, 1H), 7.45 (dt, J=2.6, 8.3 Hz, 1H), 7.29 (dd, J=3.7, 9.1 Hz, 1H), 4.47-4.38 (m, 1H), 4.35-4.28 (m, 1H), 3.69 (s, 3H), 3.27 (s, 3H), 3.53-1.37 (m, 11H).

LCMS: Exact mass calculated for C₂₄H₂₇BrClN₅O₂ is 531.10, found m/z=532.2 (M+H).

Example 1.33: Preparation of N-[3-(4-chloro-2-methyl-2H-pyrazol-3-yl)-4-(2-morpholin-4-yl-ethoxy)-phenyl]-3-fluoro-4-methyl-benzamide (Compound 559)

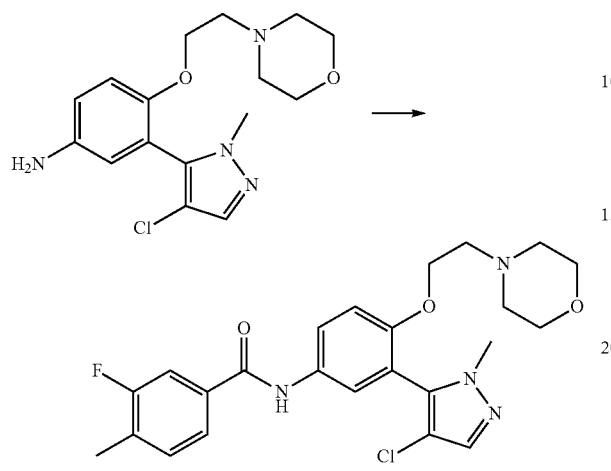

To a solution of 3-(4-Chloro-2-methyl-2H-pyrazol-3-yl)-4-(2-morpholin-4-yl-ethoxy)-phenylamine (0.040 g, 0.12 mmol) in $CH_2Cl_2$ (1.8 mL) was added 3-fluoro-4-methyl-benzoyl chloride (0.025 mL, 0.14 mmol) and triethylamine (0.022 mL, 0.15 mmol). The reaction was stirred for 1 h, and concentrated and purified by RP-HPLC. Lyophilization afforded a TFA salt as a brown oil (0.0096 g, 14%). LCMS m/z (%)=473 (M+H $^{35}$Cl, 100), 475 (M+H $^{37}$Cl, 27). $^1$H NMR (400 MHz, DMSO-$d_6$) δ: 10.31 (s, 1H), 7.96 (dd, J=2.6, 11.6 Hz, 1H), 7.76-7.72 (m, 3H), 7.67 (s, 1H), 7.49-7.44 (m, 1H), 7.30 (d, J=9.1 Hz, 1H), 4.48-4.44 (m, 1H), 4.38-4.30 (m, 1H), 3.66 (s, 3H), 4.00-2.90 (m, 10H), 2.32 (s, 3H).

Example 1.34: Preparation of 1-(3-(4-chloro-1-methyl-1H-pyrazol-5-yl)-4-(2-morpholinoethoxy)phenyl)-3-(3-chlorophenyl)urea (Compound 231)

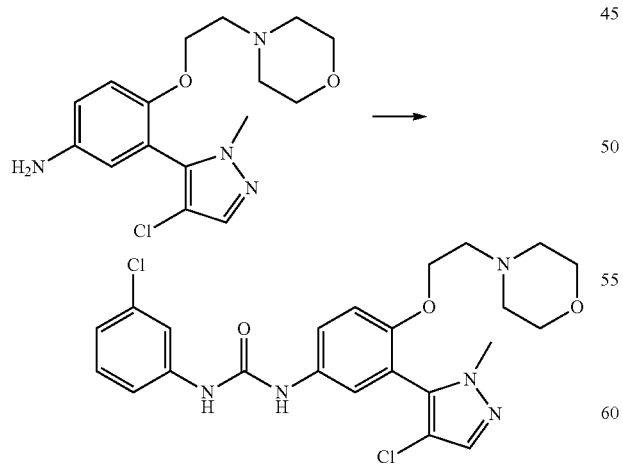

A solution of 3-(4-chloro-2-methyl-2H-pyrazol-3-yl)-4-(2-morpholin-4-yl-ethoxy)-phenylamine (0.040 g, 0.12 mmol) in $CH_2Cl_2$ (1 mL) was treated with 3-chlorophenyl isocyanate (0.015 mL, 0.125 mmol). The reaction was stirred overnight, and concentrated and purified by RP-HPLC. Lyophilization afforded a TFA salt as a brown solid (0.016 g, 27%). LCMS m/z (%)=490 (M+H $^{35}$Cl$^{35}$Cl, 100), 492 (M+H $^{35}$Cl$^{37}$Cl, 76), 494 (M+H $^{37}$Cl$^{37}$Cl, 15). $^1$H NMR (400 MHz, DMSO-$d_6$) δ: 8.92 (s, 1H), 8.79 (s, 1H), 7.74 (t, J=2.0 Hz, 1H), 7.70-7.63 (m, 1H), 7.57 (dd, J=2.7, 6.3 Hz, 1H), 7.41 (d, J=2.7 Hz, 1H), 7.36-7.28 (m, 2H), 7.21 (d, J=9.0 Hz, 1H), 7.04 (dt, J=1.9, 7.4 Hz, 1H), 4.22-4.15 (m, 1H), 4.11-4.05 (m, 1H), 3.70 (s, 3H), 3.56-3.51 (m, 4H), 2.66-2.48 (m, 2H), 2.42-2.30 (m, 4H).

Example 1.35: Preparation of 1-(4-chloro-benzyl)-3-[3-(2-methyl-2H-pyrazol-3-yl)-4-(3-morpholin-4-yl-propoxy)-phenyl]-urea (Compound 666)

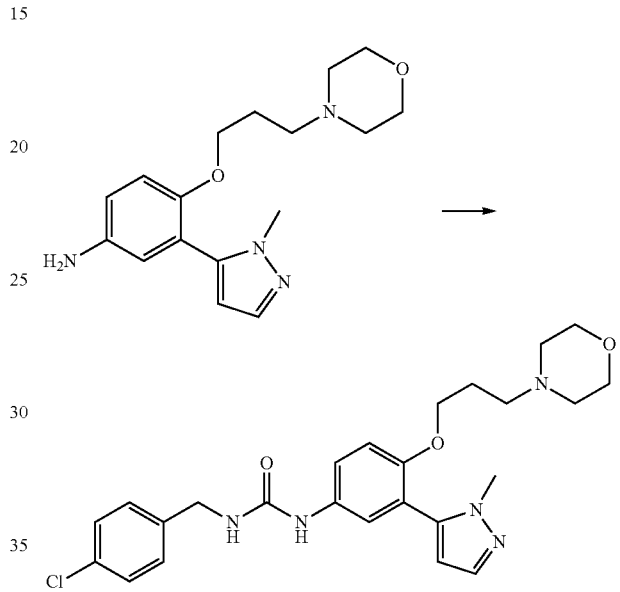

A solution of 3-(1-methyl-1H-pyrazol-5-yl)-4-(3-morpholinopropoxy) benzenamine (0.025 g, 0.079 mmol) in $CH_2Cl_2$ (0.6 mL) was treated with 4-chlorobenzyl isocyanate (0.012 mL, 0.083 mmol). The reaction was stirred for 1 h, and concentrated and purified by RP-HPLC. Lyophilization afforded a TFA salt as a white solid (0.037 g, 78%). LCMS m/z (%)=484 (M+H $^{35}$Cl, 100), 486 (M+H $^{37}$Cl, 38). $^1$H NMR (400 MHz, DMSO-$d_6$) δ: 9.60 (s, 1H), 8.63 (s, 1H), 7.46 (d, J=1.8 Hz, 1H), 7.43 (dd, J=2.6, 8.9 Hz, 1H), 7.40-7.29 (m, 4H), 7.07 (d, J=9.0 Hz, 1H), 6.75-6.70 (m, 1H), 6.25 (d, J=1.8 Hz, 1H), 4.26 (d, J=5.8 Hz, 2H), 4.02-3.90 (m, 4H), 3.65 (s, 3H), 3.58 (t, J=12.0 Hz, 2H), 3.34 (d, J=12.4 Hz, 2H), 3.09-2.92 (m, 4H), 2.06-1.97 (m, 2H).

Example 1.36: Preparation of 3-chloro-N-[3-(2-methyl-2H-pyrazol-3-yl)-4-(2-pyrrolidin-1-yl-ethoxy)-phenyl]-benzamide (Compound 512)

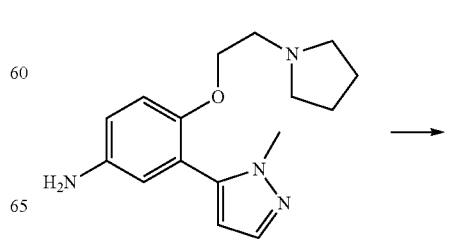

-continued

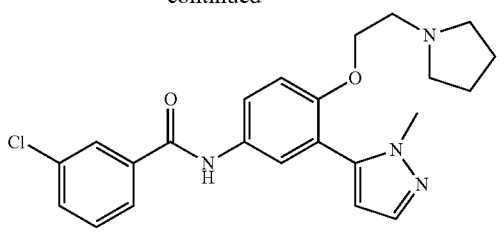

To a solution of 3-(1-methyl-1H-pyrazol-5-yl)-4-(2-(pyrrolidin-1-yl)ethoxy)benzenamine (0.029 g, 0.10 mmol) in CH$_2$Cl$_2$ (1.5 mL) was added 3-chlorobenzoyl chloride (0.015 mL, 0.12 mmol) and triethylamine (0.018 mL, 0.13 mmol). The reaction was stirred for 1 h, and concentrated and purified by RP-HPLC. Lyophilization afforded a TFA salt as a brown oil (0.037 g, 87%). LCMS m/z (%)=425 (M+H $^{35}$Cl, 100), 427 (M+H $^{37}$Cl, 42). $^1$H NMR (400 MHz, DMSO-d$_6$) δ: 10.40 (s, 1H), 8.01-8.00 (m, 1H), 7.94-7.87 (m, 2H), 7.72 (d, J=2.6 Hz, 1H), 7.70-7.67 (m, 1H), 7.60-7.55 (m, 1H), 7.49 (d, J=1.8 Hz, 1H), 7.25 (d, J=9.0 Hz, 1H), 6.31 (d, J=1.8 Hz, 1H), 4.32-4.28 (m, 2H), 3.69 (s, 3H), 3.58-3.52 (m, 2H), 3.35-3.25 (m, 2H), 2.95-2.82 (m, 2H), 1.95-1.85 (m, 2H), 1.78-1.68 (m, 2H).

Example 1.37: Preparation of 3-fluoro-N-[3-(2-methyl-2H-pyrazol-3-yl)-4-(2-pyrrolidin-1-yl-ethoxy)-phenyl]-4-trifluoromethyl-benzamide (Compound 487)

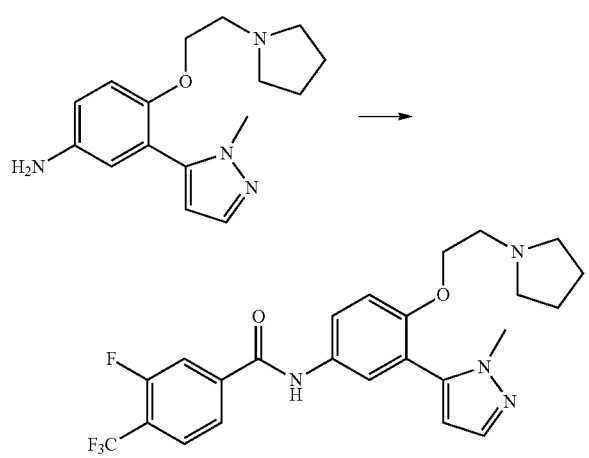

To a solution of 3-(1-methyl-1H-pyrazol-5-yl)-4-(2-(pyrrolidin-1-yl)ethoxy)benzenamine (0.029 g, 0.10 mmol) in CH$_2$Cl$_2$ (1.5 mL) was added 3-fluoro-4-(trifluoromethyl) benzoyl chloride (0.018 mL, 0.12 mmol) and triethylamine (0.018 mL, 0.13 mmol). The reaction was stirred for 1 h, and concentrated and purified by RP-HPLC. Lyophilization afforded a TFA salt as a brown oil (0.042 g, 88%). LCMS m/z (%)=477 (M+H, 100). $^1$H NMR (400 MHz, DMSO-d$_6$) δ: 10.55 (s, 1H), 8.07-7.95 (m, 3H), 7.88 (dd, J=2.6, 9.0 Hz, 1H), 7.73 (d, J=2.6 Hz, 1H), 7.49 (d, J=1.8 Hz, 1H), 7.27 (d, J=9.0 Hz, 1H), 6.31 (d, J=1.8 Hz, 1H), 4.33-4.29 (m, 2H), 3.69 (s, 3H), 3.58-3.52 (m, 2H), 3.35-3.25 (m, 2H), 2.92-2.81 (m, 2H), 1.95-1.85 (m, 2H), 1.80-1.69 (m, 2H).

Example 1.38: Preparation of 1-{3-(4-chloro-2-methyl-2H-pyrazol-3-yl)-4-[2-(3-hydroxy-azetidin-1-yl)-ethoxy]-phenyl}-3-(4-chloro-phenyl)-urea (Compound 298)

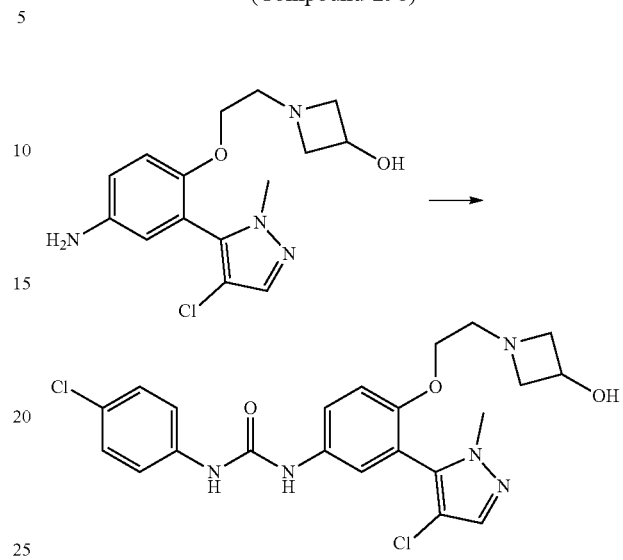

4-Chlorophenylisocyanate (19.0 mg, 0.124 mmol) was added to a solution of 1-{2-[4-amino-2-(4-chloro-2-methyl-2H-pyrazol-3-yl)-phenoxy]-ethyl}-azetidin-3-ol (40.0 mg, 0.124 mmol) in dichloromethane (2.0 mL) and DMF (0.1 mL), and the mixture stirred at room temperature overnight. The solution was concentrated and purified by RP-HPLC. The collected fractions were concentrated and 12% sodium hydroxide (aq) (0.2 mL) was added to give pH 9. The solution was extracted into ethyl acetate and the organic layer was dried over sodium sulfate, filtered, and evaporated to dryness to give a white solid (28 mg, 47%). LCMS m/z (%)=476 (M+H $^{35}$Cl, 100), 478 (M+H $^{37}$Cl, 67). $^1$H NMR (400 MHz, DMSO-d$_6$) δ: 8.81 (bs, 1H), 8.71 (bs, 1H), 7.60 (s, 1H), 7.53-7.50 (m, 1H), 7.47 (d, J=2.08 Hz, 1H), 7.46 (d, J=2.10 Hz, 1H), 7.36 (d, J=2.71 Hz, 1H), 7.32 (d, J=2.11 Hz, 1H), 7.30 (d, J=2.04 Hz, 1H), 7.11 (d, J=9.06 Hz, 1H), 5.19 (d, J=8.00 Hz, 1H), 4.10-4.00 (m, 1H), 3.99-3.85 (m, 2H), 3.65 (s, 3H), 3.40-3.30 (m, 2H), 2.70-2.55 (m, 4H).

Example 1.39: Preparation of 1-[4-[2-(7-aza-bicyclo [2.2.1]hept-7-yl)-ethoxy]-3-(4-bromo-2-methyl-2H-pyrazol-3-yl)-phenyl]-3-(3-trifluoromethyl-benzyl)-urea (Compound 710)

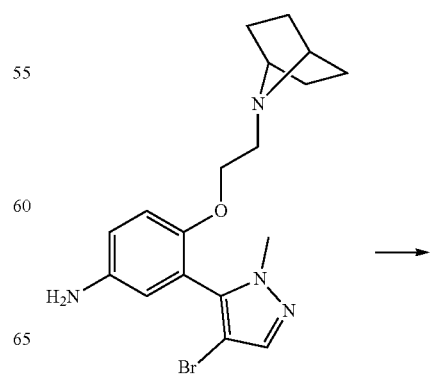

123

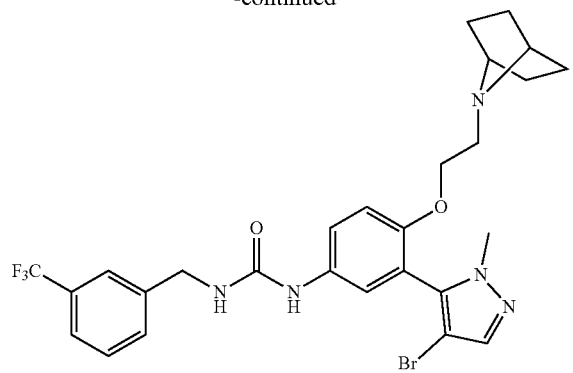

4-[2-(7-Aza-bicyclo[2.2.1]hept-7-yl)-ethoxy]-3-(4-bromo-2-methyl-2H-pyrazol-3-yl)-phenylamine (50.0 mg, 0.13 mmol) was added to a solution of 4-nitrophenylchloroformate (26.0 mg, 0.13 mmol) in 1,2-dichloroethane (4.0 mL) and the mixture stirred at room temperature for 1 hour. To the resulting precipitate mixture was added 3-trifluoromethylbenzylamine (0.022 mL, 0.15 mmol) and N,N-diisopropylethylamine (0.030 mL, 0.17 mmol), and the mixture stirred an additional 1 hour. The mixture was concentrated and purified by RP-HPLC. The collected fractions were concentrated and 12% sodium hydroxide (aq) (0.2 mL) was added to give pH 9. The solution was extracted into ethyl acetate and the organic layer was dried over sodium sulfate, filtered, and evaporated to dryness to give a white solid (49 mg, 65%). LCMS m/z (%)=592 (M+H $^{79}$Br, 100), 594 (M+H $^{81}$Br, 67). $^1$H NMR (400 MHz, DMSO-d$_6$) δ: 8.67 (bs, 1H), 7.67 (bs, 1H), 7.65-7.59 (m, 4H), 7.53-7.50 (m, 1H), 7.33 (d, J=2.69 Hz, 1H), 7.12 (d, J=9.04 Hz, 1H), 6.77-6.74 (m, 1H), 4.40 (d, J=4.0 Hz, 2H), 4.08-3.98 (m, 2H), 3.67 (s, 3H), 3.12 (m, 2H), 2.59-2.55 (m, 2H), 1.56-1.54 (m, 4H), 1.17-1.15 (m, 4H).

Example 1.40: Preparation of 1-[4-[2-(7-aza-bicyclo[2.2.1]hept-7-yl)-ethoxy]-3-(4-bromo-2-methyl-2H-pyrazol-3-yl)-phenyl]-3-(2,4-difluoro-benzyl)-urea (Compound 734)

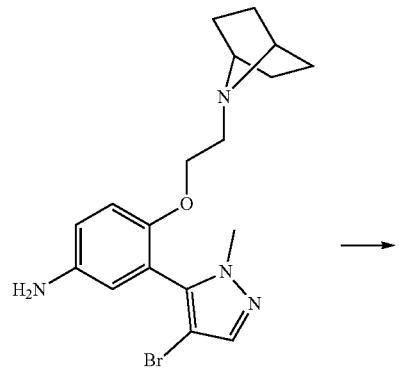

124

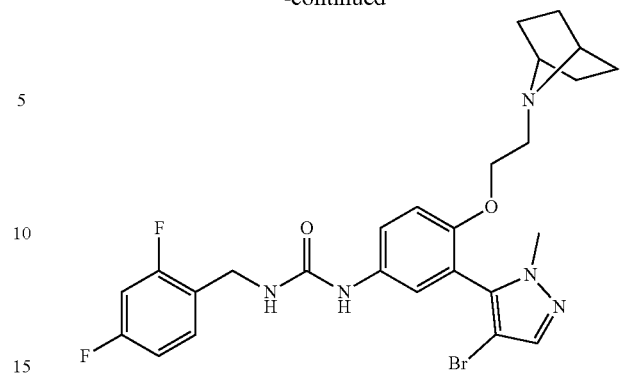

4-[2-(7-Aza-bicyclo[2.2.1]hept-7-yl)-ethoxy]-3-(4-bromo-2-methyl-2H-pyrazol-3-yl)-phenylamine (50.0 mg, 0.13 mmol) was added to a solution of 4-nitrophenylchloroformate (26.0 mg, 0.13 mmol) in 1,2-dichloroethane (4.0 mL) and the mixture stirred at room temperature for 1 hour. To the resulting precipitate mixture was added 2,4-difluorobenzylamine (0.030 mL, 0.25 mmol) and N,N-diisopropylethylamine (0.030 mL, 0.17 mmol), and the mixture stirred an additional 1 hour. The mixture was concentrated and purified by RP-HPLC. The collected fractions were concentrated and 12% sodium hydroxide (aq) (0.2 mL) was added to give pH 9. The solution was extracted into ethyl acetate and the organic layer was dried over sodium sulfate, filtered, and evaporated to dryness to give a white solid (62 mg, 87%). LCMS m/z (%)=560 (M+H $^{79}$Br, 100), 562 (M+H $^{81}$Br, 91). $^1$H NMR (400 MHz, DMSO-d$_6$) δ: 8.59 (bs, 1H), 7.58 (bs, 1H), 7.48-7.38 (m, 2H), 7.29 (bs, 1H), 7.24-7.18 (m, 1H), 7.10-7.04 (m, 2H), 6.60-5.59 (m, 1H), 4.29 (d, J=4.0 Hz, 2H), 4.06-3.96 (m, 2H), 3.64 (s, 3H), 3.11 (bs, 2H), 2.58-2.54 (m, 2H), 1.54-1.52 (m, 4H), 1.15-1.13 (m, 4H).

Example 1.41: Preparation of 4-fluoro-N-[3-(2-methyl-2H-pyrazol-3-yl)-4-(2-morpholin-4-yl-ethoxy)-phenyl]-benzamide (Compound 281)

Step 1.41a: General Procedure of Mitsunobu. Preparation of 4-{2-[2-(2-Methyl-2H-pyrazol-3-yl)-4-nitro-phenoxy]-ethyl}-morpholine

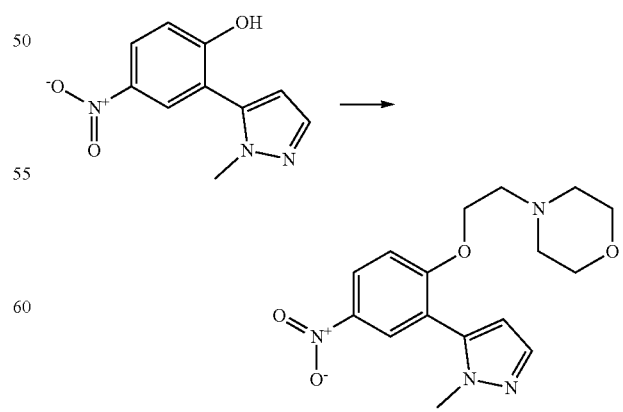

A mixture of triphenylphosphine (7.5 g, 1.8 eq), and diisopropylazodicarboxylate (5.66 mL, 1.8 eq) in 50 mL THF was stirred at 0° C. for 10 minutes, then 2-(2-methyl-2H-pyrazol-3-yl)-4-nitro-phenol (3.5 g, 15.9 mmole), and 2-morpholin-4-yl-ethanol (3.66 mL, 1.8 eq) was added into the mixture at 0° C. Reaction mixture was stirred at room temp for another 1 hour. The mixture was purified by HPLC to give title compound as a yellow gummy solid (9.436 g, 89%). Exact mass calculated for $C_{16}H_{20}N_4O_5$ 332.2, found 333.3 (MH$^+$).

Step 1.41b: Preparation of 3-(2-Methyl-2H-pyrazol-3-yl)-4-(2-morpholin-4-yl-ethoxy)-phenylamine

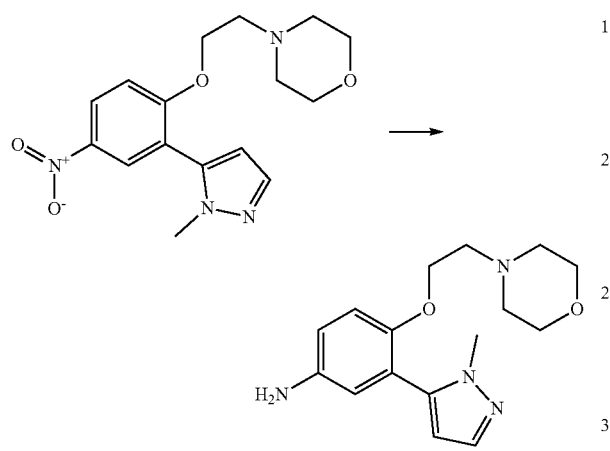

To a solution of 4-{2-[2-(2-methyl-2H-pyrazol-3-yl)-4-nitro-phenoxy]-ethyl}-morpholine (1.913 g, 2.88 mmole), in saturated ammonium chloride solution (6 mL), water (6 mL) and THF (12 mL) was added zinc dust (1.123 g, 6 eq) at 0° C. The mixture was stirred at room temp for 1 hour and then filtered off through celite. The solution was dried in vacuo to give title compound as a yellow gummy solid (1.87 g, 99%). Exact mass calculated for $C_{16}H_{22}N_4O_2$ 302.2, found 303.4 (MH$^+$).

Step 1.41c: Preparation of 2,4-Difluoro-N-[3-(2-methyl-2H-pyrazol-3-yl)-4-(2-morpholin-4-yl-ethoxy)-phenyl]-benzamide. (Compound 281)

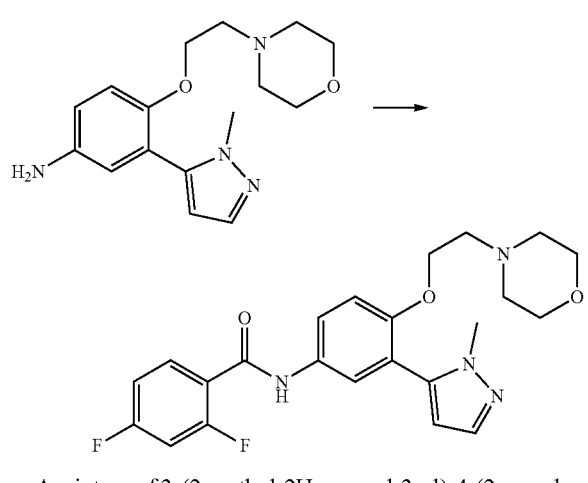

A mixture of 3-(2-methyl-2H-pyrazol-3-yl)-4-(2-morpholin-4-yl-ethoxy)-phenylamine (200 mg, 0.66 mmole), 2,4-difluoro-benzoyl chloride (140 mg, 1.2 eq), and triethylamine (0.2 mL, 2 eq) in 3 mL THF was stirred at room temperature for 10 minutes. The mixture was purified by HPLC to give title compound as a white solid (99 mg, 34%). $^1$H NMR (Acetone-d$_6$, 400 MHz) δ 2.92-3.06 (m, 2H), 3.13-3.17 (m, 2H), 3.50-3.58 (m, 4H), 3.68 (s, 3H), 3.82-3.85 (m, 2H), 4.36 (t, 2H), 6.29 (s, 1H), 7.24 (d, J=9.09 Hz, 2H), 7.44 (dt, J=10.1, 2.78 Hz, 1H), 7.49 (s, 1H), 7.67 (s, 1H), 7.72-7.79 (m, 1H), 7.81 (dd, J=9.09, 2.78 Hz, 1H). Exact mass calculated for $C_{23}H_{24}F_2N_4O_3$ 442.2, found 443.5 (MH$^+$).

Example 1.42: Preparation of N-[3-(2-methyl-2H-pyrazol-3-yl)-4-(2-morpholin-4-yl-ethoxy)-phenyl]-4-trifluoromethyl-benzamide (Compound 282)

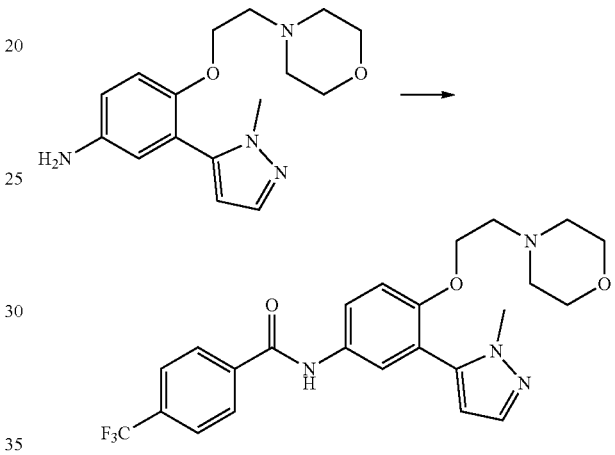

A solution of HATU (98.0 mg, 0.260 mmol), triethylamine (55.7 µl, 0.400 mmol) and 4-trifluoromethyl-benzoic acid (49.0 mg, 0.260 mmol) in THF (1.0 mL) was stirred at room temperature. After 15 min, 3-(2-methyl-2H-pyrazol-3-yl)-4-(2-morpholin-4-yl-ethoxy)-phenylamine (60.0 mg, 0.200 mmol) was added, and the mixture was stirred at 100° C. for 10 minutes in microwave. The mixture was purified by HPLC to give title compound as a white solid (TFA salt, 27 mg, 28%). $^1$H NMR (DMSO-d$_6$, 400 MHz) δ2.96-3.10 (m, 2H), 3.16-3.19 (m, 2H), 3.52-3.60 (m, 4H), 3.70 (s, 3H), 3.84-3.87 (m, 2H), 4.39 (t, J=5.05 Hz, 2H), 6.31 (d, J=1.77 Hz, 1H), 7.28 (d, J=9.09 Hz, 1H), 7.51 (d, J=1.77 Hz, 1H), 7.75 (d, J=2.78 Hz, 1H), 7.94 (d, J=8.34 Hz, 2H), 8.16 (d, J=8.84 Hz, 2H), 8.89 (s, 1H), 10.5 (s, 1H). Exact mass calculated for $C_{24}H_{25}F_3N_4O_3$ 474.2, found 475.4 (MH$^+$).

Example 1.43: Preparation of N-[3-(2-methyl-2H-pyrazol-3-yl)-4-(2-pyrrolidin-1-yl-ethoxy)-phenyl]-3-trifluoromethyl-benzamide (Compound 435)

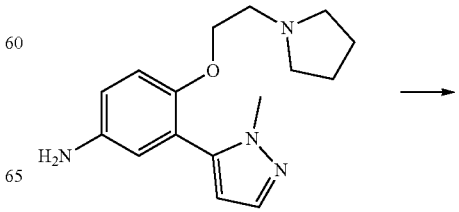

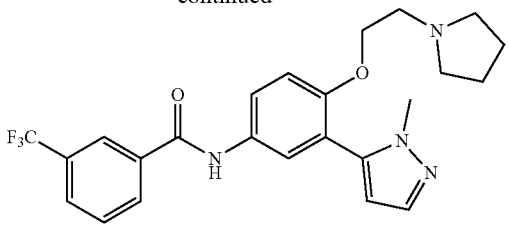

A solution of HATU (113 mg, 0.30 mmol), triethylamine (55.7 µl, 0.400 mmol) and 3-trifluoromethyl-benzoic acid (57 mg, 0.30 mmol) in DMF (1.0 mL) was stirred at room temperature. After 15 min, 3-(2-Methyl-2H-pyrazol-3-yl)-4-(2-pyrrolidin-1-yl-ethoxy)-phenylamine (57.0 mg, 0.200 mmol) was added, and the mixture was stirred at 100° C. for 10 minutes in microwave. The mixture was purified by HPLC to give title compound as a burgundy oil (TFA salt, 42 mg, 46% yield). Exact mass calculated for $C_{24}H_{25}F_3N_4O_2$ 458.2, found 459.4 (MH$^+$).

Example 1.44: Preparation of N-[4-[2-(3,3-difluoro-pyrrolidin-1-yl)-ethoxy]-3-(2-methyl-2H-pyrazol-3-yl)-phenyl]-4-fluoro-3-methyl-benzamide (Compound 546)

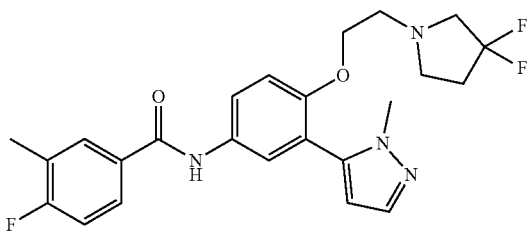 [SMILES: Cc1cc(C(=O)Nc2ccc(OCCN3CCC(F)(F)C3)c(-c3ccnn3C)c2)ccc1F]

A mixture of 4-[2-(3,3-Difluoro-pyrrolidin-1-yl)-ethoxy]-3-(2-methyl-2H-pyrazol-3-yl)-phenylamine (64 mg, 0.20 mmole), 4-fluoro-3-methyl-benzoyl chloride (52 mg, 0.30 mmole), and triethylamine (56.5 µL, 0.40 mmole) in 1 mL THF was stirred at room temperature for 10 minutes. The mixture was purified by HPLC to give the title compound as a white solid (TFA salt, 29 mg, 32/o yield). Exact mass calculated for $C_{24}H_{25}F_3N_4O_2$ 458.2, found 459.3 (MH$^+$).

Example 1.45: Preparation of 4-fluoro-3-methyl-N-[3-(2-methyl-2H-pyrazol-3-yl)-4-((S)-1-methyl-pyrrolidin-2-ylmethoxy)-phenyl]-benzamide (Compound 547)

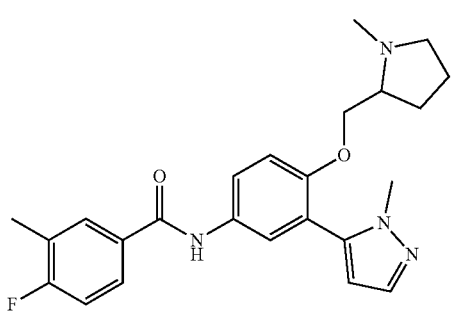 [SMILES: Cc1cc(C(=O)Nc2ccc(OCC3CCCN3C)c(-c3ccnn3C)c2)ccc1F]

A mixture of 3-(2-Methyl-2H-pyrazol-3-yl)-4-(1-methyl-pyrrolidin-2-ylmethoxy)-phenylamine (64 mg, 0.23 mmole), 4-fluoro-3-methyl-benzoyl chloride (60 mg, 0.35 mmole), and triethylamine (63.4 µL, 0.46 mmole) in 1 mL THF was stirred at room temperature for 10 minutes. The mixture was purified by HPLC to give the title compound as a white solid (TFA salt, 92 mg, 95% yield). Exact mass calculated for $C_{24}H_{27}FN_4O_2$ 422.2, found 423.2 (MH$^+$).

Example 1.46: Preparation of N-{3-(4-bromo-2-methyl-2H-pyrazol-3-yl)-4-[2-(2-methyl-pyrrolidin-1-yl)-ethoxy]-phenyl}-3, 4-difluoro-benzamide (Compound 579)

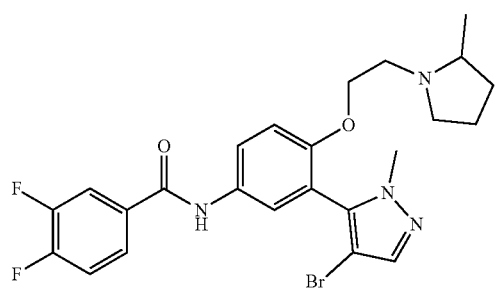 [SMILES: CC1CCCN1CCOc1ccc(NC(=O)c2ccc(F)c(F)c2)cc1-c1c(Br)cnn1C]

A mixture of 3-(4-Bromo-2-methyl-2H-pyrazol-3-yl)-4-[2-(2-methyl-pyrrolidin-1-yl)-ethoxy]-phenylamine (95 mg, 0.25 mmole), 3,4-difluoro-benzoyl chloride (40 µL, 0.301 mmole), and triethylamine (70.2 µL, 0.501 mmole) in 1 mL THF was stirred at room temperature for 10 minutes. The mixture was purified by HPLC to give the title compound as a white solid (TFA salt, 60 mg, 46% yield). $^1$H NMR (DMSO-d$_6$, 400 MHz) δ 1.22 (dd, J=19.71, 6.57 Hz, 3H), 1.45-1.53 (m, 1H), 1.72-1.89 (m, 2H), 2.07-2.14 (m, 1H), 2.79-2.98 (m, 1H), 3.08-3.15 (m, 1H), 3.31-3.44 (m, 2H), 3.59-3.65 (m, 1H), 3.68 (d, J=4.80 Hz, 3H), 4.21-4.46 (m, 2H), 7.29 (dd, J=9.85 Hz, 6.82 Hz, 1H), 7.60-7.67 (m, 1H), 7.66 (s, 1H), 7.70-7.72 (m, 1H), 7.84-7.88 (m, 1H), 7.94 (dt, J=9.09, 2.78, 2.53 Hz, 1H), 8.01-8.06 (m, 1H), 9.22-9.48 (m, 1H from TFA), 10.4 (s, NH). Exact mass calculated for $C_{24}H_{25}^{79}BrF_2N_4O_2$, 518.1, found 519.3, 521.5 (MH$^+$).

Example 1.47: Preparation of N-[3-(4-bromo-2-methyl-2H-pyrazol-3-yl)-4-((R)-1-methyl-pyrrolidin-3-yloxy)-phenyl]-3,4-difluoro-benzamide (Compound 585)

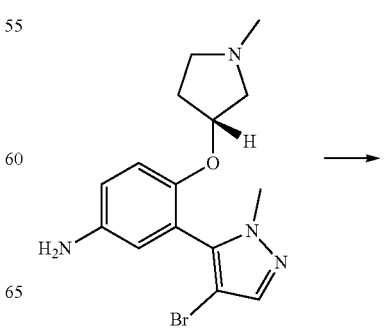

-continued

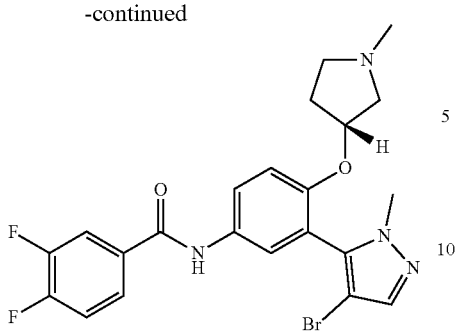

A mixture of 3-(4-bromo-2-methyl-2H-pyrazol-3-yl)-4-((R)-1-methyl-pyrrolidin-3-yloxy)-phenylamine (88 mg, 0.25 mmole), 3,4-difluoro-benzoyl chloride (40 μL, 0.30 mmole), and triethylamine (70 μL, 0.5 mmole) in 1 mL THF was stirred at room temperature for 10 minutes. The mixture was purified by HPLC to give the title compound as a white solid (TFA salt, 24 mg, 19% yield). $^1$H NMR (CD$_3$OD, 400 MHz) δ 2.17-2.31 (m, 1H), 2.71-2.84 (m, 2H), 2.87-2.97 (m, 2H), 3.14-3.25 (m, 1H), 3.38-3.48 (m, 1H), 3.72-3.79 (m, 1H), 3.75 (s, 3H), 3.89-3.97 (m, 1H), 5.17-5.24 (m, 1H), 7.17-7.30 (m, 1H), 7.41-7.47 (m, 1H), 7.56-7.62 (m, 1H), 7.63-7.69 (m, 1H), 7.78-89 (m, 1H), 7.88-7.93 (m, 2H). Exact mass calculated for $C_{22}BrH_{21}F_2N_4O_2$ 490.1, found 491.5, 493.5 (MH$^+$).

Example 1.48: Preparation of N-[4-[2-((S)-3-hydroxy-pyrrolidin-1-yl)-ethoxy]-3-(2-methyl-2H-pyrazol-3-yl)-phenyl]-4-trifluoromethyl-benzamide (Compound 586)

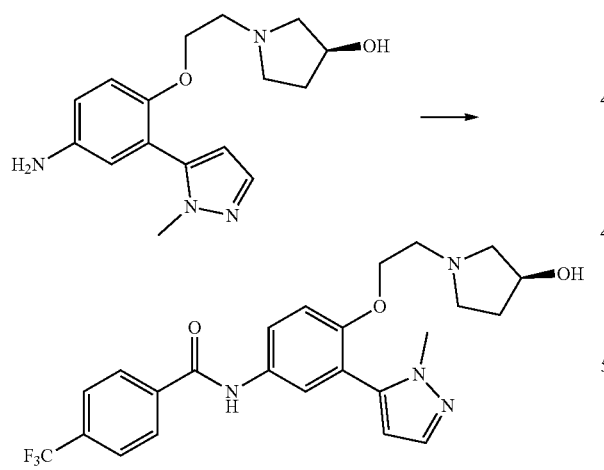

A solution of HATU (183 mg, 0.482 mmol), triethylamine (100 μl, 0.741 mmol) and 4-trifluoromethyl benzoic acid (92 mg, 0.482 mmol) in THF (1.0 mL) was stirred at room temperature. After 15 min, (S)-1-{2-[4-Amino-2-(2-methyl-2H-pyrazol-3-yl)-phenoxy]-ethyl}-pyrrolidin-3-ol (112 mg, 0.370 mmol) was added, and the mixture was stirred at 100° C. for 10 minutes in microwave. The mixture was purified by HPLC to give the title compound as a white solid (TFA salt, 58 mg, 33% yield). $^1$H NMR (DMSO-d$_6$, 400 MHz) δ 1.67-1.74 (m, 1H), 1.78-1.90 (m, 1H), 2.09-2.18 (m, 1H), 2.88-2.97 (m, 1H), 3.31-3.37 (m, 1H), 3.47-3.61 (m, 2H), 3.69 (s, 3H), 4.31-4.36 (m, 4H), 6.31 (s, 1H), 7.24-7.28 (m, 1H), 7.50 (s, 1H), 7.75 (s, 1H), 7.90 (d, J=8.84 Hz, 1H), 7.94 (d, J=8.34 Hz, 2H), 8.16 (d, J=8.34 Hz, 2H), 9.93-10.11 (m, 1H), 10.5 (s, 1H). Exact mass calculated for $C_{24}H_{25}F_3N_4O_3$ 474.2, found 475.3 (MH$^+$).

Example 1.49: Preparation of 3-fluoro-N-[4-[2-(4-formyl-piperazin-1-yl)-ethoxy]-3-(2-methyl-2H-pyrazol-3-yl)-phenyl]-benzamide (Compound 752)

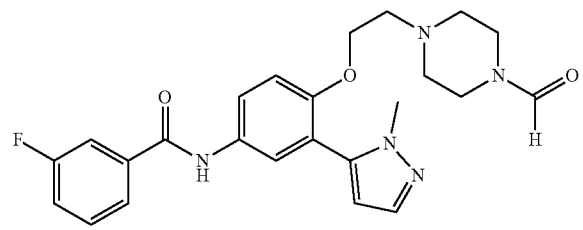 [SMILES: Cn1nccc1-c1cc(NC(=O)c2cccc(F)c2)ccc1OCCN1CCN(C=O)CC1]

A mixture of N-[4-(2-Bromo-ethoxy)-3-(2-methyl-2H-pyrazol-3-yl)-phenyl]-3-fluoro-benzamide (83 mg, 0.198 mmole), and piperazine-1-carbaldehyde (27 mg, 0.238 mmole), and K$_2$CO$_3$ (110 mg, 0.794 mmole) in 2 mL DMF was stirred at 120° C. for 20 minutes in microwave. The mixture was purified by HPLC to give title compound as a white solid as a TFA salt. Exact mass calculated for $C_{24}FH_{26}N_5O_3$ 451.2, found 452.2 (MH$^+$), $^1$HNMR (CD$_3$CN, 400 MHz) δ 3.15-3.32 (m, 4H), 3.66-3.71 (m, 4H), 3.71-3.76 (m, 2H), 3.74 (s, 3H), 4.60 (t, J=4.80 Hz, 2H), 6.30 (d, J=1.77 Hz, 1H), 7.23 (d, J=8.84 Hz, 1H), 7.37 (dd, J=8.59, 2.78 Hz, 1H), 7.50 (d, J=1.77 Hz, 1H), 7.54-7.61 (m, 1H), 7.73-7.77 (m, 1H), 7.81 (d, J=2.53 Hz, 1H), 7.85 (d, J=7.83 Hz, 1H), 7.94 (dd, J=9.09, 2.53 Hz, 1H), 8.08 (s, 1H), 9.68 (s, NH).

Example 1.50: Preparation of N-[4-[2-(4-acetyl-piperazin-1-yl)-ethoxy]-3-(2-methyl-2H-pyrazol-3-yl)-phenyl]-3-methoxy-benzamide (Compound 755)

Step 1.50a: Preparation of 4-(2-bromo-ethoxy)-3-(2-methyl-2H-pyrazol-3-yl)-phenylamine

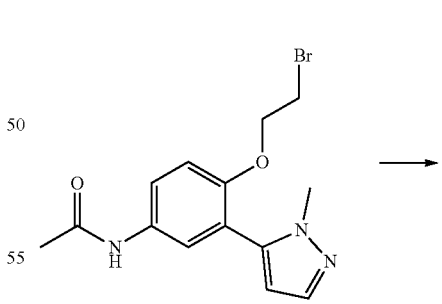

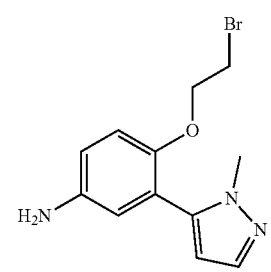

To a solution of N-[4-(2-Bromo-ethoxy)-3-(2-methyl-2H-pyrazol-3-yl)-phenyl]-acetamide (3 g, 8.9 mmole) in methanol (6 mL) was added Sulfuric acid (2.2 mL, 42 mmole, 4.78 eq) at 0° C. while stirring. The reaction mixture was refluxed at 90° C. for 1 hour 20 minutes. Crude was quenched with water, neutralized with saturated sodium hydroxide solution until pH 8, extracted with ethyl acetate, and then concentrated in vacuo to give title compound as a solid (2.6 g, 99%). Exact mass calculated for $C_{12}H_{14}BrN_3O$ 295.0, found 296.1 (M+H $^{79}$Br, 100), 298.2 (M+H 81Br, 98).

Step 1.50b: Preparation of N-[4-(2-bromo-ethoxy)-3-(2-methyl-2H-pyrazol-3-yl)-phenyl]-3-methoxy-benzamide

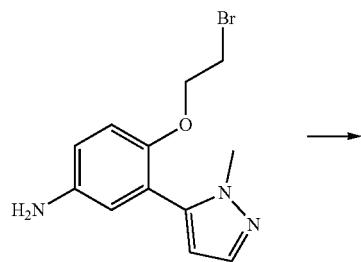

A mixture of 4-(2-Bromo-ethoxy)-3-(2-methyl-2H-pyrazol-3-yl)-phenylamine (1.012 g, 3.417 mmole), 3-methoxy-benzoyl chloride (700 mg, 1.2 eq), and triethylamine (1.0 mL, 2 eq) in 5 mL THF was stirred at room temperature for 10 minutes. The mixture was purified by HPLC to give title compound as white solid (957 mg, 52%). Exact mass calculated for $C_{20}H_{20}BrN_3O_3$ 429.1, found 430.3 (M+H $^{79}$Br, 100), 432.5 (M+H $^{81}$Br, 98).

Step 1.50c: Preparation of N-[4-[2-(4-acetyl-piperazin-1-yl)-ethoxy]-3-(2-methyl-2H-pyrazol-3-yl)-phenyl]-3-methoxy-benzamide

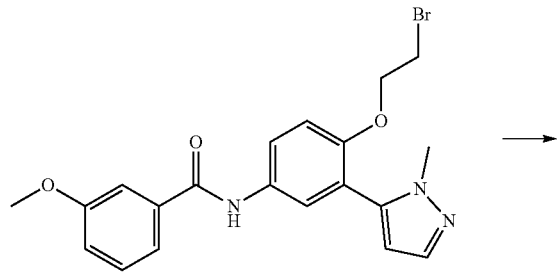

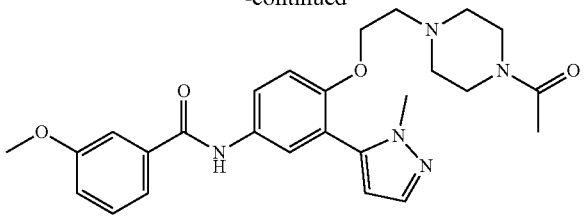

A mixture of N-[4-(2-Bromo-ethoxy)-3-(2-methyl-2H-pyrazol-3-yl)-phenyl]-3-methoxy-benzamide (90 mg, 0.21 mmole), and 1-Piperazin-1-yl-ethanone (32 mg, 1.2 eq), and $K_2CO_3$ (116 mg, 4.0 eq) in 2 mL DMF was stirred at 120° C. for 20 minutes in microwave. The mixture was purified by HPLC to give title compound as a white solid as TFA salt (97 mg, 97%). $^1$H NMR (Acetone-$d_6$, 400 MHz) δ 2.07 (s, 3H), 3.30 (sb, 4H), 3.71 (t, J=4.80 Hz, 2H), 3.75 (s, 3H), 3.79 (sb, 2H), 3.87 (s, 3H), 4.60 (t, J=4.80 Hz, 2H), 4.99 (sb, 2H), 6.32 (s, 1H), 7.13 (d, J=8.08 Hz, 1H), 7.23 (d, J=9.09 Hz, 1H), 7.42 (t, J=8.08 Hz, 1H), 7.53 (m, 2H), 7.56 (d, J=7.83 Hz, 1H), 7.82 (s, 1H), 7.94 (dd, J=8.84, 2.53 Hz, 1H), 9.56 (s, NH). Exact mass calculated for $C_{26}H_{31}N_5O_4$ 477.2, found 478.3 (MH$^+$).

Example 1.51: Preparation of N-[3-(2-methyl-2H-pyrazol-3-yl)-4-(2-morpholin-4-yl-ethoxy)-phenyl]-2-phenyl-acetamide) (Compound 762)

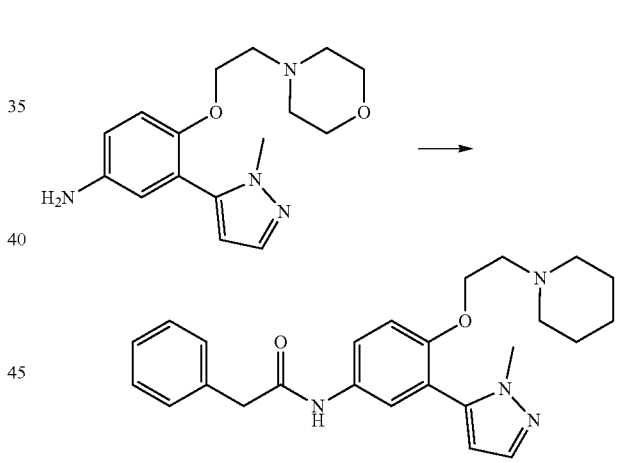

A solution of HATU (57.0 mg, 0.150 mmol), triethylamine (41.8 µl, 0.300 mmol) and phenylacetic acid (20.4 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (49 mg, 92%). LCMS m/z (%)=421.3 (M+H 100). $^1$H NMR (500 MHz, MeOH-$d_4$) δ 2.96-3.26 (m, 4H) 3.51-3.55 (m, 2H) 3.55-3.97 (m, 4H) 3.67 (s, 2H) 3.70 (s, 3H) 4.36-4.41 (m, 2H) 6.32 (d, J=1.89 Hz, 1H) 7.14 (d, J=8.83 Hz, 1H) 7.21-7.26 (m, 1H) 7.29-7.36 (m, 4H) 7.53 (d, J=1.89 Hz, 1H) 7.56 (d, J=2.52 Hz, 1H) 7.66 (dd, J=8.83, 2.52 Hz, 1H).

Example 1.52: Preparation of 2-(3-fluoro-phenyl)-N-[3-(2-methyl-2H-pyrazol-3-yl)-4-(2-morpholin-4-yl-ethoxy)-phenyl]-acetamide (Compound 766)

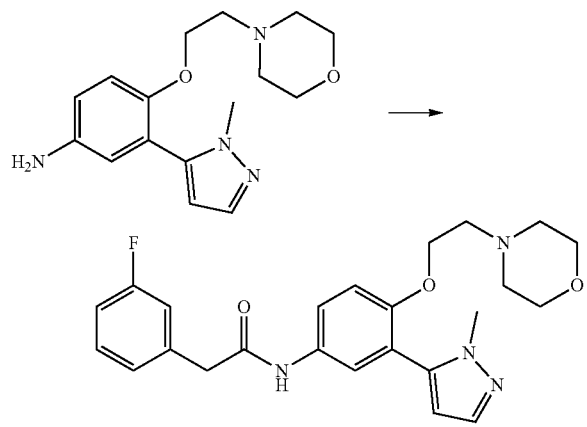

A solution of HATU (57.0 mg, 0.150 mmol), triethylamine (41.8 µl, 0.300 mmol) and 3-fluorophenylacetic acid (23.1 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (39 mg, 71%). LCMS m/z (%)=439.5 (M+H 100). $^1$H NMR (500 MHz, MeOH-d$_4$) δ 2.92-3.28 (m, 2H), 3.50-3.57 (m, 2H), 3.59-3.95 (m, 2H), 3.69 (s, 2H), 3.71 (s, 3H), 4.37-4.43 (m, 2H), 6.32 (d, J=2.21 Hz, 1H), 6.96-7.02 (m, 1H), 7.07-7.13 (m, 1H), 7.13-7.18 (m, 2H), 7.29-7.36 (m, 1H), 7.52 (d, J=1.89 Hz, 1H), 7.56 (d, J=2.84 Hz, 1H), 7.67 (dd, J=8.99, 2.68 Hz, 1H).

Example 1.53: Preparation of 2-(3-chloro-phenyl)-N-[3-(2-methyl-2H-pyrazol-3-yl)-4-(2-morpholin-4-yl-ethoxy)-phenyl]-acetamide (Compound 767)

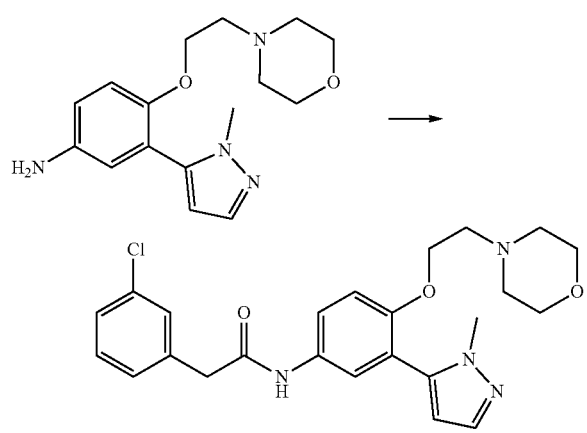

A solution of HATU (57.0 mg, 0.150 mmol), triethylamine (41.8 µl, 0.300 mmol) and 3-chlorophenylacetic acid (25.6 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (33 mg, 58%). LCMS m/z (%)=455.3 (M+H 100). $^1$H NMR (500 MHz, MeOH-d$_4$) δ 2.95-3.28 (m, 2H), 3.50-3.56 (m, 2H), 3.57-4.05 (m, 2H), 3.68 (s, 2H), 3.71 (s, 3H), 4.37-4.42 (m, 2H), 6.32 (d, J=1.89 Hz, 1H), 7.15 (d, J=8.83 Hz, 1H), 7.24-7.33 (m, 3H), 7.37-7.39 (m, 1H), 7.52 (d, J=1.89 Hz, 1H), 7.56 (d, J=2.84 Hz, 1H), 7.67 (dd, J=8.99, 2.68 Hz, 2H).

Example 1.54: Preparation of N-[3-(2-methyl-2H-pyrazol-3-yl)-4-(2-morpholin-4-yl-ethoxy)-phenyl]-2-(3-trifluoromethyl-phenyl)-acetamide (Compound 768)

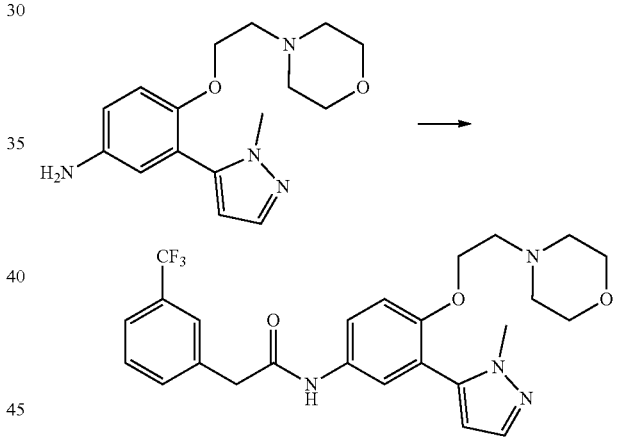

A solution of HATU (57.0 mg, 0.150 mmol), triethylamine (41.8 µl, 0.300 mmol) and 3-trifluoromethyl phenylacetic acid (30.6 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (36 mg, 60%). LCMS m/z (%)=489.3 (M+H 100). $^1$H NMR (500 MHz, MeOH-d$_4$) δ 2.96-3.27 (m, 2H), 3.51-3.56 (m, 2H), 3.58-3.98 (m, 2H), 3.71 (s, 2H), 3.78 (s, 3H), 4.37-4.43 (m, 2H), 6.32 (d, J=1.89 Hz, 1H), 7.16 (d, J=9.14 Hz, 1H), 7.49-7.59 (m, 4H), 7.61 (d, J=7.57 Hz, 1H), 7.65-7.70 (m, 2H).

Example 1.55: Preparation of 2-(3-methoxy-phenyl)-N-[3-(2-methyl-2H-pyrazol-3-yl)-4-(2-morpholin-4-yl-ethoxy)-phenyl]-acetamide (Compound 769)

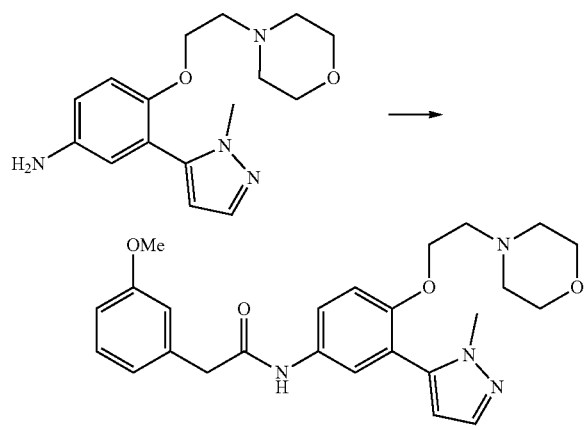

A solution of HATU (57.0 mg, 0.150 mmol), triethylamine (41.8 µl, 0.300 mmol) and 3-methoxy-phenylacetic acid (24.9 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (57 mg, 80%). LCMS m/z (%)=451.2 (M+H 100). $^1$H NMR (500 MHz, MeOH-d$_4$) δ 2.91-3.27 (m, 4H), 3.50-3.55 (m, 2H), 3.57-3.99 (m, 4H), 3.64 (s, 2H), 3.70 (s, 3H), 3.77 (s, 3H), 4.35-4.42 (m, 2H), 6.31 (d, J=1.89 Hz, 1H), 6.79-6.85 (m, 1H), 6.89-6.95 (m, 2H), 7.14 (d, J=8.83 Hz, 1H), 7.22 (t, J=8.20 Hz, 1H), 7.52 (d, J=1.89 Hz, 1H), 7.56 (d, J=2.84 Hz, 1H), 7.67 (dd, J=8.98, 2.68 Hz, 1H).

Example 1.56: Preparation of N-[3-(2-methyl-2H-pyrazol-3-yl)-4-(2-morpholin-4-yl-ethoxy)-phenyl]-2-m-tolyl-acetamide (Compound 770)

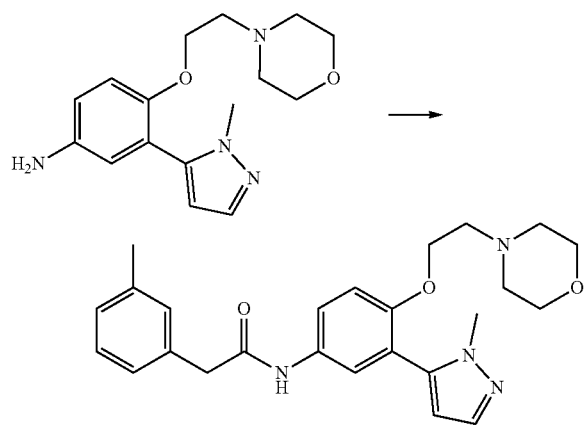

A solution of HATU (57.0 mg, 0.150 mmol), triethylamine (41.8 µl, 0.300 mmol) and m-tolylacetic acid (22.5 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (49 mg, 89%). LCMS m/z (%)=435.3 (M+H 100). $^1$H NMR (500 MHz, MeOH-d$_4$) δ 2.31 (s, 3H), 2.89-3.27 (m, 2H), 3.47-3.54 (m, 2H), 3.58-4.00 (m, 2H), 3.63 (s, 2H), 3.70 (s, 3H), 4.36-4.41 (m, 2H), 6.31 (d, J=1.89 Hz, 1H), 7.04-7.08 (m, 1H), 7.10-7.22 (m, 4H), 7.52 (d, J=1.89 Hz, 1H), 7.56 (d, J=2.52 Hz, 1H), 7.66 (dd, J=8.83, 2.52 Hz, 1H).

Example 1.57: Preparation of N-[3-(2-methyl-2H-pyrazol-3-yl)-4-(2-morpholin-4-yl-ethoxy)-phenyl]-2-p-tolyl-acetamide (Compound 771)

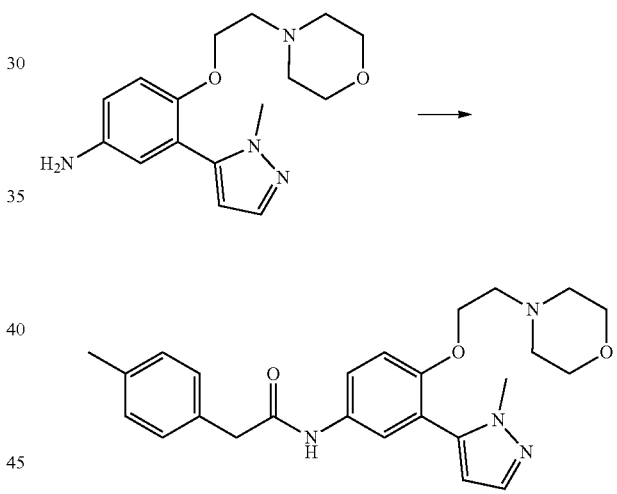

A solution of HATU (57.0 mg, 0.150 mmol), triethylamine (41.8 µl, 0.300 mmol) and p-tolylacetic acid (22.5 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (50 mg, 91%). LCMS m/z (%)=435.3 (M+H 100). $^1$H NMR (500 MHz, MeOH-d$_4$) δ 2.31 (s, 3H), 3.01-3.23 (m, 2H), 3.49-4.00 (m, 2H), 3.51-3.57 (m, 2H), 3.62 (s, 2H), 3.71 (s, 3H), 4.35-4.42 (m, 2H), 6.31 (d, J=1.89 Hz, 1H), 7.12-7.18 (m, 3H), 7.22 (d, J=8.20 Hz, 2H), 7.52 (d, J=1.89 Hz, 1H), 7.53 (d, J=2.84 Hz, 1H), 7.69 (dd, J=8.98, 2.68 Hz, 1H).

Example 1.58: Preparation of 2-benzo[1,3]dioxol-5-yl-N-[3-(2-methyl-2H-pyrazol-3-yl)-4-(2-morpholin-4-yl-ethoxy)-phenyl]-acetamide (Compound 772)

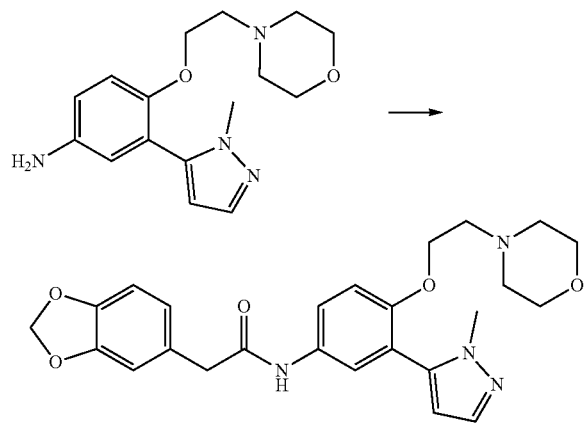

A solution of HATU (57.0 mg, 0.150 mmol), triethylamine (41.8 μl, 0.300 mmol) and 3,4-methylenedioxy-phenylacetic acid (27.0 mg, 0.150 mmol) in DMF (0.3 mL) was stirred at room temperature. After 15 min, 3-(2-methyl-2H-pyrazol-3-yl)-4-(2-morpholin-4-yl-ethoxy)-aniline (30.2 mg, 0.100 mmol) was added, and the mixture was stirred at room temperature overnight. The solution was diluted with dichloromethane and washed with saturated sodium bicarbonate. The organic layer was dried with sodium sulfate, filtered, and evaporated to dryness. The crude product was purified by RP-HPLC and lyophilized to give a TFA-salt as a yellow oil (48 mg, 83%). LCMS m/z (%)=465.4 (M+H 100). $^1$H NMR (500 MHz, MeOH-d$_4$) δ 2.94-3.24 (m, 2H), 3.48-4.05 (m, 2H), 3.51-3.56 (m, 2H), 3.58 (s, 2H), 3.71 (s, 3H), 4.35-4.43 (m, 2H), 5.92 (s, 2H), 6.32 (d, J=1.89 Hz, 1H), 6.74-6.83 (m, 2H), 6.83-6.87 (m, 1H), 7.16 (d, J=8.83 Hz, 1H), 7.52-7.54 (m, 3H), 7.69 (dd, J=8.98, 2.68 Hz, 1H).

Example 1.59: Preparation of N-[3-(2-methyl-2H-pyrazol-3-yl)-4-(2-morpholin-4-yl-ethoxy)-phenyl]-2-(4-trifluoromethyl-phenyl)-acetamide (Compound 794)

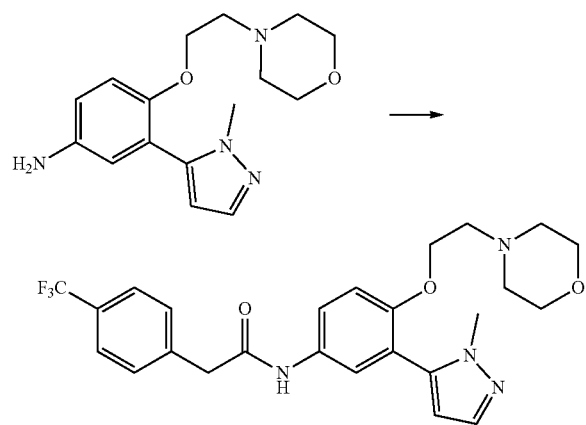

1-Propanephosphonic acid cyclic anhydride (50% in EtOAc, 106 μl, 0.20 mmol) was added to 3-(2-methyl-2H-pyrazol-3-yl)-4-(2-morpholin-4-yl-ethoxy)-aniline (30.2 mg, 0.10 mmol), 4-trifluoromethylphenylacetic acid (18 mg, 0.09 mmol), and triethylamine (123 μl, 0.9 mmol) in ethyl acetate (0.1 mL), and the mixture was stirred at room temperature. After 1 h, the reaction was quenched with saturated sodium bicarbonate, and the product was extracted with ethyl acetate. The organic layer was washed with brine, dried with sodium sulfate, filtered, and evaporated to dryness. The residue was dissolved in methanol (0.5 mL), a solution of acetyl chloride (13 μl, 0.2 mmol) in methanol added, and the solution was evaporated to dryness. The residue was redissolved in methanol and evaporated. The residue was dissolved in water and lyophilized to give a HCl-salt as a white solid (17 mg, 36%). LCMS m/z (%)=489.3 (M+H 100). $^1$H NMR (500 MHz, MeOH-d$_4$) δ 3.05-3.14 (m, 2H), 3.21-3.28 (m, 2H), 3.56-3.61 (m, 2H), 3.65-3.74 (m, 2H), 3.79 (s, 3H), 3.81 (s, 2H), 3.90-3.98 (m, 2H), 4.42-4.49 (m, 2H), 6.47 (d, J=2.21 Hz, 1H), 7.22 (d, J=9.14 Hz, 1H), 7.57 (d, J=8.20 Hz, 2H), 7.64 (d, J=2.84 Hz, 1H), 7.66 (d, J=7.88 Hz, 2H), 7.70-7.74 (m, 2H).

Example 1.60: Preparation of N-[3-(2-methyl-2H-pyrazol-3-yl)-4-(2-morpholin-4-yl-ethoxy)-phenyl]-2-thiophen-2-yl-acetamide (Compound 795)

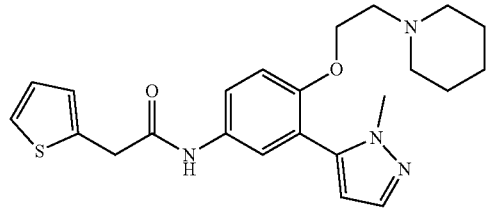 [SMILES: Cn1nccc1-c1cc(NC(=O)Cc2cccs2)ccc1OCCN1CCCCC1]

1-Propanephosphonic acid cyclic anhydride (50% in EtOAc, 106 L1, 0.20 mmol) was added to 3-(2-methyl-2H-pyrazol-3-yl)-4-(2-morpholin-4-yl-ethoxy)-aniline (30.2 mg, 0.10 mmol), 2-thienylacetic acid (13 mg, 0.09 mmol), and triethylamine (123 μl, 0.9 mmol) in ethyl acetate (0.1 mL), and the mixture was stirred at room temperature. After 1 h, the reaction was quenched with saturated sodium bicarbonate, and the product was extracted with ethyl acetate. The organic layer was washed with brine, dried with sodium sulfate, filtered, and evaporated to dryness. The residue was dissolved in methanol (0.5 mL), a solution of acetyl chloride (13 μl, 0.2 mmol) in methanol added, and the solution was evaporated to dryness. The residue was redissolved in methanol and evaporated. The residue was dissolved in water and lyophilized to give a HCl-salt as a yellow solid (22 mg, 54%). LCMS m/z (%)=427.2 (M+H 100). $^1$H NMR (500 MHz, MeOH-d$_4$) δ 3.06-3.15 (m, 2H), 3.25-3.31 (m, 2H), 3.56-3.61 (m, 2H), 3.67-3.75 (m, 2H), 3.82 (s, 3H), 3.92 (s, 2H), 3.95 (dd, J=12.61, 2.52 Hz, 2H), 4.45-4.50 (m, 2H), 6.52 (d, J=2.21 Hz, 1H), 6.99 (d, J=3.47 Hz, 1H), 7.00 (d, J=3.47 Hz, 1H), 7.01-7.04 (m, 1H), 7.24 (d, J=9.14 Hz, 1H), 7.31 (dd, J=5.04, 1.26 Hz, 1H), 7.66 (d, J=2.52 Hz, 1H), 7.71 (dd, J=8.99, 2.68 Hz, 1H), 7.80 (d, J=2.21 Hz, 1H).

Example 1.61: Preparation of 1-[4-(2-azetidin-1-yl-ethoxy)-3-(2-methyl-2H-pyrazol-3-yl)-phenyl]-3-(2, 4-difluoro-phenyl)-urea (Compound 86)

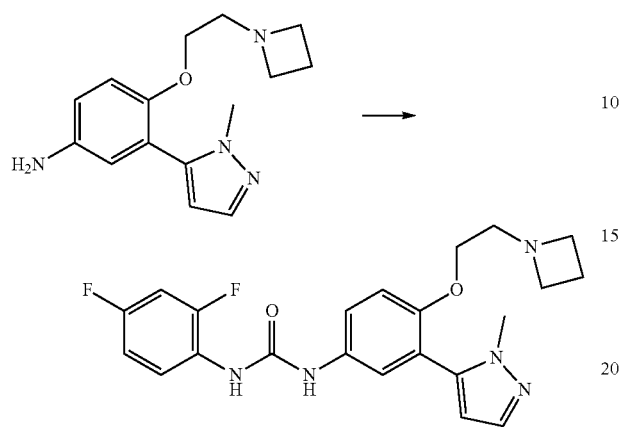

To a solution of 4-(2-(azetidin-1-yl)ethoxy)-3-(1-methyl-1H-pyrazol-5-yl)benzenamine (40.1 mg, 0.147 mmol) in CH$_2$Cl$_2$ (2 mL) was added 2,4-difluorophenyl isocyanate (18 µL, 0.152 mmol) and stirred for two hours. The crude reaction mixture was purified by SiO$_2$ column chromatography (Eluent: methanol/CH$_2$Cl$_2$=1/6) to afford the title compound (50.4 mg, 80%). LCMS m/z (%)=428 (MH$^+$, 100), $^1$H NMR (400 MHz, DMSO-d$_6$) δ: 8.96 (bs, 1H), 8.47 (bs, 1H), 8.09-7.98 (m, 1H), 7.45-7.39 (m, 2H), 7.36 (d, J=2.71 Hz, 1H), 7.34-7.26 (m, 1H), 7.06 (d, J=8.94 Hz, 1H), 7.06-6.98 (m, 1H), 6.23 (d, J=1.85 Hz, 1H), 3.89 (t, J=5.49 Hz, 2H), 3.67 (s, 3H), 2.98 (t, J=6.92 Hz, 4H), 2.60 (t, J=5.47 Hz, 2H), 1.86 (quintet, J=6.99 Hz, 2H).

Example 1.62: Preparation of 1-{3-(4-bromo-2-methyl-2H-pyrazol-3-yl)-4-[2-(3-methoxy-azetidin-1-yl)-ethoxy]-phenyl}-3-(4-chloro-phenyl)-urea (Compound 267)

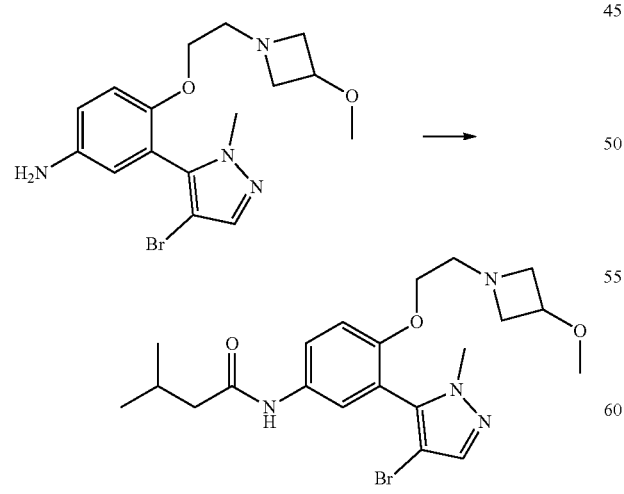

To a solution of 3-(4-bromo-1-methyl-1H-pyrazol-5-yl)-4-(2-(3-methoxyazetidin-1-yl)ethoxy)benzenamine (39.2 mg, 0.103 mmol) in CH$_2$Cl$_2$ (4 mL) was added 4-chlorophenyl isocyanate (18.0 mg) and stirred for two hours. The resulting material was purified by HPLC. The product was dried in vacuo to afford the title compound as a white solid (50.7 mg, 92%). LCMS m/z (%)=534 (M+H $^{79}$Br, 74), 536 (M+H $^{81}$Br, 100). $^1$H NMR (400 MHz, DMSO-d$_6$) δ: 8.79 (bs, 1H), 8.70 (bs, 1H), 7.60 (s, 1H), 7.52 (dd, J=8.95, 2.71 Hz, 1H), 7.47 (d, J=8.94 Hz, 2H), 7.35 (d, J=2.70 Hz, 1H), 7.31 (d, J=8.91 Hz, 2H), 7.09 (d, J=9.03 Hz, 1H), 4.02-3.86 (m, 2H), 3.83 (quint, J=5.80 Hz, 1H), 3.66 (s, 3H), 3.35-3.29 (m, 1H), 3.27-3.18 (m, 1H), 3.08 (s, 3H), 2.74-2.56 (m, 4H).

Example 1.63: Preparation of N-{3-(4-bromo-2-methyl-2H-pyrazol-3-yl)-4-[2-(3-methoxy-azetidin-1-yl)-ethoxy]-phenyl}-3-methyl-butyramide (Compound 326)

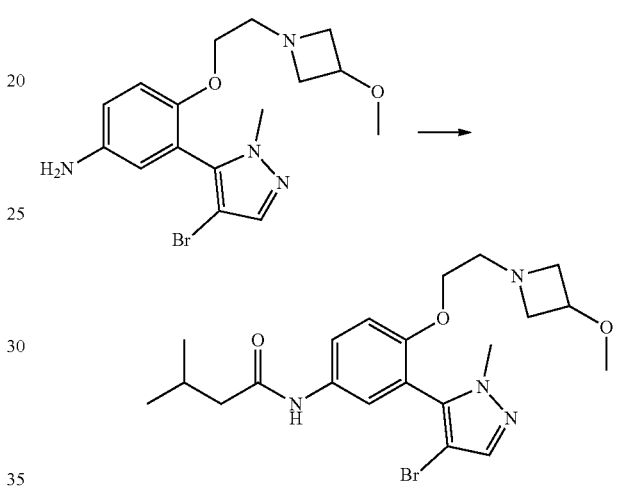

To a solution of 3-(4-bromo-1-methyl-1H-pyrazol-5-yl)-4-(2-(3-methoxyazetidin-1-yl)ethoxy)benzenamine (40.3 mg, 0.107 mmol) and pyridine (35 µL) in CH$_2$Cl$_2$ (2 mL) was added isovaleryl chloride (15 µL, 0.122) and stirred for two hours. The resulting material was purified by HPLC. The product was dried in vacuo to afford the title compound as a white solid (36.0 mg, 73%). LCMS m/z (%)=465 (M+H $^{79}$Br, 75), 467 (M+H $^{81}$Br, 90). $^1$H NMR (400 MHz, DMSO-d$_6$) δ: 10.00 (bs, 1H), 7.69 (dd, J=8.99, 2.65 Hz, 1H), 7.60 (s, 1H), 7.48 (d, J=2.63 Hz, 1H), 7.09 (d, J=9.06 Hz, 1H), 4.03-3.86 (m, 2H), 3.82 (quint, J=5.76 Hz, 1H), 3.65 (s, 3H), 3.35-3.28 (m, 1H), 3.24-3.17 (m, 1H), 3.08 (s, 3H), 2.73-2.55 (m, 4H), 2.16 (d, J=6.96 Hz, 2H), 2.12-2.00 (m, 1H), 0.92 (d, J=6.55 Hz, 6H).

Example 1.64: Preparation of benzooxazol-2-yl-[3-(4-bromo-2-methyl-2H-pyrazol-3-yl)-4-(2-piperidin-1-yl-ethoxy)-phenyl]-amine (Compound 199)

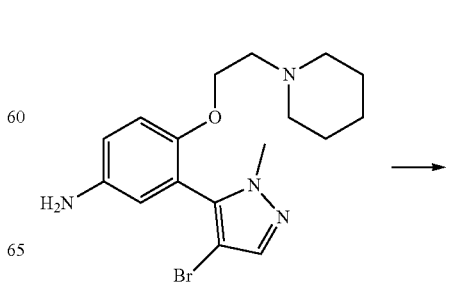

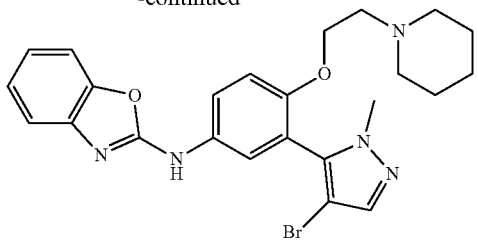

To a mixture of 3-(4-bromo-2-methyl-2H-pyrazol-3-yl)-4-(2-piperidin-1-yl-ethoxy)-phenylamine (0.034 g, 0.09 mmol) and 2-chlorobenzoxazole (0.016 g, 0.11 mmol) in isopropanol (1 mL), DIEA (0.031 mL, 0.18 mmol)) was added. The reaction mixture was heated at 60° C. for 4 days, concentrated then subjected to a purification by prep HPLC. The corresponding fractions were collected and lyophilized to afford Compound 199 (TFA salt) as an off-white solid in 18.4% yield. LCMS m/z (%)=496 (M+H $^{79}$Br, 90), 498 (M+H $^{81}$Br, 100). $^1$H NMR (400 MHz, Acetone-d$_6$) δ: 11.80 (bs, 1H), 8.04 (dd, J=2.8, 9.0 Hz, 1H), 7.91 (d, J=2.8 Hz, 1H), 7.61 (s, 1H), 7.48-7.42 (m, 2H), 7.36 (d, J=9.0 Hz, 1H), 7.27 (dt, J=1.0, 7.6 Hz, 1H), 7.18 (dt, J=1.2, 7.8 Hz, 1H), 4.72-4.63 (m, 1H), 4.60-4.5 (m, 1H), 3.80 (s, 3H), 3.81-3.42 (m, 4H and water), 2.95-2.82 (m, 2H), 1.95-1.80 (m, 4H), 1.55-1.30 9 (m, 2H).

Example 1.65: Preparation of 5-chloro-thiophene-2-carboxylic acid [3-(4-chloro-2-methyl-2H-pyrazol-3-yl)-4-(2-morpholin-4-yl-ethoxy)-phenyl]-amide (Compound 333)

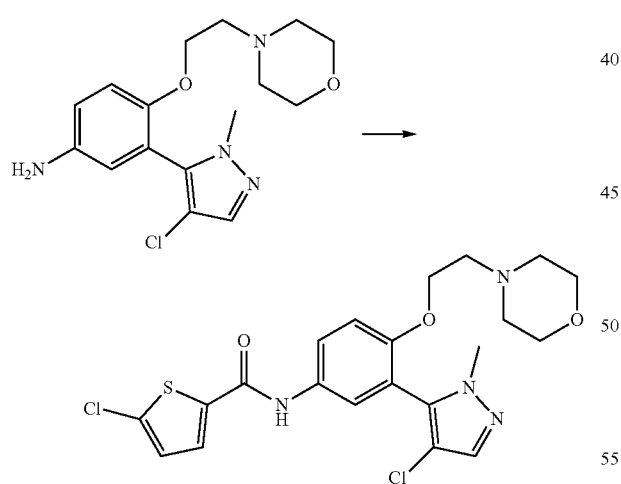

To a mixture of 3-(4-chloro-2-methyl-2H-pyrazol-3-yl)-4-(2-morpholin-4-yl-ethoxy)-phenylamine (0.100 g, 0.3 mmol), 5-chlorothiophene-2-carboxylic acid (0.049 g, 0.3 mmol), and HATU (0.114 g, 0.3 mmol) in DMF (4 mL), DIEA (0.157 mL, 0.9 mmol) was added, then the reaction mixture stirred at room temperature overnight. The crude product was purified by prep HPLC. The corresponding fractions were collected and lyophilized to give a TFA-salt of Compound 333 as a brown solid in 15.1% yield. LCMS m/z (%)=481.2 (M+H, 100). $^1$H NMR (400 MHz, DMSO-d$_6$) δ: 10.41 (s, 1H), 9.95 (bs, 1H), 7.90-7.87 (m, 2H), 7.66 (s, 1H), 7.63 (d, J=2.6 Hz, 1H), 7.31-7.23 (m, 2H), 4.48-4.27 (m, 2H), 3.66 (s, 3H), 3.81-2.87 (m, 10H and water).

Example 1.66: Preparation of 3,4-difluoro-N-[4-[2-(2-methyl-piperidin-1-yl)-ethoxy]-3-(2-methyl-2H-pyrazol-3-yl)-phenyl]-benzamide (Compound 459)

A mixture of 4-[2-(2-Methyl-piperidin-1-yl)-ethoxy]-3-(2-methyl-2H-pyrazol-3-yl)-phenylamine (0.031 g, 0.1 mmol), 3,4-difluorobenzoyl chloride (0.015 mL, 0.12 mmol) and triethylamine (0.018 mL, 0.13 mmol)) in methylene chloride (1.5 mL) was stirred at room temperature overnight and concentrated to give a crude product that was subjected to a purification by prep HPLC. The corresponding fractions were collected and lyophilized to give a TFA-salt of Compound 459 as a white solid in 88.2% yield. LCMS m/z (%)=455.5 (M+H, 100).

Example 1.67: Preparation of N-[3-(4-chloro-2-methyl-2H-pyrazol-3-yl)-4-(1-methyl-piperidin-4-yloxy)-phenyl]-4-fluoro-3-methyl-benzamide (Compound 745)

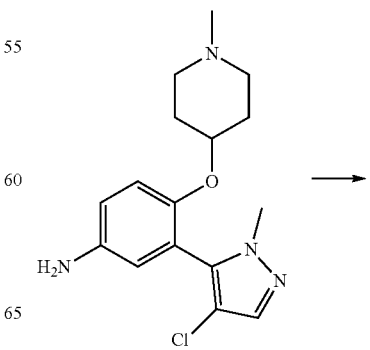

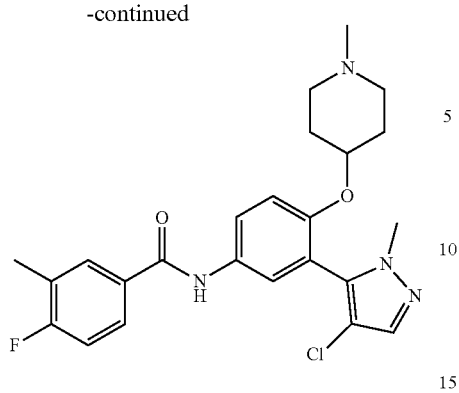

A mixture of 3-(4-Chloro-2-methyl-2H-pyrazol-3-yl)-4-(1-methyl-piperidin-4-yloxy)-phenylamine (0.040 g, 0.12 mmol), 4-fluoro-3-methylbenzoyl chloride (0.026 g, 0.12 mmol) and triethylamine (0.016 mL, 0.13 mmol)) in methylene chloride (1.5 mL) was stirred at room temperature overnight and concentrated to give a crude product that was subjected to a purification by prep HPLC. The corresponding fractions were collected and lyophilized to give a TFA-salt of Compound 745 as a white solid in 57.0% yield. LCMS m/z (%)=457.4 (M+H, 100).

Example 1.68: Preparation of 1-(2-fluoro-phenyl)-3-[3-(2-methyl-2H-pyrazol-3-yl)-4-(2-piperidin-1-yl-ethoxy)-phenyl]-urea (Compound 65)

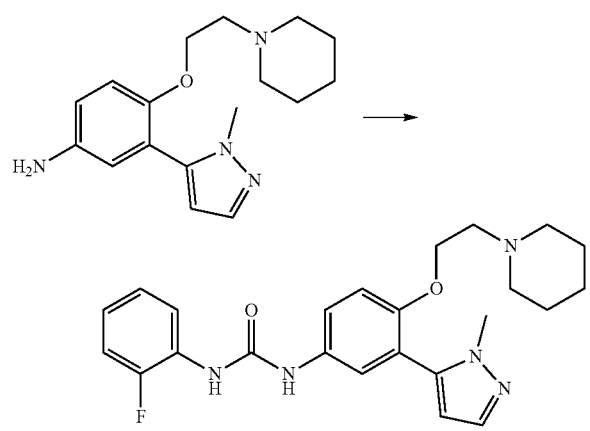

A solution of 3-(2-Methyl-2H-pyrazol-3-yl)-4-(2-piperidin-1-yl-ethoxy)-phenylamine (21.0 mg, 0.07 mmol) in methylene chloride (1 mL) was treated with 2-fluorophenyl isocyanate (0.074 mmol), then the reaction mixture stirred at room temperature overnight and concentrated to give an oily residue that was subjected to a purification by flash chromatography (SiO$_2$, CH$_2$Cl$_2$/MeOH gradient elution) to afford Compound 65 as a white solid in 45.1% yield. LCMS m/z (%)=438.4 (M+H, 100). H NMR (400 MHz, DMSO-d$_6$) δ: 8.52 (bs, 1H), 8.32-8.28 (m, 1H), 8.02 (bs, 1H), 7.57 (dd, J=2.7, 8.9 Hz, 1H), 7.48 (d, J=2.7 Hz, 1H), 7.39 (d, J=1.8 Hz, 1H), 7.18-7.06 (m, 3H), 7.00-6.92 (m, 1H), 6.22 (d, J=1.8 Hz, 1H), 4.11-4.08 (m, 2H), 3.75 (s, 3H), 2.67-2.60 (m, 2H), 2.42-2.31 (m, 4H), 1.52-1.43 (m, 4H), 1.40-1.32 (m, 2H).

Example 1.69: Preparation of N-[3-(4-bromo-2-methyl-2H-pyrazol-3-yl)-4-(2-pyrrolidin-1-yl-ethoxy)-phenyl]-3-fluoro-benzamide (Compound 455)

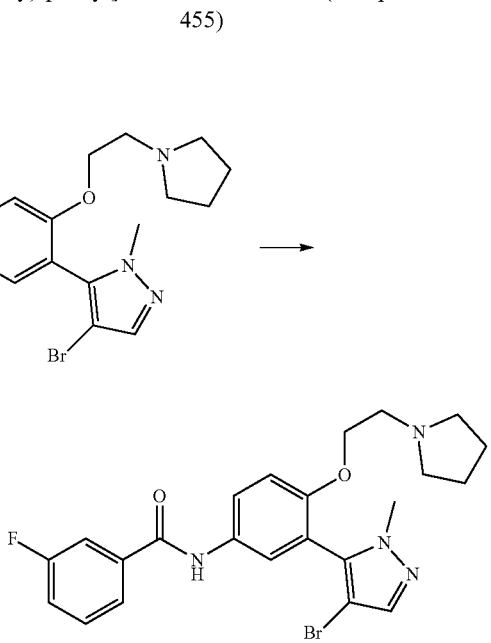

A mixture of 3-(4-Bromo-2-methyl-2H-pyrazol-3-yl)-4-(2-pyrrolidin-1-yl-ethoxy)-phenylamine (0.036 g, 0.1 mmol), 3-fluoro-benzoyl chloride (14.6 µL, 0.12 mmol) and triethylamine (18.1 µL, 0.13 mmol)) in methylene chloride (2 mL) was stirred at room temperature overnight and concentrated to give a crude product that was subjected to a purification by prep HPLC. The corresponding fractions were collected and lyophilized to give a TFA-salt of Compound 455 as a tan solid in 85.4% yield. LCMS m/z (%)=487 (M+H $^{79}$Br, 97), 489 (M+H $^{81}$Br, 100). $^1$H NMR (400 MHz, DMSO-d$_6$) δ: 10.42 (s, 1H), 9.71 (bs, 1H), 7.96 (d, J=9.0 Hz, 1H), 7.83-7.73 (m, 3H), 7.66 (s, 1H), 7.63-7.57 (m, 1H), 7.46 (t, J=8.7 Hz, 1H), 7.30 (d, J=9.1 Hz, 1H), 4.45-4.21 (m, 2H), 3.68 (s, 3H), 3.51-3.42 (m, 2H and water), 3.43-3.20 (m, 2H), 2.93-2.60 (m, 2H), 1.97-1.68 (m, 4H).

Example 1.70: Preparation of cyclopentanecarboxylic Acid [3-(4-bromo-2-methyl-2H-pyrazol-3-yl)-4-(2-morpholin-4-yl-ethoxy)-phenyl]-amide (Compound 310)

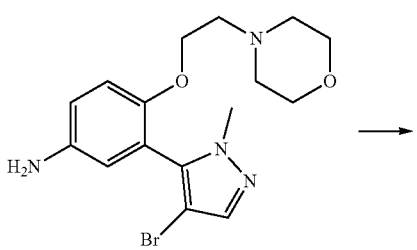

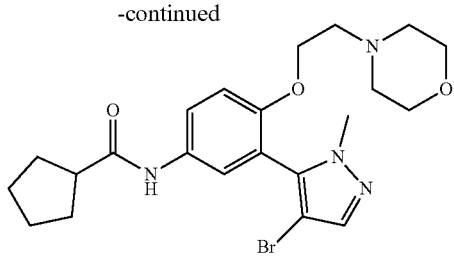

A mixture of 3-(4-Bromo-2-methyl-2H-pyrazol-3-yl)-4-(2-morpholin-4-yl-ethoxy)-phenylamine (76 mg, 0.2 mmol), cyclopentyl carboxylic acid (27 mg, 0.24 mmol), HATU (99 mg, 0.26 mmol) and triethylamine (0.3 mL) in DMF (2 mL) was heated in microwave at 100° C. for 30 min. The crude was purified by HPLC to give title compound (20 mg, 21%) as a brown solid as TFA salt. $^1$H NMR (CD$_3$CN, 400 MHz) δ 1.66-1.95 (m, 8H), 2.70-2.80 (m, 1H), 2.85-3.02 (m, 2H), 3.13-3.27 (m, 2H), 3.43 (t, 2H), 3.73 (s, 3H), 3.74-3.80 (m, 2H), 3.82-3.90 (m, 2H), 4.34-4.48 (m, 2H), 7.13 (d, J=9.09 Hz, 1H), 7.55 (d, J=2.53 Hz, 1H), 7.57 (s, 1H), 7.76 (dd, J=2.78, 9.35 Hz, 1H), 8.38 (s, 1H). Exact mass calculated for C$_{22}$H$_{29}$$^{79}$BrN$_4$O$_3$ 476.1, found 477.3 (M+H $^{79}$Br, 100), 479.3 (M+H $^{81}$Br, 98).

Example 1.71: Preparation of N-[3-(2-methyl-2H-pyrazol-3-yl)-4-(2-pyrrolidin-1-yl-ethoxy)-phenyl]-4-trifluoromethyl-benzamide (Compound 343)

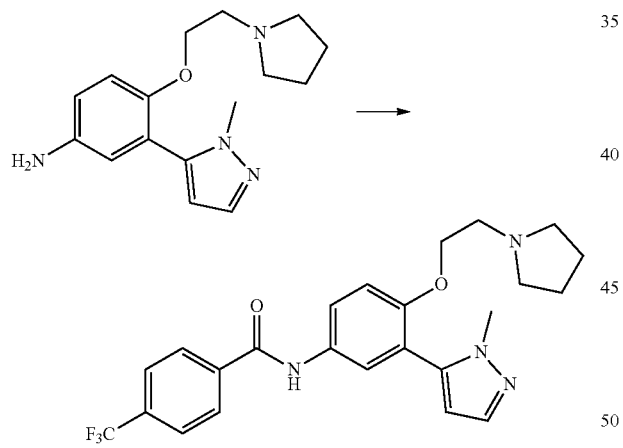

A mixture of 3-(2-Methyl-2H-pyrazol-3-yl)-4-(2-pyrrolidin-1-yl-ethoxy)-phenylamine (57 mg, 0.2 mmol), 4-trifluoromethyl-benzoic acid (42 mg, 0.22 mmol), HATU (91 mg, 0.24 mmol) and triethylamine (0.3 mL) in DMF (2 mL) was heated in microwave at 100° C. for 15 min. The crude was purified by HPLC to give the title compound (65 mg, 71%) as a brown solid as TFA salt. $^1$H NMR (DMSO-d$_6$, 400 MHz) δ 1.73-1.76 (m, 2H), 1.87-1.92 (m, 2H), 2.85-2.90 (m, 2H), 3.29-3.32 (m, 2H), 3.53-3.57 (m, 2H), 3.69 (s, 3H), 4.32 (t, J=4.80 Hz, 2H), 6.32 (d, J=2.02 Hz, 1H), 7.26 (d, J=8.59 Hz, 1H), 7.50 (d, J=1.78 Hz, 1H), 7.75 (d, J=2.53 Hz, 1H), 7.88-7.94 (m, 3H), 8.15 (d, J=8.84 Hz, 2H), 9.81 (s, 1H), 10.5 (s, 1H). Exact mass calculated for C$_{24}$H$_{25}$F$_3$N$_4$O$_2$ 458.2, found 459.4 (MH$^+$).

Example 1.72: Preparation of N-{3-(4-bromo-2-methyl-2H-pyrazol-3-yl)-4-[2-((S)-3-fluoro-pyrrolidin-1-yl)-ethoxy]-phenyl}-3-fluoro-benzamide (Compound 475)

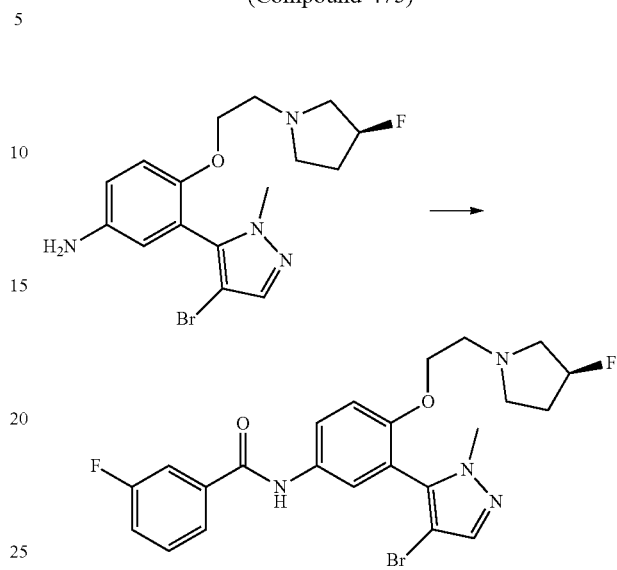

A mixture of 3-(4-bromo-2-methyl-2H-pyrazol-3-yl)-4-[2-((S)-3-fluoro-pyrrolidin-1-yl)-ethoxy]-phenylamine (76 mg, 0.2 mmol), 3-fluorobenzoyl chloride (32 mg, 0.22 mmol), triethylamine (0.3 mL) in THF (2 mL) was stirred at r.t. for 20 min. The solvent was concentrated in vacuo and the crude was purified by HPLC to give the title compound (40 mg, 40%) as a yellow solid as TFA salt. $^1$H NMR (DMSO-d$_6$, 400 MHz) δ 1.98-2.10 (m, 2H), 2.90-3.45 (m, 6H), 3.68 (s, 3H), 4.28-4.30 (m, 1H), 4.39-4.42 (m, 1H), 5.28-5.42 (m, 1H), 7.28-7.31 (m, 1H), 7.44-7.49 (m, 1H), 7.57-7.63 (m, 1H), 7.67 (d, 1H), 7.73-7.82 (m, 3H), 7.94 (dd, 1H), 10.4 (s, 2H). Exact mass calculated for C$_{23}$H$_{23}$BrF$_2$N$_4$O$_2$ 504.1, found 505.5/507.5 (MH$^+$).

Example 1.73: Preparation of 3-chloro-4-fluoro-N-[4-[2-(4-fluoro-piperidin-1-yl)-ethoxy]-3-(2-methyl-2H-pyrazol-3-yl)-phenyl]-benzamide (Compound 538)

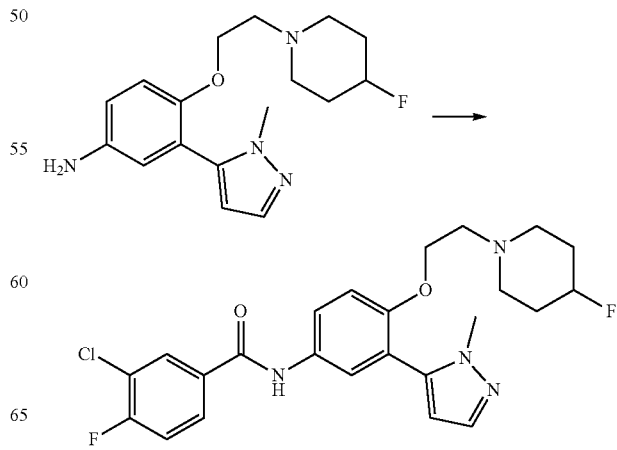

A mixture of 4-[2-(4-fluoro-piperidin-1-yl)-ethoxy]-3-(2-methyl-2H-pyrazol-3-yl)-phenylamine (80 mg, 0.25 mmol), 4-fluoro-3-chlorobenzoyl chloride (48 mg, 0.25 mmol), and triethylamine (0.3 mL) in THF (3 mL) was stirred at r.t. for 10 min. The solvent was concentrated in vacuo and the crude was purified by HPLC to give the title compound (58 mg, 50%) as a white solid as TFA salt. $^1$H NMR (acetone-d$_6$, 400 MHz) δ 2.02-2.24 (m, 4H), 3.08-3.18 (m, 2H), 3.32-3.42 (m, 2H), 3.63 (t, J=4.55 Hz, 2H), 3.80 (s, 3H), 4.59 (t, J=4.55 Hz, 2H), 4.91-5.03 (m, 1H), 6.30 (d, J=1.77 Hz, 1H), 7.23 (d, J=8.84 Hz, 1H), 7.43-7.51 (m, 2H), 7.81 (t, J=2.27 Hz, 1H), 7.91-7.97 (m, 1H), 8.02-8.08 (m, 1H), 8.18 (dd, J=2.53, 7.33 Hz, 1H), 9.71 (s, 1H). Exact mass calculated for C$_{24}$H$_{25}$ClF$_2$N$_4$O$_2$ 503.1, found 504.1/506.1 (MH$^+$).

Example 1.74: Preparation of N-[3-(4-bromo-2-methyl-2H-pyrazol-3-yl)-4-(piperidin-3-yloxy)-phenyl]-4-fluoro-benzamide (Compound 396)

Step 1.74a: Preparation of 3-[2-(4-bromo-2-methyl-2H-pyrazol-3-yl)-4-(4-fluoro-benzoylamino)-phenoxy]-piperidine-1-carboxylic Acid Tert-Butyl Ester

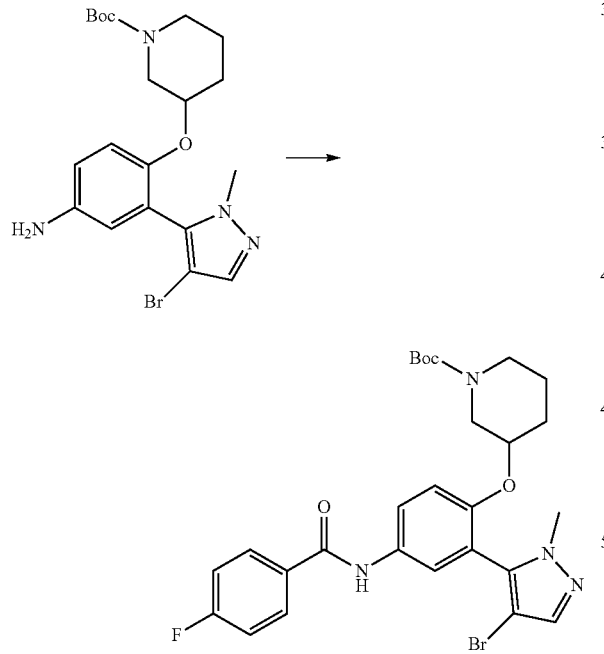

A mixture of 3-[4-amino-2-(4-bromo-2-methyl-2H-pyrazol-3-yl)-phenoxy]-piperidine-1-carboxylic acid tert-butyl ester (90 mg, 0.2 mmol), 4-fluorobenzoic acid (34 mg, 0.24 mmol), HATU (99 mg, 0.26 mmol) and triethylamine (0.3 mL) in DMF (2 mL) was heated in microwave at 100° C. for 15 min. The crude was purified by HPLC to give 3-[2-(4-bromo-2-methyl-2H-pyrazol-3-yl)-4-(4-fluoro-benzoylamino)-phenoxy]-piperidine-1-carboxylic acid tert-butyl ester (36 mg, 32%) as a white solid. MS found, 573.5 and 575.5.

Step 1.74b: Preparation of N-[3-(4-bromo-2-methyl-2H-pyrazol-3-yl)-4-(piperidin-3-yloxy)-phenyl]-4-fluoro-benzamide (Compound 396)

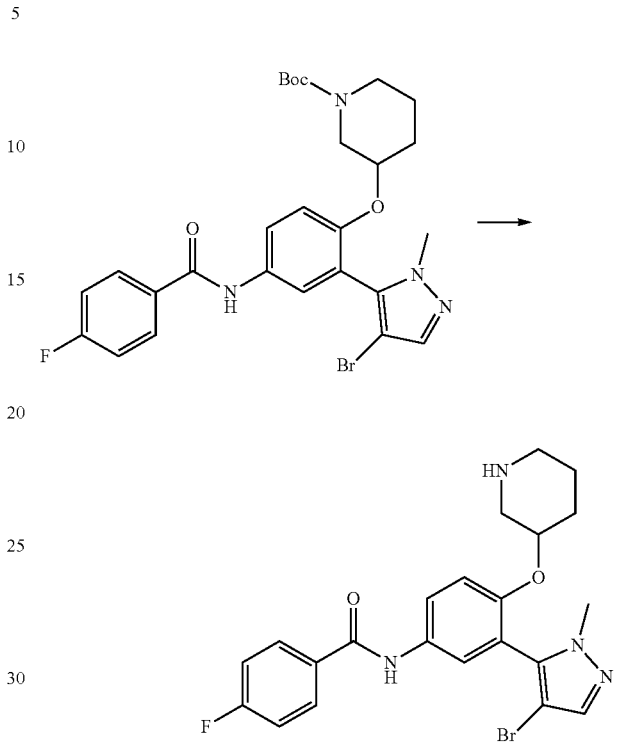

To 3-[2-(4-bromo-2-methyl-2H-pyrazol-3-yl)-4-(4-fluoro-benzoylamino)-phenoxy]-piperidine-1-carboxylic acid tert-butyl ester (36 mg) was added HCl in dioxane (4 M, 1 mL), the mixture was stirred at r.t. for a few hours. The solvent was concentrated in vacuo to give the title compound (36 mg) as HCl salt. $^1$H NMR (DMSO-d$_6$, 400 MHz) δ 1.42-2.08 (m, 4H), 2.72-3.38 (m, 4H), 3.73 (d, 3H), 4.45 (m, 1H), 7.33-7.39 (m, 3H), 7.65 (d, J=2.53 Hz, 1H), 7.74 (t, J=3.03 Hz, 1H), 7.90-7.95 (m, 1H), 8.03-8.07 (m, 2H), 8.85-9.02 (m, 1H), 9.15-9.30 (m, 1H), 10.4 (s, 1H). Exact mass calculated for C$_{22}$H$_{22}$BrFN$_4$O$_2$ 472.1, found 473.3/475.3 (MH$^+$).

Example 1.75: Preparation of N-[4-[2-(4-acetyl-piperazin-1-yl)-ethoxy]-3-(2-methyl-2H-pyrazol-3-yl)-phenyl]-3-fluoro-benzamide (Compound 660)

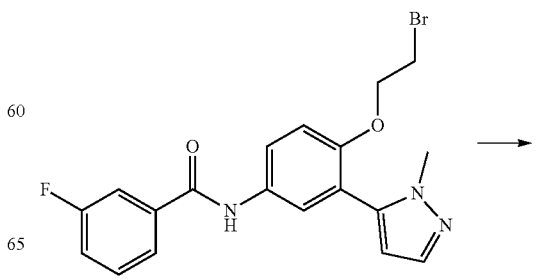

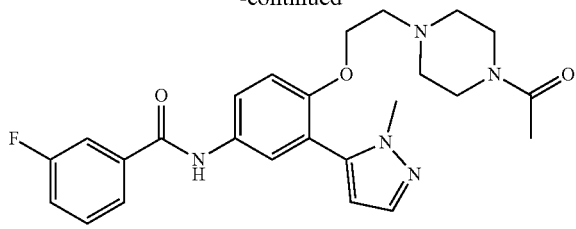

A mixture of N-[4-(2-Bromo-ethoxy)-3-(2-methyl-2H-pyrazol-3-yl)-phenyl]-3-fluoro-benzamide (105 mg, 0.251 mmol), 1-acetylpiperazine (34 mg, 0.264 mmol) and potassium carbonate (42 mg, 0.301 mmol) in DMF (3 mL) was heated in microwave at 120° C. for 20 min. The mixture was purified by HPLC to give title compound (75 mg, 64%) as a white solid as TFA salt. $^1$H NMR (CD$_3$CN, 400 MHz) δ 2.09 (s, 3H), 3.32-3.38 (m, 6H), 3.48 (t, J=5.05 Hz, 4H), 3.79 (s, 3H), 4.43 (t, J=4.55 Hz, 2H), 6.39 (d, J=2.02 Hz, 1H), 7.18 (d, J=9.09 Hz, 1H), 7.40 (dt, J=2.78, 8.59 Hz, 1H), 7.57-7.63 (m, 2H), 7.70-7.74 (m, 2H), 7.80-7.82 (m, 1H), 7.85 (dd, J=2.78, 9.09 Hz, 1H), 8.93 (s, 1H). Exact mass calculated for C$_{25}$H$_{28}$FN$_5$O$_3$ 465.2, found 466.4 (MH$^+$).

Example 1.76: Preparation of N-[4-[2-(4,4-difluoro-piperidin-1-yl)-ethoxy]-3-(2-methyl-2H-pyrazol-3-yl)-phenyl]-3-fluoro-benzamide (Compound 778)

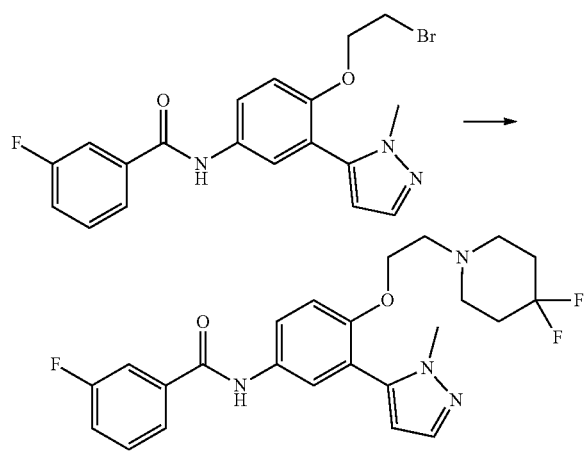

A mixture of N-[4-(2-bromo-ethoxy)-3-(2-methyl-2H-pyrazol-3-yl)-phenyl]-3-fluoro-benzamide (104 mg, 0.25 mmol), 4,4-difluoropiperidine hydrochloride (43 mg, 0.275 mmol) and potassium carbonate (103 mg, 0.75 mmol) in DMF (2 mL) was heated in microwave at 120° C. for 20 min. The crude was purified by HPLC to give the title compound (20 mg, 18%) as a white solid as TFA salt. $^1$H NMR (DMSO-d$_6$, 400 MHz) δ 2.10-2.23 (m, 4H), 3.10-3.40 (m, 4H), 3.57 (t, 2H), 3.68 (s, 3H), 4.37 (t, 2H), 6.30 (d, 1H), 7.25 (d, 1H), 7.45 (dt, 1H), 7.50 (d, 1H), 7.57-7.62 (m, 1H), 7.72 (d, 1H), 7.74-7.82 (m, 2H), 7.89 (dd, 1H), 10.3 (s, 1H). Exact mass calculated for C$_{24}$H$_{25}$F$_3$N$_4$O$_2$ 458.2, found 459.4 (MH$^+$).

Example 1.77: Preparation of 1-[3-(4-bromo-2-methyl-2H-pyrazol-3-yl)-4-(2-pyrrolidin-1-yl-ethoxy)-phenyl]-3-(4-chloro-phenyl)-urea (Compound 1)

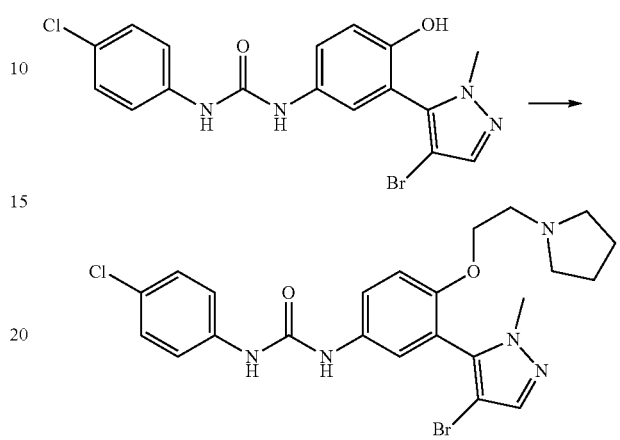

To a solution of 1-(3-(4-bromo-1-methyl-1H-pyrazol-5-yl)-4-hydroxyphenyl)-3-(4-chlorophenyl)urea (44.3 mg, 0.105 mmol) in THF (5 mL), was added triphenyl phosphine (66.2 mg, 0.252 mmol) and 1-(2-hydroxyethyl)pyrrolidine (28.0 mg, 0.243 mmol) followed by dropwise addition of diisopropyl azodicarboxylate (DIAD) (50 μL, 0.258 mmol). After 1 hour, an LC/MS showed only partial conversion so extra triphenyl phosphine (36.9 mg, 0.141 mmol) and 1-(2-hydroxyethyl)pyrrolidine (17 μL, 0.145 mmol) was added followed by dropwise addition of diisopropyl azodicarboxylate (DIAD) (27 μL, 0.139 mmol). The reaction mixture was stirred at room temperature for 1 more hour and then concentrated. The resulting material was purified by HPLC. The product was dried in vacuo to afford the title compound as a light brown solid (31.3 mg, 57%). LCMS m/z (%)=520 (M+H$^{81}$Br, 100), 518 (M+H$^{79}$Br, 73), $^1$H NMR (400 MHz, DMSO-d$_6$) δ 8.81 (bs, 1H), 8.71 (bs, 1H), 7.60 (s, 1H), 7.53 (dd, J=8.98, 2.72 Hz, 1H), 7.47 (d, J=8.95 Hz, 2H), 7.35 (d, J=2.71 Hz, 1H), 7.31 (d, J=8.90 Hz, 2H), 7.15 (d, J=9.05 Hz, 1H), 4.15-4.07 (m, 1H), 4.06-3.98 (m, 1H), 3.66 (s, 3H), 2.80-2.69 (m, 1H), 2.69-2.58 (m, 1H), 2.42-2.31 (m, 4H), 1.66-1.55 (m, 4H).

Example 1.78: Preparation of 1-[3-(4-bromo-2-methyl-2H-pyrazol-3-yl)-4-(2-pyrrolidin-1-yl-ethoxy)-phenyl]-3-(2,4-difluoro-phenyl)-urea (Compound 5)

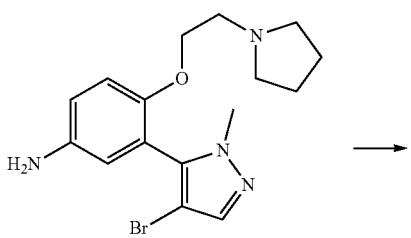

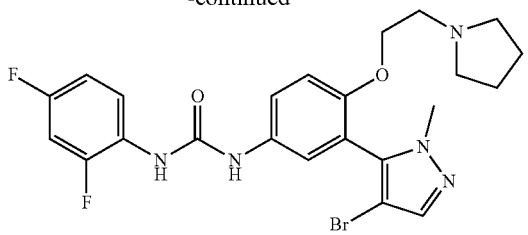

To a solution of 3-(4-Bromo-2-methyl-2H-pyrazol-3-yl)-4-(2-pyrrolidin-1-yl-ethoxy)-phenylamine (0.96 g, 2.47 mmol) in 10 mL of DMA was added 2,4-difluoro phenyl isocyanate (0.42 g, 2.71 mmol), and the mixture was stirred at ambient temperature overnight. The reaction mixture was diluted with DMSO and was purified by RP-HPLC. The fractions containing the product were pooled and evaporated to a small volume. The aqueous solution was neutralized with 1N NaOH to a pH of 9.0 and the product was extracted with ethyl acetate (2×, 50 mL). The organic layer was dried with sodium sulfate, filtered and evaporated to dryness to produce 1-[3-(4-bromo-2-methyl-2H-pyrazol-3-yl)-4-(2-pyrrolidin-1-yl-ethoxy)-phenyl]-3-(2,4-difluoro-phenyl)-urea as a colorless solid in 59% yield. LCMS m/z (%)=520 (M+H $^{79}$Br, 100), 522 (M+H $^{81}$Br, 98). $^1$H NMR (400 MHz. DMSO-d$_6$) δ: 9.03 (bs, 1H), 8.49 (bs, 1H), 8.01-8.1 (m, 1H), 7.61 (s, 1H), 7.51 (dd, J=8.96 and 2.73 Hz, 1H), 7.35 (d, J=2.72 Hz, 1H), 7.27-7.33 (m, 1H), 7.15 (d, J=9.04 Hz, 1H), 7.04-7.09 (m, 1H), 4.01-4.11 (m, 2H), 3.67 (s, 3H), 2.51-2.73 (m, 2H), 2.34-2.38 (bs, 4H), 1.59-1.63 (bs, 4H).

Example 1.79: Preparation of 1-[3-(4-bromo-2-methyl-2H-pyrazol-3-yl)-4-(2-pyridin-4-yl-ethoxy)-phenyl]-3-(4-chloro-phenyl)-urea (Compound 145)

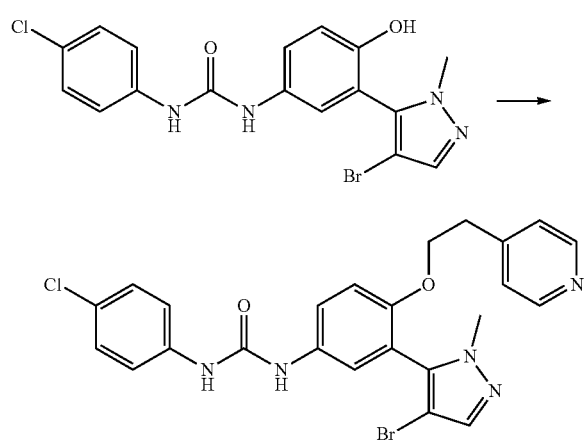

To a solution of 1-[3-(4-bromo-2-methyl-2H-pyrazol-3-yl)-4-hydroxy-phenyl]-3-(4-chloro-phenyl)-urea (0.1 g, 0.24 mmol), 4-(2-hydroxyethyl)-pyridine (0.0443 g, 0.36 mmol), and triphenylphosphine (0.0944 g, 0.36 mmol) in 10 mL of dry THF was added diisopropylazodicarboxylate (0.0728 g, 0.36 mmol) at ambient temperature. The mixture was stirred for 2 hours. Next, additional triphenylphosphine (0.0944 g, 0.36 mmol), 4-(2-hydroxyethyl)-pyridine (0.0443 g, 0.36 mmol), and diisopropylazodicarboxylate were added and the reaction mixture further stirred at room temperature overnight. The solvent from the reaction mixture was evaporated and the crude residue was dissolved in 5.0 mL of DMSO and purified by RP-HPLC. The proper fractions were collected and concentrated to ¼ volume. The aqueous solution was neutralized with 1N NaOH and extracted with ethyl acetate (2×, 59 mL). The organic layer was dried with sodium sulfate, filtered and evaporated to dryness to afford 1-[3-(4-Bromo-2-methyl-2H-pyrazol-3-yl)-4-(2-pyridin-4-yl-ethoxy)-phenyl]-3-(4-chloro-phenyl)-urea as a brown solid in 44% yield. LCMS m/z (%)=526 (M+H $^{79}$Br, 100), 528 (M+H $^{81}$Br, 67). $^1$H NMR (DMSO-d$_6$) δ: 9.33 (bs, 1H), 9.24 (bs, 1H), 8.39 (dd, J=4.44 and 1.48 Hz, 2H), 7.63 (d, J=7.28 Hz, 1H), 7.59 (s, 1H), 7.56 (dd, J=8.94 and 2.71 Hz, 2H), 7.48 (m, 1H), 7.34 (d, J=2.67, 1H), 7.31 (d, J=2.67, 1H), 7.28 (dd, J=6.88 and 4.87 Hz, 2H), 7.14 (d, J=9.05 Hz, 1H), 7.09 (d, J=5.93 Hz, 1H), 4.01-4.2 (m, 2H), 3.48 (s, 3H), 2.96-2.91 (m, 2H).

Example 1.80: Preparation of 1-(2,4-difluoro-phenyl)-3-[4-(2-imidazol-1-yl-ethoxy)-3-(2-methyl-2H-pyrazol-3-yl)-phenyl]-urea (Compound 219)

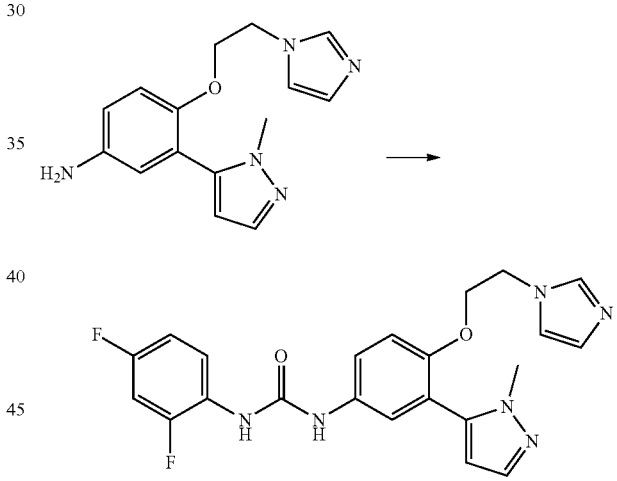

To a solution of 4-(2-imidazol-1-yl-ethoxy)-3-(2-methyl-2H-pyrazol-3-yl)-phenylamine (0.08 g, 0.256 mmol) in 2.0 mL of dichloromethane was added 2,4-difluoro phenyl isocyanate (0.042 g, 0.280 mmol), and the mixture was stirred at ambient temperature overnight. The DCM was evaporated from the reaction mixture, the crude residue was dissolved in 5.0 mL of DMSO and purified by RP-HPLC. The proper fractions were collected and lyophilized to afford the 1-(2,4-difluoro-phenyl)-3-[4-(2-imidazol-1-yl-ethoxy)-3-(2-methyl-2H-pyrazol-3-yl)-phenyl]-urea as an off-white solid in 75% yield. LCMS m/z (%)=439 (M+H). $^1$H NMR (400 MHz, Acetone-d$_6$) δ: 8.46 (bs, 1H), 7.96-8.02 (m, 1H), 7.48 (dd, J=8.9 and 2.72 Hz, 1H), 7.39-7.41 (m, 2H), 7.31 (d, J=1.81 Hz, 1H), 7.17 (t, J=1.42 Hz, 1H), 6.94 (d, J=8.94 Hz, 1H), 6.7-6.8 (m, 2H), 6.01 (d, J=1.78 Hz, 1H), 4.62 (t, J=4.74 Hz, 2H), 4.33 (t, J=5.07 Hz, 2H), 3.48 (s, 3H).

Example 1.81: Preparation of [4-(2-azepan-1-yl-ethoxy)-3-(4-bromo-2-methyl-2H-pyrazol-3-yl)-phenyl]-carbamic Acid Isopropyl Ester (Compound 352)

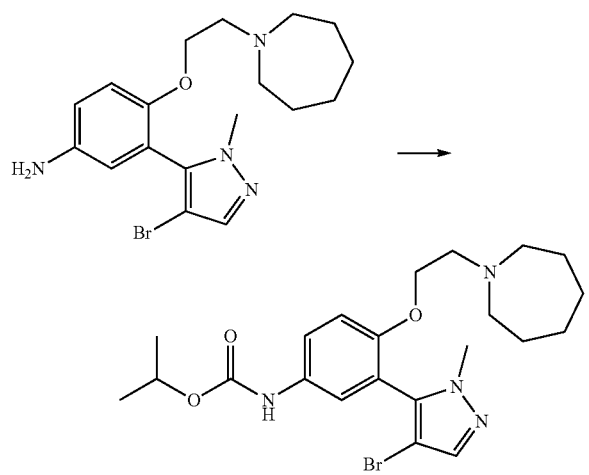

To a solution of 4-(2-azepan-1-yl-ethoxy)-3-(4-bromo-2-methyl-2H-pyrazol-3-yl)-phenylamine (0.06 g, 0.1539 mmol) 2.0 mL of DMA was added isopropyl chloroformate (0.021 g, 0.1687 mmol), and the mixture was stirred at ambient temperature overnight. The reaction mixture was diluted to 5.0 mL with DMSO and purified by RP-HPLC. The proper fractions were collected and evaporated to ¼ volume and the aqueous was neutralized with 1N NaOH to a pH 9.0. Next, the product was extracted with ethyl acetate (2×, 30 mL). The pooled organic layer was dried with sodium sulfate, filtered and evaporated to dryness to afford [4-(2-Azepan-1-yl-ethoxy)-3-(4-bromo-2-methyl-2H-pyrazol-3-yl)-phenyl]-carbamic acid isopropyl ester as a colorless solid in 69% yield. LCMS m/z (%)=478 (M+H $^{79}$Br, 100), 480 (M+H $^{81}$Br, 98). $^1$H NMR (400 MHz, DMSO-d$_6$) δ: 8.79 (bs, 1H), 8.69 (bs, 1H), 7.59 (s, 1H), 7.34 (d, J=2.62 Hz, 1H), 7.21-7.31 (m, 1H), 7.14 (d, J=9.04 Hz, 1H), 4.02-4.12 (m, 1H), 3.92-4.12 (m, 2H), 3.67 (s, 3H), 2.69-2.78 (m, 2H), 2.53-2.59 (m, 2H), 1.4-1.58 (bs, 8H), 1.26 (d, J=6.82 Hz, 6H).

Example 1.82: Preparation of N-[3-(2-methyl-2H-pyrazol-3-yl)-4-(2-[1,4]oxazepan-4-yl-ethoxy)-phenyl]-3-trifluoromethyl-benzamide (Compound 568)

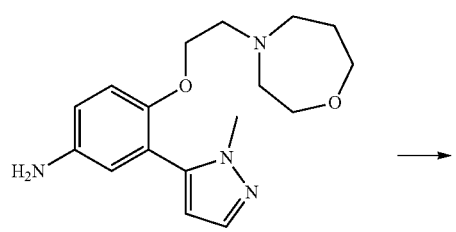

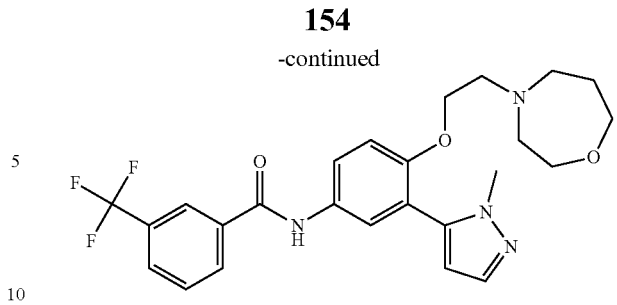

To a solution 3-(2-methyl-2H-pyrazol-3-yl)-4-(2-[1,4]oxazepan-4-yl-ethoxy)-phenylamine (0.07 g, 0.2215 mmol) in 2.0 mL of DMA was added DIEA (0.057 g, 0.443 mmol), followed by m-trifluoromethyl benzoyl chloride (0.056 g, 0.266 mmol), and the reaction mixture was stirred at ambient temperature overnight. The reaction mixture was diluted to 5.0 mL with DMSO and purified by RP-HPLC. The proper fractions were collected and lyophilized to afford N-[3-(2-Methyl-2H-pyrazol-3-yl)-4-(2-[1,4]oxazepan-4-yl-ethoxy)-phenyl]-3-trifluoromethyl-benzamide as an off-white semisolid in 87% yield. LCMS m/z (%)=489 (M+H, 100). $^1$H NMR (400 MHz, DMSO-d$_6$) δ: 10.5 (bs, 1H), 8.29 (s, 1H), 8.26 (d, J=7.94 Hz, 1H), 7.98 (d, J=7.83 Hz, 1H), 7.89 (dd, J=8.93 and 2.55 Hz, 1H), 7.79 (t, J=7.82 Hz, 1H), 7.72 (d, J=2.53 Hz, 1H), 7.49 (s, 1H), 7.26 (d, J=9.14 Hz, 1H), 6.31 (d, J=1.79 Hz, 1H), 4.29-4.43 (m, 2H), 3.69 (s, 3H), 3.55-3.64 (m, 5H), 3.01-3.18 (m, 5H), 1.8-2.1 (m, 2H).

Example 1.83: Preparation of N-[3-(4-bromo-2-methyl-2H-pyrazol-3-yl)-4-(2-[1,4]oxazepan-4-yl-ethoxy)-phenyl]-3-fluoro-4-trifluoromethyl-benzamide (Compound 606)

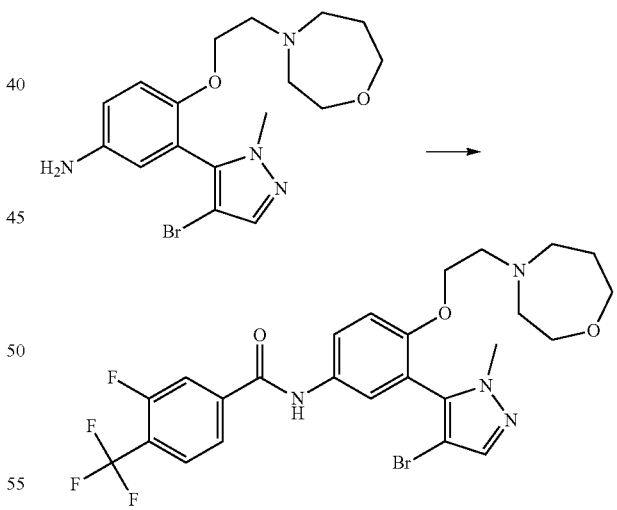

To a solution of 3-(4-bromo-2-methyl-2H-pyrazol-3-yl)-4-(2-[1,4]oxazepan-4-yl-ethoxy)-phenylamine (0.06 g, 0.152 mmol), and N,N-diisopropylethylamine (0.0529 mL, 0.304 mmol) in 3.0 mL of DMA was added slowly 3-fluoro-4-(trifluoromethyl)benzoyl chloride (0.0278 mL, 0.182 mmol) and the reaction mixture was stirred at ambient temperature overnight. The reaction mixture was diluted to 5.0 mL with DMSO and subjected to purification on a RP-HPLC. The proper fractions were collected and lyophilized to furnish N-[3-(4-Bromo-2-methyl-2H-pyrazol-3-yl)-4-(2-[1,4]oxazepan-4-yl-ethoxy)-phenyl]-3-fluoro-4-trifluoromethyl-benzamide as an off-white semisolid in 53% yield. LCMS m/z (%)=585 (M+H $^{79}$Br, 100), 587 (M+H $^{81}$Br, 98). $^1$H NMR (400 MHz, DMSO-d$_6$) δ: 10.3 (bs, 1H), 8.06 (d, J=11.27 Hz, 1H), 7.95-8.01 (m, 3H), 7.72 (d, J=2.60 Hz, 1H), 7.68 (d, J=2.36 Hz, 1H), 7.31 (d, J=9.48 Hz, 1H), 4.35-4.44 (m, 2H), 3.5-3.9 (m, 10H), 2.51-2.69 (m, 5H).

Example 1.84: Preparation of [3-(2-methyl-2H-pyrazol-3-yl)-4-(2-thiomorpholin-4-yl-ethoxy)-phenyl]-carbamic Acid Isopropyl Ester (Compound 214)

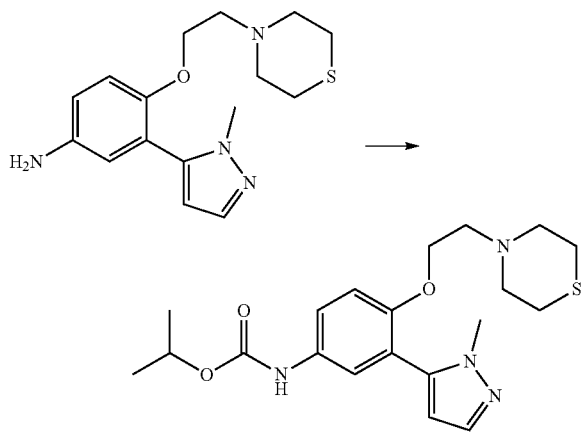

To a solution of 3-(2-methyl-2H-pyrazol-3-yl)-4-(2-thiomorpholin-4-yl-ethoxy)-phenylamine (0.14 g, 0.443 mmol) in 2.0 mL/1.0 mL DCM/Pyridine mixture was added isopropyl chloroformate (0.06 g, 0.487 mmol), and the reaction mixture was stirred at room temperature overnight. The DCM/Pyridine mixture was evaporated to give a brown residue. The residue was dissolved in 5.0 mL of DMSO and was subjected to purification on RP-HPLC. The proper fractions were collected and lyophilized to produce [3-(2-Methyl-2H-pyrazol-3-yl)-4-(2-thiomorpholin-4-yl-ethoxy)-phenyl]-carbamic acid isopropyl ester as a solid in 84% yield. LCMS m/z (%)=405 (M+H, 100). $^1$H NMR (400 MHz, Acetone-d$_6$) δ: 8.58 (bs, 1H), 7.66 (dd, J=8.4 and 2.6 Hz, 1H), 7.55 (s, 1H), 7.47 (d, J=1.81 Hz, 1H), 7.28 (d, J=1.8 Hz, 1H), 7.16 (d, J=8.9 Hz, 1H), 6.05 (d, J=1.86 Hz, 1H), 4.92-4.98, (m, 1H), 4.53 (t, J=4.3 Hz, 2H), 3.72 (s, 3H), 3.59 (dd, J=9.63 and 4.86 Hz, 2H), 3.28-3.42 (m, 4H), 2.93-2.99 (m, 4H), 1.25 (d, J=6.12 Hz, 6H).

Example 1.85: Preparation of [3-(2-methyl-2H-pyrazol-3-yl)-4-(2-[1,4]oxazepan-4-yl-ethoxy)-phenyl]-carbamic Acid Isopropyl Ester (Compound 215)

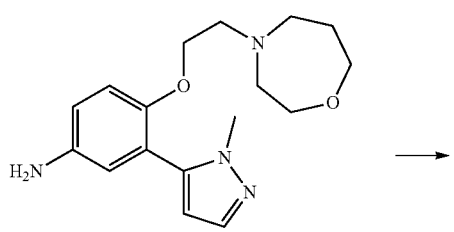

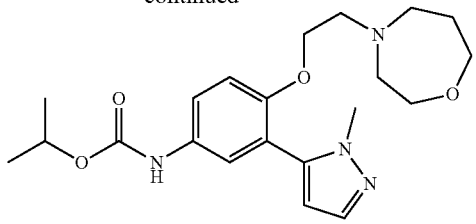

To a solution of 3-(2-methyl-2H-pyrazol-3-yl)-4-(2-[1,4]oxazepan-4-yl-ethoxy)-phenylamine (0.08 g, 0.253 mmol) in 2.0 mL of DMA was added isopropyl chloroformate (0.034 g, 0.278 mmol), and the reaction mixture was stirred at room temperature overnight. The reaction mixture was diluted to 5.0 mL with DMSO and was subjected to purification on RP-HPLC. The proper fractions were collected and lyophilized to afford [3-(2-methyl-2H-pyrazol-3-yl)-4-(2-[1,4]oxazepan-4-yl-ethoxy)-phenyl]-carbamic acid isopropyl ester as an off-white semisolid in 80% yield. LCMS m/z (%)=403 (M+H, 100). $^1$H NMR (400 MH, Acetone-d$_6$) δ: 8.35 (bs. 1H), 7.45 (dd, J=8.4 and 2.6 Hz, 1H), 7.33 (s, 1H), 7.23 (d, J=1.8 Hz, 1H), 6.94 (d, J=8.95 Hz, 1H), 6.05 (d, J=1.82 Hz, 1H), 4.69-4.76, (m, 1H), 4.31 (t, J=4.36 Hz, 2H), 3.52 (s, 3H), 3.41 (t, J=4.93 Hz, 2H), 3.10-3.30 (m, 4H), 2.71-2.80 (m, 4H), 1.05 (d, J=6.12 Hz, 6H).

Example 1.86: Preparation of N-[3-(4-chloro-2-methyl-2H-pyrazol-3-yl)-4-(2-morpholin-4-yl-ethoxy)-phenyl]-3-trifluoromethyl-benzamide (Compound 527)

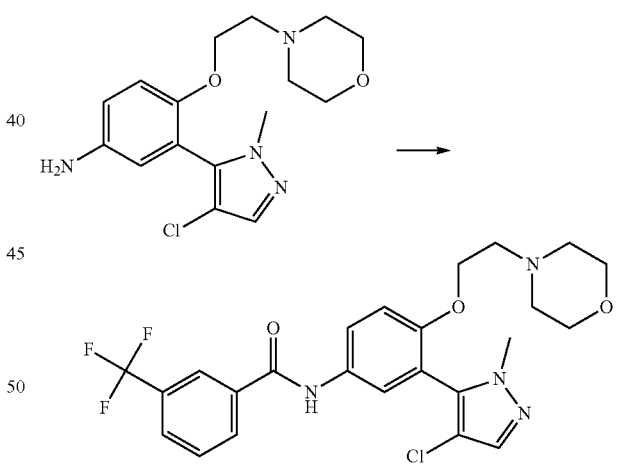

To a clear solution of 3-(4-chloro-2-methyl-2H-pyrazol-3-yl)-4-(2-morpholin-4-yl-ethoxy)-phenylamine (60.1 g, 178 mmol) in a mixture of n-propanol/ethyl acetate (600/200 mL) at 30-35° C. was added 3-trifluoromethyl benzoyl chloride slowly with stirring. The reaction mixture became turbid initially and solids were separated after the mixture was stirred at ambient temperature for 3 to 5 hours. The solids were filtered, washed with n-propanol, and dried in vacuo at 40° C. overnight to produce N-[3-(4-Chloro-2-methyl-2H-pyrazol-3-yl)-4-(2-morpholin-4-yl-ethoxy)-phenyl]-3-trifluoromethyl-benzamide as a white solid in 72% yield (as the HCl salt). LCMS m/z (%)=509 (M+H $^{35}$Cl, 100), 511 (M+H $^{37}$Cl, 33) $^1$H NMR (400 MHz, DMSO-d$_6$)

δ: 10.7 (bs, 1H), 8.39-8.44 (m, 2H), 8.01 (d, J=2.61 Hz, 1H), 7.98 (s, 1H), 7.75-7.83 (m, 2H), 7.69 (s, 1H), 7.35 (d, J=9.01, 1H), 4.45-4.65 (m, 2H), 3.79-3.89 (m, 4H), 3.69 (s, 3H), 3.36-3.53 (m, 4H with water), 3.05-3.25 (m, 2H), 2.99-3.05 (m, 2H).

Example 1.87: Preparation of N-(3-(4-chloro-1-methyl-1H-pyrazol-5-yl)-4-(2-morpholinoethoxy) phenyl)cyclopropanecarboxamide (Compound 271)

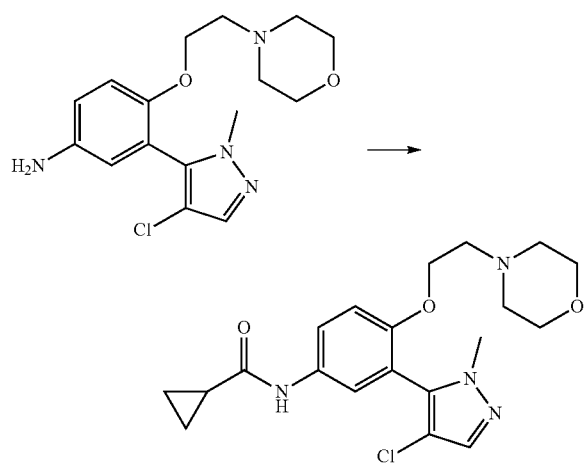

To a solution of 3-(4-Chloro-2-methyl-2H-pyrazol-3-yl)-4-(2-morpholin-4-yl-ethoxy)-phenylamine (0.20 g, 0.60 mmol) in $CH_2Cl_2$ (14.0 mL) was added cyclopropanecarbonyl chloride (0.075 mL, 0.72 mmol) and pyridine (0.061 mL, 0.78 mmol). The reaction was stirred for 20 min., and concentrated and purified by RP-HPLC. Lyophilization afforded the TFA salt of the title compound as a brown oil (0.027 g, 56%). LCMS m/z (%)=405 (M+H$^{35}$Cl, 100), 407 (M+H$^{37}$Cl, 38). $^1$H NMR (400 MHz, DMSO-d$_6$) δ: 10.28 (s, 1H), 7.74 (dd, J=2.6, 9.0 Hz, 1H), 7.65 (s, 1H), 7.54 (d, J=2.6 Hz, 1H), 7.23 (d, J=9.0 Hz, 1H), 4.43-4.37 (m, 1H), 4.32-4.25 (m, 1H), 3.63 (s, 3H), 3.92-2.92 (m, 10H), 1.78-1.70 (m, 1H), 0.78 (d, J=6.3 Hz, 4H).

Example 1.88: Preparation of 3-methoxy-N-[3-(2-methyl-2H-pyrazol-3-yl)-4-(2-morpholin-4-yl-ethoxy)-phenyl]-benzamide (Compound 733)

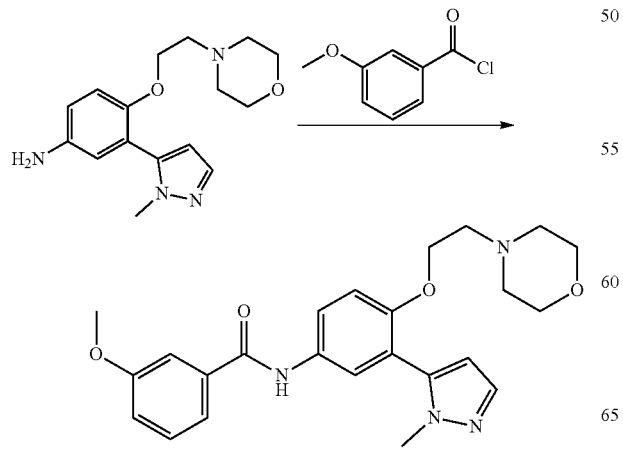

A mixture of 3-(2-methyl-2H-pyrazol-3-yl)-4-(2-morpholin-4-yl-ethoxy)-phenylamine (120 mg, 0.40 mmole), 3-methoxy-benzoyl chloride (81 mg, 0.48 mmole), and triethylamine (0.1 mL, 0.79 mmole) in 5 mL THF was stirred at room temperature for 10 minutes. The mixture was purified by HPLC to give the title compound as a white solid (TFA salt, 88 mg, 51%). $^1$H NMR (Acetone-d$_6$, 400 MHz) 2.99-3.21 (m, 2H), 3.22-3.45 (m, 2H), 3.66 (t, J=4.80 Hz, 2H), 3.75 (s, 3H), 3.85 (s, 3H), 3.79-3.89 (m, 4H), 4.58 (t, J=4.80 Hz, 2H), 6.29 (d, J=2.02 Hz 1H), 7.13 (dd, J=8.34, 2.53 Hz, 1H), 7.22 (d, J=8.84 Hz, 1H), 7.42 (t, J=7.83 Hz, 1H), 7.47 (d, J=1.77 Hz, 1H), 7.52 (t, J=1.77 Hz, 1H), 7.56 (d, J=7.07 Hz, 1H), 7.80-7.83 (m, 1H), 7.91-7.96 (m, 1H), 9.54 (s, NH). Exact mass calculated for $C_{24}H_{28}N_4O_4$ 436.2, found 437.5 (MH$^+$).

Example 1.89: Analytical Data for Additional Compounds of the Present Invention

Certain compounds of the present invention were prepared in a similar manner as described herein. The general synthetic methods and analytical data for these compounds are shown in the tables below, the calculated mass (i.e., Mass Calc) is MH$^+$.

| Cmpd No. | Method | Mass Calc | Mass Observed |
|---|---|---|---|
| 2 | B | 532.1 | 534 |
| 3 | B | 534.1 | 534 & 536 |
| 4 | F | 440.2 | 440 |
| 6 | B | 534.1 | 534 & 536 |
| 7 | B | 451.1 | 451 |
| 8 | F | 456.2 | 456 |
| 9 | B | 547.1 | 549 |
| 10 | B | 518.1 | 518 & 520 |
| 11 | B | 536.1 | 536 & 538 |
| 12 | B | 465.1 | 465 & 467 |
| 14 | B | 490.2 | 490 & 492 |
| 15 | B | 505.2 | 505 & 507 |
| 16 | B | 492.2 | 492 & 494 |
| 18 | B | 490.1 | 490 |
| 19 | B | 488.2 | 487 & 489 |
| 20 | B | 329.2 | 329 |
| 21 | F | 502.1 | 502 & 504 |
| 22 | F | 518.1 | 520 |
| 23 | D | 465.1 | 465 & 467 |
| 24 | Y | 564.1 | 564 & 566 |
| 26 | Z | 534.1 | 534 & 536 |
| 27 | F | 442.2 | 442 |
| 29 | F | 436.2 | 436.2 |
| 30 | D | 367.2 | 367.3 |
| 31 | F | 514.2 | 445 |
| 32 | A, B | 343.2 | 343 |
| 34 | D | 401.2 | 401 |
| 36 | B | 429.2 | 429 |
| 37 | D | 445.2 | 445 |
| 38 | B, Q, F | 496.2 | 496.5 |
| 39 | F | 512.2 | 512.6 |
| 40 | F | 528.2 | 528.4 |
| 41 | F | 510.2 | 510.5 |
| 42 | F | 526.2 | 526.3 |
| 43 | E | 453.2 | 453 |
| 45 | F | 468.2 | 468 & 470 |
| 46 | F | 438.2 | 438 |
| 47 | F | 438.2 | 438 |
| 48 | F | 540.2 | 540 & 542 |
| 49 | F | 524.3 | 524 |
| 50 | F | 542.2 | 542 |
| 51 | F | 436.2 | 436.5 |
| 52 | M | 440.2 | 440 & 442 |
| 53 | M | 424.2 | 424 |
| 54 | M | 442.2 | 442 |
| 55 | M | 414.2 | 414.5 |
| 56 | M | 396.2 | 396.2 |

| Cmpd No. | Method | Mass Calc | Mass Observed |
|---|---|---|---|
| 57 | M | 412.1 | 412.5 |
| 58 | M | 428.2 | 428.3 |
| 59 | M | 410.2 | 410.3 |
| 60 | M | 426.2 | 426.3 |
| 61 | F | 558.2 | 558.3 |
| 62 | F | 556.2 | 556.3 |
| 63 | M | 458.2 | 458.3 |
| 64 | M | 456.1 | 456.5 |
| 66 | F | 454.2 | 454 & 456 |
| 67 | F | 454.2 | 454 & 456 |
| 68 | F | 420.2 | 420 |
| 69 | F | 498.1 | 498 & 500 |
| 70 | F | 456.2 | 456 |
| 71 | F | 450.2 | 450 |
| 72 | F | 488.2 | 488 |
| 73 | F | 556.2 | 556 |
| 74 | F | 452.2 | 452 |
| 75 | F | 450.2 | 450 |
| 76 | F | 462.2 | 462 |
| 77 | F | 558.2 | 558.4 |
| 78 | F | 556.2 | 556.2 |
| 79 | M | 458.2 | 458.3 |
| 80 | F | 434.2 | 434 |
| 81 | F | 488.2 | 488 |
| 82 | M | 456.1 | 456.3 |
| 83 | F | 410.2 | 410 |
| 84 | F | 426.2 | 426 |
| 85 | A, B, C, F | 440.2 | 442 |
| 88 | R | 483.2 | 483 & 485 |
| 89 | E | 539.2 | 540 & 542 |
| 90 | D | 487.3 | 487 |
| 91 | D | 473.3 | 473 |
| 92 | M | 373.2 | 373 |
| 93 | M | 439.2 | 439 |
| 94 | M | 387.2 | 387 |
| 96 | R | 371.2 | 371.4 |
| 97 | F | 454.2 | 454 |
| 98 | J | 526.2 | 526.0 |
| 99 | J | 569.3 | 568.6 |
| 100 | J | 470.2 | 569.7 |
| 101 | F | 458.2 | 458 |
| 102 | F | 440.2 | 440 |
| 103 | K | 498.2 | 498.3 |
| 104 | M | 469.2 | 469.5 |
| 105 | B | 379.1 | 379.4 |
| 107 | R | 569.2 | 568.9 |
| 108 | E | 569.2 | 568.7 |
| 109 | K | 555.2 | 555.3 |
| 110 | K | 555.2 | 555.3 |
| 111 | J | 512.2 | 512.4 |
| 112 | F | 490.2 | 490 |
| 113 | D | 389.2 | 389 |
| 114 | K | 498.2 | 498.5 |
| 115 | F | 456.2 | 456 |
| 116 | F | 440.2 | 440.6 |
| 117 | E | 455.2 | 455 |
| 118 | R | 569.2 | 569.6 |
| 119 | K | 555.2 | 555.1 |
| 120 | J | 470.2 | 470.5 |
| 121 | E | 478.2 | 478.4 |
| 122 | R | 457.3 | 457.5 |
| 123 | R | 443.3 | 443.5 |
| 124 | R | 457.3 | 457.5 |
| 126 | G, H, F | 528.2 | 528 |
| 127 | Y | 586.2 | 486 |
| 128 | B, C, F | 469.2 | 569 |
| 129 | F | 471.2 | 471 |
| 130 | F | 453.2 | 453 |
| 131 | F | 483.2 | 483 |
| 132 | H, F | 474.2 | 474 |
| 133 | H, F | 472.1 | 472 & 474 |
| 134 | R | 546.2 | 546.5 |
| 135 | E | 584.2 | 584.5 |
| 136 | E | 568.3 | 567.8 |
| 137 | A, B | 476.2 | 476 |
| 138 | J | 540.2 | 540.4 |
| 139 | M | 486.2 | 486 |
| 140 | G, H, F | 486.2 | 486 |
| 141 | F | 484.2 | 484 |
| 142 | K | 512.2 | 511.6 |
| 143 | F | 442.2 | 442 & 444 |
| 144 | R | 465.1 | 467 |
| 146 | M | 532.1 | 532 & 534 |
| 147 | D | 437.2 | 437 & 438 |
| 148 | E | 584.2 | 583.6 |
| 149 | F | 444.2 | 444 |
| 150 | R | 421.2 | 421.3 |
| 152 | F | 472.2 | 472 |
| 153 | F | 470.2 | 471 |
| 154 | D | 403.2 | 403 |
| 155 | D | 417.2 | 417 |
| 156 | J | 456.2 | 454.4 |
| 157 | J | 540.2 | 540.4 |
| 158 | J | 555.2 | 555.4 |
| 159 | J | 484.2 | 484.6 |
| 160 | E | 439.2 | 439 |
| 161 | E | 451.2 | 451 |
| 162 | H, F | 470.2 | 470 |
| 163 | H, F | 470.2 | 470 |
| 164 | J | 484.2 | 484.4 |
| 165 | R | 457.2 | 457 |
| 166 | G | 373.2 | 373 |
| 167 | J | 497.2 | 496.7 |
| 168 | R | 421.2 | 420.9 |
| 169 | R | 458.2 | 457.9 |
| 170 | R | 510.1 | 509.5 |
| 171 | R | 456.2 | 455.7 |
| 172 | J | 567.2 | 566.9 |
| 173 | B | 576.2 | 575.4 |
| 178 | R | 458.2 | 457.2 |
| 180 | U | 435.2 | 435.4 |
| 181 | R | 470.2 | 470.3 |
| 182 | F | 486.2 | 486 |
| 183 | F | 468.2 | 468.6 |
| 184 | F | 484.2 | 484 |
| 185 | U | 429.2 | 428.7 |
| 186 | R | 475.1 | 474.9 |
| 187 | L | 581.2 | 581.2 |
| 188 | M | 455.2 | 454.8 |
| 189 | F | 468.2 | 468.6 |
| 190 | E | 483.2 | 483.5 |
| 191 | K | 555.2 | 555.4 |
| 192 | F | 442.2 | 442 |
| 193 | D | 417.2 | 417 |
| 194 | R | 500.3 | 500 |
| 195 | K | 486.3 | 486 |
| 197 | L | 462.2 | 462.3 |
| 198 | I | 512.1 | 512 & 514 |
| 200 | R | 533.2 | 533.5 |
| 201 | L | 490.2 | 490.4 |
| 202 | K | 519.2 | 519.4 |
| 204 | W | 486.3 | 486.4 |
| 205 | V | 428.2 | 428.4 |
| 206 | W | 444.3 | 444.5 |
| 207 | K | 458.3 | 458.4 |
| 208 | R, W | 490.2 | 490.4 |
| 210 | K | 567.2 | 567.5 |
| 211 | K | 526.2 | 526.2 |
| 212 | K | 513.2 | 513.5 |
| 213 | W | 449.2 | 449.3 |

The general synthetic methods and analytical data for additional compounds of the present invention are shown in the table below, the calculated mass (i.e., Mass Calc) is MH$^+$.

| Cmpd No. | Method | Mass Calc | Mass Observed |
|---|---|---|---|
| 214 | D | 405.2 | 405.8 |
| 215 | D | 403.2 | 403.7 |
| 216 | F | 470.2 | 470.5 |
| 217 | F | 472.2 | 472.8 |
| 218 | F | 437.1 | 437.9 |
| 219 | F | 439.2 | 439.8 |
| 220 | F | 506.2 | 506.3 |
| 221 | R | 387.2 | 386.8 |
| 222 | G | 345.2 | 345 |
| 223 | R | 493.2 | 492.7 & 494.7 |
| 224 | F | 456.2 | 455.7 |
| 225 | C, P, E, X, J | 543.2 | 543.5 |
| 226 | C, P, E, X, J | 583.2 | 583.4 |
| 227 | F | 458.2 | 458.3 |
| 228 | E | 455.2 | 455.5 |
| 229 | F | 474.2 | 474 |
| 230 | F | 474.2 | 474 |
| 231 | F | 490.1 | 490 |
| 232 | F | 456.2 | 456 |
| 233 | F | 492.2 | 492 |
| 234 | F | 524.1 | 524 |
| 235 | F | 558.1 | 558 |
| 236 | F | 470.2 | 470 |
| 237 | F | 486.2 | 486 |
| 238 | W | 457.3 | 456.7 |
| 239 | C, P, E, X, J | 586.1 | 586.3 |
| 240 | K | 443.3 | 442.9 |
| 241 | B | 421.1 | 421.2 |
| 242 | B | 377.2 | 377.2 |
| 243 | D | 402.2 | 402 |
| 244 | D | 416.3 | 416 |
| 245 | F | 424.2 | 424.8 |
| 246 | F | 424.2 | 424.5 |
| 247 | F | 436.2 | 436.8 |
| 248 | F | 440.2 | 440.7 |
| 249 | G | 359.2 | 359.2 |
| 250 | F | 504.1 | 504.3 |
| 251 | F | 488.2 | 488.3 |
| 252 | F | 550.1 | 550.6 |
| 253 | F | 552.1 | 552.3 |
| 254 | F | 582.0 | 582.2 |
| 255 | F | 584.1 | 584.3 |
| 256 | F | 548.1 | 548.3 |
| 257 | F | 550.1 | 550.2 |
| 258 | F | 492.2 | 492 |
| 259 | F | 524.2 | 524 |
| 260 | F | 486.2 | 486 |
| 261 | F | 498.2 | 498 |
| 262 | F | 492.2 | 492 |
| 263 | F | 492.2 | 492 |
| 264 | F | 592.1 | 592 |
| 265 | F | 506.2 | 506 |
| 266 | G | 423.1 | 422.8 |
| 267 | F | 534.1 | 534.2 |
| 268 | F | 536.1 | 536.2 |
| 269 | E | 533.1 | 533.3 |
| 270 | F | 518.1 | 518.4 |
| 271 | E | 405.2 | 404.9 |
| 272 | E | 447.1 | 447 |
| 273 | E | 459.2 | 459 |
| 274 | E | 489.1 | 489 |
| 275 | J | 449.1 | 449.2 & 451.2 |
| 276 | J | 506.2 | 506.3 & 508.3 |
| 277 | J | 479.2 | 479.3 & 481.2 |
| 278 | G | 409.1 | 408.7 |
| 279 | F | 520.1 | 520.4 |
| 280 | B, Q, R | 425.2 | 425.4 |
| 283 | B, Q, E | 491.2 | 491.3 |
| 284 | F | 522.1 | 522.2 |
| 285 | F | 504.1 | 504.3 |
| 286 | F | 504.1 | 504.3 |
| 287 | E | 431.1 | 431 |
| 288 | E | 459.2 | 459 |
| 289 | E | 459.2 | 459 |
| 290 | F | 420.2 | 420.4 |
| 291 | F | 431.2 | 431.9 |
| 292 | F | 438.2 | 438.2 |
| 293 | G | 371.2 | 370.8 |
| 294 | E | 369.2 | 368.9 |
| 295 | E | 411.2 | 410.8 |
| 296 | E | 395.2 | 394.8 |
| 297 | E | 423.2 | 423 |
| 298 | F | 476.1 | 476.1 |
| 299 | F | 478.1 | 478.3 |
| 300 | J | 546.2 | 546.4 |
| 301 | K | 532.2 | 532.2 |
| 302 | E | 423.2 | 423.3 |
| 303 | E | 423.2 | 423.2 |
| 304 | F | 456.2 | 456.4 |
| 305 | AF | 447.1 | 447.1 |
| 306 | R | 463.1 | 463.4 & 465.4 |
| 307 | R | 491.2 | 491.3 & 493.3 |
| 308 | E | 449.1 | 448.6 & 450.6 |
| 309 | R | 463.1 | 462.7 & 464.7 |
| 310 | R | 477.1 | 477.3 & 479.3 |
| 311 | F | 455.2 | 455.8 |
| 312 | F | 457.2 | 457.7 |
| 313 | R | 491.2 | 491.3 |
| 314 | F | 472.2 | 472.2 |
| 315 | F | 484.2 | 484.4 |
| 316 | F | 484.1 | 484 |
| 317 | F | 490.2 | 490 |
| 318 | F | 474.2 | 474 |
| 319 | F | 482.2 | 481.6 |
| 320 | F | 484.2 | 484.4 |
| 321 | F | 466.3 | 465.8 |
| 322 | B | 632.2 | 632.3 |
| 323 | B | 618.1 | 618.4 |
| 324 | F | 478.3 | 478.3 |
| 325 | E | 481.2 | 481.3 |
| 326 | E | 465.1 | 465.3 |
| 327 | E | 427.2 | 427.2 |
| 328 | F | 505.2 | 505.5 |
| 329 | J | 454.2 | 454.4 & 456.4 |
| 330 | J | 385.3 | 385.3 |
| 331 | F, B | 554.2 | 554.4 |
| 332 | E | 497.2 | 497 |
| 333 | R | 481.1 | 481.2 |
| 334 | L | 560.1 | 560.2 |
| 335 | AG | 532.1 | 532.2 |
| 336 | E | 397.2 | 396.8 |
| 337 | E | 441.2 | 441.4 |
| 338 | E | 413.2 | 413.5 |
| 339 | V | 454.2 | 454.5 |
| 340 | F | 482.2 | 482.5 |
| 341 | R | 519.1 | 519.4 |
| 342 | R | 509.1 | 509.4 |
| 343 | Q, R | 459.2 | 459.4 |
| 344 | E & M | 397.2 | 397 |
| 345 | E | 431.1 | 431.2 |
| 346 | F | 476.2 | 476.1 |
| 347 | E | 427.2 | 427.4 |
| 348 | E | 445.1 | 445.1 |
| 349 | J | 602.3 | 602.7 |
| 350 | F | 546.1 | 546.3 |
| 351 | D | 548.1 | 548.4 |
| 352 | E | 479.2 | 479.4 |
| 353 | AI | 468.2 | 468.5 |
| 354 | R | 569.1 | 569.3 |
| 355 | F | 470.2 | 470.4 |
| 356 | Y | 492.1 | 492.3 |
| 357 | AG | 411.2 | 411 |
| 358 | F | 472.2 | 472.4 |
| 359 | F | 454.2 | 454.5 |
| 360 | E | 487.1 | 487 |
| 361 | E | 517.1 | 517 |
| 362 | R | 475.2 | 475.3 |
| 363 | AG | 454.2 | 454 |
| 364 | B, Q, R | 527.2 | 527.4 |
| 365 | B, Q, F | 496.2 | 496.3 |
| 366 | B, Q, R | 531.2 | 531.6 |
| 367 | E | 469.2 | 469.5 |
| 368 | R | 505.2 | 505.4 |
| 369 | AG | 453.2 | 453 |

| Cmpd No. | Method | Mass Calc | Mass Observed |
|---|---|---|---|
| 370 | F | 470.2 | 470.5 |
| 371 | B, Q, R, V | 427.1 | 427.2 |
| 372 | B, Q, F, V | 396.2 | 396.2 |
| 373 | B, Q, R, V | 431.2 | 431.3 |
| 374 | T | 507.2 | 507 |
| 375 | F | 472.2 | 472.4 |
| 376 | E | 469.2 | 469.5 |
| 377 | E | 473.1 | 473.2 |
| 378 | F, M | 504.1 | 504.1 & 506.1 |
| 379 | Y | 476.2 | 476.4 |
| 380 | E & M | 475.1 | 475 |
| 381 | E & M | 517.1 | 517 |
| 382 | AG | 489.1 | 489 |
| 383 | AG | 531.1 | 531 |
| 384 | Y | 494.1 | 494.4 |
| 385 | Y | 494.1 | 494.4 |
| 386 | B, T, Q, R, V | 509.1 | 511.3 |
| 387 | B, T, Q, R, V | 475.0 | 477.4 |
| 388 | B, T, Q, R, V | 459.1 | 459.2 |
| 389 | B, T, Q, R, V | 477.1 | 479.3 |
| 390 | R | 459.1 | 459.3 |
| 391 | B, T, Q, F, V | 490.1 | 492.3 |
| 392 | B, T, Q, F, V | 492.1 | 494.3 |
| 393 | F, M | 426.2 | 426.3 & 428.3 |
| 394 | F, M | 488.1 | 488.4 & 490.4 |
| 395 | R, M | 489.1 | 489.3 & 491.3 |
| 396 | R, M | 473.1 | 473.3 & 475.3 |
| 397 | R, M | 491.1 | 491.4 & 493.4 |
| 398 | R, M | 503.1 | 503.2 & 504.2 |
| 399 | E | 443.2 | 443.3 |
| 400 | E | 473.1 | 473.1 |
| 401 | F | 468.2 | 468.4 |
| 402 | B, Q, R, M | 445.2 | 445.5 |
| 403 | F | 452.2 | 452.4 |
| 404 | E | 467.2 | 467.6 |
| 405 | F | 466.2 | 466.2 |
| 406 | F | 450.2 | 450.4 |
| 407 | F | 470.2 | 470.4 |
| 408 | E | 441.2 | 441.4 |
| 409 | E | 473.1 | 473.3 |
| 410 | E | 473.1 | 473.6 |
| 411 | E | 491.2 | 491.3 |
| 412 | E | 491.2 | 491.4 |
| 413 | E | 441.2 | 441.5 |
| 414 | E | 473.2 | 473.3 |
| 415 | R | 481.2 | 481.4 |
| 416 | R | 479.2 | 479.3 |
| 417 | R | 545.1 | 545.1 |
| 418 | R | 543.1 | 543.6 |
| 419 | R | 533.1 | 533 |
| 420 | Q, F, B, V, X, Y | 502.2 | 502.3 |
| 421 | J | 458.2 | 458.3 |
| 422 | F, M | 426.2 | 426.2 |
| 423 | E, M | 425.2 | 425.4 |
| 424 | E | 441.2 | 441.3 |
| 425 | E | 473.2 | 473.6 |
| 426 | E | 473.2 | 473.6 |
| 427 | E | 465.2 | 465.4 |
| 428 | F | 468.2 | 468.5 |
| 429 | F | 468.2 | 468.5 |
| 430 | E | 451.2 | 451.1 |
| 431 | E | 435.2 | 435.3 |
| 432 | E | 461.2 | 461.5 |
| 433 | B, Q, R, M | 425.2 | 425.3 & 427.3 |
| 434 | B, Q, R, M | 441.2 | 441.5 & 443.5 |
| 435 | P, Q, R | 459.2 | 459.4 |
| 436 | E | 425.2 | 425.2 |
| 437 | R | 529.2 | 529.2 |
| 438 | F & M | 428.2 | 428 |
| 439 | F & M | 426.2 | 426 |
| 440 | E | 509.1 | 509 |
| 441 | E | 477.1 | 477 |
| 442 | F | 468.2 | 468.6 |
| 443 | E | 467.2 | 467.6 |
| 444 | E & M | 413.2 | 413 |
| 445 | E & M | 445.2 | 445 |
| 446 | E | 487.2 | 487.7 |
| 447 | R | 531.1 | 531.3 |
| 448 | R | 547.1 | 547.3 |
| 449 | E | 501.1 | 501.4 |
| 450 | E | 501.1 | 501 |
| 451 | E | 485.2 | 485.4 |
| 452 | E | 551.1 | 551.5 |
| 453 | E | 519.1 | 519.4 |
| 454 | E | 537.1 | 537.4 |
| 455 | E | 487.1 | 487.4 |
| 456 | E | 505.1 | 505.4 |
| 457 | E | 487.2 | 487.4 |
| 458 | E | 437.2 | 437.5 |
| 459 | E | 455.2 | 455.5 |
| 460 | F | 468.2 | 468.6 |
| 461 | E | 531.1 | 531.5 |
| 462 | E | 565.1 | 565.3 |
| 463 | E | 504.1 | 504.4 |
| 464 | E | 498.1 | 498.4 |
| 465 | E | 513.1 | 513.4 |
| 466 | E | 527.2 | 527.5 |
| 467 | E & M | 425.2 | 425 |
| 468 | P, Q, R | 427.2 | 427.4 |
| 469 | E | 459.1 | 459.3 |
| 470 | P, Q, R | 477.2 | 477.3 |
| 471 | P, Q, R | 477.2 | 477.2 |
| 472 | J, Q, E | 423.2 | 423.5 |
| 473 | J, Q, E | 427.2 | 427.4 |
| 474 | G, Q, R | 505.1 | 505.5 & 507.5 |
| 475 | G, Q, E | 505.1 | 505.5 & 507.5 |
| 476 | R | 453.2 | 453.4 |
| 477 | E | 493.2 | 493.4 |
| 478 | F | 490.2 | 490.5 |
| 479 | E | 441.2 | 441.4 |
| 480 | E | 475.2 | 475 |
| 481 | G, Q, E | 491.2 | 491.4 |
| 482 | G, Q, E | 491.2 | 491.4 |
| 483 | E | 427.2 | 427 |
| 484 | E | 443.2 | 443 |
| 485 | E | 477.2 | 477 |
| 486 | E | 423.2 | 423 |
| 487 | E | 477.2 | 477 |
| 488 | E | 423.2 | 423 |
| 489 | E | 425.2 | 425 |
| 490 | E | 475.1 | 475.2 |
| 491 | E | 493.2 | 493.3 |
| 492 | E | 485.2 | 485.3 |
| 493 | E | 457.2 | 457.3 |
| 494 | E | 491.2 | 491.5 |
| 495 | E | 437.2 | 437.5 |
| 496 | E | 437.2 | 437.5 |
| 497 | E | 505.3 | 505.3 |
| 498 | E | 503.3 | 503.3 |
| 499 | E | 483.1 | 483.3 |
| 500 | E | 537.1 | 537.3 |
| 501 | E | 503.1 | 503.3 |
| 502 | E | 469.1 | 469.3 |
| 503 | E | 519.1 | 419.4 |
| 504 | E | 517.1 | 517.3 |
| 505 | E | 497.1 | 497.5 |
| 506 | E | 551.1 | 551.5 |
| 507 | E | 517.1 | 517.3 |
| 508 | E | 483.1 | 483.3 |
| 509 | E | 409.2 | 409 |
| 510 | E | 405.2 | 405 |
| 511 | E | 475.2 | 475 |
| 512 | E | 425.2 | 425 |
| 513 | E | 409.2 | 409 |
| 514 | F | 484.2 | 484.3 |
| 515 | E | 503.2 | 503.2 |
| 516 | B, T, Q, E | 503.2 | 505.3 |
| 517 | B, T, Q, E | 503.1 | 505.1 |
| 518 | E | 503.2 | 503.6 |
| 519 | R | 457.2 | 457.3 |
| 520 | R | 493.1 | 493 |
| 521 | R | 487.2 | 487 |

| Cmpd No. | Method | Mass Calc | Mass Observed |
|---|---|---|---|
| 522 | R | 487.2 | 487 |
| 523 | R | 503.2 | 503 |
| 524 | E | 477.1 | 477 |
| 525 | E | 509.1 | 509 |
| 526 | E | 493.1 | 493 |
| 527 | E | 509.1 | 509 |
| 528 | E | 475.1 | 475 |
| 529 | E | 455.2 | 455 |
| 530 | E | 525.1 | 525 |
| 531 | E | 471.2 | 471 |
| 532 | E | 455.2 | 455 |
| 533 | P, Q, E | 473.2 | 473.2 |
| 534 | P, Q, R | 441.2 | 441.4 |
| 535 | P, Q, E | 457.2 | 457.2 |
| 536 | P, J, Q, E | 495.2 | 495.3 |
| 537 | G, Q, E | 455.2 | 455.4 |
| 538 | G, Q, E | 475.2 | 475.2 |
| 539 | P, Q, E | 459.2 | 459.2 |
| 540 | P, Q, E | 443.2 | 443.3 |
| 541 | R | 443.2 | 443 |
| 542 | R | 470.2 | 470 |
| 543 | R | 475.1 | 475 |
| 544 | R | 476.1 | 476 |
| 545 | P, J, Q, E | 479.1 | 479.2 |
| 546 | P, J, Q, E | 459.2 | 459.3 |
| 547 | P, Q, E | 423.2 | 423.2 |
| 548 | B, Q, E | 521.1 | 521.3 & 523.3 |
| 549 | B, Q, E | 490.1 | 490.1 & 492.1 |
| 550 | R | 537.1 | 537 |
| 551 | R | 503.2 | 503 |
| 552 | R | 537.1 | 537 |
| 553 | R | 499.2 | 499 |
| 554 | R | 485.2 | 485 |
| 555 | B, Q, E | 445.2 | 445.3 |
| 556 | B, Q, E | 429.1 | 429.1 |
| 557 | B, Q, E | 382.2 | 382.3 |
| 558 | E | 527.1 | 527 |
| 559 | E | 473.2 | 473 |
| 560 | E | 527.1 | 527 |
| 561 | E | 473.2 | 473 |
| 562 | E | 442.2 | 442 |
| 563 | E | 442.2 | 442 |
| 564 | E | 441.2 | 441 |
| 565 | E | 466.2 | 466 |
| 566 | E | 489.2 | 489.2 |
| 567 | E | 505.2 | 505.3 |
| 568 | E | 489.2 | 489.2 |
| 569 | E | 457.2 | 457.2 |
| 570 | E | 439.2 | 439.1 |
| 571 | E | 453.2 | 453.1 |
| 572 | E | 473.2 | 473.6 |
| 573 | E | 527.1 | 527 |
| 574 | R | 537.2 | 537 |
| 575 | P, J, Q, E | 475.2 | 475.2 |
| 576 | P, J, Q, E | 459.2 | 459.3 |
| 577 | P, J, T, Q, E | 523.1 | 525.4 |
| 578 | J, Q, E | 457.2 | 457.2 |
| 579 | P, J, T, Q, E | 519.1 | 521.5 |
| 580 | P, J, T, Q, E | 519.1 | 519.3 |
| 581 |  | 345.2 | 345.2 |
| 582 | E | 521.2 | 521 |
| 583 | B, T, Q, E | 491.1 | 491.2 |
| 584 | R | 475.2 | 475.6 |
| 585 | B, T, Q, E | 491.1 | 491.5 |
| 586 | P, J, Q, R | 475.2 | 475.3 |
| 587 | B, Q, E | 551.2 | 551.3 |
| 588 | E | 563.1 | 563.2 |
| 589 | E | 563.1 | 563.3 |
| 590 | F | 502.2 | 502.6 |
| 591 | F | 502.2 | 502.6 |
| 592 | B, Q, E, A, E | 461.2 | 461.4 |
| 593 | B, Q, E, A, E | 461.2 | 461.5 |
| 594 | B | 551.2 | 551.3 |
| 595 | E | 513.1 | 513.4 |
| 596 | E | 513.1 | 513.2 |
| 597 | E | 521.2 | 521.5 |
| 598 | E | 471.2 | 471.5 |
| 599 | E | 543.1 | 545.3 |
| 600 | E | 503.2 | 503.4 |
| 601 | E | 529.1 | 529.2 |
| 602 | E | 503.2 | 503.4 |
| 603 | E | 529.1 | 529.2 |
| 604 | E | 567.1 | 567.1 |
| 605 | E | 567.1 | 567.2 |
| 606 | E | 585.1 | 585.3 |
| 607 | E | 531.1 | 531.5 |
| 608 | E | 585.1 | 585.4 |
| 609 | E | 569.1 | 569.43 |
| 610 | E | 569.1 | 569.43 |
| 611 | F | 518.2 | 518.5 |
| 612 | F | 587.1 | 587.4 |
| 613 | F | 518.2 | 518.5 |
| 614 | E | 587.1 | 587.3 |
| 615 | P, J, T, Q, R | 521.1 | 521.3 |
| 616 | P, J, T, Q, R | 519.1 | 521.5 |
| 617 | B, Q, F | 532.2 | 532.4 |
| 618 | R | 441.2 | 441.3 & 443.3 |
| 619 | R | 455.2 | 455.3 & 457.3 |
| 620 | E | 581.1 | 581.2 |
| 621 | E | 581.1 | 581.2 |
| 622 | P, J, Q, E | 488.2 | 488.2 |
| 623 | P, J, Q, E | 468.2 | 468.3 |
| 624 | P, J, Q, E | 452.2 | 452.3 |
| 625 | R | 489.2 | 489.3 |
| 626 | R | 489.2 | 489.3 |
| 627 | J, Q, E | 555.2 | 555.7 |
| 628 | J, Q, E | 535.2 | 535.4 |
| 629 | J, Q, E | 519.2 | 519.6 |
| 630 | E | 483.2 | 483.4 |
| 631 | F | 498.2 | 498.5 |
| 632 | F | 482.2 | 482.4 |
| 633 | E | 537.2 | 537 |
| 634 | E | 537.2 | 537 |
| 635 | E | 505.2 | 505 |
| 636 | E | 531.1 | 531 |
| 637 | E | 531.1 | 531 |
| 638 | E | 531.1 | 531.1 |
| 639 | E | 563.1 | 563.2 |
| 640 | E | 521.2 | 521 |
| 641 | E | 489.2 | 489 |
| 642 | F | 516.2 | 516 |
| 643 | F | 500.2 | 500 |
| 644 | E | 565.1 | 565 |
| 645 | E | 533.1 | 533 |
| 646 | F | 544.2 | 544 |
| 647 | P, J, X, Q, E | 488.1 | 488.2 |
| 648 | F | 504.1 | 504.1 |
| 649 | F | 488.2 | 488.2 |
| 650 | F | 488.2 | 488.2 |
| 651 | J, Q, E | 546.2 | 546.6 |
| 652 | P, J, X, Q, E | 472.1 | 472.3 |
| 653 | J, Q, E | 496.2 | 496.4 |
| 654 | J, Q, E | 527.2 | 527.6 |
| 655 | P, J, Q, E | 538.3 | 538.5 |
| 656 | P, J, Q, E | 588.3 | 588.6 |
| 657 | E | 568.3 | 568.3 |
| 658 | F | 524.2 | 524.3 |
| 659 | J, Q, E | 516.2 | 516.4 |
| 660 | E | 466.2 | 466.4 |
| 660 | E | 466.2 | 466 |
| 661 | J, Q, E | 496.2 | 496.3 |
| 662 | P, J, Q, E, V, D | 510.2 | 510.5 |
| 663 | P, J, Q, E, V, D | 560.2 | 560.5 |
| 664 | F | 504.2 | 504 |
| 665 | F | 504.2 | 504 |
| 666 | F | 484.2 | 484 |
| 667 | E | 469.2 | 469 |
| 668 | E | 489.2 | 489 |
| 669 | E | 489.2 | 489 |
| 670 | P, J, T, Q, E | 532.1 | 534.2 |
| 671 | F | 468.2 | 468 |
| 672 | E | 455.2 | 455 |

-continued

| Cmpd No. | Method | Mass Calc | Mass Observed |
|---|---|---|---|
| 673 | E | 457.2 | 457 |
| 674 | J, T, Q, E | 566.1 | 566.2 & 568.2 |
| 675 | J, T, Q, F | 547.1 | 547.3 & 549.3 |
| 676 | F | 468.2 | 468 |
| 677 | J, T, Q, E | 516.1 | 516.3 & 518.3 |
| 678 | X, J, Q, E | 536.2 | 536.3 & 538.3 |
| 679 | E | 473.2 | 473.2 |
| 680 | E | 473.2 | 473.2 |
| 681 | E | 439.2 | 439.5 |
| 682 | E | 441.2 | 441.5 |
| 683 | E | 453.2 | 453.3 |
| 684 | F | 456.2 | 456.3 |
| 685 | F | 454.2 | 454.2 |
| 686 | F | 468.2 | 468.4 |
| 687 | J, X, Q, E | 522.1 | 522.3 & 524.3 |
| 688 | E | 470.2 | 470 |
| 689 | E | 470.2 | 470 |
| 690 | E | 450.2 | 450 |
| 691 | F | 451.2 | 451 |
| 692 | P, F | 550.2 | 550.6 |
| 693 | P, F, A, E | 460.1 | 460.2 |
| 694 | B, C, E | 585.2 | 585.5 |
| 695 | X, J, Q, E | 502.1 | 502.6 & 504.6 |
| 696 | B, C, E, A, E | 495.1 | 495.4 |
| 698 | F | 542.1 | 542.5 |
| 699 | J | 542.1 | 542.3 |
| 700 | F | 542.1 | 542.6 |
| 701 | F | 592.1 | 594.5 |
| 702 | F | 538.2 | 540.5 |
| 703 | P, X, J, Q, E | 550.2 | 550.6 |
| 704 | P, X, J, Q, E | 500.2 | 500.7 |
| 705 | P, X, J, Q, E | 516.1 | 516.3 |
| 706 | P, J, Q, E | 500.2 | 500.3 |
| 707 | P, J, Q, E | 516.2 | 516.4 |
| 708 | P, J, Q, E | 482.2 | 482.3 |
| 709 | Y | 592.1 | 592.3 |
| 710 | Y | 592.1 | 592.3 |
| 711 | P, J, Q, F | 481.2 | 481.3 |
| 712 | F | 558.1 | 560.3 |
| 713 | J | 536.2 | 536.4 & 538.4 |
| 714 | C, P, E, X, J | 536.2 | 536.5 |
| 715 | C, P, E, X, J | 550.2 | 550.4 |
| 716 | C, P, E, X, J | 551.2 | 551.3 |
| 717 | B | 363.2 | 363 |
| 718 | G | 622.2 | 622 |
| 719 | M | 522.2 | 522 |
| 720 | E | 564.2 | 564 |
| 721 | F | 558.1 | 558.2 |
| 722 | F | 464.2 | 464.3 |
| 723 | C, P, E, X, J | 579.2 | 579.5 |
| 724 | C, P, E, X, J | 550.2 | 550.4 |
| 725 | C, P, E, X, J | 529.1 | 529.3 |
| 726 | E | 493.2 | 493 |
| 727 | B, Q, E | 441.2 | 441.3 |
| 728 | B | 507.2 | 507 |
| 729 | E | 425.2 | 425 |
| 730 | B, Q, E | 443.2 | 443.3 |
| 731 | J, Q, E | 484.2 | 484.3 |
| 732 | B, Q, E | 439.2 | 439.5 |
| 733 | E | 437.2 | 437 |
| 734 | Y | 560.1 | 560.3 |
| 735 | C, P, E, X, J | 515.1 | 515.3 |
| 736 | F | 498.2 | 498.3 |
| 737 | F | 498.2 | 498.2 |
| 738 | F | 498.2 | 498.3 |
| 739 | E | 443.2 | 443.5 |
| 740 | E | 443.2 | 443.5 |
| 741 | E | 443.2 | 443.5 |
| 742 | E | 455.2 | 455.3 |
| 743 | E | 439.2 | 439.4 |
| 744 | E | 457.2 | 457.3 |
| 745 | E | 457.2 | 457.4 |
| 746 | F | 480.2 | 480.3 |
| 747 | P, V, E, J | 466.2 | 466.4 |
| 748 | P, V, E, J | 467.2 | 467.4 |
| 749 | F | 494.2 | 494.5 |

-continued

| Cmpd No. | Method | Mass Calc | Mass Observed |
|---|---|---|---|
| 750 | E | 451.2 | 451.2 |
| 751 | R | 536.2 | 536.2 |
| 752 | P, V, E, J | 452.2 | 452.2 |
| 753 | P, V, E, J | 502.2 | 502.1 |
| 754 | V, E, J | 491.2 | 491.3 |
| 755 | P, V, E, J | 478.2 | 478.3 |
| 756 | M | 522.1 | 522.4 |
| 758 | J | 532.2 | 532.4 |
| 759 | B, Q, E | 443.2 | 443.4 |
| 760 | B, Q, E | 467.2 | 467.5 |
| 761 | B, Q, E | 443.2 | 443.3 |
| 762 | R | 421.2 | 421.3 |
| 763 | R | 455.2 | 455.4 |
| 764 | R | 489.2 | 489.5 |
| 765 | R | 451.2 | 451.1 |
| 766 | R | 439.2 | 439.5 |
| 767 | R | 455.2 | 455.3 |
| 768 | R | 489.2 | 489.3 |
| 769 | R | 451.2 | 451.2 |
| 770 | R | 435.2 | 435.3 |
| 771 | R | 435.2 | 435.3 |
| 772 | R | 465.2 | 465.4 |
| 773 | R | 435.2 | 435.4 |
| 774 | J | 490.2 | 490.3 |
| 775 | G | 504.2 | 504.2 |
| 776 | G | 518.2 | 518.4 |
| 777 | J | 532.2 | 532.4 |
| 778 | V, E, J | 459.2 | 459.4 |
| 779 | E | 419.2 | 419 |
| 780 | E | 433.2 | 433 |
| 781 | E | 447.2 | 447 |
| 782 | J | 518.2 | 518.4 |
| 783 | G | 573.2 | 573.6 |
| 784 | E | 461.1 | 461.3 |
| 785 | E | 439.2 | 439.5 |
| 786 | G | 485.2 | 485 |
| 787 | G | 500.2 | 500 |
| 788 | G | 500.2 | 500 |
| 789 | V, E, J | 503.2 | 503.6 |
| 790 | J | 476.2 | 476.2 |
| 791 | P, V, E, J | 479.2 | 479.4 |
| 792 | R | 422.2 | 422.3 |
| 793 | R | 439.2 | 439.4 |
| 794 | R | 489.2 | 489.3 |
| 795 | R | 427.2 | 427.2 |
| 796 | V, E, J | 424.2 | 424.2 |
| 797 | L | 492.2 | 492.5 |
| 798 | L | 494.2 | 494.4 |
| 799 | R | 422.2 | 422.4 |
| 800 | J, Q, E | 502.2 | 502.2 |
| 801 | J, Q, E | 486.2 | 486.2 & 488.2 |
| 802 | P, J, Q, E | 502.2 | 502.6 |
| 803 | P, J, Q, E | 486.2 | 486.4 |
| 804 | P, J, Q, E | 502.2 | 502.3 |
| 805 | P, J, Q, E, V | 438.2 | 438.4 |
| 806 | P, J, Q, E, V | 488.2 | 488.3 |
| 807 | E, M | 468.2 | 468.5 & 470.5 |
| 808 | AF | 509.1 | 509.1 |
| 809 | AF | 475.1 | 475.1 |
| 810 | AF | 459.1 | 459.1 |
| 811 | AF | 459.1 | 459 |
| 812 | AF | 481.2 | 481.2 |
| 813 | AF | 431.2 | 431.3 |
| 814 | AF | 447.1 | 447.2 |
| 815 | AF | 431.2 | 431.3 |
| 816 | AF | 449.1 | 449.2 |
| 817 | AF | 497.1 | 497.1 |
| 818 | AF | 414.2 | 414.4 |
| 819 | AG | 546.1 | 546.4 |
| 820 | E | 475.1 | 475.1 |
| 821 | E | 487.1 | 487 |
| 822 | E | 517.1 | 517 |
| 823 | E | 473.1 | 473.6 |
| 824 | E | 473.2 | 473.3 |
| 825 | E | 501.1 | 501 |
| 826 | E | 521.2 | 521 |

-continued

| Cmpd No. | Method | Mass Calc | Mass Observed |
|---|---|---|---|
| 831 | B, Q, F | 514.2 | 514.6 |
| 832 | B, Q, F | 512.1 | 512.4 |
| 833 | B, Q, F | 528.2 | 528.4 |
| 834 | B, Q, F | 510.2 | 510.5 |
| 834 | B, Q, F, M | 412.1 | 412.5 |
| 836 | B, Q, F, M | 410.2 | 410.3 |

Example 2

Receptor Expression

A. pCMV

Although a variety of expression vectors are available to those in the art, it is preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of patent Procedure. The DNA was tested by the ATCC and determined to be viable. The ATCC has assigned the following deposit number to pCMV: ATCC #203351.

B. Transfection Procedure

For the IP accumulation assay (Example 3), HEK293 cells were transfected while for the DOI binding assay (Example 4) COS7 cells were transfected. Several protocols well known in the art can be used to transfect cells. The following protocol is representative of the transfection procedures used herein for COS7 or 293 cells.

On day one, COS-7 cells were plated onto 24 well plates, usually $1 \times 10^5$ cells/well or $2 \times 10^5$ cells/well, respectively. On day two, the cells were transfected by first mixing 0.25 ug cDNA in 50 µl serum-free DMEM/well and then 2 µl lipofectamine in 50 µl serum-free DMEM/well. The solutions ("transfection media") were gently mixed and incubated for 15-30 minutes at room temperature. The cells were washed with 0.5 mL PBS and then 400 µl of serum free media was mixed with the transfection media and added to the cells. The cells were then incubated for 3-4 hours at 37° C./5% $CO_2$. Then the transfection media was removed and replaced with 1 mL/well of regular growth media.

For 293 cells, on day one, $13 \times 10^6$ 293 cells per 150 mm plate were plated out. On day two, 2 mL of serum OptimemI (Invitrogen Corporation) was added per plate followed by addition of 60 µL of lipofectamine and 16 µg of cDNA. Note that lipofectamine must be added to the OptimemI and mixed well before addition of cDNA. While complexes between lipofectamine and the cDNA are forming, media was carefully aspirated and cells were gently rinsed with 5 mL of OptimemI media followed by careful aspiration. Then 12 mL of Optimem was added to each plate and 2 mL of transfection solution was added followed by a 5 hour incubation at 37° C. in a 5% $CO_2$ incubator. Plates were then carefully aspirated and 25 mL of Complete Media were added to each plate and cells were then incubated until used.

Example 3

Inositol Phosphate (IP) Accumulation Assays

A. 5-$HT_{2A}$ Receptor

Compounds of the invention were tested for their ability to activate a 5-$HT_{2A}$ receptor clone using an IP accumulation assay. Briefly, HEK293 cells were transiently transfected with a pCMV expression vector containing a human 5-$HT_{2A}$ receptor (for the sequence of the receptor see U.S. Pat. No. 6,541,209, SEQ ID NO:24) as described in Example 2. An IP accumulation assay was performed as described below. Certain compounds of the invention had activity values ranging from about 75 µM to about 0.6 nM in this assay.

B. Constitutively Active 5-$HT_{2A}$ Receptor

Compounds of the invention were tested for their ability to inhibit a constitutively active 5-$HT_{2A}$ receptor clone using an IP accumulation assay. Briefly, 293 cells were transiently transfected with a pCMV expression vector containing a constitutively active human 5-$HT_{2A}$ receptor (for the sequence of the receptor see U.S. Pat. No. 6,541,209, SEQ ID NO:30) as described in Example 2. The constitutively active human 5-$HT_{2A}$ receptor contained the human 5-$HT_{2A}$ receptor described in part A except that intracellular loop 3 (IC3) and the cytoplasmic tail were replaced by the corresponding human INI 5-HT2C cDNA. An IP accumulation assay was performed as described below. Certain compounds of the invention had activity values ranging from about 10 µM to about 0.1 nM in this assay.

C. IP Accumulation Assay Protocol

On the day after transfections, media was removed and the cells were washed with 5 mL PBS followed by careful aspiration. Cells were then trypsinized with 2 mL of 0.05% trypsin for 20-30 seconds followed by addition of 10 mL of warmed media, gently triturated to dissociate cells, and an additional 13 mL of warmed media was gently added. Cells were then counted and 55,000 cells were added to 96-well sterile poly-D-lysine treated plates. Cells were allowed to attach over a six hour incubation at 37° C. in a 5% $CO_2$ incubator. Media was then carefully aspirated and 100 µL of warm inositol-free media plus 0.5 µCi $^3$H-inositol was added to each well and the plates were incubated for 18-20 hours at 37° C. in a 5% $CO_2$ incubator.

On the next day, media was carefully aspirated and then 0.1 mL of assay medium was added containing inositol-free/serum free media, 10 µM pargyline, 10 mM lithium chloride, and test compound at indicated concentrations. The plates were then incubated for three hours at 37° C. and then wells were carefully aspirated. Then 200 µL of ice-cold 0.1M formic acid was added to each well. Plates can then be frozen at this point at −80° C. until further processed. Frozen plates were then thawed over the course of one hour, and the contents of the wells (approximately 220 µL) were placed over 400 µL of washed ion-exchange resin (AG 1-X8) contained in a Multi Screen Filtration plate and incubated for 10 minutes followed by filtration under vacuum pressure. Resin was then washed nine times with 200 µL of water and then tritiated inositol phosphates (IP, IP2, and IP3) were eluted into a collecting plate by the addition of 200 ul of 1M ammonium formate and an additional 10 minute incubation. The eluant was then transferred to 20 mL scintillation vials, 8 mL of SuperMix or Hi-Safe scintillation cocktails was added, and vials were counted for 0.5-1 minutes in a Wallac 1414 scintillation counter.

Example 4

Binding Assays

Compounds of the invention were tested for their ability to bind to a 5-$HT_{2A}$ receptor clone membrane preparation using a radioligand binding assay. Briefly, COS cells were transiently transfected with a pCMV expression vector containing a human 5-$HT_{2A}$ receptor (for the sequence of the receptor see U.S. Pat. No. 6,541,209, SEQ ID NO:24) as described in Example 2.

A. Preparation of Crude Membrane Preparations for Radioligand Binding Assays

COS7 cells transfected with recombinant human 5-HT$_{2A}$ receptors were cultured for 48 hr post transfection, collected, washed with ice-cold phosphate buffered saline, pH7.4 (PBS), and then centrifuged at 48,000×g for 20 min at 4° C. The cell pellet was then resuspended in wash buffer containing 20 mM HEPES pH 7.4 and 0.1 mM EDTA, homogenized on ice using a Brinkman polytron, and recentrifuged at 48,000×g for 20 min. at 4° C. The resultant pellet was then resuspended in 20 mM HEPES, pH 7.4, homogenized on ice, and centrifuged (48,000×g for 20 min at 4° C.). Crude membrane pellets were stored at −80° C. until used for radioligand binding assays.

B. [$^{125}$I]DOI Radioligand Binding Assay

Radioligand binding assays for human 5-HT$_{2A}$ receptor was conducted using the 5-HT$_2$ agonist [$^{125}$I]DOI as radioligand. To define nonspecific binding, 10 µM DOI was used for all assays. For competitive binding studies, 0.5 nM [$^{125}$I]DOI was used and compounds were assayed over a range of 0.01 nM to 10 µM. Assays were conducted in a total volume of 200 µl in 96-well Perkin Elmer GF/C filter plates in assay buffer (50 mM Tris-HCl, pH 7.4, 0.5 mM EDTA, 5 mM MgCl$_2$, and 10 µM pargyline). Assay incubations were performed for 60 min at room temperature and were terminated by rapid filtration under vacuum pressure of the reaction mixture over Whatman GF/C glass fiber filters presoaked in 0.5% PEI using a Brandell cell harvestor. Filters were then washing several times with ice-cold wash buffer (50 mM Tris-HCl, pH 7.4). Plates were then dried at room temperature and counted in a Wallac microBeta scintillation counter. Certain compounds of the present invention and their corresponding activity values are shown in following table.

| Compound No. | IC$_{50}$ DOI Binding Assay (nM) |
|---|---|
| 23 | 1.1 |
| 45 | 10.2 |
| 76 | 5.0 |
| 160 | 13.7 |

Certain other compounds of the invention had activity values ranging from about 10 µM to about 0.1 nM in this assay.

Example 5

In Vitro Human Platelet Aggregation Assays

Compounds of the invention were tested for their ability to aggregate human platelets. Aggregation assays were performed using a Chrono-Log Optical aggregometer model 410. Human blood (~100 mL) was collected from human donors into glass Vacutainers containing 3.8% sodium citrate (light blue tops) at room temperature. Platelet rich plasma (PRP) was isolated via centrifugation at 100 g for 15 min at room temperature. After removal of the aqueous PRP layer, the platelet poor plasma (PPP) was prepared via high speed centrifugation at 2400 g for 20 min. Platelets were counted and their concentration was set to 250,000 cells/µl by dilution with PPP. Aggregation assays were conducted according to the manufacturer's specifications. Briefly, a suspension of 450 µl PRP was stirred in a glass cuvette (1200 rpm) and, after baseline was established, 1 µM ADP followed by either saline or 1 µM 5HT and compound of interest (at desired concentrations) were added and the aggregation response recorded. The concentration of ADP used causes approximately 10-20% of maximal aggregation. The 5-HT concentration corresponded to the concentration which produced maximal potentiation. Percent inhibition of aggregation was calculated from the maximum decrease in optical density of the controls and of the samples containing inhibitors. Only the synergistic effect was assessed. Certain compounds of the invention had activity values ranging from about 80 µM to about 1 nM in this assay. Other compounds of the invention had activity values ranging from about 8 µM to about 2 nM in this assay.

Example 6

Efficacy of Compounds of the Invention in the Attenuation of DOI-Induced Hypolocomotion in Rats.

In this example, compounds of the invention can be tested for inverse agonist activity by determining whether these compounds could attenuate DOI-induced hypolocomotion in rats in a novel environment. DOI is a potent 5-HT$_{2A/2C}$ receptor agonist that crosses the blood-brain barrier. The standard protocol used is described briefly below.

Animals:

Male Sprague-Dawley rats weighing between 200-300 g are used for all tests. Rats are housed three to four per cage. These rats are naïve to experimental testing and drug treatment. Rats are handled one to three days before testing to acclimate them to experimental manipulation. Rats are fasted overnight prior to testing.

Compounds:

(R)-DOI HCl (C$_{11}$H$_{16}$INO$_2$HCl) can be obtained from Sigma-Aldrich, and is dissolved in 0.9% saline. Compounds of the invention are synthesized at Arena Pharmaceuticals Inc. and are dissolved in 100% PEG400. DOI is injected s.c. in a volume of 1 mL/kg, while compounds of the invention are administered p.o. in a volume of 2 mL/kg.

Procedure:

The "Motor Monitor" (Hamilton-Kinder, Poway, Calif.) is used for all activity measurement. This apparatus recorded rears using infrared photobeams.

Locomotor activity testing is conducted during the light cycle (0630-1830) between 9:00 a.m. and 4:00 p.m. Animals are allowed 30 min acclimation to the testing room before testing began.

In determining the effects of compounds of the invention on DOI-induced hypoactivity, animals are first injected with vehicle or the compound of the invention (50 µmol/kg) in their home cages. Sixty minutes later, saline or DOI (0.3 mg/kg salt) is injected. 10 min after DOI administration, animals are placed into the activity apparatus and rearing activity is measured for 10 minutes.

Statistics and Results:

Results (total rears over 10 minutes) are analyzed by t-test. P<0.05 is considered significant.

Example 7

In Vitro Binding of 5-HT$_{2A}$ Receptor

Animals:

Animals (Sprague-Dawley rats) are sacrificed and brains are rapidly dissected and frozen in isopentane maintained at −42° C. Horizontal sections are prepared on a cryostat and maintained at −20° C.

LSD Displacement Protocol:

Lysergic acid diethylamide (LSD) is a potent 5-HT$_{2A}$ receptor and dopamine D$_2$ receptor ligand. An indication of the selectivity of compounds for either or both of these receptors involves displacement of radiolabeled-bound LSD from pre-treated brain sections. For these studies, radiolabeled $^{125}$I-LSD (NEN Life Sciences, Boston, Mass., Catalogue number NEX-199) can be utilized; spiperone (RBI, Natick, Mass. Catalogue number s-128) a 5-HT$_{2A}$ receptor and dopamine D$_2$ receptor antagonist, can also utilized. Buffer consists of 50 nanomolar TRIS-HCl, pH 7.4.

Brain sections are incubated in (a) Buffer plus 1 nanomolar $^{125}$I-LSD; (b) Buffer plus 1 nanomolar $^{125}$I-LSD and 1 micromolar spiperone; or Buffer plus 1 nanomolar $^{125}$I-LSD and 1 micromolar Compound of interest for 30 minutes at room temperature. Sections are then washed 2×10 minutes at 4° C. in Buffer, followed by 20 seconds in distilled H$_2$O. Slides are then air-dried.

After drying, sections are apposed to x-ray film (Kodak Hyperfilm) and exposed for 4 days.

Example 8

Serotonin 5-HT$_{2A}$ Receptor Occupancy Studies in Monkey

In this example, the 5-HT$_{2A}$ receptor occupancy of a compound of the invention can be measured. The study can be carried out in rhesus monkeys using PET and $^{18}$F-altanserin.

Radioligand:

The PET radioligand used for the occupancy studies is $^{18}$F-altanserin. Radiosynthesis of $^{18}$F-altanserin is achieved in high specific activities and is suitable for radiolabeling 5-HT$_{2A}$ receptors in vivo (see Staley et al., *Nucl. Med. Biol.*, 28:271-279 (2001) and references cited within). Quality control issues (chemical and radiochemical purity, specific activity, stability etc) and appropriate binding of the radioligand are verified in rat brain slices prior to use in PET experiments.

Drug Doses and Formulations:

Briefly, the radiopharmaceutical is dissolved in sterile 0.9% saline, pH approx 6-7. The compounds of the invention are dissolved in 60% PEG 400-40% sterile saline on the same day of the PET experiment.

Serotonin 5-HT$_{2A}$ occupancy studies in humans have been reported for M100,907 (Grunder et al., *Neuropsychopharmacology*, 17:175-185 (1997), and Talvik-Lofti et al., *Psychopharmacology*, 148:400-403 (2000)). High occupancies of the 5-HT$_{2A}$ receptors have been reported for various oral doses (doses studied ranged from 6 to 20 mg). For example, an occupancy of >90% was reported for a dose of 20 mg (Talvik-Lofti et al., supra), which translates to approx. 0.28 mg/kg. It may therefore be anticipated that an i.v. dose of 0.1 to 0.2 mg/kg of M100,907 is likely to provide high receptor occupancy. A 0.5 mg/kg dose of a Compound of the invention can be used in these studies.

PET Experiments:

The monkey is anesthetized by using ketamine (10 mg/kg) and is maintained using 0.7 to 1.25% isoflurane. Typically, the monkey has two i.v. lines, one on each arm. One i.v. line is used to administer the radioligand, while the other line is used to draw blood samples for pharmacokinetic data of the radioligand as well as the cold drugs. Generally, rapid blood samples are taken as the radioligand is administered which then taper out by the end of the scan. A volume of approximately 1 mL of blood is taken per time point, which is spun down, and a portion of the plasma is counted for radioactivity in the blood.

An initial control study is carried out in order to measure baseline receptor densities. PET scans on the monkey are separated by at least two weeks. Unlabeled Compound of the invention is administered intravenously, dissolved in 80% PEG 400:40% sterile saline.

PET Data Analysis:

PET data are analyzed by using cerebellum as the reference region and using the distribution volume region (DVR) method. This method has been applied for the analysis of $^{18}$F-altanserin PET data in nonhuman primate and human studies (Smith et al., Synapse, 30:380-392 (1998).

Example 9

The Effect of Compounds of the Invention and Zolpidem on Delta Power in Rats

In this example, the effect of Compounds of the invention on sleep and wakefulness can be compared to the reference drug zolpidem. Drugs are administered during the middle of the light period (inactivity period).

Briefly, Compounds of the invention are tested for their effects on sleep parameters and are compared to zolpidem (5.0 mg/kg, Sigma, St. Louis, Mo.) and vehicle control (80% Tween 80, Sigma, St. Louis, Mo.). A repeated measures design is employed in which each rat is to receive seven separate dosings via oral gavage. The first and seventh dosings are vehicle and the second through sixth are the test compounds and zolpidem given in counter-balanced order. Since all dosings are administered while the rats are connected to the recording apparatus, 60% CO$_2$/40% O$_2$ gas is employed for light sedation during the oral gavage process. Rats are fully recovered within 60 seconds following the procedure. A minimum of three days elapses between dosings. In order to test the effect of the compounds on sleep consolidation, dosing occurs during the middle of the rats' normal inactive period (6 hours following lights on). Dosing typically occurs between 13:15 and 13:45 using a 24 hour notation. All dosing solutions are made fresh on the day of dosing. Following each dosing, animals are continuously recorded until lights out the following day (~30 hours).

Animal Recording and Surgical Procedures:

Animals are housed in a temperature controlled recording room under a 12/12 light/dark cycle (lights on at 7:00 am) and have food and water available ad libitum. Room temperature (24+2° C.), humidity (50+20% relative humidity) and lighting conditions are monitored continuously via computer. Drugs are administered via oral gavage as described above, with a minimum of three days between dosings. Animals are inspected daily in accordance with NIH guidelines.

Eight male Wistar rats (300+25 g; Charles River, Wilmington, Mass.) are prepared with chronic recording implants for continuous electroencephalograph (EEG) and electromyograph (EMG) recordings. Under isoflurane anesthesia (1-4%), the fur is shaved from the top of the skull and the skin was disinfected with Betadine and alcohol. A dorsal midline incision is made, the temporalis muscle retracted, and the skull cauterized and thoroughly cleaned with a 2% hydrogen peroxide solution. Stainless steel screws (#000) are implanted into the skull and served as epidural electrodes. EEG electrodes are positioned bilaterally at +2.0 mm AP from bregma and 2.0 mm ML and at −6.0 mm AP and 3.0 mm ML. Multi-stranded twisted stainless steel wire electrodes are sutured bilaterally in the neck muscles for recording of the EMG. EMG and EEG electrodes are soldered to a head plug connector that was affixed to the skull with dental acrylic. Incisions are closed with suture (silk 4-0) and antibiotics administered topically. Pain is relieved by a long-lasting analgesic (Buprenorphine) administered intramuscularly once post-operatively. Post-surgery, each animal is placed in a clean cage and observed until it is recovered. Animals are permitted a minimum of one week post-operative recovery before study.

For sleep recordings, animals are connected via a cable and a counter-balanced commutator to a Neurodata model 15 data collection system (Grass-Telefactor, West Warwick, R.I.). The animals are allowed an acclimation period of at least 48 hours before the start of the experiment and are connected to the recording apparatus continuously throughout the experimental period except to replace damaged cables. The amplified EEG and EMG signals are digitized and stored on a computer using SleepSign software (Kissei Comtec, Irvine Calif.).

Data Analysis:

EEG and EMG data are scored visually in 10 second epochs for waking (W), REMS, NREMS. Scored data are analyzed and expressed as time spent in each state per half hour. Sleep bout length and number of bouts for each state are calculated in hourly bins. A "bout" consists of a minimum of two consecutive epochs of a given state. EEG delta power (0.5-3.5 Hz) within NREMS is also analyzed in hourly bins. The EEG spectra during NREMS are obtained offline with a fast Fourier transform algorithm on all epochs without artifact. The delta power is normalized to the average delta power in NREMS between 23:00 and 1:00, a time when delta power is normally lowest.

Data are analyzed using repeated measures ANOVA. Light phase and dark phase data are analyzed separately. Both the treatment effect within each rat and the time by treatment effect within each rat is analyzed. Since two comparisons are made, a minimum value of $P<0.025$ is required for post hoc analysis. When statistical significance is found from the ANOVAs, t-tests are performed comparing all compounds to vehicle and the test compounds to zolpidem.

Example 10

Efficacy of Compounds of the Invention in the Inhibition of JC Virus Infection of Human Glial Cells A compound of the invention can be shown to inhibit JC virus infection of human glial cells using the in vitro model of Elphick et al. [*Science* (2004) 306:1380-1383], essentially as described briefly here.

Cells and JC Virus

The human glial cell line SVG (or a suitable subclone thereof, such as SVG-A) is used for these experiments. SVG is a human glial cell line established by transformation of human fetal glial cells by an origin defective SV40 mutant [Major et al., *Proc. Natl. Acad. Sci. USA* (1985) 82:1257-1261]. SVG cells are cultured in Eagle's minimum essential medium (Mediatech Inc., Herndon, Va.) supplemented with 10% heat-inactivated fetal bovine serum, and kept in a humidified 37° C. 5% $CO_2$ incubator.

The Mad-1/SVEΔ strain of JC virus [Vacante et al., *Virology* (1989) 170:353-361] is used for these experiments. While the host range of JC virus is typically limited to growth in human fetal glial cells, the host range of Mad-1/SVEΔ extends to human kidney and monkey cell types. Mad-1/SVEΔ is propagated in HEK cells. Virus titer is measured by hemagglutination of human type O erythrocytes.

Assay for Inhibition of JC Virus Infection

SVG cells growing on coverslips are pre-incubated at 37° C. for 45 min with or without the compound of the invention diluted in media containing 2% FCS. By way of illustration and not limitation, the compound of the invention is used at a concentration of about 1 nM to about 100 μM, at a concentration of about 10 nM to about 100M, at a concentration of about 1 nM to about 10M, or at a concentration of about 10 nM to about 10 μM.

JC virus (Mad-1/SVEΔ) is then added at an MOI of 1.0 and the cells are incubated for 1 hr at 37° C. in the continued presence of the compound of the invention. The cells are then washed 3× in PBS and fed with growth media containing the compound of the invention. At 72 hr post-infection, V antigen positive cells are scored by indirect immunofluorescence (see below). Controls include the addition of the compound of the invention at 24 and 48 h post-infection. The percentage of infected cells in untreated cultures is set at 100%.

Indirect Immunofluorescence

For indirect immunofluorescence analysis of V antigen expression, SVG cells growing on coverslips are fixed in ice cold acetone. To detect V antigen expression, the cells are then incubated for 30 min at 37° C. with a 1:10 dilution of hybridoma supernatant from PAB597. The PAB597 hybridoma produces a monoclonal antibody against the SV40 capsid protein VP1 which has been shown to cross-react with JC virus VP1. The cells are then washed and incubated with goat anti-mouse Alexa Fluor 488 secondary antibody for an additional 30 min. After a final wash, the cells are counterstained with 0.05% Evan's blue, mounted onto glass slides using 90% glycerol in PBS and visualized on Nikon E800 epifluorescent scope. Images are captured using a Hamamatsu digital camera and analyzed using Improvision software.

Example 11

In Vitro Dog Platelet Aggregation Assays

Approximately 50 mL of blood was pooled from 3 male beagles. The protocol for analyzing the effects of compounds on platelet aggregation were identical to those used for human platelets (see Example 5, supra) except 5 μM ADP and 2 μM 5-HT were used to stimulate amplification of platelet aggregation. Results: $IC_{50}$ curves were generated for each compound tested which ranged from about 2 nM to greater than about 10 μM.

Example 12

Ex-Vivo Dog Whole Blood Aggregation

One hour following PO dosing with a test compound whole blood was collected from male beagle dogs in a 5 mL vacutainer with exogenous heparin (5 U/mL) added to vacutainer. Aggregation studies were evaluated by using whole blood Aggregometer (Chronolog Corp.). Briefly, whole blood (400 uL) was added to saline (600 uL) with constant stirring and activated with 5 ug of Collagen (Chronolog Corp.). The serotonin response was obtained by adding 5-HT (Sigma) to final concentration of 2.5 μM. Results: Selected compounds were tested for antiplatelet aggregation activity after single bolus oral dosing. The dose that afforded maximal inhibition of 5-HT amplified platelet aggregation was identified and used for comparison. Certain compounds demonstrated significant inhibition of 5-HT amplified collagen platelet aggregation at a range of concentrations from 0.1 mg/kg to 5 mg/kg.

Example 12

Rat In Vivo Thrombosis, Bleeding, Aggregation, PK Assay Thrombosis Formation and Bleeding Time:

This model concomitantly measures thrombus formation, bleeding time, platelet aggregation and drug exposure in a single live dosed rat. Test compounds where administered to male rats (weighing 250-350 g) via PO injection at varying concentrations depending on compound potency ranging from 1 mpk-100 mpk. Animals where then anesthetized using Nembutal approximately 30 min post PO. Once the animal was fully anesthetized using approved surgical techniques the animal's right femoral artery was isolated in 2 different sections approximately 4-6 mm in length, one area for probe placement and one for Ferric Chloride patch positioning. The artery was then allowed to stabilize to allow recovery from the surgery. During stabilization the animal was then intubated and placed on a ventilator (Harvard Apparatus, Inc.) at 75 strokes/min with a volume of 2.5 cubic cm. Following intubation and after stabilization a micro arterial probe (Transonic Systems, Inc) was then placed on the distal isolated femoral artery. Once the probe was in place the flow was monitored using a Powerlab recording system (AD Instruments) to monitor rate of pulsatile flow. A small piece of filter paper soaked in 30% ferric chloride was placed on the area of the artery upstream of the probe for 10 min. After 5 min of Ferric Chloride patch placement the last 3 mm of the rat's tail was removed. The tail was then placed in a saline filled glass vial at 37 degree and the time it took for bleeding to stop was recorded. After the Ferric chloride patch was removed the flow was recorded until the artery was occluded and time to occlusion was recorded.

Whole Blood Aggregation and PK:

Following measurement of bleeding and time to occlusion 5 mL of blood was obtained for ex-vivo aggregation analysis by cardiac puncture in heparin (5 U/mL). An additional 500 µL of blood was collected in a separate vacutainer for PK analysis (plasma drug concentration). Ex-vivo aggregation studies were evaluated by using whole blood Aggregometer (Chronolog Corp.). Briefly, whole blood (400 µL) was added to saline (600 µL) with constant stirring and activated with 2.55 µg of Collagen (Chronolog Corp.). The serotonin response was obtained by adding 5-HT (Sigma) to final concentration of 2.5 µM. Results: Test compounds or reference compounds with acceptable levels of binding to rat 5-HT2A receptors were evaluated for effects of thrombus formation, bleeding and platelet activity in a single model. This allowed for the most accurate demonstration of separation of the test compound effects on platelet mediated thrombus formation from effects on bleeding. For example the $ED_{50}$ generated for Compound 5 for the time to occlusion and bleeding time in this model demonstrated a ~7-fold separation (log scale) in this therapeutic index.

Those skilled in the art will recognize that various modifications, additions, substitutions, and variations to the illustrative examples set forth herein can be made without departing from the spirit of the invention and are, therefore, considered within the scope of the invention. All documents referenced above, including, but are not limited to, printed publications, and provisional and regular patent applications, are incorporated herein by reference in their entirety.

What is claimed is:
1. A compound of Formula (Ia):

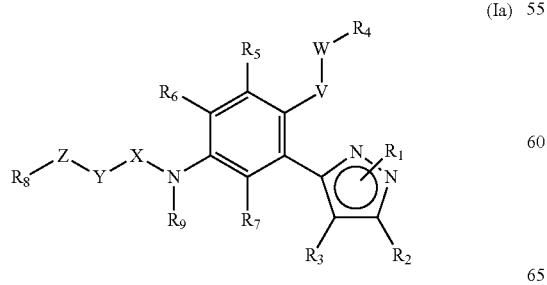

(Ia)

or a pharmaceutically acceptable salt, hydrate or solvate thereof;

wherein:
V is O, S, S(=O), S(=O)$_2$, or NR$_{10}$;
W is $C_{1-4}$ alkylene optionally substituted with 1 to 8 substituents selected independently from the group consisting of $C_{1-3}$ alkyl, $C_{1-4}$ alkoxy, carboxy, cyano, $C_{1-3}$ haloalkyl, halogen, and oxo; or W is absent;
X is C(=O), C(=S), or absent;
Y is O, NR$_{11}$, or absent;
Z is $C_{1-4}$ alkylene, or $C_{3-6}$ cycloalkylene, each optionally substituted with 1 to 8 substituents selected independently from the group consisting of $C_{1-3}$ alkyl, $C_{1-4}$ alkoxy, carboxy, cyano, $C_{1-3}$ haloalkyl, halogen, hydroxyl, and oxo; or Z is absent;
R$_1$ is selected from the group consisting of H, $C_{1-6}$ alkyl, $C_{2-6}$ alkenyl, $C_{2-6}$ alkynyl, and $C_{3-7}$ cycloalkyl;
R$_2$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro, and sulfonamide;
R$_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro, and sulfonamide;
R$_4$ is heterobicyclic, heterocyclic, or heteroaryl each optionally substituted with substituents selected independently from the group consisting of $C_{1-6}$ acyl, $C_{1-12}$ acyloxy, $C_{2-6}$ alkenyl, $C_{1-4}$ alkoxy, $C_{1-6}$ alkoxycarbonylamino, $C_{1-6}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{3-7}$ cycloalkylcarbonyl, $C_{2-6}$ dialkylcarboxamide, formyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, hydroxyl, nitro, phenyl and sulfonamide; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy, and heteroaryl are each optionally substituted with substituents selected independently from the group consisting of $C_{1-6}$ alkyl, $C_{1-5}$ acyl, $C_{1-4}$ alkoxy, $C_{1-6}$ alkylamino, $C_{2-8}$ dialkylamino, $C_{1-4}$ alkylcarboxamide, $C_{1-4}$ alkylsulfonyl, amino, carbo-$C_{1-6}$- alkoxy, carboxamide, carboxy, cyano, $C_{3-6}$ cycloalkyl, halogen, $C_{1-4}$ haloalkoxy, $C_{1-4}$ haloalkyl, hydroxyl, and phenyl;

$R_5$, $R_6$, and $R_7$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy, and phenyl;

$R_8$ is $C_{1-8}$ alkyl, $C_{2-6}$ alkenyl, aryl, $C_{3-7}$ cycloalkyl, or heteroaryl each optionally substituted with substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent substituents together with said aryl or said heteroaryl form a $C_{5-7}$ cycloalkyl optionally comprising 1 to 2 oxygen atoms and optionally substituted with F, Cl or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro; and $R_9$, $R_{10}$, and $R_{11}$ are each independently H or $C_{1-8}$ alkyl; provided that $R_4$ is a group other than an oxiranyl group.

2. The compound according to claim 1 having Formula (Ic):

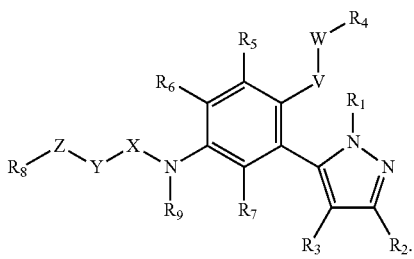

(Ic)

3. The compound according to claim 1, wherein V is O.

4. The compound according to claim 1, wherein W is —CH$_2$—, —CH$_2$CH$_2$—, —CH$_2$C(=O)—, —CH$_2$CH$_2$CH$_2$—, —C(CH$_3$)$_2$C(=O)—, —CH$_2$CH(CH$_3$)—, —CH(CH$_3$)CH$_2$—, —C(CH$_3$)$_2$CH$_2$—, or —CH$_2$C(CH$_3$)$_2$—.

5. The compound according to claim 1, wherein W is absent.

6. The compound according to claim 1, wherein X is C(=O).

7. The compound according to claim 1, wherein X is absent.

8. The compound according to claim 1, wherein Y is NH, O or absent.

9. The compound according to claim 1, wherein Z is absent, —CH$_2$—, —CH(OH)—, —CF$_2$—, —C(CH$_3$)$_2$—, 1,1-cyclopropyl, —CH$_2$CH$_2$—, —CH$_2$CH$_2$CH$_2$—, —CH(CH$_3$)—, or —C(=O)—.

10. The compound according to claim 1, wherein $R_1$ is —CH$_3$.

11. The compound according to claim 1, wherein $R_2$ is H.

12. The compound according to claim 1, wherein $R_3$ is H, F, Cl or Br.

13. The compound according to claim 1, wherein $R_4$ is heterobicyclic, heterocyclic, or heteroaryl each optionally substituted with substituents selected independently from the group consisting of $C_{1-6}$ acyl, $C_{1-12}$ acyloxy, $C_{1-6}$ alkoxycarbonylamino, $C_{1-4}$ alkoxy, $C_{1-6}$ alkyl, $C_{1-4}$ alkylcarboxamide, $C_{1-4}$ alkylsulfonamide, $C_{1-4}$ alkylsulfonyl, $C_{1-4}$ alkylureyl, amino, carbo-$C_{1-6}$-alkoxy, carboxamide, carboxy, $C_{2-6}$ dialkylcarboxamide, formyl, halogen, $C_{1-4}$ haloalkyl, heteroaryl, hydroxyl and phenyl; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy and heteroaryl are each optionally substituted with substituents selected independently from the group consisting of $C_{1-6}$ alkyl, carbo-$C_{1-6}$-alkoxy, carboxy, and phenyl.

14. The compound according to claim 1, wherein $R_4$ is selected from the group consisting of pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl, pyridin-4-yl, azetidin-1-yl, thiomorpholin-4-yl, morpholin-2-yl, 2,5-diaza-bicyclo[2.2.1]hept-2-yl, [1,4]oxazepan-4-yl, 1,1-dioxo-1$\lambda^6$-thiomorpholin-4-yl, piperidin-2-yl, azepan-1-yl, pyrrolidin-3-yl, 3-oxo-piperazin-1-yl, 7-aza-bicyclo[2.2.1]hept-7-yl, and imidazol-1-yl each optionally substituted with substituents selected independently from the group consisting of CH$_3$, C(=O)O-t-butyl, C(=O)OH, C(=O)OEt, NHC(=O)O-t-butyl, OH, C(=O)NHCH$_2$C(=O)OCH$_3$, NHC(=O)CH$_2$C(=O)OCH$_3$, C(=O)NHCH$_2$C(=O)OH, NHC(=O)CH$_2$C(=O)OH, C(=O)OCH$_3$, OC(=O)CH$_2$CH$_2$C(=O)OCH$_3$, OC(=O)CH$_2$CH$_2$CH$_2$CH$_3$, CH$_2$C(=O)OCH$_2$CH$_3$, OCH$_3$, CH$_2$C(=O)OH, OC(=O)CH$_2$CH$_2$C(=O)OCH$_3$, CH$_2$CH$_2$C(=O)OCH$_3$, C(=O)CH$_3$, and C(=O)OCH$_2$-phenyl, C(=O)CH$_2$CH$_2$C(=O)OCH$_3$, C(=O)CH$_2$CH$_2$C(=O)OH, F, phenyl, CH$_2$C(=O)OCH$_3$, S(=O)$_2$CH$_3$, OCH$_2$-phenyl, CH$_2$-phenyl, C(=O)NH$_2$, CHO, —NH$_2$, NHC(=O)CH$_3$, C(=O)N(CH$_3$)$_2$, NHS(=O)$_2$CH$_3$, —CF$_3$, 3-methyl-[1,2,4]oxadiazol-5-yl, and CH(CH$_3$)$_2$.

15. The compound according to claim 1, wherein $R_5$, $R_6$ and $R_7$ are all H.

16. The compound according to claim 1, wherein $R_8$ is $C_{1-8}$ alkyl, $C_{2-6}$ alkenyl, aryl, $C_{3-7}$ cycloalkyl, or heteroaryl each optionally substituted with substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, and hydroxyl, or two adjacent substituents together with said aryl or said heteroaryl form a $C_{5-7}$ cycloalkyl optionally comprising 1 to 2 oxygen atoms and optionally substituted with F.

17. The compound according to claim 1, wherein $R_8$ is selected from the group consisting of methyl, iso-propyl, iso-butyl, n-propyl, n-butyl, 2-methyl-propenyl, phenyl, naphthalen-1-yl, cyclopropyl, cyclobutyl, cyclopentyl, pyridin-2-yl, pyridin-3-yl, 1H-benzoimidazol-2-yl, benzooxazol-2-yl, benzothiazol-2-yl, thiophen-2-yl, furan-2-yl, benzothiophen-2-yl, thiazol-2-yl, isoxazol-3-yl, and pyridin-4-yl each optionally substituted with substituents selected independently from the group consisting of $C(=O)CH_3$, $OCH_3$, $CH_3$, F, Cl, Br, $CF_3$, hydroxyl, $OCF_3$, and CN, or two adjacent substituents together with said phenyl form a $C_5$ cycloalkyl comprising 2 oxygen atoms and optionally substituted with F.

18. The compound according to claim 1, wherein $R_8$ is selected from the group consisting of 4-chloro-phenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluoro-phenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, 2,5-dichloro-phenyl, and benzo[1,3]dioxol-5-yl.

19. The compound according to claim 1, wherein $R_8$ is selected from the group consisting of methyl, iso-propyl, iso-butyl, n-propyl, n-butyl, 2-methyl-propenyl, 3-methyl-butyl, cyclopropyl, cyclobutyl, and cyclopentyl.

20. The compound according to claim 1, wherein $R_8$ is selected from the group consisting of pyridin-3-yl, 6-trifluoromethyl-pyridin-3-yl, 3-hydroxy-pyridin-2-yl, 6-methyl-pyridin-3-yl, 6-hydroxy-pyridin-3-yl, 1H-benzoimidazol-2-yl, benzooxazol-2-yl, benzothiazol-2-yl, thiophen-2-yl, furan-2-yl, 5-chloro-thiophen-2-yl, benzothiophen-2-yl, thiazol-2-yl, 5-methyl-isoxazol-3-yl, and pyridin-4-yl.

21. The compound according to claim 1, wherein $R_9$ is H.
22. The compound according to claim 1, wherein $R_{11}$ is H.
23. The compound according to claim 1 having Formula

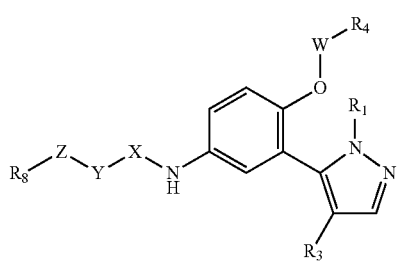

(Ik)

or a pharmaceutically acceptable salt, hydrate or solvate thereof;

wherein:
W is $-CH_2-$, $-CH_2CH_2-$, $-CH_2C(=O)-$, $-CH_2CH_2CH_2-$, $-C(CH_3)_2C(=O)-$, $-CH_2CH(CH_3)-$, $-CH(CH_3)CH_2-$, $-C(CH_3)_2CH_2-$, or $-CH_2C(CH_3)_2-$; or W is absent;

X is $C(=O)$ or absent;
Y is NH, O or absent;
Z is absent, $-CH_2-$, $-CH(OH)-$, $-CF_2-$, $-C(CH_3)_2-$, 1,1-cyclopropyl, $-CH_2CH_2-$, $-CH_2CH_2CH_2-$, $-CH(CH_3)-$, or $-C(=O)-$;
$R_1$ is $C_{1-6}$ alkyl;
$R_3$ is H or halogen;
$R_4$ is heterobicyclic, heterocyclic, or heteroaryl, each optionally substituted with substituents selected independently from the group consisting of $C_{1-6}$ acyl, $C_{1-12}$ acyloxy, $C_{1-4}$ alkoxy, $C_{1-6}$ alkoxycarbonylamino, $C_{1-6}$ alkyl, $C_{1-4}$ alkylcarboxamide, $C_{1-4}$ alkylsulfonamide, $C_{1-4}$ alkylsulfonyl, $C_{1-4}$ alkylureyl, amino, carbo-$C_{1-6}$-alkoxy, carboxamide, carboxy, $C_{2-6}$ dialkylcarboxamide, formyl, halogen, $C_{1-4}$ haloalkyl, heteroaryl, hydroxyl and phenyl; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy and heteroaryl are each optionally substituted with substituents selected independently from the group consisting of $C_{1-6}$ alkyl, carbo-$C_{1-6}$-alkoxy, carboxy, and phenyl; and
$R_8$ is $C_{1-8}$ alkyl, $C_{2-6}$ alkenyl, aryl, $C_{3-7}$ cycloalkyl, or heteroaryl, each optionally substituted with substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent substituents together with said aryl or said heteroaryl form a $C_{5-7}$ cycloalkyl optionally comprising 1 to 2 oxygen atoms and optionally substituted with F.

24. The compound according to claim 1 having Formula

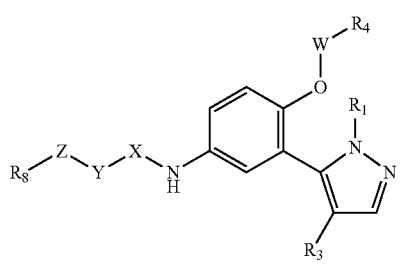

(Ik)

or a pharmaceutically acceptable salt, hydrate or solvate thereof;

wherein:
W is $-CH_2-$, $-CH_2CH_2-$, $-CH_2C(=O)-$, $-CH_2CH_2CH_2-$, $-C(CH_3)_2C(=O)-$, $-CH_2CH(CH_3)-$, $-CH(CH_3)CH_2-$, $-C(CH_3)_2CH_2-$, or $-CH_2C(CH_3)_2-$; or W is absent;

X is $C(=O)$ or absent;
Y is NH, O or absent;
Z is absent, $-CH_2-$, $-CH(OH)-$, $-CF_2-$, $-C(CH_3)_2-$, 1,1-cyclopropyl, $-CH_2CH_2-$, $-CH_2CH_2CH_2-$, $-CH(CH_3)-$, or $-C(=O)-$;
$R_1$ is $C_{1-6}$ alkyl;
$R_3$ is H or halogen;

R₄ is heterobicyclic, heterocyclic, or heteroaryl, each optionally substituted with substituents selected independently from the group consisting of $C_{1-6}$ acyl, $C_{1-12}$ acyloxy, $C_{1-4}$ alkoxy, $C_{1-6}$ alkoxycarbonylamino, $C_{1-6}$ alkyl, $C_{1-4}$ alkylcarboxamide, $C_{1-4}$ alkylsulfonamide, $C_{1-4}$ alkylsulfonyl, $C_{1-4}$ alkylureyl, amino, carbo-$C_{1-6}$-alkoxy, carboxamide, carboxy, $C_{2-6}$ dialkylcarboxamide, formyl, halogen, $C_{1-4}$ haloalkyl, heteroaryl, hydroxyl and phenyl; wherein said $C_{1-5}$ acyl, $C_{1-5}$ acyloxy, $C_{1-4}$ alkoxy, $C_{1-6}$ alkyl, $C_{1-4}$ alkylcarboxamide, amino, carbo-$C_{1-6}$-alkoxy and heteroaryl are each optionally substituted with substituents selected independently from the group consisting of $C_{1-6}$ alkyl, carbo-$C_{1-6}$-alkoxy, carboxy, and phenyl; and R₈ is selected from the group consisting of 4-chloro-phenyl, 2,4-difluoro-phenyl, 4-fluoro-phenyl, 3-chloro-phenyl, 2,2-difluoro-benzo[1,3]dioxol-5-yl, 4-hydroxy-phenyl, 4-chloro-2-hydroxy-phenyl, phenyl, 3-fluoro-phenyl, 2-fluoro-phenyl, 2-chloro-phenyl, 4-bromo-phenyl, 4-methoxy-phenyl, 4-trifluoromethyl-phenyl, 3,5-bis-trifluoromethyl-phenyl, 2-fluoro-5-methyl-phenyl, 3-methoxy-phenyl, 3-acetyl-phenyl, 4-methyl-phenyl, 3-trifluoromethyl-phenyl, 3,5-difluoro-phenyl, 2,4-dichloro-phenyl, 4-chloro-2-trifluoromethyl-phenyl, 3,4-difluoro-phenyl, 2,5-difluoro-phenyl, 2,6-difluoro-phenyl, naphthalen-1-yl, 4-trifluoromethoxy-phenyl, 3-cyano-phenyl, 2-trifluoromethoxy-phenyl, 4-chloro-2-fluoro-phenyl, 2,3-difluoro-phenyl, 2,4,5-trifluoro-phenyl, 2,3,4-trifluoro-phenyl, 3,4-dichloro-phenyl, 4-fluoro-3-trifluoromethyl-phenyl, 5-fluoro-2-trifluoromethyl-phenyl, 2-trifluoromethyl-phenyl, 3-methyl-phenyl, 2-fluoro-4-trifluoromethyl-phenyl, 4-chloro-3-fluoro-phenyl, 3-fluoro-4-methyl-phenyl, 4-fluoro-3-methyl-phenyl, 3-fluoro-4-trifluoromethyl-phenyl, 3-chloro-4-fluoro-phenyl, 2,6-dichloro-phenyl, 4-cyano-phenyl, 2,5-dichloro-phenyl, and benzo[1,3]dioxol-5-yl.

25. The compound according to claim 1 having Formula (Io):

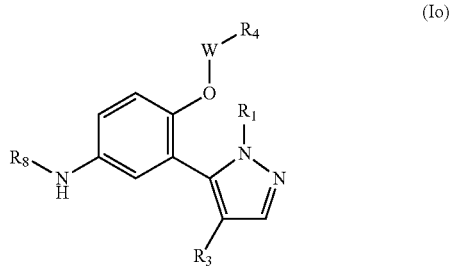

or a pharmaceutically acceptable salt, hydrate or solvate thereof;
wherein:
W is —CH₂—, —CH₂CH₂— or —CH₂C(=O)—;
R₁ is $C_{1-6}$ alkyl;
R₃ is H or halogen;
R₄ is pyrrolidin-1-yl, pyrrolidin-2-yl, piperidin-1-yl, piperidin-4-yl, piperidin-3-yl, morpholin-4-yl, piperazin-1-yl, pyridin-3-yl, pyridin-2-yl or pyridin-4-yl, each optionally substituted with substituents selected independently from the group consisting of CH₃, C(=O)O-t-butyl, C(=O)OH, C(=O)OEt, NHC(=O)O-t-butyl, OH, C(=O)NHCH₂C(=O)OCH₃, NHC(=O)CH₂C(=O)OCH₃, C(=O)NHCH₂C(=O)OH, NHC(=O)CH₂C(=O)OH, C(=O)OCH₃, OC(=O)CH₂CH₂C(=O)OCH₃, OC(=O)CH₂CH₂CH₂CH₂CH₃, CH₂C(=O)OCH₂CH₃, OCH₃, CH₂C(=O)OH, OC(=O)CH₂CH₂C(=O)OCH₃, CH₂CH₂C(=O)OCH₃, C(=O)CH₃, and C(=O)OCH₂-phenyl; and R₈ is selected from the group consisting of 1H-benzoimidazol-2-yl, benzooxazol-2-yl and benzothiazol-2-yl.

26. The compound according to claim 1, wherein the compound is selected from the group consisting of:
1-[3-(4-Bromo-2-methyl-2H-pyrazol-3-yl)-4-(2-pyrrolidin-1-yl-ethoxy)-phenyl]-3-(4-chloro-phenyl)-urea (Compound 1);
N-(3-(4-chloro-1-methyl-1H-pyrazol-5-yl)-4-(2-morpholinoethoxy)phenyl) cyclopropanecarboxamide (Compound 271);
N-{3-(4-Bromo-2-methyl-2H-pyrazol-3-yl)-4-[2-(4-methoxy-piperidin-1-yl)-ethoxy]-phenyl}-3-fluoro-benzamide (Compound 637);
N-[3-(4-chloro-2-methyl-2H-pyrazol-3-yl)-4-(2-morpholin-4-yl-ethoxy)-phenyl]-3-fluoro-4-methyl-benzamide (Compound 559);
1-(3-(4-chloro-1-methyl-1H-pyrazol-5-yl)-4-(2-morpholinoethoxy)phenyl)-3-(3-chlorophenyl)urea (Compound 231);
1-(4-Chloro-benzyl)-3-[3-(2-methyl-2H-pyrazol-3-yl)-4-(3-morpholin-4-yl-propoxy)-phenyl]-urea (Compound 666);
3-Chloro-N-[3-(2-methyl-2H-pyrazol-3-yl)-4-(2-pyrrolidin-1-yl-ethoxy)-phenyl]-benzamide (Compound 512);
3-Fluoro-N-[3-(2-methyl-2H-pyrazol-3-yl)-4-(2-pyrrolidin-1-yl-ethoxy)-phenyl]-4-trifluoromethyl-benzamide (Compound 487);
1-{3-(4-Chloro-2-methyl-2H-pyrazol-3-yl)-4-[2-(3-hydroxy-azetidin-1-yl)-ethoxy]-phenyl}-3-(4-chloro-phenyl)-urea (Compound 298);
1-[4-[2-(7-Aza-bicyclo[2.2.1]hept-7-yl)-ethoxy]-3-(4-bromo-2-methyl-2H-pyrazol-3-yl)-phenyl]-3-(3-trifluoromethyl-benzyl)-urea (Compound 710);
1-[4-[2-(7-Aza-bicyclo[2.2.1]hept-7-yl)-ethoxy]-3-(4-bromo-2-methyl-2H-pyrazol-3-yl)-phenyl]-3-(2,4-difluoro-benzyl)-urea (Compound 734);
4-Fluoro-N-[3-(2-methyl-2H-pyrazol-3-yl)-4-(2-morpholin-4-yl-ethoxy)-phenyl]-benzamide (Compound 281);
N-[3-(2-Methyl-2H-pyrazol-3-yl)-4-(2-morpholin-4-yl-ethoxy)-phenyl]-4-trifluoromethyl-benzamide (Compound 282);
N-[3-(2-Methyl-2H-pyrazol-3-yl)-4-(2-pyrrolidin-1-yl-ethoxy)-phenyl]-3-trifluoromethyl-benzamide (Compound 435);
N-[4-[2-(3,3-Difluoro-pyrrolidin-1-yl)-ethoxy]-3-(2-methyl-2H-pyrazol-3-yl)-phenyl]-4-fluoro-3-methyl-benzamide (Compound 546);
4-Fluoro-3-methyl-N-[3-(2-methyl-2H-pyrazol-3-yl)-4-(1-methyl-pyrrolidin-2-ylmethoxy)-phenyl]-benzamide (Compound 547);
N-{3-(4-Bromo-2-methyl-2H-pyrazol-3-yl)-4-[2-(2-methyl-pyrrolidin-1-yl)-ethoxy]-phenyl}-3, 4-difluoro-benzamide (Compound 579);
N-[3-(4-Bromo-2-methyl-2H-pyrazol-3-yl)-4-(1-methyl-pyrrolidin-3-yloxy)-phenyl]-3, 4-difluoro-benzamide (Compound 585);
N-[4-[2-(3-Hydroxy-pyrrolidin-1-yl)-ethoxy]-3-(2-methyl-2H-pyrazol-3-yl)-phenyl]-4-trifluoromethyl-benzamide (Compound 586);

3-Fluoro-N-[4-[2-(4-formyl-piperazin-1-yl)-ethoxy]-3-(2-methyl-2H-pyrazol-3-yl)-phenyl]-benzamide (Compound 752);
N-[4-[2-(4-Acetyl-piperazin-1-yl)-ethoxy]-3-(2-methyl-2H-pyrazol-3-yl)-phenyl]-3-methoxy-benzamide (Compound 755);
N-[3-(2-Methyl-2H-pyrazol-3-yl)-4-(2-morpholin-4-yl-ethoxy)-phenyl]-2-phenyl-acetamide) (Compound 762);
2-(3-Fluoro-phenyl)-N-[3-(2-methyl-2H-pyrazol-3-yl)-4-(2-morpholin-4-yl-ethoxy)-phenyl]-acetamide (Compound 766);
2-(3-Chloro-phenyl)-N-[3-(2-methyl-2H-pyrazol-3-yl)-4-(2-morpholin-4-yl-ethoxy)-phenyl]-acetamide (Compound 767);
N-[3-(2-Methyl-2H-pyrazol-3-yl)-4-(2-morpholin-4-yl-ethoxy)-phenyl]-2-(3-trifluoromethyl-phenyl)-acetamide (Compound 768);
2-(3-Methoxy-phenyl)-N-[3-(2-methyl-2H-pyrazol-3-yl)-4-(2-morpholin-4-yl-ethoxy)-phenyl]-acetamide (Compound 769);
N-[3-(2-Methyl-2H-pyrazol-3-yl)-4-(2-morpholin-4-yl-ethoxy)-phenyl]-2-m-tolyl-acetamide (Compound 770);
N-[3-(2-Methyl-2H-pyrazol-3-yl)-4-(2-morpholin-4-yl-ethoxy)-phenyl]-2-p-tolyl-acetamide (Compound 771);
2-Benzo[1,3]dioxol-5-yl-N-[3-(2-methyl-2H-pyrazol-3-yl)-4-(2-morpholin-4-yl-ethoxy)-phenyl]-acetamide (Compound 772);
N-[3-(2-Methyl-2H-pyrazol-3-yl)-4-(2-morpholin-4-yl-ethoxy)-phenyl]-2-(4-trifluoromethyl-phenyl)-acetamide (Compound 794);
N-[3-(2-Methyl-2H-pyrazol-3-yl)-4-(2-morpholin-4-yl-ethoxy)-phenyl]-2-thiophen-2-yl-acetamide (Compound 795);
1-[4-(2-Azetidin-1-yl-ethoxy)-3-(2-methyl-2H-pyrazol-3-yl)-phenyl]-3-(2,4-difluoro-phenyl)-urea (Compound 86);
1-{3-(4-Bromo-2-methyl-2H-pyrazol-3-yl)-4-[2-(3-methoxy-azetidin-1-yl)-ethoxy]-phenyl}-3-(4-chloro-phenyl)-urea (Compound 267);
N-{3-(4-Bromo-2-methyl-2H-pyrazol-3-yl)-4-[2-(3-methoxy-azetidin-1-yl)-ethoxy]-phenyl}-3-methyl-butyramide (Compound 326);
Benzooxazol-2-yl-[3-(4-bromo-2-methyl-2H-pyrazol-3-yl)-4-(2-piperidin-1-yl-ethoxy)-phenyl]-amine (Compound 199);
5-Chloro-thiophene-2-carboxylic acid [3-(4-chloro-2-methyl-2H-pyrazol-3-yl)-4-(2-morpholin-4-yl-ethoxy)-phenyl]-amide (Compound 333);
3,4-Difluoro-N-[4-[2-(2-methyl-piperidin-1-yl)-ethoxy]-3-(2-methyl-2H-pyrazol-3-yl)-phenyl]-benzamide (Compound 459);
N-[3-(4-Chloro-2-methyl-2H-pyrazol-3-yl)-4-(1-methyl-piperidin-4-yloxy)-phenyl]-4-fluoro-3-methyl-benzamide (Compound 745);
1-(2-Fluoro-phenyl)-3-[3-(2-methyl-2H-pyrazol-3-yl)-4-(2-piperidin-1-yl-ethoxy)-phenyl]-urea (Compound 65);
N-[3-(4-Bromo-2-methyl-2H-pyrazol-3-yl)-4-(2-pyrrolidin-1-yl-ethoxy)-phenyl]-3-fluoro-benzamide (Compound 455);
Cyclopentanecarboxylic acid [3-(4-bromo-2-methyl-2H-pyrazol-3-yl)-4-(2-morpholin-4-yl-ethoxy)-phenyl]-amide (Compound 310);
N-[3-(2-Methyl-2H-pyrazol-3-yl)-4-(2-pyrrolidin-1-yl-ethoxy)-phenyl]-4-trifluoromethyl-benzamide (Compound 343);
N-{3-(4-Bromo-2-methyl-2H-pyrazol-3-yl)-4-[2-(3-fluoro-pyrrolidin-1-yl)-ethoxy]-phenyl}-3-fluoro-benzamide (Compound 475);
3-Chloro-4-fluoro-N-[4-[2-(4-fluoro-piperidin-1-yl)-ethoxy]-3-(2-methyl-2H-pyrazol-3-yl)-phenyl]-benzamide (Compound 538);
N-[3-(4-Bromo-2-methyl-2H-pyrazol-3-yl)-4-(piperidin-3-yloxy)-phenyl]-4-fluoro-benzamide (Compound 396);
N-[4-[2-(4-Acetyl-piperazin-1-yl)-ethoxy]-3-(2-methyl-2H-pyrazol-3-yl)-phenyl]-3-fluoro-benzamide (Compound 660);
N-[4-[2-(4,4-Difluoro-piperidin-1-yl)-ethoxy]-3-(2-methyl-2H-pyrazol-3-yl)-phenyl]-3-fluoro-benzamide (Compound 778);
3-Fluoro-N-[3-(2-methyl-2H-pyrazol-3-yl)-4-(2-morpholin-4-yl-ethoxy)-phenyl]-benzamide (Compound 729);
3-Methoxy-N-[3-(2-methyl-2H-pyrazol-3-yl)-4-(2-morpholin-4-yl-ethoxy)-phenyl]-benzamide (Compound 733);
1-[3-(4-Bromo-2-methyl-2H-pyrazol-3-yl)-4-(2-pyrrolidin-1-yl-ethoxy)-phenyl]-3-(2,4-difluoro-phenyl)-urea (Compound 5);
1-[3-(4-Bromo-2-methyl-2H-pyrazol-3-yl)-4-(2-pyridin-4-yl-ethoxy)-phenyl]-3-(4-chloro-phenyl)-urea (Compound 145);
1-(2,4-Difluoro-phenyl)-3-[4-(2-imidazol-1-yl-ethoxy)-3-(2-methyl-2H-pyrazol-3-yl)-phenyl]-urea (Compound 219);
[4-(2-Azepan-1-yl-ethoxy)-3-(4-bromo-2-methyl-2H-pyrazol-3-yl)-phenyl]-carbamic acid isopropyl ester (Compound 352);
N-[3-(2-Methyl-2H-pyrazol-3-yl)-4-(2-[1,4]oxazepan-4-yl-ethoxy)-phenyl]-3-trifluoromethyl-benzamide (Compound 568);
N-[3-(4-Bromo-2-methyl-2H-pyrazol-3-yl)-4-(2-[1,4]oxazepan-4-yl-ethoxy)-phenyl]-3-fluoro-4-trifluoromethyl-benzamide (Compound 606);
[3-(2-Methyl-2H-pyrazol-3-yl)-4-(2-thiomorpholin-4-yl-ethoxy)-phenyl]-carbamic acid isopropyl ester (Compound 214);
[3-(2-Methyl-2H-pyrazol-3-yl)-4-(2-[1,4]oxazepan-4-yl-ethoxy)-phenyl]-carbamic acid isopropyl ester (Compound 215); and
N-[3-(4-Chloro-2-methyl-2H-pyrazol-3-yl)-4-(2-morpholin-4-yl-ethoxy)-phenyl]-3-trifluoromethyl-benzamide (Compound 527);
or a pharmaceutically acceptable salt, hydrate or solvate thereof.

27. A pharmaceutical composition comprising a compound according to claim 1 and a pharmaceutically acceptable carrier.

28. A method for treating a 5-HT$_{2A}$ mediated disorder in an individual comprising administering to said individual in need thereof a therapeutically effective amount of a compound according to claim 1 or a pharmaceutical composition according to claim 27, wherein said 5-HT$_{2A}$ mediated disorder is selected from the group consisting of coronary artery disease, myocardial infarction, transient ischemic attack, angina, stroke, and atrial fibrillation.

29. A method for treating a condition associated with platelet aggregation in an individual comprising administering to said individual in need thereof a therapeutically effective amount of a compound according to claim 1 or a pharmaceutical composition according to claim 27.

30. A method for reducing the risk of blood clot formation in an angioplasty or coronary bypass surgery individual comprising administering to said individual in need thereof a therapeutically effective amount of a compound according to claim 1 or a pharmaceutical composition according to claim 27.

31. A method for reducing the risk of blood clot formation in an individual suffering from atrial fibrillation, comprising administering to said individual in need thereof a therapeutically effective amount of a compound according to claim 1 or a pharmaceutical composition according to claim 27.

32. A method for treating a sleep disorder in an individual comprising administering to said individual in need thereof a therapeutically effective amount of a compound according to claim 1 or a pharmaceutical composition according to claim 27.

33. The method according to claim 32, wherein said sleep disorder is a dyssomnia.

34. The method according to claim 32, wherein said sleep disorder is a parasomnia.

35. A method for treating a diabetic-related disorder in an individual comprising administering to said individual in need thereof a therapeutically effective amount of a compound according to claim 1 or a pharmaceutical composition according to claim 27.

36. A method for treating progressive multifocal leukoencephalopathy in an individual comprising administering to said individual in need thereof a therapeutically effective amount of a compound according to claim 1 or a pharmaceutical composition according to claim 27.

37. A method for treating hypertension in an individual comprising administering to the individual in need thereof a therapeutically effective amount of a compound according to claim 1 or a pharmaceutical composition according to claim 27.

38. A method for treating pain in an individual comprising administering to the individual in need thereof a therapeutically effective amount of a compound according to claim 1 or a pharmaceutical composition according to claim 27.

39. A process for preparing a composition comprising admixing a compound according to claim 1 and a pharmaceutically acceptable carrier.

\* \* \* \* \*